United States Patent
Hicks et al.

(10) Patent No.: US 7,572,607 B2
(45) Date of Patent: Aug. 11, 2009

(54) POLYPEPTIDES AND BIOSYNTHETIC PATHWAYS FOR THE PRODUCTION OF MONATIN AND ITS PRECURSORS

(75) Inventors: Paula M. Hicks, Bend, OR (US); Sara C. McFarlan, St. Paul, MN (US); Timothy W. Abraham, Minnetonka, MN (US); Douglas C. Cameron, Plymouth, MN (US); James R. Millis, Plymouth, MN (US); John Rosazza, Iowa City, IA (US); Lishan Zhao, Carlsbad, CA (US); David Paul Weiner, Del Mar, CA (US)

(73) Assignee: Cargill, Incorporated, Wayzata, MN (US)

( * ) Notice: Subject to any disclaimer, the term of this patent is extended or adjusted under 35 U.S.C. 154(b) by 278 days.

(21) Appl. No.: 11/114,922

(22) Filed: Apr. 26, 2005

(65) Prior Publication Data

US 2005/0282260 A1 Dec. 22, 2005

Related U.S. Application Data

(63) Continuation-in-part of application No. 10/422,366, filed on Apr. 23, 2003, now abandoned.

(60) Provisional application No. 60/374,831, filed on Apr. 23, 2002.

(51) Int. Cl.
C12P 13/22 (2006.01)
C12N 1/21 (2006.01)

(52) U.S. Cl. ................ 435/121; 435/108; 435/193; 435/69.1; 435/325; 435/320.1; 435/252.3; 536/23.2

(58) Field of Classification Search ............ 435/108, 435/193, 69.1, 325, 320.1, 252.3, 121; 536/23.2
See application file for complete search history.

(56) References Cited

U.S. PATENT DOCUMENTS

| | | | |
|---|---|---|---|
| 3,002,889 A | 10/1961 | Kinoshita et al. | |
| 3,128,237 A | 4/1964 | Motozaki et al. | |
| 3,399,114 A | 8/1968 | Ohsawa et al. | |
| 3,751,458 A | 8/1973 | Wiley | |
| 4,371,614 A | 2/1983 | Anderson et al. | |
| 4,975,298 A | 12/1990 | Van Wyk et al. | |
| 5,128,164 A | 7/1992 | Van Wyk et al. | |
| 5,128,482 A | 7/1992 | Olivier et al. | |
| 5,300,437 A | 4/1994 | Stirling et al. | |
| 5,728,555 A | 3/1998 | Fotheringham et al. | |
| 5,985,617 A | 11/1999 | Liao | |
| 5,994,559 A | 11/1999 | Abushanab et al. | |
| 6,207,427 B1 | 3/2001 | Hashimoto et al. | |
| 6,489,100 B1 | 12/2002 | Liao | |
| 7,064,219 B2 | 6/2006 | Kawahara et al. | |
| 2003/0228403 A1 | 12/2003 | Amino et al. | |
| 2004/0063175 A1 | 4/2004 | Abraham et al. | |
| 2005/0004394 A1 | 1/2005 | Kawahara et al. | |
| 2005/0009153 A1 | 1/2005 | Sugiyama et al. | |
| 2005/0020508 A1 | 1/2005 | Amino et al. | |
| 2005/0095670 A1 | 5/2005 | Ikeda et al. | |
| 2005/0106305 A1 | 5/2005 | Abraham et al. | |
| 2005/0112260 A1 | 5/2005 | Abraham et al. | |
| 2005/0118317 A1 | 6/2005 | Amino et al. | |
| 2005/0137246 A1 | 6/2005 | Amino et al. | |
| 2005/0153405 A1 | 7/2005 | Sugiyama et al. | |
| 2005/0170041 A1 | 8/2005 | Abraham et al. | |
| 2005/0221453 A1 | 10/2005 | Takagi et al. | |
| 2005/0221455 A1 | 10/2005 | McFarlan et al. | |
| 2005/0244937 A1 | 11/2005 | Abraham et al. | |
| 2005/0244939 A1 | 11/2005 | Sugiyama et al. | |
| 2005/0272939 A1 | 12/2005 | Amino et al. | |
| 2005/0282260 A1* | 12/2005 | Hicks et al. .............. | 435/121 |
| 2006/0003411 A1 | 1/2006 | Sugiyama et al. | |
| 2006/0003426 A1 | 1/2006 | Sugiyama et al. | |
| 2006/0009394 A1 | 1/2006 | Amino | |
| 2006/0014819 A1 | 1/2006 | Mori et al. | |
| 2006/0074249 A1 | 4/2006 | Kawahara et al. | |
| 2006/0083695 A1 | 4/2006 | Mori | |
| 2006/0154343 A1 | 7/2006 | Mori et al. | |
| 2006/0172396 A1 | 8/2006 | Sugiyama et al. | |
| 2006/0252135 A1 | 11/2006 | Brazeau et al. | |
| 2007/0099277 A1 | 5/2007 | Anderson et al. | |
| 2007/0105938 A1 | 5/2007 | Anderson et al. | |
| 2008/0020435 A1 | 1/2008 | Burke et al. | |

FOREIGN PATENT DOCUMENTS

EP 0 438 314 A1 7/1991

(Continued)

OTHER PUBLICATIONS

Ackerman, L.G., "Structure Elucidation of and Synthetic Approaches to Monatin, a Metabolite from *Schlerochiton illicifolius*," Ph.D. Dissertation, University of Stellenbosch 175 pages (1990).

Ager, D.J., et al., "Commercial, Synthetic Nonnutritive Sweeteners," *Angew. Chem. Int. Ed.* 37:1802-1817, Verlag Chemie (1998).

Ager, D.J., et al., "Novel biosynthetic routes to non-proteinogenic amino acids as chiral pharmaceutical intermediates," *J. Mol. Catal., B: Enzym.* 11:199-205, Elsevier Science (Jan. 2001).

(Continued)

*Primary Examiner*—Chih-Min Kam

(57) ABSTRACT

Methods and compositions that can be used to make monatin from glucose, tryptophan, indole-3-lactic acid, indole-3-pyruvate, and 2-hydroxy 2-(indol-3-ylmethyl)-4-keto glutaric acid, are provided. Methods are also disclosed for producing the indole-3-pyruvate and 2-hydroxy 2-(indol-3-ylmethyl)-4-keto glutaric acid intermediates. Compositions provided include nucleic acid molecules, polypeptides, chemical structures, and cells. Methods include in vitro and in vivo processes, and the in vitro methods include chemical reactions.

45 Claims, 9 Drawing Sheets

FOREIGN PATENT DOCUMENTS

| | | |
|---|---|---|
| EP | 1 045 029 A2 | 10/2000 |
| EP | 1 445 323 A1 | 8/2004 |
| EP | 1 449 832 | 8/2004 |
| EP | 1 533 376 | 5/2005 |
| EP | 1 580 268 | 9/2005 |
| EP | 1 605 041 | 12/2005 |
| EP | 1 350 79 | 9/2006 |
| EP | 1 719 758 A1 | 11/2006 |
| JP | 2002/060382 | 2/2002 |
| JP | 2003/171365 | 6/2003 |
| JP | 2004/222657 | 8/2004 |
| JP | 2004/331644 | 11/2004 |
| JP | 2004/331650 | 11/2004 |
| WO | WO 87/01130 A1 | 2/1987 |
| WO | WO 99/55877 A1 | 11/1999 |
| WO | WO 03/000913 A2 | 1/2003 |
| WO | WO 03/045914 | 6/2003 |
| WO | WO 03/056026 | 7/2003 |
| WO | WO 03/056026 A1 | 7/2003 |
| WO | WO 03/059865 A1 | 7/2003 |
| WO | WO 03/091396 A2 | 11/2003 |
| WO | WO 2004/018672 A1 | 3/2004 |
| WO | WO 2004/053125 A1 | 6/2004 |
| WO | WO 2005/001105 | 1/2005 |
| WO | WO 2005/014839 A2 | 2/2005 |
| WO | WO 2005/016022 A1 | 2/2005 |
| WO | WO 2005/020721 A1 | 3/2005 |
| WO | WO 2005/042756 A1 | 5/2005 |
| WO | WO 2005/082850 A1 | 9/2005 |
| WO | WO 2006/011613 A1 | 2/2006 |
| WO | WO 2006/058893 A2 | 6/2006 |
| WO | WO 2006/113897 | 10/2006 |
| WO | WO 2007/103389 | 9/2007 |
| WO | WO 2007/133183 | 11/2007 |
| WO | WO 2007/133184 | 11/2007 |

OTHER PUBLICATIONS

Bae, H., et al., "Production of aromatic D-amino acids from α-keto acids and ammonia by coupling of four enzyme reactions," *J. Mol. Catal., B: Enzym.* 6:241-247, Elsevier Science (1999).

Bassoli, A., et al., "Design and Synthesis of New Monatin Derivatives," *Abstracts presented at the 13th International Symposium on Olfaction and Taste and 14th European Chemoreception Research Organisation Congress*, Brighton, UK, Jul. 20-24, 2000.

Bassoli, A., "'Chemistry-Nature,' still an open match for the discovery of new intensive sweeteners," *European Journal of Nutraceuticals & Functional Foods* 15:27-29, Tekno Scienze (Jul./Aug. 2004).

Bongaerts, J., et al., "Metabolic Engineering for Microbial Production of Aromatic Amino Acids and Derived Compounds," *Metab. Eng.* 3:289-300, Academic Press (Oct. 2001).

Buldain, G., et al., "Carbon-13 Nuclear Magnetic Resonance Spectra of the Hydrate, Keto and Enol forms of Oxalacetic Acid," *Magnetic Resonance in Chemistry* 23:478-481, Wiley Heden Ltd. (1985).

DeLuna, A., et al., "NADP-Glutamate Dehydrogenase Isoenzymes of *Saccharomyces cerevisiae*," *J. Biol. Chem.* 276:43775-43783, The American Society for Biochemistry and Molecular Biology, Inc. (Nov. 2001).

Flores, N., et al., "Pathway engineering for the production of aromatic compounds in *Escherichia coli*," *Nat. Biotechnol.* 14:620-623, Nature America Publishing (1996).

Floyd, N.C., et al., "A Simple Strategy for obtaining both Enantiomers from an Aldolase Reaction: Preparation of L- and D-4-Hydroxy-2-ketogluterate," *J. Chem. Soc. Perkin Trans. 1* 9:1085-1086, Chemical Society (1992).

Galkin, A., et al., "Synthesis of Optically Active Amino Acids from α-Keto Acids with *Escherichia coli* Cells Expressing Heterologous Genes," *Appl. Environ. Microbiol.* 63:4651-4656, American Society for Microbiology (1997).

Gosset, G., et al., "A direct comparison of approaches for increasing carbon flow to aromatic biosynthesis in *Escherichia coli*," *J. Ind. Microbiol.* 17:47-52, Stockton Press on behalf of the Society for Industrial Microbiology (1996).

Hayashi, H., et al., "*Escherichia coli* Aromatic Amino Acid Aminotransferase: Characterization and Comparison with Aspartate Aminotransferase," *Biochemistry* 32:12229-12239, American Chemical Society (1993).

Hibino, S. and Choshi, T., "Simple indole alkaloids and those with a nonrearranged monoterpenoid unit," *Nat. Prod. Rep.* 19:148-180, Royal Society of Chemistry (Apr. 2002).

Holzapfel, C. and Olivier, J., "The Synthesis of a γ-Keto-α-Amino Acid, a Key Intermediate in the Sythesis of Monatin, A New Natural Sweetener," *Synthetic Communications* 23:2511-2526, Marcel Dekker (1993).

Holzapfel, C., et al., "A Simple Cycloaddition Approach to a Racemate of the Natural Sweetener Monatin," *Synthetic Communications* 24:3197-3211, Marcel Dekker (1994).

Izumi, Y., *Amino-san Kogyo—Gosei to Riyo*, Kaneko, T., et al., eds., Kodansha Ltd., pp. 8-9 (1973).

Izumi, Y., *Synthetic production and utilization of amino acids*, Kaneko, T., et al., eds., Kodansha Ltd., pp. 3-16 (1974) (republished English translation that includes NPL18).

Juhl, K., et al., "Catalytic asymmetric homo-aldol reaction of pyruvate-a chiral Lewis acid catalyst that mimics aldolase enzymes," *Chem. Commun.*, No. 22, pp. 2211-2212, Royal Society of Chemistry (2000).

Katsumata, R. and Ikeda, M., "Hyperproduction of Tryptophan in *Corynebacterium glutamicum* by Pathway Engineering," *Bio/Technology* 11:921-925, Nature Publishing Co. (1993).

Koeller, K.M. and Wong, C.-H., "Enzymes for chemical synthesis," *Nature* 409:232-240, Nature Publishing Group (Jan. 2001).

Kogiso, K., et al., "Control of Lactamization during the Synthesis of the Monatin Analogue," *Peptide Science 2003*, The Proceedings of the 40th Symposium on Japanese Peptide Symposium, pp. 195-198, The Japanese Peptide Society (Mar. 2004).

Koshiba, T. and Mito, N., "Partial Purification and some Properties of L- and D-Tryptophan Aminotransferases form Maize Coleoptiles," Proceedings of the 8th International Symposium on Vitamin $B_6$ and Carbonyl Catalysis, Osaka, Japan, pp. 245-247, Pergamon Press, Oct. 15-19, 1990.

Li, T., et al., "Nonproteinogenic α-Amino Acid Preparation Using Equilibrium Shifted Transamination," *Organic Process Research & Development* 6:533-538, American Chemical Society (Jul./Aug. 2002).

Liao, J.C., et al., "Pathway Analysis, Engineering, and Physiological Considerations for Redirecting Central Metabolism," *Biotechnol. Bioeng.* 52:129-140, John Wiley & Sons, Inc. (1996).

Nakamura, K., et al., "Total Synthesis of Monatin," *Org. Lett.* 2:2967-2970, American Chemical Society (2000).

Nakamura, K., et al., "Total Synthesis of Monatin and the Taste Expression," *Peptide Science 2003*, The Proceedings of the 40th Symposium on Japanese Peptide Symposium, pp. 61-64, The Japanese Peptide Society (Mar. 2004).

Oliveira, D. and Coelho, F., "Highly Diastereoselective Alkylation of a Pyroglutamate Derivative with an Electrophile Obained from Indole. Synthesis of a Potential Intermediate for the Preparation of the Natural Sweetener (−)-Monatin," *Synthetic Communications* 30:2143-2159, Marcel Dekker (2000).

Oliveira, D. and Coelho, F., "Diastereoselective formation of a quanternary center in a pyroglutamate derivative. Formal synthesis of Monatin," *Tetrahedron Lett.* 42:6793-6796, Elsevier Science Ltd. (Sep. 2001).

Azuma et al., "Hyper-production of L-tryptophan via fermentation with crystallization," *Appl. Microbiol. Biotechnol.*, 1993, 39:471-476.

Bassoli et al., "General Pseudoreceptor Model for Sweet Compounds: A Semiquantitative Prediction of Binding Affinity for Sweet-Tasting Molecules," *J. Med. Chem.*, 2002, 45:4402-4409.

Bassoli et al., "Monatin and Its Stereoisomers: Chemoenzymatic Synthesis and Taste Properties," *Eur. J. Org. Chem.*, 2005, 8:1652-1658.

Bhatnagar et al., "The Broad-specificity, Membrane-bound Lactate Dehydrogenase of *Neisseria gonorrhoeae*: Ties to Aromatic Metabolism," *J. Gen. Microbiol.*, 1989, 135:353-360.

Bommarius et al., "Some new developments in reductive amination with cofactor regeneration," *Biocatalysis*, 1994, 10:37-47.

Brandl and Lindow, "Cloning and characterization of a locus encoding an indolepyruvate decarboxylase involved in indole-3-acetic acid synthesis in *Erwinia herbicola*," *Appl. Environ. Microbiol.*, 1996, 62:4121-4128.

Camargo (Ediclea Cristina Fregonese Camargo), "Preparation of amino acids not proteinogênicos, structurally related to adoçante natural Monatina" [translated by Google], Jan. 2003, Universidade Estadual de Campinas Instituto de Quimica, Dissertation of Masters, English abstract only.

Eggeling and Sahm, "Amino-acid production: principles of metabolic engineering," *Metabolic Engineering*, 1999, Lee & Papoutsakis (eds.), Marcel Dekker, Inc., New York.

Eikmanns et al., "Cloning, sequence analysis, and inactivation of the *Corynebacterium glutamicum* icd gene encoding isocitrate dehydrogenase and biochemical characterization of the enzyme," *J. Bacteriol.*, 1995, 177:774-782.

El-Abyad and Farid, "Optimization of culture conditions for indole-3-pyruvic acid production by *Streptomyces griseoflavus*," *Can. J. Microbiol.*, 1994, 40:754-760.

Fotheringham et al., "The cloning and sequence analysis of the aspC and tyrB genes from *Escherichia coli* K12," *Biochem J.*, 1986, 234:593-604.

Furuya et al., "A Novel Enzyme, L-Tryptophan Oxidase, from a Basidiomycete, Coprinus sp. SF-1: Purification and Characterization," *Biosci. Biotechnol. Biochem.*, 2000, 64(7):1486-1493.

Holzapfel et al., "The synthesis of a gamma-keto-alpha-amino acid, a key intermediate in the synthesis of monatin, a new natural sweetener," *Synthetic Communications*, 1993, 23(18):2511-2526.

Jetten et al., "Metabolic Engineering of *Corynebacterium glutamicum*," *Ann. N.Y. Acad. Sci.*, 1994, 721:12-29.

Jetten et al., "Recent advances in the physiology and genetics of amino acid-producing bacteria," *Critical Reviews in Biotechnology*, 1995, 15:73-103.

Kawasaki et al., "L-Tryptophan Production by Pyruvic Acid-Producing *Escherichia coli* Strain Carrying the Enterobacter aerogenes Tryptophanase Gene," *Journal of Fermentation and Bioengineering*, 1996, 82(6):604-606.

Koffas et al., "Engineering metabolism and product formation in *Corynebacterium glutamicum* by coordinated gene overexpression," *Metabolic Engineering*, 2003, 5:32-41.

Koga et al., "Involvement of L-tryptophan aminotransferase in indole-3-acetic acid biosynthesis in *Enterobacter cloacae*," *Biochim. Biophys. Acta*, 1994, 1209:241-247.

Kumagai et al., "Racemization of D- or L-Alanine by Crystalline Tyrosine Phenol-Lyase from *Escherichia intermedia*," *Biochem. Biophys. Res. Commun.*, 1970, 39:796-801.

Labrou et al., "Oxaloacetate Decarboxylase from *Pseudomonas stutzeri*: Purification and Characterization," *Archives of Biochemistry and Biophysics*, 1999, 365(1):17-24.

Lee et al., "Functional and structural characterization of D-amino acid aminotransferases from *Geobacillus* spp.," *Appl. Environ. Microbiol.*, 2006, 72:1588-1594.

Patnaik et al., "Engineering of *Escherichia coli* Central Metabolism for Aromatic Metabolite Production with Near Theoretical Yield," *Appl. Environ. Microbiol.*, 1994, 60(11):3903-3908.

Rijnen et al., "Genetic Characterization of the Major Lactococcal Aromatic Aminotransferase and Its Involvement in Conversion of Amino Acids to Aroma Compounds," *Appl. Environ. Biol.*, 1999, 65(11):4873-4880.

Tamura et al., "Stereoselective Synthesis of 4-Hydroxy 4-Substituted Glutamic Acids," *J. Org. Chem.*, 2005, 70(12):4569-77.

Wolf et al., "A Biocatalytic Route to Enantiomerically Pure Unsaturated -H—Amino Acids," *Adv. Synth. & Catalysis*, 2001, 343:662-674.

Yonaha et al., "D-Amino Acid Aminotransferase of *Bacillus sphaericus*," *J. Biol. Chem.*, 1975, 250(17):6983-6989.

Passerat, N. and Bolte, J., "Large-Scale Enzymatic Synthesis of Diastereoisomeric γ-Hydroxy L-Glutamic Acids," *Tetrahedron Lett.* 28:1277-1280, Elsevier (1987).

Patil, R. and Dekker, E., "Cloning Nucleotide Sequence, Overexpression, and Inactivation of the *Escherichia coli* 2-Keto-4-Hydroxyglutarate Aldolase Gene," *J. Bacteriol.* 174:102-107, American Society for Microbiology (1992).

Patrick, W.M., et al., "Site-Directed Mutagenesis of Tyr354 in *Geobacillus stearothermophilus* Alanine Racemase Identifies a Role in Controlling Substrate Specificity and a Possible Role in the Evolution of Antibiotic Resistance," *Chembiochem* 3:789-792, Wiley-VCH-Verlag GmbH (2002).

Shelton, M.C., et al., "2-Keto3-deoxy6-phosphogluconate Aldolases as Catalysts for Stereocontrolled Carbon—Carbon Bond Formation," *J. Am. Chem. Soc.* 118:2117-2125, American Chemical Society (1996).

Tamura, O., et al., "Highly stereoselective synthesis of (−)-monatin, a high-intensity sweetener, using chelation-controlled nitrone cycloaddition," *Chem. Commun. (Camb.)* 21:2678-2679, The Royal Society of Chemistry (Nov. 2003).

Vleggaar, R., et al., "Structure Elucidation of Monatin, a High-intensity Sweetener Isolated from the Plant *Schlerochiton ilicifolius*," *J. Chem. Soc. Perkin Trans.I 22*:3095-3098, Royal Society of Chemistry (1992).

Zeman, R., et al., "Enzyme Synthesis of L-Tryptophan," *Folia Microbiol.* 35:200-204, Slovak Academy of Sciences (1990).

"Bacteria: *Corynebacterium glutamicum*," ATCC No. 13058, available online @ www.atcc.org/SearchCatalogs/longview.cfm?atccsearch=yes (accessed on Mar. 11, 2005).

Dialog File 351, Accession No. 12442290, Derwent WPI English language abstract for JP 2002/060382 (listed on accompanying PTO/SB/08A as document FP5), (2002).

Dialog File 351, Accession No. 13542893, Derwent WPI English language abstract for WO 03/056026 A1 (listed on accompanying PTO/SB/08A as document FP8), 2003.

Dialog File 351, Accession No. 13655060, Derwent WPI English language abstract for JP 2003/171365 (listed on accompanying PTO/SB/08A as document FP7).

Dialog File 351, Accession No. 14386782, Derwent WPI English language abstract for JP 2004/222657 (listed on accompanying PTO/SB/08A as document FP14).

Dialog File 351, Accession No. 14644791, Derwent WPI English language abstract for JP 2004/331644 (listed on accompanying PTO/SB/08A as document FP15).

Dialog File 351, Accession No. 14655288, Derwent WPI English language abstract for JP 2004/331650 (listed on accompanying PTO/SB/08A as document FP16).

Dialog File 351, Accession No. 15288756, Derwent WPI English language abstract for WO 2005/082850 A1 (listed on accompanying PTO/SB/08A as document FP21), (2005).

Dialog File 351, Accession No. 15581479, Derwent WPI English language abstract for WO 2006/011613 A1 (listed on accompanying PTO/SB/08A as document FP22), (2006).

Office Action issued by the United States Patent and Trademark Office in U.S. Appl. No. 10/979,821, dated Jun. 15, 2007.

Office Action issued by the United States Patent and Trademark Office in U.S. Appl. No. 10/969,245, dated Apr. 17, 2007.

Office Action issued by the United States Patent and Trademark Office in U.S. Appl. No. 10/903,582, dated Jun. 21, 2007.

* cited by examiner

Indole-3-lactic acid

EC 1.1.1.110 indolelactate dehydrogenase

EC 1.1.1.222 R-4-hydroxyphenyllactate dehydrogenase

EC 1.1.1.237 3-(4)-hydroxyphenylpyruvate reductase

EC 1.1.1.27, 1.1.1.28, 1.1.2.3 lactate dehydrogenase

EC 1.1.1.111 (3-imidazol-5-yl) lactate dehydrogenase

EC 1.1.3.- lactate oxidase

Chemical oxidation

Indole-3-pyruvate $R_1$ = Boc, Cbz, etc.
$R_2$ and $R_3$ = Alkyl, Aryl, etc.

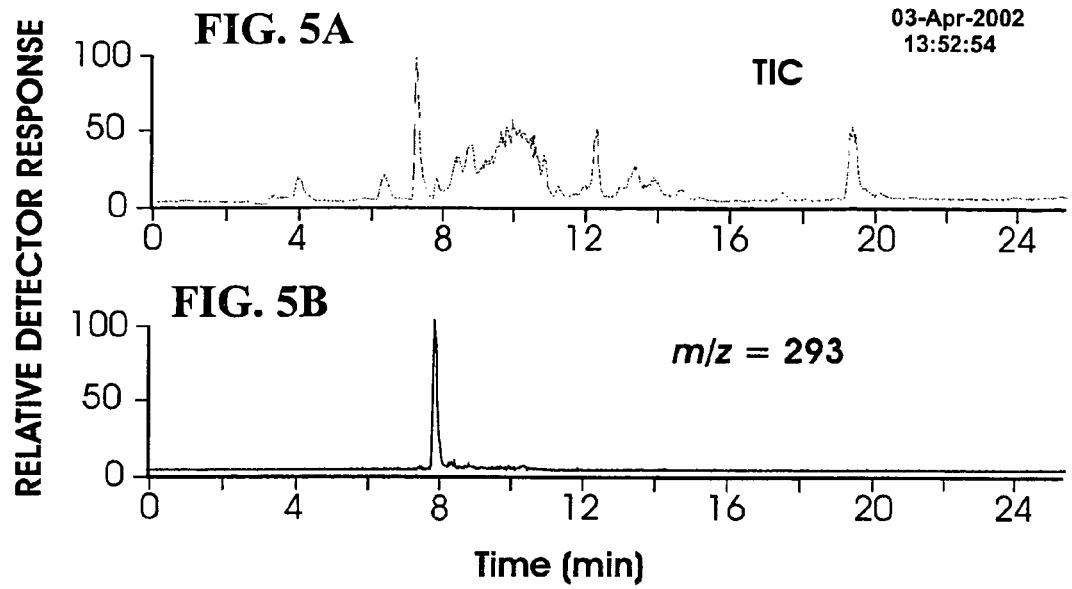
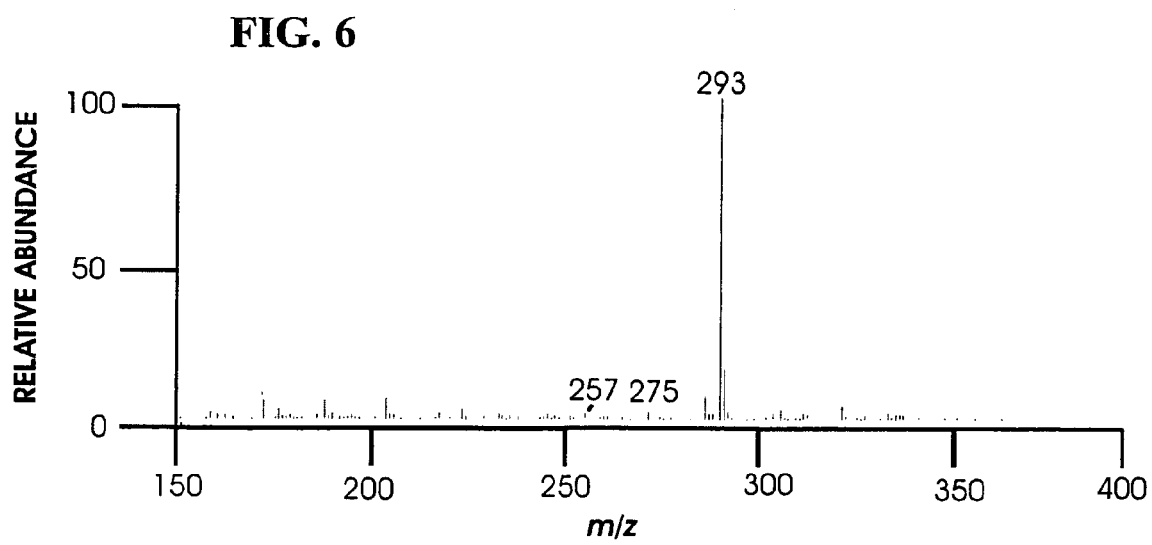

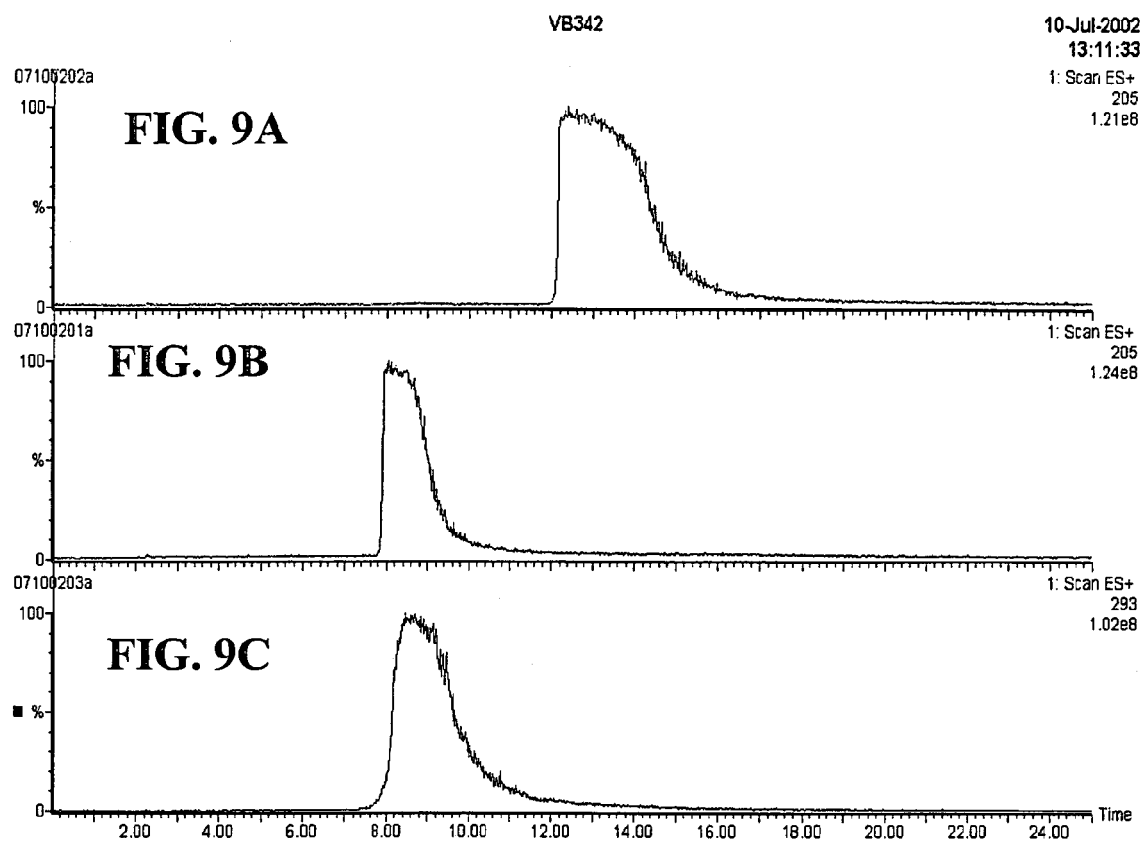
FIG. 9A
FIG. 9B
FIG. 9C
FIG. 10
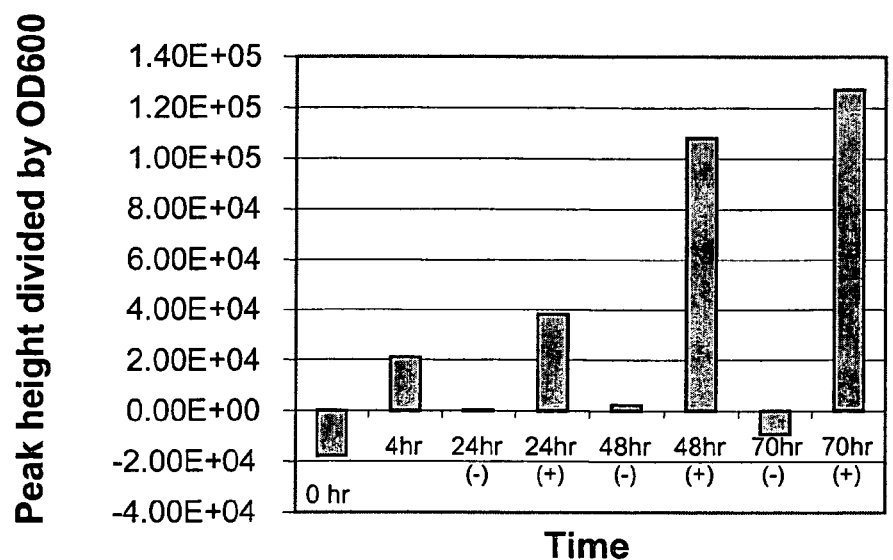

POLYPEPTIDES AND BIOSYNTHETIC PATHWAYS FOR THE PRODUCTION OF MONATIN AND ITS PRECURSORS

CROSS-REFERENCE TO RELATED APPLICATION

This application is a continuation-in-part of application Ser. No. 10/422,366, filed Apr. 23, 2003, now abandoned, which claims the benefit of U.S. Provisional Patent Application No. 60/374,831, filed Apr. 23, 2002. In addition, this application is related to application Ser. No. 10/979,821, filed Nov. 3, 2004, which is also a continuation-in-part of application Ser. No. 10/422,366. The aforementioned applications are incorporated by reference in their entireties.

FIELD

This disclosure provides polypeptides and biosynthetic pathways that are useful in the production of indole-3-pyruvate, 2-hydroxy 2-(indol-3ylmethyl)-4-keto glutaric acid (MP) and/or monatin.

BACKGROUND

Indole pyruvate.

Indole-3-pyruvate is a strong antioxidant that is believed to counter act oxidative stress in tissues with high oxygen concentrations (Politi et al. "Recent advances in Tryptophan Research", edited by G. A. Filippini et al. Plenum Press, New York, 1996, pp 291-8). Indole pyruvate also is an intermediate in a pathway to produce indole-acetic acid (IAA), the primary plant growth hormone auxin (diffusible growth promoting factor). IAA is active in submicrogram amounts in a range of physiological processes including apical dominance, tropisms, shoot elongation, induction of cambial cell division, and root initiation. Synthetic auxins are used in horticulture to induce rooting and to promote the set and development of fruit. At high concentrations the synthetic auxins are effective herbicides against broad-leafed plants. Natural auxins produced by fermentation may be considered more environmentally friendly than chemically produced herbicides. Growth regulators had world sales in 1999 of 0.4 billion pounds (1.4 billion U.S. dollars).

Some examples of patents on indole acetic acid and derivatives thereof include: U.S. Pat. No. 5,843,782 Micropropagation of rose plants, auxin used in culture medium and U.S. Pat. No. 5,952,231 Micropropagation of rose plants.

In addition to plant related utilities, indole acetic acid is useful in pharmaceutical applications. For example, U.S. Pat. No. 5,173,497 "Method of preparing alpha-oxopyrrolo[2,3-B]indole acetic acids and derivatives" proposes the use of these compounds in the treatment of memory impairment such as that associated with Alzheimer's disease and senile dementia. The mechanism proposed in U.S. Pat. No. 5,173,497 is that these compounds inhibit the polypeptide acetylcholinesterase and increase acetylcholine levels in the brain.

Indole-3-carbinol is produced from indole-3-acetic acid by peroxidase-catalyzed oxidation, and can easily be converted into diindolylmethane. Both compounds are reported to eliminate toxins and promote the production of hormones beneficial to women's health.

Tryptophan Derivatives

Chlorinated D-tryptophan has been identified as a nonnutritive sweetener, and there is increasing interest in pursuing other derivatives as well. Monatin is a natural sweetener that is similar in composition to the amino acid tryptophan. It can be extracted from the bark of the roots of the South African shrub, *Sclerochiton ilicifolius*, and has promise in the food and beverage industry as a high-intensity sweetener. Some examples of patents on monatin include: U.S. Pat. No. 5,994,559 Synthesis of monatin-A high intensity natural sweetener, U.S. Pat. No. 4,975,298 3-(1-amino-1,3-dicarboxy-3-hydroxy-but-4-yl)-indole compounds, U.S. Pat. No. 5,128,164 Composition for human consumption containing 3-(1-amino-1,3-dicarboxy-3-hydroxy-but-4-yl)-indole compounds; and U.S. Pat. No. 5,128,482 Process for the production of 3-1(1-amino-1,3-dicarboxy-3-hydroxy-but-4-yl) indole.

Some of the precursors of monatin described here can also be useful as synthetic sweeteners or as intermediates in the synthesis of monatin derivatives.

SUMMARY

The disclosure provides several biosynthetic routes for making monatin from glucose, tryptophan, indole-3-lactic acid, and/or through monatin precursors such as indole-3-pyruvate and 2-hydroxy 2-(indole-3-ylmethyl)-4-keto glutaric acid. Polypeptides and nucleic acid sequences that can be used to make monatin, indole-3-pyruvate, and 2-hydroxy 2-(indole-3-ylmethyl)-4-keto glutaric acid are disclosed. In an effort to be concise, where ever intermediates/products are identified in the specification and claims (e.g. monatin or monatin precursor) as being formed, the term "and/or salts thereof" should be understood to be included where applicable. In other words, for example, the phrase "indole-3-pyruvate is converted to monatin precursor" should be understood to read "indole-3-pyruvic acid is converted to monatin precursor and and/or salts thereof." A person of ordinary skill, in fact, would appreciate that under reaction conditions shown the salts of the intermediates/products are in fact present or also present.

Monatin can be produced by reacting a reaction mixture that includes one or more suitable substrates and one or more selected polypeptides. Suitable substrates may include, but are not limited to, glucose, tryptophan, indole-3-lactic acid, monatin precursors (such as indole-3-pyruvate and 2-hydroxy 2-(indole-3-ylmethyl)-4-keto glutaric acid), and mixtures thereof. Suitable substrates that are present in the reaction mixture for producing monatin, may be added to the reaction mixture and/or may be produced in situ in the reaction mixture. The selected polypeptides may be added to the reaction mixture and/or may be produced by microorganisms present in the reaction mixture (e.g., by fermenting the reaction mixture with a microorganism that expresses the selected polypeptide).

Monatin can be produced through indole-3-pyruvate, 2-hydroxy 2-(indole-3-ylmethyl)-4-keto glutaric acid (monatin precursor, MP, the alpha-keto form of monatin), indole-3-lactic acid, tryptophan, and/or glucose (FIG. 1). Methods of producing or making monatin or its intermediates shown in FIGS. 1-3 and 11-13 that involve converting a substrate to a first product, and then converting the first product to a second product, and so on, until the desired end product is created, are disclosed.

FIGS. 1-3 and 11-13 show potential intermediate products and end products in boxes. For example, a conversion from one product to another, such as glucose to tryptophan, tryptophan to indole-3-pyruvate, indole-3-pyruvate to MP, MP to monatin, or indole-3-lactic acid (indole-lactate) to indole-3-pyruvate, can be performed by using these methods. These conversions can be facilitated chemically or biologically. The term "convert" refers to the use of either chemical means or polypeptides in a reaction which changes a first intermediate to a second intermediate. The term "chemical conversion" refers to reactions that are not actively facilitated by polypeptides. The term "biological conversion" refers to reactions that are actively facilitated by polypeptides (e.g., enzymes). Conversions can take place in vitro or in vivo (e.g., by fermenting a nutrient broth with an suitable microorganism). When biological conversions are used the polypeptides and/or cells can be immobilized on supports such as by chemical attachment on polymer supports. The conversion can be accomplished using any reactor known to one of ordinary skill in the art, for example in a batch or a continuous reactor.

Methods are also provided that include contacting a first polypeptide with a substrate and making a first product, and then contacting the first product created with a second polypeptide and creating a second product, and then contacting the second product created with a third polypeptide and creating a third product, for example monatin. The polypeptides used and the products produced are shown in FIGS. 1-3 and 11-13.

Polypeptides, and their coding sequences, that can be used to perform the conversions shown in FIGS. 1-3 and 11-13 are disclosed. In some examples, polypeptides having one or more point mutations that allow the substrate specificity and/or activity of the polypeptides to be modified, are used to make monatin.

Isolated and recombinant cells that produce monatin are disclosed. These cells can be any cell, such as a plant, animal, bacterial, yeast, algal, archaeal, or fungal cell. These cells may be used to synthesize monatin by fermenting a nutrient medium that includes the cell. The nutrient medium may include any suitable molecule for synthesizing monatin, including but not limited to, glucose, tryptophan, indole-3-lactic acid, and/or monatin precursors such as indole-3-pyruvate and 2-hydroxy 2-(indole-3-ylmethyl)-4-keto glutaric acid.

In a particular example, the disclosed cells include one or more of the following activities, for example two or more or three or more of the following activities: tryptophan aminotransferase (EC 2.6.1.27), tyrosine (aromatic) aminotransferase (EC 2.6.1.5), multiple substrate aminotransferase (EC 2.6.1.-), aspartate aminotransferase (EC 2.6.1.1), tryptophan dehydrogenase (EC 1.4.1.19), tryptophan-phenylpyruvate transaminase (EC 2.6.1.28), L-amino acid oxidase (EC 1.4.3.2), tryptophan oxidase (no EC number, Hadar et al., *J. Bacteriol* 125:1096-1104, 1976 and Furuya et al., *Biosci Biotechnol Biochem* 64:1486-93, 2000), D-amino acid dehydrogenase (EC 1.4.99.1), D-amino acid oxidase (EC 1.4.3.3), D-alanine aminotransferase (EC 2.6.1.21), synthase/lyase (EC 4.1.3.-), such as 4-hydroxy-4-methyl-2-oxoglutarate aldolase (EC 4.1.3.17) or 4-hydroxy-2-oxoglutarate aldolase (EC 4.1.3.16), synthase/lyase (4.1.2.-), D-tryptophan aminotransferase (Kohiba and Mito, Proceedings of the 8$^{th}$ International Symposium on Vitamin B$_6$ and Carbonyl Catalysis, Osaka, Japan 1990), branched-chain aminotransferase (BCAT, EC 2.6.1.42), phenylalanine dehydrogenase (EC 1.4.1.20), glutamate dehydrogenase (EC 1.4.1.2, 1.4.1.3, 1.4.1.4) and leucine (branched-chain) dehydrogenase (EC 1.4.1.9).

In another example, cells include one or more, for example two or more, or three or more, of the following activities: indolelactate dehydrogenase (EC 1.1.1.110), R-4-hydroxyphenyllactate dehydrogenase (EC 1.1.1.222), 3-(4)-hydroxyphenylpyruvate reductase (EC 1.1.1.237), lactate dehydrogenase (EC 1.1.1.27, 1.1.1.28, 1.1.2.3), (3-imidazol-5-yl) lactate dehydrogenase (EC 1.1.1.111), lactate oxidase (EC 1.1.3.-), synthase/lyase (4.1.3.-) such as 4-hydroxy-4-methyl-2-oxoglutarate aldolase (EC 4.1.3.17) or 4-hydroxy-2-oxoglutarate aldolase (EC 4.1.3.16), synthase/lyase (4.1.2.-), tryptophan dehydrogenase (EC 1.4.1.19), tryptophan-phenylpyruvate transaminase (EC 2.6.1.28), tryptophan aminotransferase (EC 2.6.1.27), tyrosine (aromatic) aminotransferase (EC 2.6.1.5), multiple substrate aminotransferase (EC 2.6.1.-), aspartate aminotransferase (EC 2.6.1.1), branched-chain aminotransferase (BCAT, EC 2.6.1.42), phenylalanine dehydrogenase (EC 1.4.1.20), glutamate dehydrogenase (EC 1.4.1.2, 1.4.1.3, 1.4.1.4 ), leucine (branched-chain) dehydrogenase (EC 1.4.1.9), D-amino acid dehydrogenase (EC 1.4.99.1), D-tryptophan aminotransferase, and/or D-alanine aminotransferase (EC 2.6.1.21).

In addition, the disclosed cells can include one or more of the following activities, for example two or more or three or more of the following activities: tryptophan aminotransferase (EC 2.6.1.27), tyrosine (aromatic) aminotransferase (EC 2.6.1.5), multiple substrate aminotransferase (EC 2.6.1.-), aspartate aminotransferase (EC 2.6.1.1), tryptophan dehydrogenase (EC 1.4.1.19), tryptophan-phenylpyruvate transaminase (EC 2.6.1.28), L-amino acid oxidase (EC 1.4.3.2), tryptophan oxidase (no EC number), D-amino acid dehydrogenase (EC 1.4.99.1), D-amino acid oxidase (EC 1.4.3.3), D-alanine aminotransferase (EC 2.6.1.21), indolelactate dehydrogenase (EC 1.1.1.110), R-4-hydroxyphenyllactate dehydrogenase (EC 1.1.1.222), 3-(4)-hydroxyphenylpyruvate reductase (EC 1.1.1.237), lactate dehydrogenase (EC 1.1.1.27, 1.1.1.28, 1.1.2.3), (3-imidazol-5-yl) lactate dehydrogenase (EC 1.1.1.111), lactate oxidase (EC 1.1.3.-), synthase/lyase (4.1.3.-) such as 4-hydroxy-4-methyl-2-oxoglutarate aldolase (EC 4.1.3.17) or 4-hydroxy-2-oxoglutarate aldolase (EC 4.1.3.16), synthase/lyase (4.1.2.-), branched-chain aminotransferase (BCAT, EC 2.6.1.42), glutamate dehydrogenase (EC 1.4.1.2, 1.4.1.3, 1.4.1.4), phenylalanine dehydrogenase (EC 1.4.1.20), leucine (branched-chain) dehydrogenase (EC 1.4.1.9) and/or D-tryptophan aminotransferase.

Monatin can be produced by a method that includes contacting tryptophan and/or indole-3-lactic acid with a first polypeptide, wherein the first polypeptide converts tryptophan and/or indole-3-lactic acid to indole-3-pyruvate (either the D or the L form of tryptophan or indole-3-lactic acid can be used as the substrate that is converted to indole-3-pyruvate; one of skill in the art will appreciate that the polypeptides chosen for this step ideally exhibit the appropriate specificity), contacting the resulting indole-3-pyruvate with a second polypeptide, wherein the second polypeptide converts the indole-3-pyruvate to 2-hydroxy 2-(indol-3-ylmethyl)-4-keto glutaric acid (MP), and contacting the MP with a third polypeptide, wherein the third polypeptide converts MP to monatin. Exemplary polypeptides that can be used for these conversions are shown in FIGS. 2 and 3.

Another aspect of the invention provides compositions such as MP, cells that contain at least two polypeptides, or sometimes at least three or at least four polypeptides, that are encoded on at least one exogenous nucleic acid sequence.

These and other aspects of the disclosure are apparent from the following detailed description and illustrative examples.

Compounds shown in boxes are substrates and products produced in the biosynthetic pathways.

Compositions adjacent to the arrows are cofactors, or reactants that can be used during the conversion of a substrate to a product. The cofactor or reactant used will depend upon the polypeptide used for the particular step of the biosynthetic pathway. The cofactor PLP (pyridoxal 5'-phosphate) can catalyze reactions independent of a polypeptide, and therefore, merely providing PLP can allow for the progression from substrate to product.

Figure 2:
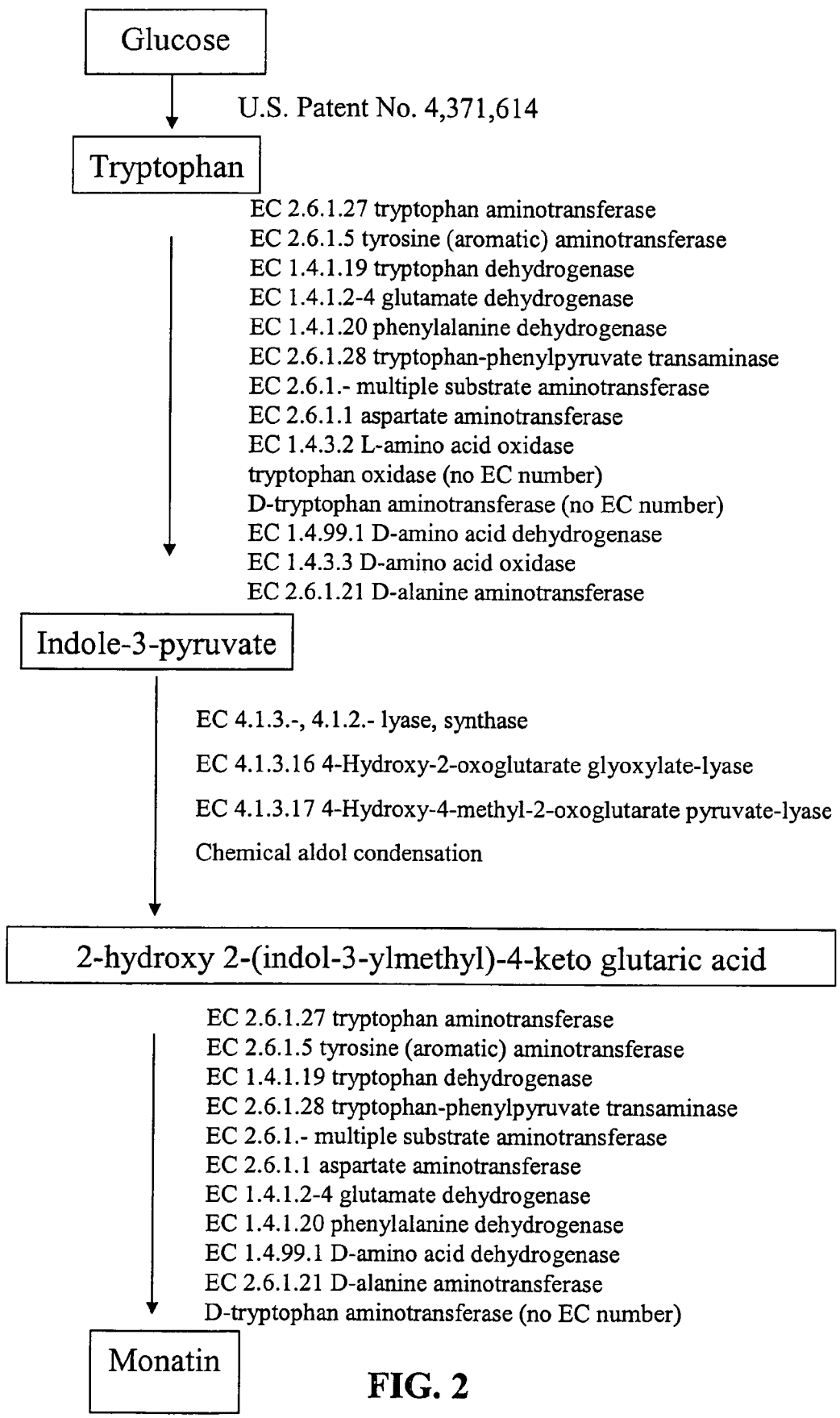

FIG. 2 is a more detailed diagram of the biosynthetic pathway that utilizes the MP intermediate. The substrates for each step in the pathways are shown in boxes. The polypeptides allowing for the conversion between substrates are listed adjacent to the arrows between the substrates. Each polypeptide is described by its common name and an enzymatic class (EC) number.

Figures 3, 4:
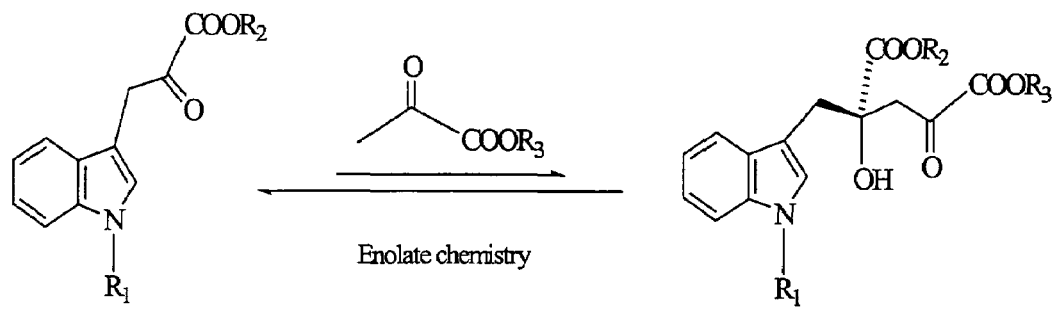

FIG. 3 shows a more detailed diagram of the biosynthetic pathway of the conversion of indole-3-lactic acid to indole-3-pyruvate. The substrates are shown in boxes, and the polypeptides allowing for the conversion between the substrates are listed adjacent to the arrow between the substrates. Each polypeptide is described by its common name and an enzymatic class (EC) number.

FIG. 4 shows one possible reaction for making MP via chemical means.

FIGS. 5A and 5B are chromatograms showing the LC/MS identification of monatin produced enzymatically.

FIG. 6 is an electrospray mass spectrum of enzymatically synthesized monatin.

Figure 7A:
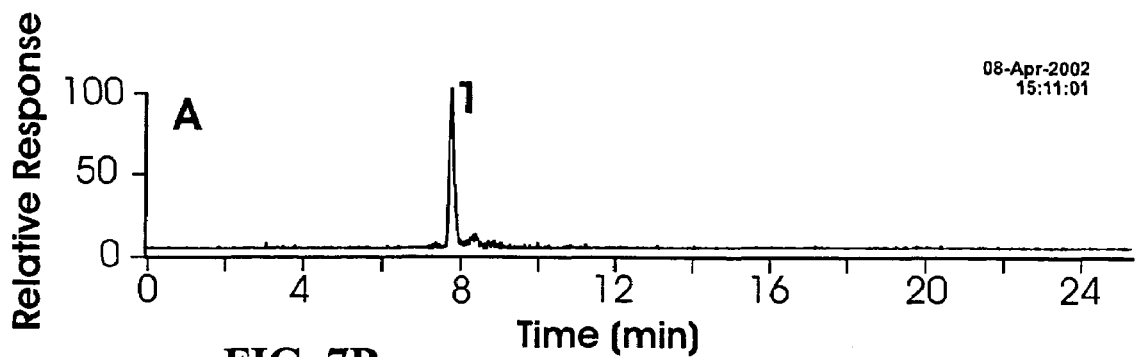
Figure 7B:
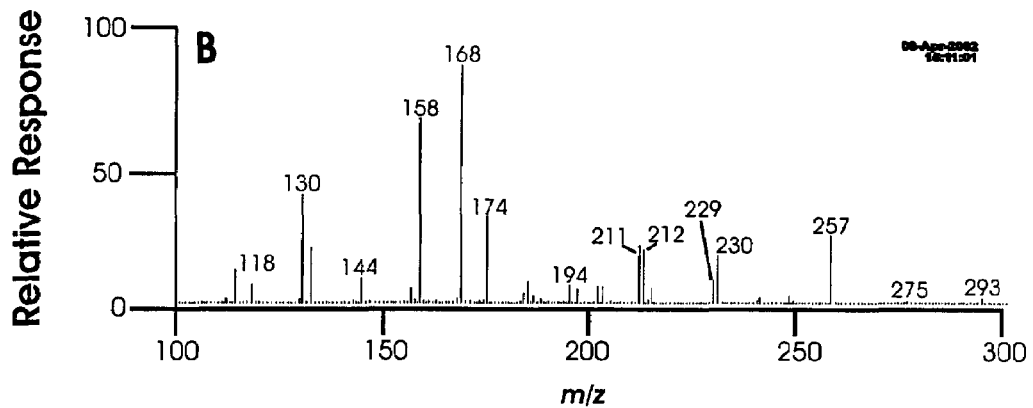

FIGS. 7A and 7B show chromatograms of the LC/MS/MS daughter ion analyses of monatin produced in an enzymatic mixture.

Figure 8:
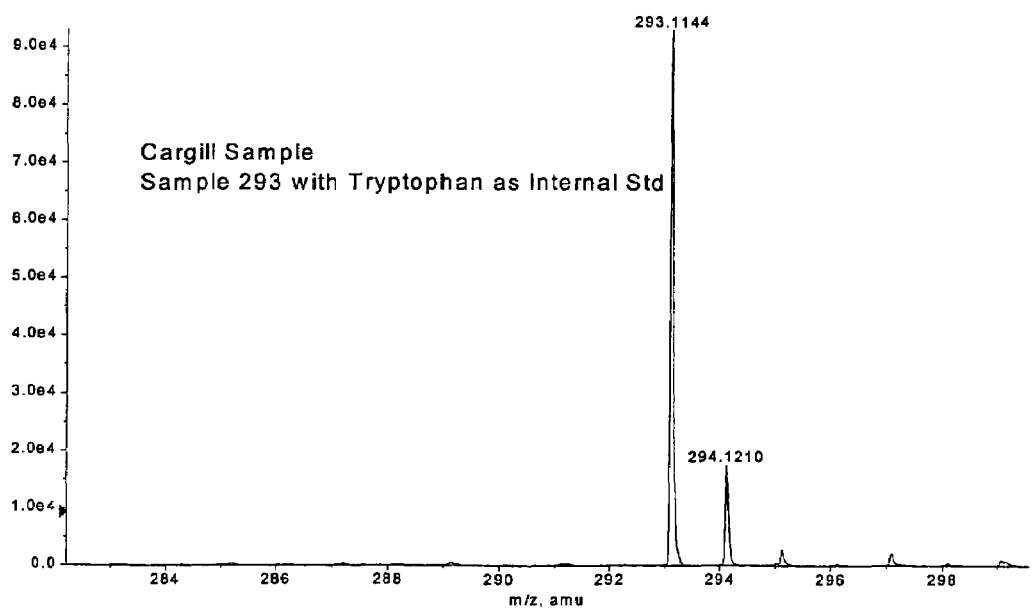

FIG. 8 is a chromatogram showing the high resolution mass measurement of monatin produced enzymatically.

FIGS. 9A-9C are chromatograms showing the chiral separation of (A) R-tryptophan, (B) S-tryptophan, and (C) monatin produced enzymatically.

FIG. 10 is a bar graph showing the relative amount of monatin produced in bacterial cells following IPTG induction. The (−) indicates a lack of substrate addition (no tryptophan or pyruvate was added).

Figure 11:
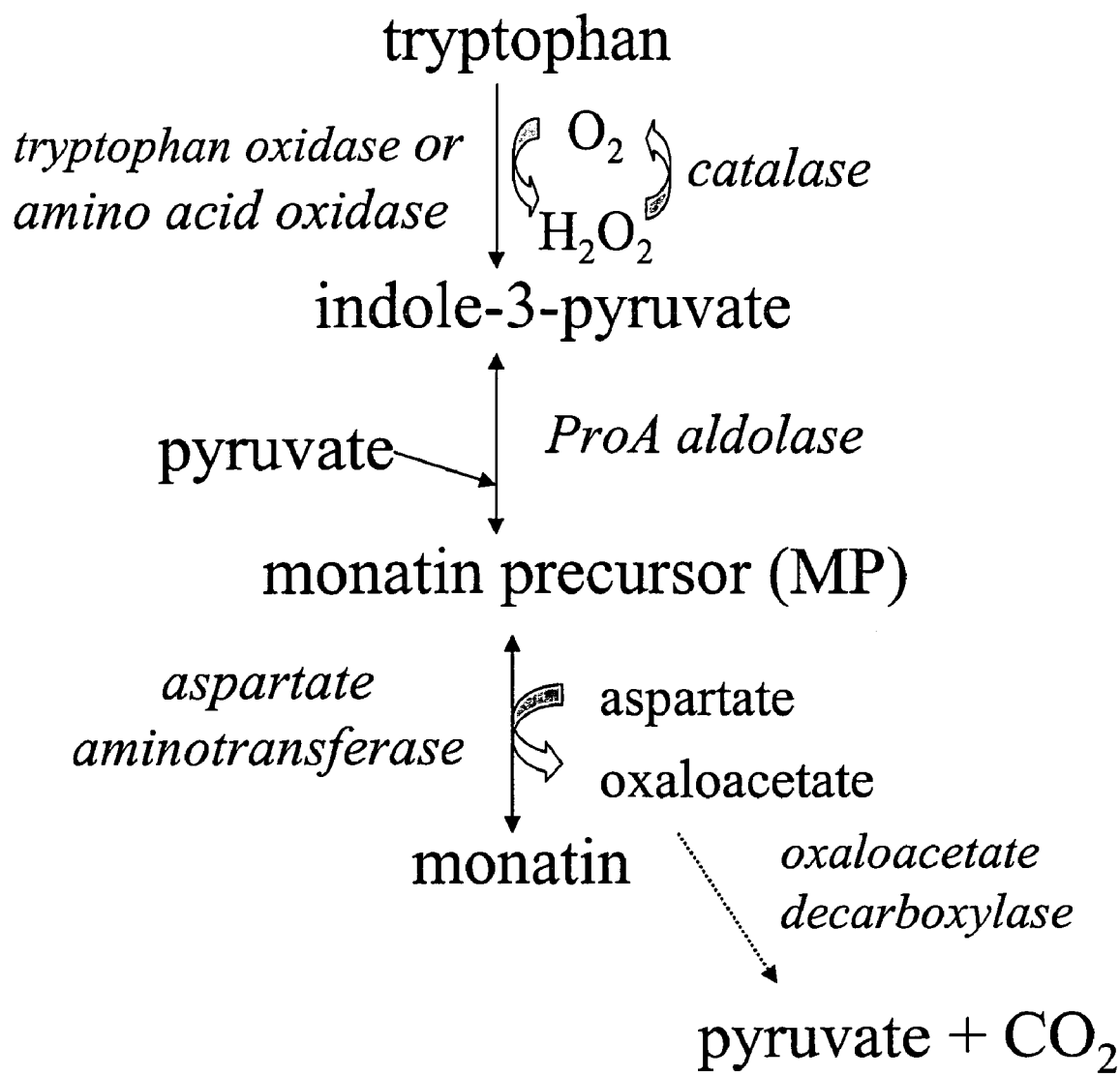
Figure 12:
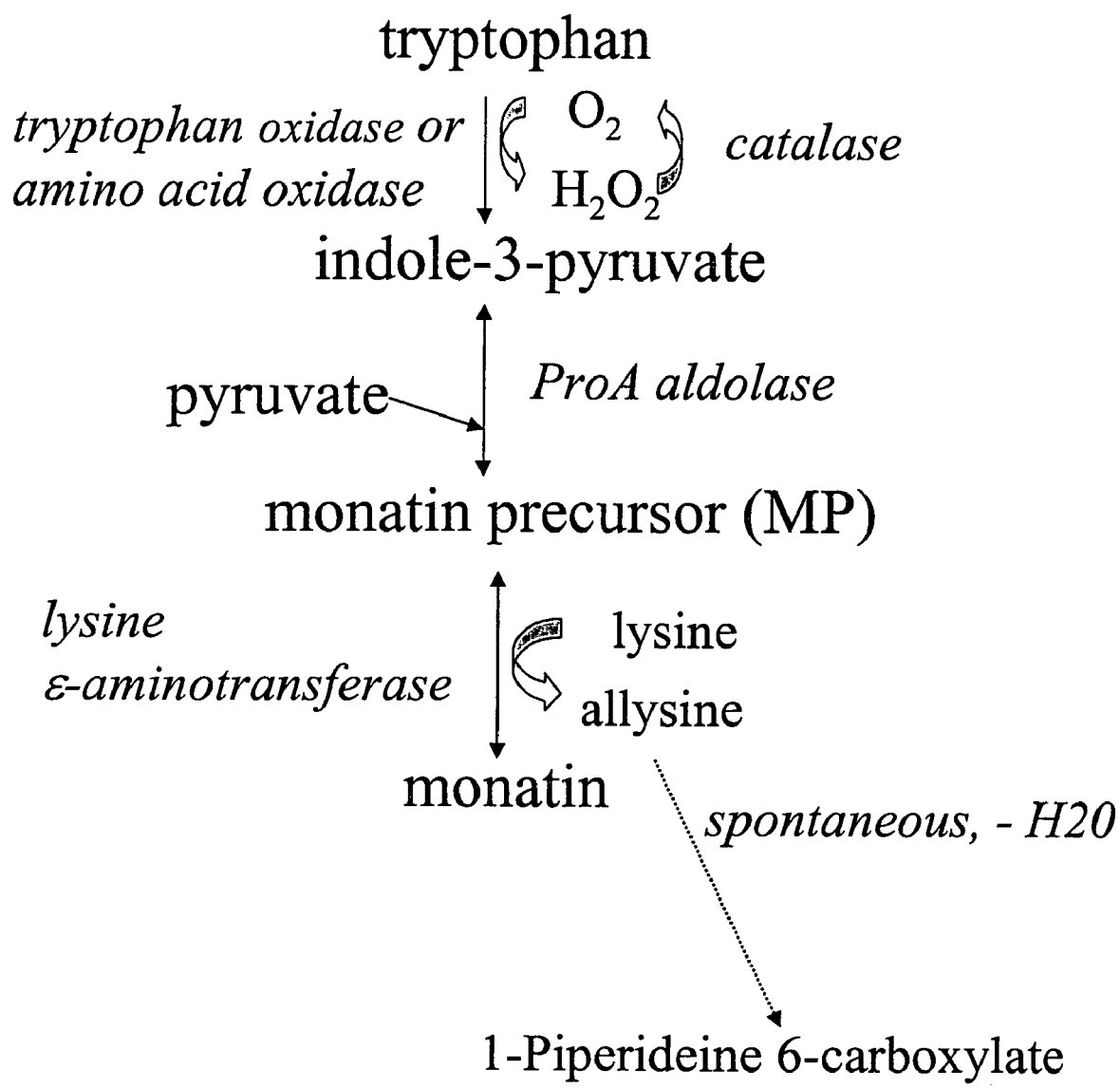

FIGS. 11-12 are schematic diagrams showing pathways used to increase the yield of monatin produced from tryptophan or indole-3-pyruvate.

Figure 13:
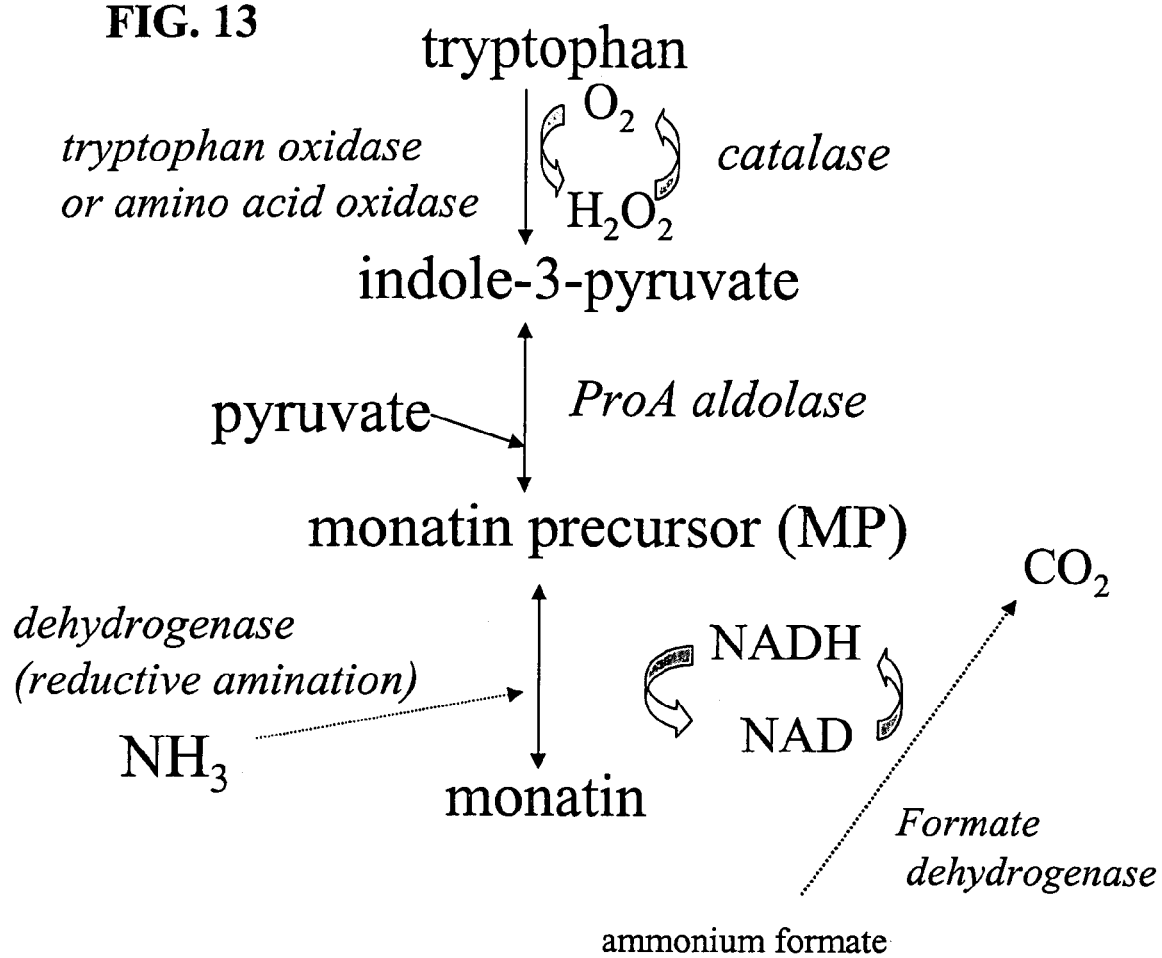

FIG. 13 is a schematic diagram showing a pathway which can be used to increase the yield of monatin produced from tryptophan or indole-3-pyruvate.

SEQUENCE LISTING

The nucleic and amino acid sequences listed in the accompanying sequence listing are shown using standard letter abbreviations for nucleotide bases, and three-letter code for amino acids. Only one strand of each nucleic acid sequence is shown, but the complementary strand is understood to be included by any reference to the displayed strand.

SEQ ID NOS: 1 and 2 show the nucleic acid and amino acid sequences of an aminotransferase from *Sinorhizobium meliloti*, respectively (tatA gene, called a tyrosine or aromatic aminotransferase in literature).

SEQ ID NOS: 3 and 4 show the nucleic acid and amino acid sequences of a tyrosine aminotransferase from *Rhodobacter sphaeroides* (2.4.1), respectively (by homology with tatA (SEQ ID NOS: 1 and 2) predicted to be an "aspartate aminotransferase" by genomics software).

SEQ ID NOS: 5 and 6 show the nucleic acid and amino acid sequences of an aminotransferase from *Rhodobacter sphaeroides* (35053), respectively (novel, cloned based on 2.4.1 sequence SEQ ID NOS 3 and 4).

SEQ ID NOS: 7 and 8 show the nucleic acid and amino acid sequences of a broad substrate aminotransferase (bsat) from *Leishmania major*, respectively.

SEQ ID NOS: 9 and 10 show the nucleic acid and amino acid sequences of an aromatic aminotransferase (araT) from *Bacillus subtilis*, respectively.

SEQ ID NOS: 11 and 12 show novel nucleic acid and amino acid sequences of an aromatic aminotransferase (araT) from *Lactobacillus amylovorus*, respectively (by homology identified as an aromatic aminotransferase).

SEQ ID NOS: 13 and 14 show the nucleic acid and amino acid sequences of a multiple substrate aminotransferase (msa) from *R. sphaeroides* (35053), respectively (identified as a multiple substrate aminotransferase by homology to Accession No. AAAE01000093.1, bp 14743-16155 and Accession No. ZP00005082.1).

SEQ ID NOS: 15-16 show primers used to clone the *B. subtilis* D-alanine aminotransferase (dat) sequence.

SEQ ID NOS: 17-18 show primers used to clone the *S. meliloti* tatA sequence.

SEQ ID NOS: 19-20 show primers used to clone the *B. subtilis* araT aminotransferase sequence.

SEQ ID NOS: 21-22 show primers used to clone the *Rhodobacter sphaeroides* (2.4.1 and 35053) multiple substrate aminotransferase sequences.

SEQ ID NOS: 23-24 show primers used to clone the *Leishmania major* bsat sequence.

SEQ ID NOS: 25-26 show primers used to clone the *Lactobacillus amylovorus* araT sequence.

SEQ ID NOS: 27-28 show primers used to clone the *R. sphaeroides* tatA sequences (both 2.4.1 and 35053).

SEQ ID NOS: 29-30 show primers used to clone the *E. coli* aspC sequence (gene sequence Genbank Accession No.: AE000195.1, protein sequence Genbank Accession No.: AAC74014.1).

SEQ ID NOS: 31 and 32 show the nucleic acid and amino acid sequences of aromatic aminotransferase (tyrB) from *E. coli*, respectively.

SEQ ID NOS: 33-34 show primers used to clone the *E. coli* tyrB sequence.

SEQ ID NOS: 35-40 show primers used to clone polypeptides with 4-hydroxy-2-oxoglutarate aldolase (KHG) (EC 4.1.3.16) activity.

SEQ ID NOS: 41 and 42 show the nucleic acid sequences of tryptophanase (tna) from *E. coli* and tyrosine phenol-lyase (tpl) from *Citrobacter freundii*, coding for proteins P00913 (GI: 401195) and P31013 (GI: 401201), respectively.

SEQ ID NOS: 43-46 show primers used to clone tryptophanase polypeptides and β-tyrosinase (tyrosine phenol-lyase) polypeptides.

SEQ ID NOS: 47-54 show primers used to mutate tryptophanase polypeptides and β-tyrosinase polypeptides.

SEQ ID NOS: 55-64 show primers used to clone polypeptides with 4-hydroxy-4-methyl-2-oxoglutarate aldolase (EC 4.1.3.17) activity.

SEQ ID NOS: 65 and 66 show the nucleic acid and amino acid sequences of 4-hydroxy-4-methyl-2-oxoglutarate aldolase (proA) from *C. testosteroni*, respectively.

SEQ ID NOS: 67-68 show primers used to clone *C. testosteroni* 4-hydroxy-4-methyl-2-oxoglutarate aldolase (proA) in an operon with *E. coli* aspC in pET30 Xa/LIC.

SEQ ID NOS: 69-72 show primers used to clone *E. coli* aspC and *C. testosteroni* proA in pESC-his.

SEQ ID NOS: 73-74 show sequences added to the 5' end of primers used to clone the genes disclosed herein.

SEQ ID NOS: 75 and 76 show the nucleic acid and amino acid sequences of the HEX gene and gene product (NCBI accession number 1AHF_A GI: 1127190) (HEXAspC aminotransferase amino acid sequence), respectively.

SEQ ID NOS: 77-78 show primers used to clone the *E. coli* aspartate aminotransferase (aspC) or the mutated aspC aminotransferase (HEX) gene sequence.

SEQ ID NOS: 79-80 show primers used to clone the *E. coli* tyrosine aminotransferase (tyrb).

SEQ ID NOS: 81-82 show primers used to clone the khg gene of *Z. mobilis* (ATCC 29191).

SEQ ID NOS 83 and 84 show the nucleic acid and amino acid sequences of the *Z. mobilis* khg gene (Accession No: AE008692.1 GI: 56542470) and gene product (Accession No.: AAV89621.1 GI: 56543467), respectively.

SEQ ID NOS: 85-86 show primers used to clone the *E. coli* yfdZ gene sequence deposited in NCBI as GI: 48994873 bases 2496317-2495079, coding for protein GI: 1788722 (protein ID AAC75438.1).

SEQ ID NOS: 87 and 88 show the nucleic acid and amino acid sequences of an aldolase from *Rhizobium leguminosarum* biovar viciae rhiz23g02-plk_1009_341 (Sanger Institute), respectively.

SEQ ID NO: 89 shows the nucleic acid sequence of a representative target sequence.

SEQ ID NO: 90 shows the nucleic acid sequence of a representative identified sequence.

SEQ ID NO: 91 shows the amino acid sequence of a His tag.

SEQ ID NO: 92 shows the amino acid sequence of GenBanik Accession No. CAC46344.

SEQ ID NO: 93 shows the amino acid sequence of GenBanik Accession No. CAB14127.1

SEQ ID NO: 94 shows the amino acid sequence of GenBanik Accession No. AAC74920.1.

SEQ ID NO: 95 shows the amino acid sequence of GenBanik Accession No. CAC47463.1.

SEQ ID NO: 96 shows the amino acid sequence of GenBanik Accession No. NP_388848.1.

SEQ ID NO: 97 shows the amino acid sequence of GenBanik Accession No. AAC74014.1.1

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. As used herein, "including" means "comprising." In addition, the singular forms "a" or "an" or "the" include plural references unless the context clearly dictates otherwise. For example, reference to "comprising a protein" includes one or a plurality of such proteins, and reference to "comprising the cell" includes reference to one or more cells and equivalents thereof known to those skilled in the art, and so forth. The term "about" encompasses the range of experimental error that occurs in any measurement. Unless otherwise stated, all measurement numbers are presumed to have the word "about" in front of them even if the word "about" is not expressly used.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features and advantages of the disclosure are apparent from the following detailed description and the claims.

cDNA (complementary DNA): A piece of DNA lacking internal, non-coding segments (introns) and regulatory sequences which determine transcription. cDNA can be synthesized in the laboratory by reverse transcription from messenger RNA extracted from cells.

Conservative substitution: a substitution of one amino acid for another amino acid in a polypeptide, which substitution has little to no impact on the activity of the polypeptide. The substitution is considered conservative independent of whether the exchanged amino acids appear structurally or functionally similar. For example, ideally, a tryptophan aminotransferase polypeptide including one or more conservative substitutions retains tryptophan aminotransferase activity. A polypeptide can be produced to contain one or more conservative substitutions by manipulating the nucleotide sequence that encodes that-polypeptide using, for example, standard procedures such as site-directed mutagenesis or PCR or other methods known to those in the art.

Non-limiting examples of amino acids which may be substituted for an original amino acid in a protein and which may be regarded as conservative substitutions if there is little to no impact on the activity of the polypeptide include: Ala substituted with ser or thr; arg substituted with gln, his, or lys; asn substituted with glu, gln, lys, his, asp; asp substituted with asn, glu, or gln; cys substituted with ser or ala; gln substituted with asn, glu, lys, his, asp, or arg; glu substituted with asn, gln lys, or asp; gly substituted with pro; his substituted with asn, lys, gln, arg, tyr; ile substituted with leu, met, val, phe; leu substituted with ile, met, val, phe; lys substituted with asn, glu, gln, his, arg; met substituted with ile, leu, val, phe; phe substituted with trp, tyr, met, ile, or leu; ser substituted with thr, ala; thr substituted with ser or ala; trp substituted with phe, tyr; tyr substituted with his, phe, or trp; and val substituted with met, ile, leu.

Further information about conservative substitutions can be found in, among other locations, Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (*Bio/Technology* 6:1321-5, 1988), WO 00/67796 (Curd et al.) and in standard textbooks of genetics and molecular biology.

Derived: For purposes of the specification and claims, a substance is "derived" from organism or source if any one or more of the following are true: 1) the substance is present in the organism/source; 2) the substance is removed from the native host; or, 3) the substance is removed from the native host and is evolved, for example, by mutagenesis.

Enzymatically Producing: The phrase "enzymatically producing," or similar phrases, such as "produced enzymatically" or "enzymatically synthesized," refers to the production of product (such as monatin) using at least one polypeptide, either in vitro (e.g., in test tube or reactor using one or more polypeptides) or in vivo (e.g., in a whole cell or fermentation reaction). While "enzymatically producing" a product does not exclude the use of chemical reagents or reactions, it includes the use of at least one polypeptide that facilitates at least one reaction in the production of that product.

Exogenous: The term "exogenous" as used herein with reference to nucleic acid and a particular cell refers to any nucleic acid that does not originate from that particular cell as found in nature. Thus, non-naturally-occurring nucleic acid is considered to be exogenous to a cell once introduced into the cell. Nucleic acid that is naturally-occurring also can be exogenous to a particular cell. For example, an entire chromosome isolated from a cell of person X is an exogenous nucleic acid with respect to a cell of person Y once that chromosome is introduced into Y's cell.

Functionally Equivalent: Having an equivalent function. In the context of an enzyme, functionally equivalent molecules include different molecules that retain the function of the enzyme. For example, functional equivalents can be provided by sequence alterations in an enzyme sequence, wherein the peptide with one or more sequence alterations retains a function of the unaltered peptide, such that it retains its enzymatic activity. In a particular example, a tryptophan aminotransferase functional equivalent retains the ability to convert tryptophan to indole-3-pyruvate.

Examples of sequence alterations include, but are not limited to, conservative substitutions, deletions, mutations, frameshifts, and insertions. In one example, a given polypeptide binds an antibody, and a functional equivalent is a polypeptide that binds the same antibody. Thus a functional equivalent includes peptides that have the same binding specificity as a polypeptide, and that can be used as a reagent in place of the polypeptide. In one example a functional equivalent includes a polypeptide wherein the binding sequence is discontinuous, wherein the antibody binds a linear epitope. Thus, if the peptide sequence is MPELANDLGL (amino acids 1-10 of SEQ ID NO: 12) a functional equivalent includes discontinuous epitopes, that can appear as follows (=any number of intervening amino acids): NH2--MPELANDLG**L-COOH. In this example, the polypeptide is functionally equivalent to amino acids 1-10 of SEQ ID NO: 12 if the three dimensional structure of the polypeptide is such that it can bind a monoclonal antibody that binds amino acids 1-10 of SEQ ID NO: 12.

Hybridization: The term "hybridization" as used herein refers to a method of testing for complementarity in the nucleotide sequence of two nucleic acid molecules, based on the ability of complementary single-stranded DNA and/or RNA to form a duplex molecule. Nucleic acid hybridization techniques can be used to obtain an isolated nucleic acid within the scope of the disclosure. Briefly, any nucleic acid having some homology to a sequence set forth in SEQ ID NO: 11 can be used as a probe to identify a similar nucleic acid by hybridization under conditions of moderate to high stringency. Once identified, the nucleic acid then can be purified, sequenced, and analyzed to determine whether it is within the scope of the present disclosure.

Hybridization can be done by Southern or Northern analysis to identify a DNA or RNA sequence, respectively, that hybridizes to a probe. The probe can be labeled with a biotin, digoxygenin, a polypeptide, or a radioisotope such as $^{32}P$. The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39-7.52 of Sambrook et al., (1989) Molecular Cloning, second edition, Cold Spring Harbor Laboratory, Plainview, N.Y. Typically, a probe is at least about 20 nucleotides in length. For example, a probe corresponding to a contiguous 20 nucleotide sequence set forth in SEQ ID NO: 11 can be used to identify an identical or similar nucleic acid. In addition, probes longer or shorter than 20 nucleotides can be used.

The disclosure also provides isolated nucleic acid sequences that are at least about 12 bases in length (e.g., at least about 13, 14, 15, 16, 17, 18, 19, 20, 25, 30, 40, 50, 60, 100, 250, 500, 750, 1000, 1500, 2000, 3000, 4000, or 5000 bases in length) and hybridize, under hybridization conditions, to the sense or antisense strand of a nucleic acid having the sequence set forth in SEQ ID NO: 11. The hybridization conditions can be moderately or highly stringent hybridization conditions.

For the purpose of this disclosure, moderately stringent hybridization conditions mean the hybridization is performed at about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% Dextran sulfate, and 1-15 ng/mL probe (about $5 \times 10^7$ cpm/µg), while the washes are performed at about 50° C. with a wash solution containing 2×SSC and 0.1% sodium dodecyl sulfate.

Highly stringent hybridization conditions mean the hybridization is performed at about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% Dextran sulfate, and 1-15 ng/mL probe (about $5 \times 10^7$ cpm/µg), while the washes are performed at about 65° C. with a wash solution containing 0.2×SSC and 0.1% sodium dodecyl sulfate.

Isolated: The term "isolated" as used herein refers to any substance removed from its native host; the substance need not be purified. For example "isolated nucleic acid" refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-ocurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

A nucleic acid existing among hundreds to millions of other nucleic acid molecules within, for example, cDNA or genomic libraries, or gel slices containing a genomic DNA restriction digest is not to be considered an isolated nucleic acid.

Nucleic acid: The term "nucleic acid" as used herein encompasses both RNA and DNA including, without limitation, cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

Operably linked: A first nucleic acid sequence is "operably linked" with a second nucleic acid sequence whenever the first nucleic acid sequence is placed in a functional relationship with the second nucleic acid sequence. For instance, a promoter is operably linked to a coding sequence if the promoter affects the transcription of the coding sequence. Generally, operably linked DNA sequences are contiguous and, where necessary to join two polypeptide-coding regions, in the same reading frame.

Peptide Modifications: The present disclosure includes enzymes, as well as synthetic embodiments thereof. In addition, analogues (non-peptide organic molecules), derivatives (chemically functionalized peptide molecules obtained starting with the disclosed peptide sequences) and variants (homologs) having the desired enzymatic activity can be utilized in the methods described herein. The peptides disclosed herein include a sequence of amino acids, that can be either L- and/or D-amino acids, naturally occurring and otherwise.

Peptides can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a C1-C16 ester, or converted to an amide of formula NR1R2 wherein R1 and R2 are each independently H or C1-C16 alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to C1-C16 alkyl or dialkyl amino or further converted to an amide.

Hydroxyl groups of the peptide side chains may be converted to C1-C16 alkoxy or to a C1-C 16 ester using well-recognized techniques. Phenyl and phenolic rings of the peptide side chains may be substituted with one or more halogen atoms, such as F, Cl, Br or I, or with C1-C16 alkyl, C1-C16 alkoxy, carboxylic acids and esters thereof, or amides of such carboxylic acids. Methylene groups of the peptide side chains can be extended to homologous C2-C4 alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclizing methods include the formation of thioethers and carboxyl- and amino-terminal amides and esters.

Peptidomimetic and organomimetic embodiments are also within the scope of the present disclosure, whereby the three-dimensional arrangement of the chemical constituents of such peptido- and organomimetics mimic the three-dimensional arrangement of the peptide backbone and component amino acid side chains, resulting in such peptido- and organomimetics of the proteins of this disclosure having detectable enzyme activity. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves (eds.), Pharmaceutical Biotechnology, 1993, Interpharm Press: Buffalo Grove, Ill., pp. 165-74 and Ch. 102 in Munson (ed.), Principles of Pharmacology, 1995, Chapman & Hall, for descriptions of techniques used in CADD. Also included within the scope of the disclosure are mimetics prepared using such techniques. In one example, a mimetic mimics the enzyme activity generated by an enzyme or a variant, fragment, or fusion thereof.

ProA Aldolase: Although "ProA" and/or "ProA aldolase" historically have been used to identify only the 4-hydroxy-4-methyl-2-oxoglutarate aldolase derived from *Comamonas testosteroni*, herein the term "ProA" and/or "ProA aldolase" are used to mean any polypeptide with 4-hydroxy-4-methyl-2-oxoglutarate aldolase activity unless otherwise stated. Suitable examples of ProA or ProA aldolase include *C. testosteroni* ProA (SEQ ID NO: 66) and *Sinorhizobium meliloti* ProA (NCBI Accession No.: CAC46344), or enzymes that display homology to *C. testosteroni* ProA (SEQ ID NO: 66) and/or *Sinorhizobium meliloti* ProA (NCBI Accession No.: CAC46344). For example, suitable enzymes may have at least about 40%, 50%, 60%, 70%, 80%, 90%, 95%, and/or 99% sequence identity with *C. testosteroni* ProA (SEQ ID NO: 66) and/or *Sinorhizobium meliloti* ProA (NCBI Accession No.: CAC46344).

Probes and primers: Nucleic acid probes and primers can be prepared readily based on the amino acid sequences and nucleic acid sequences provided herein. A "probe" includes an isolated nucleic acid containing a detectable label or reporter molecule. Exemplary labels include, but are not limited to, radioactive isotopes, ligands, chemiluminescent agents, and polypeptides. Methods for labeling and guidance in the choice of labels appropriate for various purposes are discussed in, for example, Sambrook et al. (ed.), Molecular Cloning: A Laboratory Manual 2nd ed., vol. 1-3, Cold Spring Harbor Laboratory Press, Cold Spring Harbor, N.Y., 1989, and Ausubel et al. (ed.) Current Protocols in Molecular Biology, Greene Publishing and Wiley-Interscience, New York (with periodic updates), 1987.

"Primers" are typically nucleic acid molecules having ten or more nucleotides (e.g., nucleic acid molecules having between about 10 nucleotides and about 100 nucleotides). A primer can be annealed to a complementary target nucleic acid strand by nucleic acid hybridization to form a hybrid between the primer and the target nucleic acid strand, and then extended along the target nucleic acid strand by, for example, a DNA polymerase polypeptide. Primer pairs can be used for amplification of a nucleic acid sequence, for example, by the polymerase chain reaction (PCR) or other nucleic-acid amplification methods known in the art.

Methods for preparing and using probes and primers are described, for example, in references such as Sambrook et al. (ed.), Molecular Cloning: A Laboratory Manual, 2nd ed., vol. 1-3, Cold Spring Harbor Laboratory Press, Cold Spring Harbor, N.Y., 1989; Ausubel et al. (ed.), Current Protocols in Molecular Biology, Greene Publishing and Wiley-Interscience, New York (with periodic updates), 1987; and Innis et al. (eds.), PCR Protocols: A Guide to Methods and Applications, Academic Press: San Diego, 1990. PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with the length, but that a probe or primer can range in size from a full-length sequence to sequences as short as five consecutive nucleotides. Thus, for example, a primer of 20 consecutive nucleotides can anneal to a target with a higher specificity than a corresponding primer of only 15 nucleotides. Thus, in order to obtain greater specificity, probes and primers can be selected that comprise, for example, 10, 20, 25, 30, 35, 40, 50, 60, 70, 80, 90, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 2000, 2050, 2100, 2150, 2200, 2250, 2300, 2350, 2400, 2450, 2500, 2550, 2600, 2650, 2700, 2750, 2800, 2850, 2900, 3000, 3050, 3100, 3150, 3200, 3250, 3300, 3350, 3400, 3450, 3500, 3550, 3600, 3650, 3700, 3750, 3800, 3850, 3900, 4000, 4050, 4100, 4150, 4200, 4250, 4300, 4350, 4400, 4450, 4500, 4550, 4600, 4650, 4700, 4750, 4800, 4850, 4900, 5000, 5050, 5100, 5150, 5200, 5250, 5300, 5350, 5400, 5450, or more consecutive nucleotides.

Promoter: An array of nucleic acid control sequences which direct transcription of a nucleic acid. A promoter includes necessary nucleic acid sequences near the start site of transcription, such as, in the case of a polymerase II type promoter, a TATA element. A promoter can include distal enhancer or repressor elements which can be located as much as several thousand base pairs from the start site of transcription.

Purified: The term "purified" as used herein does not require absolute purity, but rather is intended as a relative term. Thus, for example, a purified polypeptide or nucleic acid preparation can be one in which the subject polypeptide or nucleic acid is at a higher concentration than the polypeptide or nucleic acid would be in its natural environment within an organism or at a higher concentration than in the environment from which it was removed.

Recombinant: A "recombinant" nucleic acid is one having (1) a sequence that is not naturally occurring in the organism in which it is expressed or (2) a sequence made by an artificial combination of two otherwise-separated, shorter sequences. This artificial combination is often accomplished by chemical synthesis or, more commonly, by the artificial manipulation of isolated segments of nucleic acids, e.g., by genetic engineering techniques. "Recombinant" is also used to describe nucleic acid molecules that have been artificially manipulated, but contain the same regulatory sequences and coding regions that are found in the organism from which the nucleic acid was isolated.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a peptide, such as SEQ ID NO: 12, possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443-53, 1970; Pearson and Lipman, *Proc. Natl. Acad. Sci. U.S.A.* 85:2444-8, 1988; Higgins and Sharp, *Gene* 73:237-44, 1988; Higgins and Sharp, *CABIOS* 5:151-3, 1989; Corpet et al., *Nucleic Acids Research* 16:10881-90, 1988; and Altschul et al., *Nature Genet.* 6:119-29, 1994.

The NCBI Basic Local Alignment Search Tool (BLAST™) (Altschul et al., *J. Mol. Biol.* 215:403-10, 1990) is available from several sources, including the National Center for Biotechnology Information (NCBI, Bethesda, Md.) and on the Internet, for use in connection with the sequence analysis programs blastp, blastn, blastx, tblastn and tblastx.

Variants of a peptide are typically characterized by possession of at least 50% sequence identity counted over the full length alignment with the amino acid sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment is performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 90%, at least 95%, at least 98%, or even at least 99% sequence identity. When less than the entire sequence is being compared for sequence identity, homologs and variants will typically possess at least 80% sequence identity over short windows of 10-20 amino acids, and may possess sequence identities of at least 85%, at least 90%, at least 95%, or 98% depending on their similarity to the reference sequence. Methods for determining sequence identity over such short windows are described at the website that is maintained by the National Center for Biotechnology Information in Bethesda, Md. One of skill in the art will appreciate that these sequence identity ranges are provided for guidance only, it is entirely possible that strongly significant homologs could be obtained that fall outside of the ranges provided.

Similar methods can be used to determine the percent sequence identity of a nucleic acid sequence. In a particular example, a homologous sequence is aligned to a native sequence, and the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO: 11), or by an articulated length (e.g., 100 consecutive nucleotides or amino acid residues from a sequence set forth in an identified sequence), followed by multiplying the resulting value by 100. For example, a nucleic acid sequence that has 1166 matches when aligned with the sequence set forth in SEQ ID NO: 11 is 75.0 percent identical to the sequence set forth in SEQ ID NO: 11 (i.e., $1166 \div 1554 * 100 = 75.0$). It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It is also noted that the length value will always be an integer. In another example, a target sequence containing a 20-nucleotide region that aligns with 20 consecutive nucleotides from an identified sequence as follows contains a region that shares 75 percent sequence identity to that identified sequence (i.e., 15÷20*100=75).

```
                          1                  20
Target Sequence:       AGGTCGTGTACTGTCAGTCA  (SEQ ID NO: 89)
                       | || ||| |||| ||||  |
Identified Sequence:   ACGTGGTGAACTGCCAGTGA  (SEQ ID NO: 90)
```

Specific binding agent: An agent that is capable of specifically binding to any of the polypeptide described herein. Examples include, but are not limited to, polyclonal antibodies, monoclonal antibodies (including humanized monoclonal antibodies), and fragments of monoclonal antibodies such as Fab, F(ab')$_2$, and Fv fragments as well as any other agent capable of specifically binding to an epitope of such polypeptides.

Antibodies to the polypeptides provided herein (or fragments, variants, or fusions thereof) can be used to purify or identify such polypeptides. The amino acid and nucleic acid sequences provided herein allow for the production of specific antibody-based binding agents that recognize the polypeptides described herein.

Monoclonal or polyclonal antibodies can be produced to the polypeptides, portions of the polypeptides, or variants thereof. Optimally, antibodies raised against one or more epitopes on a polypeptide antigen will specifically detect that polypeptide. That is, antibodies raised against one particular polypeptide would recognize and bind that particular polypeptide, and would not substantially recognize or bind to other polypeptides. The determination that an antibody specifically binds to a particular polypeptide is made by any one of a number of standard immunoassay methods; for instance, Western blotting (See, e.g., Sambrook et al. (ed.), Molecular Cloning: A Laboratory Manual, 2nd ed., vol. 1-3, Cold Spring Harbor Laboratory Press, Cold Spring Harbor, N.Y., 1989).

To determine that a given antibody preparation (such as a preparation produced in a mouse against a polypeptide having the amino acid sequence set forth in SEQ ID NO: 12) specifically detects the appropriate polypeptide (e.g., a polypeptide having the amino acid sequence set forth in SEQ ID NO: 12) by Western blotting, total cellular protein can be extracted from cells and separated by SDS-polyacrylamide gel electrophoresis.

The separated total cellular protein can then be transferred to a membrane (e.g., nitrocellulose), and the antibody preparation incubated with the membrane. After washing the membrane to remove non-specifically bound antibodies, the presence of specifically bound antibodies can be detected using an appropriate secondary antibody (e.g., an anti-mouse antibody) conjugated to a polypeptide such as alkaline phosphatase since application of 5-bromo-4-chloro-3-indolyl phosphate/nitro blue tetrazolium results in the production of a densely blue-colored compound by immuno-localized alkaline phosphatase.

Substantially pure polypeptides suitable for use as an immunogen can be obtained from transfected cells, transformed cells, or wild-type cells. Polypeptide concentrations in the final preparation can be adjusted, for example, by concentration on an Amicon filter device, to the level of a few micrograms per milliliter. In addition, polypeptides ranging in size from full-length polypeptides to polypeptides having as few as nine amino acid residues can be utilized as immunogens. Such polypeptides can be produced in cell culture, can be chemically synthesized using standard methods, or can be obtained by cleaving large polypeptides into smaller polypeptides that can be purified. Polypeptides having as few as nine amino acid residues in length can be immunogenic when presented to an immune system in the context of a Major Histocompatibility Complex (MHC) molecule such as an MHC class I or MHC class II molecule. Accordingly, polypeptides having at least 9, 10, 11, 12, 13, 14, 15, 20, 25, 30, 35, 40, 45, 50, 55, 60, 70, 80, 90, 100, 150, 200, 250, 300, 350, 400, 450, 500, 550, 600, 650, 700, 750, 800, 900, 1000, 1050, 1100, 1150, 1200, 1250, 1300, 1350, or more consecutive amino acid residues of any amino acid sequence disclosed herein can be used as immunogens for producing antibodies.

Monoclonal antibodies to any of the polypeptides disclosed herein can be prepared from murine hybridomas according to the classic method of Kohler & Milstein (Nature 256:495-7, 1975) or a derivative method thereof.

Polyclonal antiserum containing antibodies to the heterogeneous epitopes of any polypeptide disclosed herein can be prepared by immunizing suitable animals with the polypeptide (or fragment thereof), which can be unmodified or modified to enhance immunogenicity. An effective immunization protocol for rabbits can be found in Vaitukaitis et al. (*J. Clin. Endocrinol. Metab.* 33:988-91,1971).

Antibody fragments can be used in place of whole antibodies and can be readily expressed in prokaryotic host cells. Methods of making and using immunologically effective portions of monoclonal antibodies, also referred to as "antibody fragments," are well known and include those described in Better & Horowitz (Methods Enzymol. 178:476-96,1989), Glockshuber et al. (*Biochemistry* 29:1362-7,1990), U.S. Pat. No. 5,648,237 ("Expression of Functional Antibody Fragments"), U.S. Pat. No. 4,946,778 ("Single Polypeptide Chain Binding Molecules"), U.S. Pat. No. 5,455,030 ("Immunotherapy Using Single Chain Polypeptide Binding Molecules"), and references cited therein.

Stereoinverting aminotransferase: A "stereoinverting aminotransferase" is a polypeptide capable of preferentially or selectively producing a chiral amino acid product (such as monatin) while using an opposite chirality substrate as the amino donor. For example, a stereoinverting aminotransferase may be a D-phenylglycine aminotransferase (also called D-4-hydroxyphenylglycine aminotransferase) that preferentially or selectively uses L-glutamate as a substrate to produce R,R monatin. Non-limiting examples of stereoinverting aminotransferases include D-methionine aminotransferase (EC 2.6.1.41) and enzymes having D-phenylglycine aminotransferase activity or D-4-hydroxyphenylglycine aminotransferase activity.

Transformed: A "transformed" cell is a cell into which a nucleic acid molecule has been introduced by, for example, molecular biology techniques. Transformation encompasses all techniques by which a nucleic acid molecule can be introduced into such a cell including, without limitation, transfection with a viral vector, conjugation, transformation with a plasmid vector, and introduction of naked DNA by electroporation, lipofection, and particle gun acceleration.

Variants, fragments or fusion proteins: The disclosed proteins, include variants, fragments, and fusions thereof. DNA sequences (for example, SEQ ID NO: 11) which encode for a protein (for example, SEQ ID NO: 12), fusion protein, or a fragment or variant of a protein, can be engineered to allow the protein to be expressed in eukaryotic cells, bacteria, insects, and/or plants. To obtain expression, the DNA sequence can be altered and operably linked to other regulatory sequences. The final product, which contains the regulatory sequences and the protein, is referred to as a vector. This vector can be introduced into eukaryotic, bacteria, insect, and/or plant cells. Once inside the cell the vector allows the protein to be produced.

A fusion protein including a protein, such as a tryptophan aminotransferase (or variant, polymorphism, mutant, or fragment thereof), for example SEQ ID NO: 12, linked to other amino acid sequences that do not inhibit the desired activity of the protein, for example the ability to convert tryptophan to indole-3-pyruvate. In one example, the other amino acid sequences are no more than about 10, 12, 15, 20, 25, 30, or 50 amino acids in length.

One of ordinary skill in the art will appreciate that a DNA sequence can be altered in numerous ways without affecting the biological activity of the encoded protein. For example, PCR can be used to produce variations in the DNA sequence which encodes an protein. Such variants can be variants optimized for codon preference in a host cell used to express the protein, or other sequence changes that facilitate expression.

Vector: A nucleic acid molecule as introduced into a cell, thereby producing a transformed cell. A vector may include nucleic acid sequences that permit it to replicate in the cell, such as an origin of replication. A vector may also include one or more selectable marker genes and other genetic elements known in the art.

Overview of Biosynthetic Pathways

As shown in FIGS. 1-3 and 11-13, many biosynthetic pathways can be used to produce monatin or its intermediates such as indole-3-pyruvate or MP. For the conversion of each substrate (glucose, tryptophan, indole-3-lactic acid, indole-3-pyruvate, and MP) to each product (tryptophan, indole-3-pyruvate, MP and monatin) several different polypeptides can be used. Moreover, these reactions can be carried out in vivo, in vitro, or through a combination of in vivo reactions and in vitro reactions, such as in vitro reactions that include non-enzymatic chemical reactions. Therefore, FIGS. 1-3 and 11-13 are exemplary, and show multiple different pathways that can be used to obtain desired products.

Glucose to Tryptophan

Many organisms can synthesize tryptophan from glucose. The construct(s) containing the gene(s) necessary to produce monatin, MP, and/or indole-3-pyruvate from glucose and/or tryptophan can be cloned into such organisms. It is shown herein that tryptophan can be converted into monatin.

In other examples, an organism is engineered using known polypeptides to produce tryptophan, or overproduce tryptophan. For example, U.S. Pat. No. 4,371,614 (herein incorporated by reference) describes an *E. coli* strain transformed with a plasmid containing a wild type tryptophan operon.

Maximum titers of tryptophan disclosed in U.S. Pat. No. 4,371,614 are about 230 ppm. Similarly, WO 8701130 (herein incorporated by reference) describes an *E. coli* strain that has been genetically engineered to produce tryptophan and discusses increasing fermentative production of L-tryptophan. Those skilled in the art will recognize that organisms capable of producing tryptophan from glucose are also capable of utilizing other carbon and energy sources that can be converted to glucose or fructose-6-phosphate, with similar results. Exemplary carbon and energy sources include, but are not limited to, sucrose, fructose, starch, cellulose, or glycerol.

Tryptophan to Indole-3-pyruvate

Several polypeptides can be used to convert tryptophan to indole-3-pyruvate. Exemplary polypeptides include members of the enzyme classes (EC) 2.6.1.27, 1.4.1.19, 1.4.99.1, 2.6.1.28, 1.4.3.2, 1.4.3.3, 2.6.1.5, 2.6.1.-, 2.6.1.1 and 2.6.1.21. These classes include polypeptides termed tryptophan aminotransferase (also termed L-phenylalanine-2-oxoglutarate aminotransferase, tryptophan transaminase, 5-hydroxytryptophan-ketoglutaric transaminase, hydroxytryptophan aminotransferase, L-tryptophan aminotransferase, L-tryptophan transaminase, and L-tryptophan:2-oxoglutarate aminotransferase) which converts L-tryptophan and 2-oxoglutarate to indole-3-pyruvate and L-glutamate; D-tryptophan aminotransferase which converts D-tryptophan and a 2-oxo acid to indole-3-pyruvate and an amino acid; tryptophan dehydrogenase (also termed NAD(P)-L-tryptophan dehydrogenase, L-tryptophan dehydrogenase, L-Trp-dehydrogenase, TDH and L-tryptophan:NAD(P) oxidoreductase (deaminating)) which converts L-tryptophan and NAD(P) to indole-3-pyruvate and NH3 and NAD(P)H; D-amino acid dehydrogenase, which converts D-amino acids and FAD to indole-3-pyruvate and $NH_3$ and $FADH_2$; tryptophan-phenylpyruvate transaminase (also termed L-tryptophan-α-ketoisocaproate aminotransferase and L-tryptophan:phenylpyruvate aminotransferase) which converts L-tryptophan and phenylpyruvate to indole-3-pyruvate and L-phenylalanine; L-amino acid oxidase (also termed ophio-amino-acid oxidase and L-amino-acid:oxygen oxidoreductase (deaminating)) which converts an L-amino acid and $H_2O$ and $O_2$ to a 2-oxo acid and $NH_3$ and $H_2O_2$; D-amino acid oxidase (also termed ophio-amino-acid oxidase and D-amino-acid:oxygen oxidoreductase (deaminating)) which converts a D-amino acid and $H_2O$ and $O_2$ to a 2-oxo acid and $NH_3$ and $H_2O_2$; and tryptophan oxidase which converts L-tryptophan and $H_2O$ and $O_2$ to indole-3-pyruvate and $NH_3$ and $H_2O_2$. These classes also contain tyrosine (aromatic) aminotransferase, aspartate aminotransferase, D-amino acid (or D-alanine) aminotransferase, and broad (multiple substrate) aminotransferase which have multiple aminotransferase activities, some of which can convert tryptophan and a 2-oxo acid to indole-3-pyruvate and an amino acid.

Eleven members of the aminotransferase class that have such activity are described below in Example 1, including a novel aminotransferase shown in SEQ ID NOS: 11 and 12. Therefore, this disclosure provides isolated nucleic acid and protein sequences having at least 80%, at least 85%, at least 90%, at least 95%, at least 98%, or even at least 99% sequence identity to SEQ ID NOS: 11 and 12. Also encompassed by this disclosure are fragments and fusions of SEQ ID NOS: 11 and 12 that retain aminotransferase activity or encode a protein having aminotransferase activity. Exemplary fragments include, but are not limited to at least 10, 12, 15, 20, 25, 50, 100, 200, 500, or 1000 contiguous nucleotides of SEQ ID NO: 11 or at least 6, 10, 15, 20, 25, 50, 75, 100, 200, 300 or 350 contiguous amino acids of SEQ ID NO: 12. The disclosed sequences (and variants, fragments, and fusions thereof) can be part of a vector. The vector can be used to transform host cells, thereby producing recombinant cells which can produce indole-3-pyruvate from tryptophan, and in some examples can further produce MP and/or monatin.

L-amino acid oxidases (1.4.3.2) are known, and sequences can be isolated from several different sources, such as *Vipera lebetine* (sp P81375), *Ophiophagus hannah* (sp P81383), *Agkistrodon rhodostoma* (spP81382), *Crotalus atrox* (sp P56742), *Burkholderia cepacia, Arabidopsis thaliana, Caulobacter cresentus, Chlamydomonas reinhardtii, Mus musculus, Pseudomonas syringae,* and *Rhodococcus* str. In addition, tryptophan oxidases are described in the literature and can be isolated, for example, from *Coprinus* sp. SF-1, Chinese cabbage with club root disease, *Arabidopsis thaliana*, and mammalian liver. One member of the L-amino acid oxidase class that can convert tryptophan to indole-3-pyruvate is discussed below in Example 5, as well as alternative sources for molecular cloning. Many D-amino acid oxidase genes are available in databases for molecular cloning.

Tryptophan dehydrogenases are known, and can be isolated, for example, from spinach, *Pisum sativum, Prosopis juliflora,* pea, mesquite, wheat, maize, tomato, tobacco, *Chromobacterium violaceum*, and *Lactobacilli*. Many D-amino acid dehydrogenase gene sequences are known.

U.S. Pat. No. 5,728,555 discloses phenylalanine deaminases (EC 3.5.1.-), which can also convert tryptophan to indole-3-pyruvate and ammonium in the presence of water. These broad specificity enzymes can be isolated from *Proteus* microorganisms, such as *Proteus myxofaciens, Proteus mirabilis, Proteus vulgaris* and *Proteus morganii*, and corresponding genes have been cloned and sequenced. See e.g, *Proteus vulgaris* deaminase (protein accession number: BAA90864.1 GI: 7007412; gene accession number: AB030003.1 GI: 700741 1); *Proteus mirabilis* deaminase (protein accession number: AAA86752.1 GI: 1015426; gene accession number: U35383.1 GI: 1015425). *Providencia* and *Morganella* also contain L-deaminases that can convert tryptophan to indole-3-pyruvate. See H. Drechsel, A. Thieken, R. Reissbrodt, G. Jung, and G. Winkelmann. J. Bacteriol., 175: 2727-2733 (1993).

As shown in FIGS. 11-13, if an amino acid oxidase, such as tryptophan oxidase, is used to convert tryptophan to indole-3-pyruvate, catalase can be added to reduce or even eliminate the presence of hydrogen peroxide.

Indole-3-lactate to Indole-3-pyruvate

The reaction that converts indole-3-lactate to indole-3-pyruvate can be catalyzed by a variety of polypeptides, such as members of the 1.1.1.110, 1.1.1.27, 1.1.1.28, 1.1.2.3, 1.1.1.222, 1.1.1.237, 1.1.3.-, or 1.1.1.111 classes of polypeptides. The 1.1.1.110 class of polypeptides includes indolelactate dehydrogenases (also termed indolelactic acid: $NAD^+$ oxidoreductase). The 1.1.1.27, 1.1.1.28, and 1.1.2.3 classes include lactate dehydrogenases (also termed lactic acid dehydrogenases, lactate: $NAD^+$ oxidoreductase). The 1.1.1.222 class contains (R)-4-hydroxyphenyllactate dehydrogenase (also termed D-aromatic lactate dehydrogenase, R-aromatic lactate dehydrogenase, and R-3-(4-hydroxyphenyl)lactate: $NAD(P)^+$ 2-oxidoreductase) and the 1.1.1.237 class contains 3-(4-hydroxyphenylpyruvate)reductase (also termed hydroxyphenylpyruvate reductase and 4-hydroxyphenyllactate: $NAD^+$ oxidoreductase). The 1.1.3.-class contains lactate oxidases, and the 1.1.1.111 class contains (3-imidazol-5-yl) lactate dehydrogenases (also termed (S)-3-(imidazol-5-yl) lactate:$NAD(P)^+$ oxidoreductase). It is likely that several of the polypeptides in these classes allow for the production of indole-3-pyruvate from indole-3-lactic acid. Examples of this conversion are provided in Example 4.

Chemical reactions can also be used to convert indole-3-lactic acid to indole-3-pyruvate. Such chemical reactions include an oxidation step that can be accomplished using several methods, for example: air oxidation using a B2 catalyst (China Chemical Reporter, v 13, n 28, p 18 (1), 2002), dilute permanganate and perchlorate, or hydrogen peroxide in the presence of metal catalysts.

Indole-3-pyruvate to 2-hydroxy 2-(indol-3ylmethyl)-4-keto glutaric acid (MP)

Several known polypeptides can be used to convert indole-3-pyruvate to MP. Exemplary polypeptide classes include 4.1.3.-, 4.1.3.16, 4.1.3.17, and 4.1.2.-. These classes include carbon-carbon synthases/lyases, such as aldolases that catalyze the condensation of two carboxylic acid substrates. Peptide class EC 4.1.3.- are synthases/lyases that form carbon-carbon bonds utilizing oxo-acid substrates (such as indole-3-pyruvate) as the electrophile, while EC 4.1.2.- are synthases/lyases that form carbon-carbon bonds utilizing aldehyde substrates (such as benzaldehyde) as the electrophile.

For example, the polypeptide described in EP 1045-029 (EC 4.1.3.16, 4-hydroxy-2-oxoglutarate glyoxylate-lyase also termed 4-hydroxy-2-oxoglutarate aldolase, 2-oxo-4-hydroxyglutarate aldolase or KHG aldolase) converts glyoxylic acid and pyruvate to 4-hydroxy-2-ketoglutaric acid, and the polypeptide 4-hydroxy-4-methyl-2-oxoglutarate aldolase (EC 4.1.3.17, also termed 4-hydroxy-4-methyl-2-oxoglutarate pyruvate-lyase or ProA aldolase), condenses two keto-acids such as two pyruvates to 4-hydroxy-4-methyl-2-oxoglutarate. Reactions utilizing these lyases are described herein.

FIGS. 1-2 and 11-13 show schematic diagrams of these reactions in which a 3-carbon (C3) molecule is combined with indole-3-pyruvate. Many members of EC 4.1.2.- and 4.1.3.-, particularly PLP-utilizing polypeptides, can utilize C3 molecules that are amino acids such as serine, cysteine, and alanine, or derivatives thereof. Aldol condensations catalyzed by representatives of EC 4.1.2.- and 4.1.3.- require the three carbon molecule (i.e., C3 carbon source) of this pathway to be pyruvate or a derivative of pyruvate. However, other compounds can serve as a C3 carbon source and be converted to pyruvate. Alanine can be transaminated by many PLP-utilizing transaminases, including many of those mentioned above, to yield pyruvate. Pyruvate and ammonia can be obtained by beta-elimination reactions (such as those catalyzed by tryptophanase or β-tyrosinase) of L-serine, L-cysteine, and derivatives of serine and cysteine with sufficient leaving groups, such as O-methyl-L-serine, O-benzyl-L-serine, S-methylcysteine, S-benzylcysteine, S-alkyl-L-cysteine, O-acyl-L-serine, and 3-chloro-L-alanine. Aspartate can serve as a source of pyruvate in PLP-mediated beta-lyase reactions such as those catalyzed by tryptophanase (EC 4.1.99.1) and/or β-tyrosinase (EC 4.1.99.2, also termed tyrosine-phenol lyase). The rate of beta-lyase reactions can be increased by performing site-directed mutagenesis on the (4.1.99.1-2) polypeptides as described by Mouratou et al. (*J. Biol. Chem* 274:1320-5, 1999) and in Example 18. These modifications allow the polypeptides to accept dicarboxylic amino acid substrates. Lactate can also serve as a source of pyruvate, and is oxidized to pyruvate by the addition of lactate dehydrogenase and an oxidized cofactor or lactate oxidase and oxygen. Examples of these reactions are described below. For example, as shown in FIG. 2 and FIGS. 11-13, ProA aldolase can be contacted with indole-3-pyruvate when pyruvate is used as the C3 molecule.

The MP can also be generated using chemical reactions, such as the aldol condensations provided in Example 8.

MP to Monatin

Conversion of MP to monatin can be catalyzed by one or more of: tryptophan aminotransferases (2.6.1.27), tryptophan dehydrogenases (1.4.1.19), D-amino acid dehydrogenases (1.4.99.1), glutamate dehydrogenases (1.4.1.2-4), phenylalanine dehydrogenase (EC 1.4.1.20), leucine (branched-chain) dehydrogenase (EC 1.4.1.9), tryptophan-phenylpyruvate transaminases (2.6.1.28), or more generally members of the aminotransferase family (2.6.1.-), such as aspartate aminotransferase (EC 2.6.1.1), tyrosine (aromatic) aminotransferase (2.6.1.5), D-tryptophan aminotransferase, D-alanine aminotransferase(2.6.1.21) (FIG. 2) and branched-chain aminotransferase (BCAT, EC 2.6.1.42). Eleven members of the aminotransferase class are described below (Example 1), including a novel member of the class shown in SEQ ID NOS: 11 and 12, and reactions demonstrating the activity of aminotransferase and dehydrogenase enzymes are provided in Example 15.

This reaction can also be performed using chemical reactions. Amination of the keto acid (MP) is performed by reductive amination using ammonia and sodium cyanoborohydride.

FIGS. 11-13 show additional polypeptides that can be used to convert MP to monatin, as well as providing increased yields of monatin from indole-3-pyruvate or tryptophan. For example, if aspartate is used as the amino donor, aspartate aminotransferase can be used to convert the aspartate to oxaloacetate (FIG. 11). The oxaloacetate is converted to pyruvate and carbon dioxide by a decarboxylase, such as oxaloacetate decarboxylase (FIG. 11) and 2-oxoglutarate decarboxylase (EC 4.1.1.71). In addition, if lysine is used as the amino donor, lysine epsilon aminotransferase (EC 2.6.1.36) can be used to convert the lysine to allysine (FIG. 12). The allysine is spontaneously converted to 1-piperideine 6-carboxylate (FIG. 12). An analogous process to that shown in FIG. 12 uses ornithine δ-aminotransferase (EC 2.6.1.13) in place of lysine epsilon aminotransferase, and ornithine serves as the amino donor. If a polypeptide capable of catalyzing reductive amination reactions (e.g., glutamate dehydrogenase) is used to convert MP to monatin, a polypeptide that can recycle NAD(P)H and/or produce a volatile product (FIG. 13) can be used, such as formate dehydrogenase.

Additional Considerations in the Design of the Biosynthetic Pathways

Depending on which polypeptides are used to generate indole-3-pyruvate, MP and/or monatin, cofactors, substrates, and/or additional polypeptides can be provided to the production cell to enhance product formation.

Removal of Hydrogen Peroxide

Hydrogen peroxide ($H_2O_2$) is a product that, if generated, can be toxic to production cells and can damage the polypeptides or intermediates produced. The L-amino acid oxidase described above generates $H_2O_2$ as a product. Therefore, if L-amino acid oxidase is used, the resulting $H_2O_2$ can be removed or its levels decreased to decrease potential injury to the cell or product.

Catalases can be used to reduce the level of $H_2O_2$ in the cell (FIGS. 11-13). The production cell can express a gene or cDNA sequence that encodes a catalase (EC 1.11. 1.6), which catalyzes the decomposition of hydrogen peroxide into water and oxygen gas. For example, a catalase can be expressed from a vector transfected into the production cell. Examples of catalases that can be used to include, but are not limited to: tr|Q9EV50 (*Staphylococcus xylosus*), tr|Q9KBE8 (*Bacillus halodurans*), tr|Q9URJ7 (*Candida albicans*), tr|P77948 (*Streptomyces coelicolor*), tr|Q9RBJ5 (*Xanthomonas campestris*) (SwissProt Accession Nos.). Biocatalytic reactors utilizing L-amino acid oxidase, D-amino acid oxidase, or tryptophan oxidase can also contain a catalase polypeptide.

Modulation of PLP (pyridoxal-5'-phosphate) Availability

Figure 1:
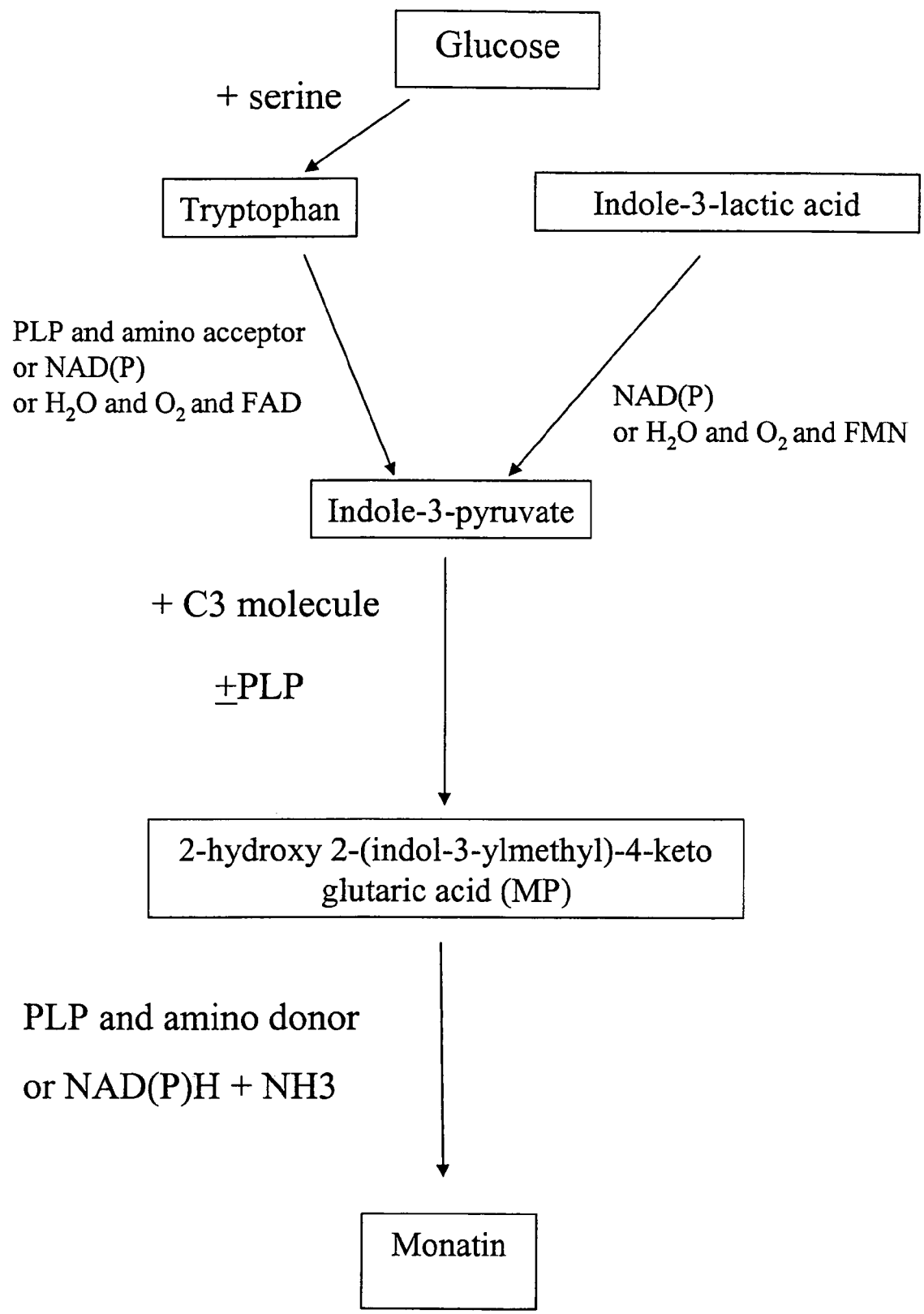
FIG. 1 shows biosynthetic pathways used to produce monatin and/or indole-3-pyruvate. One pathway produces indole-3-pyruvate via tryptophan, while another produces indole-3-pyruvate via indole-3-lactic acid. Monatin is subsequently produced via a 2-hydroxy 2-(indol-3ylmethyl)-4-keto glutaric acid (MP) intermediate.

As shown in FIG. 1, PLP can be utilized in one or more of the biosynthetic steps described herein. The concentration of PLP can be supplemented so that PLP does not become a limitation on the overall efficiency of the reaction.

The biosynthetic pathway for vitamin $B_6$ (the precursor of PLP) has been thoroughly studied in *E. coli* and some of the proteins have been crystallized (Laber et al., *FEBS Letters*, 449:45-8, 1999). Two of the genes (epd or gapB and serC) are required in other metabolic pathways, while three genes (pdxA, pdxB, and pdxJ) are unique to pyridoxal phosphate biosynthesis. One of the starting materials in the *E. coli* pathway is 1-deoxy-D-xylulose-5-phosphate (DXP). Synthesis of this precursor from common 2 and 3 carbon central metabolites is catalyzed by the polypeptide 1-deoxy-D-xylulose-5-phosphate synthase (DSX). The other precursor is a threonine derivative formed from the 4-carbon sugar, D-erythrose 4-phosphate. The genes required for the conversion to phospho-4-hydroxyl-L threonine (HTP) are epd, pdxB, and serC. The last reaction for the formation of PLP is a complex intramolecular condensation and ring-closure reaction between DXP and HTP, catalyzed by the gene products of pdxA and pdxJ.

If PLP becomes a limiting nutrient during the fermentation to produce monatin, increased expression of one or more of the pathway genes in a production host cell can be used to increase the yield of monatin. A host organism can contain multiple copies of its native pathway genes or copies of non-native pathway genes can be incorporated into the organism's genome. Additionally, multiple copies of the salvage pathway genes can be cloned into the host organism.

One salvage pathway that is conserved in all organisms recycles the various derivatives of vitamin $B_6$ to the active PLP form. The polypeptides involved in this pathway are pdxK kinase, pdxH oxidase, and pdxY kinase. Over-expression of one or more of these genes can increase PLP availability.

Vitamin $B_6$ levels can be elevated by elimination or repression of the metabolic regulation of the native biosynthetic pathway genes in the host organism. PLP represses polypeptides involved in the biosynthesis of the precursor threonine derivative in the bacterium *Flavobacterium* sp. strain 238-7. This bacterial strain, freed of metabolic control, overproduces pyridoxal derivatives and can excrete up to 20 mg/L of PLP. Genetic manipulation of the host organism producing monatin in a similar fashion will allow the increased production PLP without over-expression of the biosynthetic pathway genes.

Ammonium Utilization

Tryptophanase reactions can be driven toward the synthetic direction (production of tryptophan from indole) by making ammonia more available or by removal of water. Reductive amination reactions, such as those catalyzed by glutamate dehydrogenase, can also be driven forward by an excess of ammonium.

Ammonia can be made available as an ammonium carbonate or ammonium phosphate salt in a carbonate or phosphate buffered system. Ammonia can also be provided as ammonium pyruvate or ammonium formate. Alternatively, ammonia can be supplied if the reaction is coupled with a reaction that generates ammonia, such as glutamate dehydrogenase, tryptophan dehydrogenase or branched-chain dehydrogenase. Ammonia can be generated by addition of the natural substrates of EC 4.1.99.- (tyrosine or tryptophan), which will be hydrolyzed to phenol or indole, pyruvate and $NH_3$. This also allows for an increased yield of synthetic product over the normal equilibrium amount by allowing the enzyme to hydrolyze its preferred substrate.

Removal of Products and Byproducts

The conversion of tryptophan to indole-3-pyruvate via a tryptophan aminotransferase may adversely affect the production rate of indole-3-pyruvate because the reaction produces glutamate and requires the co-substrate 2-oxoglutarate (α-ketoglutarate). Glutamate may cause inhibition of the aminotransferase, and the reaction will consume large amounts of the co-substrate. Moreover, high glutamate concentrations are detrimental to downstream separation processes.

The polypeptide glutamate dehydrogenase (GLDH) converts glutamate to 2-oxoglutarate, thereby recycling the co-substrate in the reaction catalyzed by tryptophan aminotransferase. GLDH also generates reducing equivalents (NADH or NADPH) that can be used to generate energy for the cell (ATP) under aerobic conditions. The utilization of glutamate by GLDH also reduces byproduct formation. Additionally, the reaction generates ammonia, which can serve as a nitrogen source for the cell or as a substrate in a reductive amination for the final step shown in FIG. 1. Therefore, a production cell that over-expresses a GLDH polypeptide can be used to increase the yield and reduce the cost of media and/or separation processes.

In the tryptophan to monatin pathway, the amino donor of step three (e.g., glutamate or aspartate) can be converted back to the amino acceptor required for step 1 (e.g., 2-oxo-glutarate or oxaloacetate), if an aminotransferase from the appropriate enzyme classes is used. Utilization of two separate transaminases for this pathway, in which the substrate of one transaminase does not competitively inhibit the activity of the other transaminase, can increase the efficiency of this pathway.

Many of the reactions in the described pathways are reversible and will, therefore, reach an equilibrium between substrates and products. The yield of the pathway can be increased by continuous removal of the products from the polypeptides. For example, secretion of monatin into the fermentation broth using a permease or other transport protein, or selective crystallization of monatin from a biocatalytic reactor stream with concomitant recycle of substrates will increase the reaction yield.

The removal of byproducts by additional enzymatic reactions or by substitution of amino donor groups is another way to increase the reaction yield. Several examples are discussed in Example 21 and shown in FIGS. 11-13. Ideally a byproduct is produced that is unavailable to react in the reverse direction, either by phase change (evaporation) or by spontaneous conversion to an unreactive endproduct, such as carbon dioxide.

Modulation of the Substrate Pools

The indole pool can be modulated by increasing production of tryptophan precursors and/or altering catabolic pathways involving indole-3-pyruvate and/or tryptophan. For example, the production of indole-3-acetic acid from indole-3-pyruvate can be reduced or eliminated by functionally deleting the gene coding for EC 4.1.1.74 in the host cell. Production of indole from tryptophan can be reduced or eliminated by functionally deleting the gene coding for EC 4.1.99.1 in the host cell. Alternatively, an excess of indole can be utilized as a substrate in an in vitro or in vivo process in combination with increased amounts of the gene coding for EC 4.1.99.1 (Kawasaki et al., *J. Ferm. and Bioeng.*, 82:604-6, 1996). Genetic modifications can be made to increase the level of intermediates such as D-erythrose-4-phosphate and chorismate.

Tryptophan production is regulated in most organisms. One mechanism is via feedback inhibition of certain enzymes in the pathway; as tryptophan levels increase, the production rate of tryptophan decreases. Thus, when using a host cell engineered to produce monatin via a tryptophan intermediate, an organism can be used that is not sensitive to tryptophan concentrations. For example, a strain of *Catharanthus roseus* that is resistant to growth inhibition by various tryptophan analogs was selected by repeated exposure to high concentrations of 5-methyltryptophan (Schallenberg and Berlin, *Z Naturforsch* 34:541-5, 1979). The resulting tryptophan synthase activity of the strain was less effected by product inhibition, likely due to mutations in the gene. Similarly, a host cell used for monatin production can be optimized.

Tryptophan production can be optimized through the use of directed evolution to evolve polypeptides that are less sensitive to product inhibition. For example, screening can be performed on plates containing no tryptophan in the medium, but with high levels of non-metabolizable tryptophan analogs. U.S. Pat. Nos. 5,756,345; 4,742,007; and 4,371,614 describe methods used to increase tryptophan productivity in a fermentation organism. The last step of tryptophan biosynthesis is the addition of serine to indole; therefore the availability of serine can be increased to increase tryptophan production.

The amount of monatin produced by a fermentation organism can be increased by increasing the amount of pyruvate produced by the host organism. Certain yeasts, such as *Trichosporon cutaneum* (Wang et al., *Lett. Appl. Microbiol.* 35:338-42, 2002) and *Torulopsis glabrata* (Li et al., *Appl Microbiol. Biotechnol.* 57:451-9, 2001) overproduce pyruvate and can be used to practice the methods disclosed herein. In addition, genetic modifications can be made to organisms to promote pyruvic acid production, such as those in *E. coli* strain W1485lip2 (Kawasaki et al., *J. Ferm. and Bioeng.* 82:604-6, 1996).

Controlling Chirality

The taste profile of monatin can be altered by controlling the stereochemistry (chirality) of the molecule. For example, different monatin isomers may be desired in different blends of concentrations for different food systems. Chirality can be controlled via a combination of pH and polypeptides.

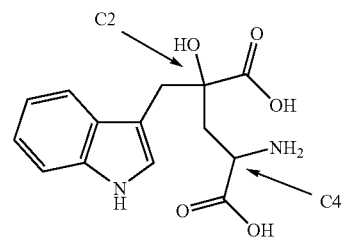

Racemization at the C-4 position of monatin (see numbered molecule above) can occur by deprotonation and reprotonation of the alpha carbon, which can occur by a shift in pH or by reaction with the cofactor PLP. In a microorganism, the pH is unlikely to shift enough to cause the racemization, but PLP is abundant. Methods to control the chirality with polypeptides depend upon the biosynthetic route utilized for monatin production.

When monatin is formed using the pathway shown in FIG. 2, the following can be considered. In a biocatalytic reaction, the chirality of carbon-2 is determined by the enzyme that converts indole-3-pyruvate to MP. Multiple enzymes (e.g.

from EC 4.1.2.-, 4.1.3.-) can convert indole-3-pyruvate to MP, thus, one can choose the enzyme that forms the desired isomer. Alternatively, the enantiospecificity of the enzyme that converts indole-3-pyruvate to MP can be modified through the use of directed evolution or catalytic antibodies can be engineered to catalyze the desired reaction. Once MP is produced (either enzymatically or by chemical condensation), the amino group can be added stereospecifically using a transaminase, such as those described herein. Either the R or S configuration of carbon-4 can be generated depending on whether a D- or L-aromatic acid aminotransferase is used. Most aminotransferases are specific for the L-isomer, however D-tryptophan aminotransferases exist in certain plants (Kohiba and Mito, Proceedings of the 8th International Symposium on Vitamin $B_6$ and Carbonyl Catalysis, Osaka, Japan 1990). Moreover, D-alanine aminotransferases (2.6.1.21), D-methionine-pyruvate aminotransferases (2.6.1.41) and both (R)-3-amino-2-methylpropanoate aminotransferase (2.6.1.61) and (S)-3-amino-2-methylpropanoate aminotransferase (2.6.1.22) have been identified. Certain aminotransferases may only accept the substrate for this reaction with a particular configuration at the C2 carbon. Therefore, even if the conversion to MP is not stereospecific, the stereochemistry of the final product can be controlled through the appropriate selection of a transaminase. Since the reactions are reversible, the unreacted MP (undesired isomer) can be recycled back to its constituents and a racemic mixture of MP can be reformed.

Activation of Substrates

Phosphorylated substrates, such as phosphoenolpyruvate (PEP), can be used in the reactions disclosed herein. Phosphorylated substrates can be more energetically favorable and, therefore, can be used to increase the reaction rates and/or yields. In aldol condensations, the addition of a phosphate group stabilizes the enol tautomer of the nucleophilic substrate, making it more reactive. In other reactions, a phosphorylated substrate often provides a better leaving group. Similarly, substrates can be activated by conversion to CoA derivatives or pyrophosphate derivatives.

Illustrative Embodiments

In one embodiment, monatin or a salt thereof may be produced by a method that includes using an aminotransferase, such as HEXAspC aminotransferase (NCBI Accession No: 1AHF_A GI: 1127190). For example, HEXAspC aminotransferase may be used to facilitate at least one reaction in which the reaction involves a substrate selected from tryptophan, 2-hydroxy 2-(indol-3-ylmethyl)-4-keto glutaric acid, and a combination thereof.

In another embodiment, monatin or a salt thereof may be produced by a method that includes using a branched-chain aminotransferase (BCAT) (EC 2.6.1.42) and/or a branched-chain dehydrogenase (EC 1.4.1.9). For example, the branched-chain aminotransferase and/or a branched-chain dehydrogenase may be used to facilitate a reaction of 2-hydroxy 2-(indol-3-ylmethyl)-4-keto glutaric acid. Suitable branched-chain aminotransferases (BCAT) (EC 2.6.1.42) may include AT-102 or AT-104. Suitable branched-chain dehydrogenases (EC 1.4.1.9) may include AADH-110.

In another embodiment, 2-hydroxy 2-(indol-3-ylmethyl)-4-keto glutaric acid or a salt thereof may be produced by a method that includes using an aldolase such as a KHG aldolase. Suitable KHG aldolases may include Z. mobilis KHG aldolase (Accession No.: AAV89621.1 GI: 56543467) and/or a polypeptide comprising an amino acid sequence that is at least about 90% identical to Z. mobilis KHG aldolase (Accession No.: AAV89621.1 GI: 56543467) and that has Z. mobilis KHG aldolase activity. In some embodiments, suitable aldolases may include polypeptides comprising an amino acid sequence that is at least about 95% identical or at least about 99% identical to Z. mobilis KHG aldolase (Accession No.: AAV89621.1 GI: 56543467), where the polypeptide has Z. mobilis KHG aldolase activity. The selected aldolase may be used to facilitate a reaction involving a substrate for synthesis of 2-hydroxy 2-(indol-3-ylmethyl)-4-keto glutaric acid, such as indole-3-pyruvate.

In other embodiments, monatin or a salt thereof may be produced by a method that includes using an aldolase to facilitate a reaction involving a substrate for synthesis of monatin, in which more than 60% of the monatin produced in the reaction is an R,R stereoisomer of monatin. Suitable aldolases for the reaction may include KHG aldolase (EC 4.1.3.16), and suitable substrates for the reaction may include indole-3-pyruvate.

In other embodiments, 2-hydroxy 2-(indol-3-ylmethyl)-4-keto glutaric acid may be produced by a method that includes reacting a suitable reaction mixture, the mixture including: (a) a suitable substrate such as tryptophan; (b) a first polypeptide chosen from HEXAspC aminotransferase (NCBI Accession No: 1AHF_A GI: 1127190), YfdZ (NCBI Accession No. AAC75438.1), and a combination thereof; and (c) a second polypeptide chosen from KHG aldolase (EC 4.1.3.16), ProA aldolase (EC 4.1.3.17), and a combination thereof. Where the substrate includes tryptophan, the tryptophan may include D-tryptophan, L-tryptophan, and a mixture thereof. The tryptophan may be added to the reaction mixture and/or producted in situ by reacting suitable substrates (e.g., glucose and serine). In some embodiments, the tryptophan includes D-tryptophan. The KHG aldolase may include Z. mobilis KHG aldolase (Accession No.: AAV8621.1 GI: 56543467) and/or a polypeptide comprising an amino acid sequence that is at least about 90% identical to Z. mobilis KHG aldolase (Accession No.: AAV89621.1 GI: 56543467) and having Z. mobilis KHG aldolase activity. In some embodiments, suitable aldolases may include polypeptides comprising an amino acid sequence that is at least about 95% identical or at least about 99% identical to Z. mobilis KHG aldolase (Accession No.: AAV89621.1 GI: 56543467), where the polypeptide has Z. mobilis KHG aldolase activity. In some embodiments, the ProA aldolase may include a C. testosteroni ProA aldolase, a S. meliloti ProA aldolase, and a combination thereof. The selected polypeptides may be added to the reaction mixture and/or expressed by microorganisms present in the reaction mixture. For example, the reaction mixture may include a nutrient medium, whereby the selected polypeptides are produced by fermenting the nutrient medium with a suitable microorganism that expresses the polypeptide.

In other embodiments, monatin or a salt thereof may be produced by reacting a reaction mixture that includes: (a) a suitable substrate such as 2-hydroxy 2-(indol-3-ylmethyl)-4-keto glutaric acid; and (b) a polypeptide chosen from YfdZ (NCBI Accession No. AAC75438.1), HEXAspC aminotransferase (NCBI Accession No: 1AHF_A GI: 1127190), a branched-chain aminotransferase (BCAT) (EC 2.6.1.42), a branched-chain dehydrogenase (EC 1.4.1.9), and a combination thereof. 2-hydroxy 2-(indol-3-ylmethyl)-4-keto glutaric acid may be added to the reaction mixture and/or may be synthesized in situ. For example, the reaction mixture may further include (c) indole-3-pyruvate; and (d) a second polypeptide that is capable of converting indole-3-pyruvate and a C3 carbon source to 2-hydroxy 2-(indol-3-ylmethyl)-4-keto glutaric acid. The indole-3-pyruvate may be added to the reaction mixture and/or may be synthesized in situ from suitable substrates. The selected polypeptides may be added to the reaction mixture and/or may be expressed by microorganisms present in the reaction mixture. For example, the reaction mixture may include a nutrient medium that is fermented with a microorganism that expresses one or more of the selected polypeptides. In some embodiments, the reaction mixture may include an unpurified cell extract, such as a cell extract that includes YfdZ (NCBI Accession No. AAC75438.1), HEXAspC aminotransferase (NCBI Accession No: 1AHF_A GI: 1127190), or a combination thereof.

In some embodiments, monatin or a salt thereof may be produced by reacting a reaction mixture that includes: (a) a suitable substrate such as 2-hydroxy 2-(indol-3-ylmethyl)-4-keto glutaric acid; and (b) a polypeptide chosen from AT-101, AT-102, AT-103, AT-104, AADH-102, AADH-110, AADH-112, AADH-113, and a combination thereof. In some embodiments, the selected polypeptide may be AT-103. The monatin or a salt thereof produced by the method may be predominantly the R,R stereoisomer of monatin. For example, in some embodiments at least about 65% of the monatin produced in the method may be an R,R stereoisomer of monatin.

In other embodiments, monatin or a salt thereof may be produced from a substrate, (such as tryptophan and/or indole-3-pyruvate), by enzymatically producing a monatin composition, in which at least about 80% of the monatin or salt thereof present in the monatin composition is an R,R stereoisomer of monatin. In suitable embodiments of the method, at least about 84% of the monatin or salt thereof present in the monatin composition is an R,R stereoisomer of monatin. Suitable substrates may include tryptophan, which may include D-tryptophan, L-tryptophan, and a mixture thereof. In some embodiments, the selected substrate is D-trytophan. The method may include providing a ProA aldolase (EC 4.1.3.17). For example, a ProA aldolase (EC 4.1.3.17) may be provided to facilitate the conversion of indole-3-pyruvate to 2-hydroxy 2-(indol-3ylmethyl)-4-keto glutaric acid. In some embodiments, the method may include providing a transaminase such as AT-103 (D-transaminase). For example, AT-103 (D-transaminase) may be provided to facilitate the conversion of 2-hydroxy 2-(indol-3ylmethyl)-4-keto glutaric acid to monatin.

In other embodiments, monatin or a salt thereof may be produced by a method that includes reacting a reaction mixture, the mixture including: (a) a substrate selected from tryptophan, 2-hydroxy 2-(indol-3-ylmethyl)-4-keto glutaric acid, and a combination thereof; and (b) an *E. coli* AspC polypeptide (NCBI Accession No. AAC74014.1). The *E. coli* AspC polypeptide (NCBI Accession No. AAC74014.1) may include at least one substitution at an amino acid position chosen from positions 39, 41, 47, 69, 109, 297, and a combination thereof, in which numbering of the amino acid positions is based on a pig cytosolic aspartate aminotransferase numbering system. In suitable embodiments, the *E. coli* AspC polypeptide may have aspartate aminotransferase activity. The *E. coli* AspC polypeptide may include at least one of the following substitutions: a Val 39 to Leu substitution; a Lys 41 to Tyr substitution; a Thr 47 to Ile substitution; an Asn 69 to Leu substitution; a Thr 109 to Ser substitution; an Asn 297 to Ser substitution; and combinations thereof. The substrate may be added to the reaction mixture and/or produced in situ from suitable substrates. The *E. coli* AspC polypeptide may be added to the reaction mixture and/or expressed by a microorganism present in the reaction mixture (e.g., by fermenting the reaction mixture, which may include a nutrient medium, with a microorganism that expresses the *E. coli* AspC polypeptide).

In further embodiments, 2-hydroxy 2-(indol-3-ylmethyl)-4-keto glutaric acid or a salt thereof may be produced by reacting a reaction mixture, the mixture including: (a) a substrate such as indole-3-pyruvate; and (b) a suitable aldolase. For example, the aldolase may be chosen from *Bradyrhizobium japonicum* str. USDA 110 (NCBI Accession No: GI: 27378953); *Sphingomonas* (*Pseudomonas*) *paucimobilis* (NCBI Accession No: GI: 19918963); *Yersinia pestis* KIM (NCBI Accession No: GI: 21956715); *Ralstonia metallidurans* CH34 (NCBI Accession No: GI: 48767386); *Yersinia pseudotuberculosis* IP 32953 (NCBI Accession No: GI: 51594436); *Rhizobium leguminosarum* biovar viciae rhiz23g02-plk_1009_341 (SEQ ID NO: 88); *Novosphingobium aromaticivorans* DSM 12444 (*Sphingomonas aromaticivorans* F199) (NCBI Accession No: GI: 48849026); *Pseudomonas putida* KT2440 (NCBI Accession No: GI: 24984081); *Magnetospirillum magnetotacticum* MS-1 (NCBI Accession No: GI: 46200890); *Rhodopseudomonas palustris* CGA009 (NCBI Accession No: GI: 39937756); *Xanthomonas campestris* ATCC-33913 (NCBI Accession No: GI: 21115297); *Xanthomonas axonopodis* citri 306 (NCBI Accession No: GI: 21110581); *Streptomyces avermitilis* MA-4680 (NCBI Accession No: GI: 29828159); and a combination thereof. The substrate (e.g., indole-3-pyruvate) may be added to the reaction mixture and/or may be produced in situ from suitable substrates. The aldolase may be added to the reaction mixture and/or may be expressed by a microorganism present in the reaction mixture (e.g., by fermenting the reaction mixture, which may include a nutrient medium, with a microorganism that expresses a selected aldolase).

In further embodiments, 2-hydroxy 2-(indol-3-ylmethyl)-4-keto glutaric acid or a salt thereof may be produced by reacting a reaction mixture, the mixture including: (a) a substrate such as indole-3-pyruvate; and (b) a suitable aldolase. For example, suitable aldolases may comprise an amino acid sequence that is at least about 49% identical to *C. testosteroni* ProA (SEQ ID NO: 66) or an amino acid sequence that is at least about 56% identical to *Sinorhizobium meliloti* ProA (NCBI Accession No.: CAC46344), where the aldolase has 4-hydroxy-4-methyl-2-oxoglutarate lyase activity. In some suitable embodiments, the aldolases may comprise an amino acid sequence that is at least about 60%, 70%, 80%, 90%, 95%, and/or 99% identical to *C. testosteroni* ProA (SEQ ID NO: 66) and/or an amino acid sequence that is at least about 60%, 70%, 80%, 90%, 95%, and/or 99% identical to *Sinorhizobium meliloti* ProA (NCBI Accession No.: CAC46344), where the aldolase has 4-hydroxy-4-methyl-2-oxoglutarate lyase activity. In some embodiments, the aldolase comprises an amino acid sequence that is at least about 60% identical to *C. testosteroni* ProA (SEQ ID NO: 66). In other embodiments, the aldolase comprises an amino acid sequence that is at least about 70% identical to *C. testosteroni* ProA (SEQ ID NO: 66). The substrate (e.g., indole-3-pyruvate) may be added to the reaction mixture and/or produced in situ from suitable substrates in the reaction mixture. The aldolase may be added to the reaction mixture and/or may be expressed by a microorganism present in the reaction mixture (e.g., by fermenting the reaction mixture, which may include a nutrient medium, with a microorganism that expresses a selected aldolase).

In further embodiments, monatin or a salt thereof may be produced by a method that includes reacting a reaction mixture, the mixture including: (a) a substrate such as tryptophan; and a suitable deaminase (EC 3.5.1.-). In some embodiments, the deaminase is derived from a microorganism chosen from: *Proteus* spp., *Providencia* spp., *Morganella* spp., or combinations thereof. Suitable deaminases may include deaminases derived from *Proteus* spp. including, but not limited to, *Proteus myxofaciens, Proteus mirabilis, Proteus vulgaris, Proteus morganii*, and combinations thereof. The tryptophan may be added to the reaction mixture and/or may be produced in situ from suitable substrates. The deaminase may be added to the reaction mixture and/or may be expressed by a microorganism present in the reaction mixture (e.g., by fermenting the reaction mixture, which may include a nutrient medium, with a microorganism that expresses a selected deaminase).

EXAMPLES

Example 1

Cloning and Expression of Tryptophan Aminotransferases

This example describes methods that were used to clone tryptophan aminotransferases, which can be used to convert tryptophan to indole-3-pyruvate. The genes were cloned into the pET 30 Xa/LIC vector to generate fusion proteins with cleavable N-terminal $HIS_6$-Tag/T7-Tags (6×His tag disclosed as SEQ ID NO: 91). The resulting proteins were purified using immobilized metal affinity chromatography.

Experimental Overview

Eleven genes encoding aminotransferases were cloned into *E. coli*. These genes were *Bacillus subtilis* D-alanine aminotransferase (dat, Genbank Accession No. Y14082.1 bp 28622-29470 and Genbank Accession No. NP_388848.1, nucleic acid sequence and amino acid sequence, respectively), *Sinorhizobium meliloti* (also termed *Rhizobium meliloti*) tyrosine aminotransferase (tatA, SEQ ID NOS: 1 and 2, nucleic acid sequence and amino acid sequence, respectively), *Rhodobacter sphaeroides* strain 2.4.1 tyrosine aminotransferase (tatA asserted by homology, SEQ ID NOS: 3 and 4, nucleic acid sequence and amino acid sequence, respectively), *R. sphaeroides* 35053 tyrosine aminotransferase (asserted by homology, SEQ ID NOS: 5 and 6, nucleic acid sequence and amino acid sequence, respectively), *Leishmania major* broad substrate aminotransferase (bsat, asserted by homology to peptide fragments from *L. mexicana*, SEQ ID NOS: 7 and 8, nucleic acid sequence and amino acid sequence, respectively), *Bacillus subtilis* aromatic aminotransferase (araT, asserted by homology, SEQ ID NOS: 9 and 10, nucleic acid sequence and amino acid sequence, respectively), *Lactobacillus amylovorus* aromatic aminotransferase (araT asserted by homology, SEQ ID NOS: 11 and 12, nucleic acid sequence and amino acid sequence, respectively), *R. sphaeroides* 35053 multiple substrate aminotransferase (asserted by homology, SEQ ID NOS: 13 and 14, nucleic acid sequence and amino acid sequence, respectively), *Rhodobacter sphaeroides* strain 2.4.1 multiple substrate aminotransferase (msa asserted by homology, Genbank Accession No. AAAE01000093.1, bp 14743-16155 and Genbank Accession No. ZP00005082:1, nucleic acid sequence and amino acid sequence, respectively), *Escherichia coli* aspartate aminotransferase (aspC, Genbank Accession No. AE000195.1 bp 2755-1565 and Genbank Accession No. AAC74014.1, nucleic acid sequence and amino acid sequence, respectively), and *E. coli* tyrosine aminotransferase (tyrB, SEQ ID NOS: 31 and 32, nucleic acid sequence and amino acid sequence, respectively).

The genes were cloned, expressed, and tested for activity in conversion of tryptophan to indole-3-pyruvate, along with commercially available enzymes. All eleven clones had activity.

Identification of Bacterial Strains that Can Contain Polypeptides with the Desired Activity No genes in the NCBI (National Center for Biotechnology Information) database were designated as tryptophan aminotransferases. However, organisms having this enzymatic activity have been identified. L-tryptophan aminotransferase (TAT) activity has been measured in cell extracts or from purified protein from the following sources: Rhizobacterial isolate from *Festuca octoflora*, pea mitochondria and cytosol, sunflower crown gall cells, *Rhizobium leguminosarum* biovar *trifoli, Erwinia herbicola* pv gypsophilae, *Pseudomonas syringae* pv. savastanoi, *Agrobacterium tumefaciens, Azospirillum lipferum* & *brasilense, Enterobacter cloacae, Enterobacter agglomerans, Bradyrhizobium elkanii, Candida maltosa, Azotobacter vinelandii*, rat brain, rat liver, *Sinorhizobium meliloti, Pseudomonas fluorescens* CHA0, *Lactococcus lactis, Lactobacillus casei, Lactobacillus helveticus*, wheat seedlings, barley, *Phaseolus aureus* (mung bean), *Saccharomyces uvarum* (carlsbergensis), *Leishmania* sp., maize, tomato shoots, pea plants, tobacco, pig, *Clostridium sporogenes*, and *Streptomyces griseus*.

Isolation of Genomic DNA for Cloning

*S. meliloti* (ATCC number 9930) was grown in TY media at 25° C., pH 7.2. Cells were grown to an optical density at 600 nm ($OD_{600}$) of 1.85 and a 2% inoculum was used for genomic DNA preparations. The Qiagen genomic tip 20/G kit (Valencia, Calif.) was used for genomic DNA isolation.

*Bacillus subtilis* 6051 (ATCC) was grown at 30° C. in Bereto Nutrient Broth (Difco; Detroit, Mich.). The Qiagen genomic tip 20/G protocol was used to isolate the genomic DNA with the following changes: the concentrations of proteinase K and lysozyme were doubled and incubation times were increased 2-3 fold.

*Leishmania major* ATCC 50122 genomic DNA was supplied by IDI, Inc. (Quebec, Canada) in TE buffer pH 8.0, 17 ng/μL.

*Rhodobacter sphaeroides* 2.4.1 (provided by Professor Sam Kaplan, University of Texas, Houston), *R. sphaeroides* 35053 (ATCC number), and *L. amylovorus* genomic DNA was prepared by standard phenol extraction. Cells were harvested in late log phase, resuspended in TEN buffer (10 mM Tris-HCl, pH 7.5, 1 mM EDTA, 100 mM NaCl), and lysed by the addition of 0.024 mL sodium lauryl sarcosine per mL cell suspension. After extracting at least three times with an equal volume of phenol saturated with TE buffer (10 mM Tris-HCl, pH 7.5, 1 mM EDTA), the DNA solution was extracted once with 9:1 chloroform:octanol and three times with chloroform. The DNA was precipitated by the addition of 0.1 volume of 3 M sodium acetate, pH 6.8 and 2 volumes ethanol. The precipitate was collected by centrifugation and washed once with 70% ethanol. Finally the DNA was dissolved in 0.10 mL distilled water.

*Escherichia coli* genomic DNA was isolated from strain DH10B (Invitrogen) and prepared using the Qiagen Genomic-tip™ (500/G) kit. From 30 mL of this strain grown in LB to an $OD_{650}$ of 1.87, 0.3 mg of purified DNA was obtained. The purified DNA was dissolved in Qiagen elution buffer (EB) at a concentration of 0.37 μg/μL.

Polymerase Chain Reaction Protocol

Primers were designed with compatible overhangs for the pET 30 Xa/LIC vector (Novagen, Madison, Wis.). The pET vector has a 12 base single stranded overhang on the 5' side of the Xa/LIC site and a 15-base single stranded overhang on the 3' side of the Xa/LIC site. The plasmid is designed for ligation independent cloning, with N-terminal His and S-tags and an optional C-terminal His-tag. The Xa protease recognition site (IEGR) sits directly in front of the start codon of the gene of interest, such that the fusion protein tags can be removed.

The following sequences were added to the 5' ends of the organism specific sequences when designing primers: forward primer, 5' GGTATTGAGGGTCGC (SEQ ID NO: 73); reverse primer: 5' AGAGGAGAGTTAGAGCC (SEQ ID NO: 74).

```
Bacillus subtilis dat primers:
N term:
                                     (SEQ ID NOS: 15 and 16)
5'-GGTATTGAGGGTCGCATGAAGGTTTTAGTCAATGG-3'
and C term:
5'-AGAGGAGAGTTAGAGCCTTATGAAATGCTAGCAGCCT-3'.

Sinorhizobium meliloti tatA primers:
N term:
                                     (SEQ ID NOS: 17 and 18)
5'-GGTATTGAGGGTCGCATGTTCGACGCCCTCGCCCG
and C term:
5'-AGAGGAGAGTTAGAGCCTCAGAGACTGGTGAACTTGC.

Bacillus subtilis araT primers:
N term:
                                     (SEQ ID NOS: 19 and 20)
5'-GGTATTGAGGGTCGCATGGAACATTTGCTGAATCC
and C term:
5'-AGAGGAGAGTTAGAGCCTTAAACGCCGTTGTTTATCG.

Rhodobacter sphaeroides msa
(both 2.4.1. and 35053):
N term:
                                     (SEQ ID NOS: 21 and 22)
5'-GGTATTGAGGGTCGCATGCGCGAGCCTCTTGCCCT
and C term:
5'-AGAGGAGAGTTAGAGCCTCAGCCGGGGAAGCTCCGGG.

Leishmania major bsat:
N term:
                                     (SEQ ID NOS: 23 and 24)
5'-GGTATTGAGGGTCGCATGTCCACGCAGGCGGCCAT
and C term:
5'-AGAGGAGAGTTAGAGCCTCACTCACGATTCACATTGC.

Lactobacillus amylovorus araT:
N term:
                                     (SEQ ID NOS: 25 and 26)
5'-GGTATTGAGGGTCGCATGCCAGAATTAGCTAATGA
and C term:
5'-AGAGGAGAGTTAGAGCCTTATTCGTCCTCTTGTAAAA.

Rhodobacter sphaeroides tatA
(both 2.4.1 and 35053 strains):
N term:
                                     (SEQ ID NOS: 27 and 28)
5'-GGTATTGAGGGTCGCATGCGCTCTACGACGGCTCC
and C term:
5'-AGAGGAGAGTTAGAGCCTCAGCCGCGCAGCACCTTGG.

Escherichia coli aspC:
N term:
                                     (SEQ ID NOS: 29 and 30)
5'-GGTATTGAGGGTCGCATGTTTGAGAACATTACCGC-3'
and C term:
5'-AGAGGAGAGTTAGAGCCTTACAGCACTGCCACAATCG-3'.

Escherichia coli tyrB:
N term:
                                     (SEQ ID NOS: 33 and 34)
5'-GGTATTGAGGGTCGCGTGTTTCAAAAAGTTGACGC
and C term:
5'-AGAGGAGAGTTAGAGCCTTACATCACCGCAGCAAACG-3'.
```

The gene derived from *S. meliloti* (tatA) was amplified using the following PCR protocol. In a 50 μL reaction 0.1-0.5 μg template, 1.5 μM of each primer, 0.4 mM each dNTP, 3.5 U Expand High Fidelity Polymerase (Roche, Indianapolis, Ind.), and 1× Expand™ buffer with Mg were used. The thermocycler program used included a hot start at 96° C. for 5 minutes, followed by 29 repetitions of the following steps: 94° C. for 30 seconds, 55° C. for 2 minutes, and 72° C. for 2.5 minutes. After the 29 repetitions the sample was maintained at 72° C. for 10 minutes and then stored at 4° C. This PCR protocol produced a product of 1199 bp.

The sequences of the genes derived from *R. sphaeroides* (msa and tatA), *L. amylovorus* araT, and *Bacillus* araT were amplified using the following PCR protocol. In a 50 μL reaction, 0.1-0.5 μg template, 1.5 μM of each primer, 0.4 mM each dNTP, 3.5 U Expand High Fidelity™ Polymerase, and 1× Expand™ buffer with Mg were added. The thermocycler program used included a hot start at 96° C. for 5 minutes, followed by 29 repetitions of the following steps: 94° C. for 30 seconds, 40-60° C. for 1 minute, 45 seconds (gradient thermocycler) and 72° C. for 2 minutes, 15 seconds. After the 29 repetitions the sample was maintained at 72° C. for 10 minutes and then stored at 4° C.

For each *R. sphaeroides* msa gene, the 42° C. and 48° C. annealing temperatures produced multiple products, but a distinct band at approximately 1464 bp. For *L. amylovorus* araT, the 42° C., 48° C., and 56° C. annealing temperatures yielded single products with intense bands at 1173 bp. For *B. subtilis* araT, the 40° C., 45° C., 50° C., 55° C. annealing temperatures generated single intense products (1173 bp), from both genomic DNA and colonies. For *L. major* bsat, the 55° C. annealing temperature gave the cleanest product (1239 bp). For *Rhodobacter* tatA genes, the 50-55° C. annealing temperatures gave clean products at the correct size (1260 bp). For both *E. coli* genes and the *B. subtilis* dat gene, an annealing temperature of 55-60° C. was used, and the annealing time was shortened to 45 seconds. Clean products of the correct sizes were obtained (approximately 1.3 kb for the *E. coli* genes, 850 bp for the dat gene).

Cloning

The PCR products were gel purified from 0.8 or 1% TAE-agarose gels using the Qiagen gel extraction kit (Valencia, Calif.). The PCR products were quantified by comparison to standards on an agarose gel, and then treated with T4 DNA polymerase following the manufacturer's recommended protocols for Ligation Independent Cloning (Novagen, Madison, Wis.).

Briefly, approximately 0.2 pmol of purified PCR product was treated with 1 U T4 DNA polymerase in the presence of dGTP for 30 minutes at 22° C. The polymerase removes successive bases from the 3' ends of the PCR product. When the polymerase encounters a guanine residue, the 5' to 3' polymerase activity of the enzyme counteracts the exonuclease activity to effectively prevent further excision. This creates single stranded overhangs that are compatible with the pET Xa/LIC vector. The polymerase is inactivated by incubating at 75° C. for 20 minutes.

The vector and treated insert were annealed as recommended by Novagen. Approximately 0.02 pmol of treated insert and 0.01 pmol vector were incubated for 5 minutes at 22° C., 6.25 mM EDTA (final concentration) was added, and the incubation at 22° C. was repeated. The annealing reaction (1 μL) was added to NovaBlue™ singles competent cells (Novagen, Madison, Wis.), and incubated on ice for 5 minutes. After mixing, the cells were transformed by heat shock for 30 seconds at 42° C. The cells were placed on ice for 2 minutes, and allowed to recover in 250 μL of room temperature SOC for 30 minutes at 37° C. with shaking at 225 rpm. Cells were plated on LB plates containing kanamycin (25-50 μg/mL).

Plasmid DNA was purified using the Qiagen spin miniprep kit and screened for the correct inserts by restriction digest with XhoI and XbaI. The sequences of plasmids that appeared to have the correct insert were verified by dideoxy chain termination DNA sequencing.

SEQ ID NOS: 1-14 and 31-32 show nucleotide and corresponding amino acid sequences of the recombinant aminotransferases, any changes from the Genbank sequences were either silent or generated conservative substitutions in the protein sequence. SEQ ID NOS: 11 and 12 are novel sequences.

Gene Expression and Assays

Plasmid DNA, verified by sequence analysis, was subcloned into *E. coli* expression hosts BLR(DE3) or BL21 (DE3) (Novagen, Madison, Wis.). The cultures were grown and the plasmids were isolated using Qiagen miniprep kit, and analyzed by restriction digest to confirm identity.

Induction was initially performed with *L. amylovorus* araT, *B. subtilis* araT, and *S. meliloti* tatA in both BLR(DE3) and BL21(DE3) cells. A time course study was performed with cultures grown in LB containing kanamycin (30 mg/L) to an $OD_{600}$ of 0.5-0.8 and induced with 1 mM IPTG (isopropyl thiogalacatoside) and sampled at 0, 1, 2, and 4 hours post induction. Cells from 2.0 mL were resuspended in 0.10 mL 120 mM Tris-HCl, pH 6.8 containing 10% sodium dodecyl sulfate, 10% 2-mercaptoethanol, and 20% glycerol, heated at 95° C. for 10 min, and cooled, and diluted with 0.10 mL $H_2O$. Aliquots of these total cellular protein samples were analyzed by SDS-PAGE using a 4-15% gradient gel. There were no significant differences in the amount of protein expressed between the 2 hour and 4 hour induction, nor between the BLR(DE3) and BL21(DE3) cells.

Cell extracts were also prepared from the 4 hour samples by suspending cell pellets from 2 mL of culture in 0.25 mL Novagen BugBuster™ reagent containing 0.25 μL benzonase nuclease, incubating at room temperature for 20 minutes with gentle shaking, and centrifuging at 16,000×g to remove cell debris. The supernatants (cell extracts) were loaded onto 4-15% gradient gels for analysis of the cellular soluble proteins.

The three clones, (*L. amylovorus* araT (SEQ ID NOS: 11 and 12), *B. subtilis* araT (SEQ ID NOS: 9 and 10), and *S. meliloti* tatA (SEQ ID NOS: 1 and 2) showed soluble protein that corresponded to the correct size (approximately 45 kDa).

The *B. subtilis* araT gene product was over-expressed at the highest level and/or was more soluble than the other two gene products.

In subsequent expression methods, plasmid DNA from positive clones was subcloned into BL21(DE3) due to the better growth characteristics of this host. Induction was repeated using 1 mM IPTG with cultures grown in LB containing kanamycin at 50 mg/L, inducing when the $OD_{600}$ reached approximately 0.8. Cells were harvested after 4 hours of growth at 37° C., centrifuged at 3000 rpm for 10 minutes (4° C.), washed with TEGGP buffer (50 mM Tris-HCl(pH 7.0), 0.5 mM EDTA, 100 mg/L glutathione, 5% glycerol, with Roche complete protease inhibitor cocktail), and flash frozen in −80° C. ethanol.

Samples were resuspended in 5 mL/g wet cell weight of BugBuster™ (Novagen) reagent containing 5 μL/mL protease inhibitor cocktail set #3 (Calbiochem-Novabiochem Corp., San Diego, Calif.) and 1 μL/mL benzonase nuclease. Samples were incubated at room temperature for 20 minutes on an orbital shaker. Insoluble cell debris was removed by centrifugation at 16,000×g for 20 minutes at 4° C.

Cell extracts were analyzed by SDS-PAGE, and assayed for tryptophan aminotransferase activity by following production of indole-pyruvic acid using the following protocol. One mL reactions were carried out in 50 mM sodium tetraborate (pH 8.5), 0.5 mM EDTA, 0.5 mM sodium arsenate, 50 μM pyridoxal phosphate, 5 mM α-ketoglutarate, and 5 mM L-tryptophan. The reactions were initiated by the addition of cell free extracts or purified enzyme and were incubated 30 minutes at 30° C. 20% TCA (200 μL) was added to stop the reaction, and the precipitated protein was removed by centrifugation. The absorbance at 327 nm was measured and compared to a standard curve of freshly prepared indole-3-pyruvate in the assay buffer. Control reactions without the substrate tryptophan or using cell-free extracts from clones transformed with pET30a alone were also performed.

Due to background from the native *E. coli* aminotransferases in cell extracts, the recombinant fusion proteins each containing an aminotransferase protein fused to the pET30 amino terminal $HIS_6$-Tag/S-Tag (6×His tag disclosed as SEQ ID NO: 91) were purified using immobilized metal affinity chromatography with His-Bind cartridges following manufacturer's protocols (Novagen, Madison, Wis.). The $HIS_6$-Tag (SEQ ID NO: 91) sequence of the fusion proteins binds to the divalent $Ni^{2+}$ cations immobilized on IDA-based His-Bind resin. The eluent fractions were desalted on PD-10 (Amersham Biosciences, Piscataway, N.J.) columns and eluted in 50 mM Tris, pH7.0. Purified proteins were analyzed by SDS-PAGE and assayed for aminotransferase activity.

Results from the 37° C. induction with 1 mM IPTG (4 hours) demonstrate that *L. major* bsat, *S. meliloti* tatA, *E. coli* aspC, and both *R. sphaeroides* tatA clones have significant levels of tryptophan aminotransferase activity. The araT protein from *B. subtilis* was over-expressed and soluble, but showed little enzymatic activity. The *L. amylovorus* araT gene product appeared to be soluble in the cell extract, but purification using a His-Bind cartridge resulted in only small amounts of protein with the correct molecular weight. The msa gene products were insoluble and further expression experiments were done at 24° C. to minimize inclusion body formation. Several concentrations of IPTG between 10 μM and 1 mM were used to maximize the amount of soluble protein.

Table 1 lists the specific activities measured in micrograms of indole-3-pyruvate (I3P) formed per milligram protein per minute. In some cases, very small amounts of recombinant protein showed high levels of activity above the effective linear range of the assay. In these cases a '>' precedes the specific activity number.

TABLE 1

Specific Activities of Clones in Cell Extracts (CE) and Purified (P) and Commercial Enzyme

| Enzyme | Specific Activity (μg I3P/mg protein/min) | Note |
|---|---|---|
| L. major bsat CE | >49.3 | |
| L. major bsat P | >4280 | |
| S. meliloti tatA CE | >28.6 | |
| S. meliloti tatA P | >931 | |
| R. sphaeroides 2.4.1 tatA CE | >41.2 | |
| R. sphaeroides 2.4.1 tatA P | 1086 | |
| R. sphaeroides 35053 tatA CE | >62.3 | |
| R. sphaeroides 35053 tatA P | >486 | |
| L. amylovorus araT CE | 1.26 | |
| L. amylovorus araT P | 0 | little protein after His-Bind cartridge |
| B. subtilis araT CE | 0 | undetectable |
| B. subtilis araT P | 1.5-4.5 | |
| R. sphaeroides 2.4.1 msa CE | 2.05 | very little soluble protein |
| R. sphaeroides 2.4.1 msa P | 0 | no protein after His-Bind cartridge |
| R. sphaeroides 35053 msa CE | 3.97 | very little soluble protein |
| R. sphaeroides 35053 msa P | 0 | no protein after His-Bind cartridge |
| E. coli aspC (P) | 800 | |
| E. coli tyrB (P) | 1 | not very soluble |
| B. subtilis D-aminotransf.(P) | 2.7 | using D-tryptophan as substrate |
| broad range transaminase | 22 | Sigma cat #T 7684 |
| Porcine type II-A | 1.5 | Sigma G7005 |
| Porcine type I | 1 | Sigma G2751 |

An alignment comparing all of the recombinant proteins cloned illustrates that there are not many highly conserved areas between the araT, tatA, bsat, and msa sequences. An alignment of highest activity recombinant proteins: *Rhodobacter* tatA gene product homologs, *L. major* broad substrate aminotransferase, and the *Sinorhizobium meliloti* tyrosine aminotransferase showed several conserved regions, however they are only approximately 30-43% identical at the protein level. The availability of the broad range, D-specific (D-alanine) aminotransferase can be useful in the production of other stereoisomers of monatin (see Examples 9-15).

Example 2

This example describes methods that were used to subclone and analyze a mutated version of the *E. coli* aspC gene, HEX, cloned in the vector pET30 Xa/LIC. The product of this gene carries 6 mutations to its active site and was rationally designed to have increased aminotransferase activity with aromatic amino acids, based on homology to the TyrB aromatic (tyrosine) aminotransferase from *E. coli*. Two of these positions (Thr 109 and Asn 297; pig cytosolic aspartate aminotransferase (AAT) numbering system) are invariant in all known aspartate aminotransferase enzymes, but were modified to mimic the *E. coli* TyrB sequence (Ser 109 and Ser 297). The other four positions (Val 39, Lys 41, Thr 47, and Asn 69) line the active site pocket of *E. coli* AspC and are replaced by amino acids with more hydrophobic side chains found in TyrB (Leu 39, Tyr 41, Ile 47, and Leu 69).

Cloning

The HEX gene cloned in pUC19 was provided by Professor J F Kirsch (Department of Molecular and Cell Biology, University of California, Berkeley, Berkeley, Calif. 94720-3206) and used as the template for the cloning of the gene into pET30 Xa/LIC. See James J. Onuffer and Jack F. Kirsch, Redesign of the substrate specificity of *Escherichia coli* aspartate aminotransferase to that of *Escherichia coli* tyrosine aminotransferase by homology modeling and site-directed mutagenesis, Protein Science, 4: 1750-1757 (1995).

The primers designed for cloning the *E. coli* aspC gene into the pET30 Xa/LIC vector (Novagen, Madison, Wis.) described in Example 1 (SEQ ID NOS: 29 and 30) were used to subclone the HEX gene into the same vector. The following PCR protocol was used for gene amplification: In a 50 μL reaction, 50 ng DNA template, 1.0 μM of each primer, 0.2 mM each dNTP, 1 U pfuUltra HF Polymerase (Stratagene), 2.1 U Expand High Fidelity™ Polymerase (Roche Molecular Biochemicals, Indianapolis, Ind. ), and 1× Expand™ buffer with Mg were added. The thermocycler program utilized a hot start of 94° C. for 5 minutes; followed by 10 cycles of a denaturing step at 94° C. (30 sec), an annealing step at 50° C. (1 min), and an extension step at 72° C. (1 min 30 sec); 15 cycles of a denaturing step at 94° C. (30 sec), an annealing step at 55° C. (1 min), and an extension step at 72° C. (1 min 30 sec) that increased 5 sec per cycle; 10 cycles of a denaturing step at 94° C. (30 sec), an annealing step at 55° C. (1 min), and an extension step at 72° C. (2 min 45 sec); and finally a finishing step at 72° C. (7 min). The amplified DNA was purified from a 1% agarose gel using a Qiagen QIAquick Gel Extraction Kit (Valencia, Calif.). The PCR product was quantified by measuring the absorbance at 260 nm, treated with T4 DNA polymerase, and annealed with the vector following the manufacturer's recommended protocols for Ligation Independent Cloning (Novagen, Madison, Wis.) and previously described in Example 1.

Transformation of the annealing reaction into electrocompetent DH10B was performed under standard conditions using a 0.1 cm cuvette and a Bio-Rad Gene Pulser II system as described in the Bio-Rad electroporation manual. Clones containing the HEX gene were identified by restriction analysis and confirmed by DNA sequencing. SEQ ID NOS 75 and 76 show nucleotide and the corresponding amino acid sequences of the HEX gene and gene product (HEXAspC aminotransferase, also called HEX protein). See also NCBI accession number 1AHF_A GI: 1127190 (amino acid sequence).

Gene Expression and Assays

Plasmid DNA (verified by sequence analysis) was subcloned into expression host BL21(DE3) (Novagen). The cultures were grown in LB medium with 50 mg/L kanamycin and the plasmids were isolated using a Qiagen spin plasmid miniprep kit and subsequently analyzed by restriction digest to confirm identity. Induction experiments were carried out with the BL21(DE3) construct grown in LB medium containing 50 mg/L kanamycin at 37° C. Protein expression was induced using 0.2 mM IPTG after the $OD_{600}$ reached approximately 0.6. The cells were grown for 4 hours at 30° C. and harvested by centrifugation. The cells were then lysed using Bugbuster™ reagent (Novagen) containing 1 μL/mL benzonase nuclease, 5 μL/mL Calbiochem protease inhibitor cocktail set III and 0.33 μL/10 mL r-Lysozyme following the Novagen recommended protocol. After incubation at 25° C. for 15 min with gentle shaking, the cell debris was pelleted by centrifugation at 21,000×g for 20 min at 4° C. The supernatant (cell free extract) was analyzed by SDS-PAGE on 4-15% gradient gels (Bio-Rad) to detect soluble protein levels of the recombinant fusion protein. The level of expression was high (approximately 30-40% of the soluble protein) and similar to that observed for the aspC aminotransferase protein.

The HIS$_6$-HEX protein (6×His tag disclosed as SEQ ID NO: 91) was purified from cell extract (prepared as described above) using immobilized metal affinity chromatography with His-Bind 900 cartridges following the manufacturer's protocol (Novagen, Madison, Wis.). (The HIS$_6$-Tag (SEQ ID NO: 91) sequence of the HIS6-HEX protein (6×His tag disclosed as SEQ ID NO : 91) binds to the divalent Ni$^{2+}$ cations immobilized on IDA-based His-Bind resin). The eluent fractions were desalted on PD-10 (Amersham Biosciences, Piscataway, N.J.) columns and eluted in 50 mM Tris-HCl, pH 7.0. The purified protein was analyzed by SDS-PAGE for purity and the amount of protein in the purification fractions was determined using the Pierce BCA assay with bovine serum albumin as the standard.

The purified HIS$_6$-HEX (6×His tag disclosed as SEQ ID NO: 91) protein and unpurified cell extracts were analyzed for tryptophan aminotransferase activity using the following protocol: The reaction mixture contained, in 1.0 mL, 50 mM sodium tetraborate, pH 8.5, 5 mM alpha-ketoglutarate, 0.05 mM pyridoxal phosphate, 0.5 mM sodium arsenate, 0.5 mM EDTA and enzyme. All components except the enzyme were mixed together, the enzyme was added to start the reaction and the reaction solution was incubated at 30° C. for 30 min. The reaction was stopped by the addition of 0.2 mL of 20% trichloroacetic acid, the mixture was centrifuged at 21,000 rpm, and the clear supernatant was carefully removed. The absorbance of the supernatant was measured at 327 nm (absorbance maximum for indole-3-pyruvate). All reactions were run in duplicate. For comparison the HIS$_6$-tyrb (6×His tag disclosed as SEQ ID NO: 91) and HIS$_6$-aspC (6×His tag disclosed as SEQ ID NO: 91) aminotransferases described in Example 1 were also analyzed using the same protocol. The results are shown in Table 2. Absorbance at 327 is proportional to indole-3-pyruvate concentration, and can be used to determine relative activities of various enzymes for a particular experiment.

TABLE 2

(6xHis tags disclosed as SEQ ID NO: 91)

| aminotransferase gene | µg aminotransferase in reaction | Absorbance at 327 nm |
|---|---|---|
| HIS$_6$-HEX, purified | 9.1 | 1.171 |
| HIS$_6$-HEX, cell extract | 22.8 | 1.683 |
| HIS$_6$-aspC purified | 9.1 | 0.834 |
| HIS$_6$-aspC, cell extract | 22.8 | 1.42 |
| HIS$_6$-tyrB purified | 9.1 | 0.008 |
| HIS$_6$-tyrB, cell extract | 22.8 | 0.346 |

The results listed in Table 2 show that the HEXAspC aminotransferase has approximately 40% higher activity for tryptophan than the AspC protein when purified enzymes are used in the assay. The increase in activity is significantly less when cell extracts are the source of the enzymes. This may be due to interfering activity from native proteins of the host E. coli strain. The tyrB gene product is less stable than the AspC protein and its lack of stability may be reflected in the low level of activity observed for this enzyme. Furthermore, the His fusion tag may interfere with the correct conformation of the protein and adversely affect its activity, see data below. The increased activity of the HEX mutant of AspC on tryptophan may explain the improvement in amounts of monatin formed when using this enzyme as described below in Examples 9-10 (Tables 6 and 7). The HEX mutant of AspC is the optimal enzyme for S,S monatin production in reactions with C. testosteroni ProA aldolase.

Example 3

This example describes methods that were used to subclone, express and analyze aspC, tyrB, and HEX aminotransferase genes and gene products that were constructed without amino terminal HIS$_6$ tags (SEQ ID NO: 91). The aminotransferase activity was measured by following the formation of the co-product of the reaction, glutamate, by HPLC as described in Example 18.

Cloning

The following primers were designed for cloning the E. coli aspC, tyrB and HEX genes into the pET30a vector (Novagen, Madison, Wis.) (the same primers were used for aspC and HEX):

```
aspC/HEX primers:
N term:
                                        (SEQ ID NO: 77)
5'-GCGGAACATATGTTTGAGAACATTACCGCC-3';

C term:
                                        (SEQ ID NO: 78)
5'-ATAACCGGATCCTTACAGCACTGCCACAATCG-3';

tyrB primers:
N term:
                                        (SEQ ID NO: 79)
5'-GCGGCGCATATGGTGTTTCAAAAAGTTGACGC-3';

C term:
                                        (SEQ ID NO: 80)
5'-CCAATAGGATCCTTACATCACCGCAGCAAACG-3'.
```

An ATG start codon was added 5' to the coding sequence of tyrB for compatibility with the restriction enzyme and for higher expression levels. The following PCR protocol was used for gene amplification: In a 100 µL reaction, 50 ng DNA template, 1.0 µM of each primer, 0.2 mM each dNTP, 1 U Pfu Turbo Polymerase Stratagene; LaJolla, Calif.), and 1× Cloned Pfu buffer were added. The thermocycler program utilized a hot start of 94° C. for 5 minutes; followed by 25 cycles of a denaturing step at 94° C. (30 sec), an annealing step at 55° C. (1 min), and an extension step at 72° C. (2 min) and finally a finishing step at 72° C. (7 min). The amplified DNA was purified using a Qiagen QIAquick® PCR Purification Kit (Valencia, CA.). The purified DNA and purified plasmid DNA (pET30 purified using a Qiagen QIAprep® Spin Miniprep Kit) was digested with the NdeI and BamHI according to the manufacturer's directions (NEB; Beverly, Mass.). Digestion of the pET30a vector with NdeI removes the amino terminal HIS$_6$-tag (SEQ ID NO: 91) region. The digested DNA was purified from a 1% agarose gel using a Qiagen QIAquick® Gel Extraction Kit (Valencia, Calif.). The purified DNA product was quantified by measuring the absorbance at 260 nm, and ligated using a Quick Ligation kit (NEB). The ligated DNA was transformed into chemically competent TOP10F' cells (Invitrogen; Carlsbad, Calif.). Clones with an insert were identified by running purified plasmid DNA on a 1% agarose gel. Clones with an insert were confirmed by DNAn sequencing.

Gene Expression and Assays

Plasmid DNA (verified by sequence analysis) was subcloned into expression host BL21(DE3) (Novagen). The cultures were grown in LB medium with 50 mg/L kanamycin.

Induction experiments were carried out with the BL21(DE3) construct grown in LB medium containing 50 mg/L kanamycin at 37° C. Protein expression was induced using 0.1 mM IPTG after the $OD_{600}$ reached approximately 0.5. The cells were grown for 4 hours at 30° C. and harvested by centrifugation. The cells were then lysed using Bugbuster™ reagent (Novagen) containing 1 µL/mL benzonase nuclease, 5 µL/mL Calbiochem protease inhibitor cocktail set III and 0.33 µL/10 mL r-Lysozyme following the Novagen recommended protocol. After incubation at 25° C. for 15 min with gentle shaking, the cell debris was pelleted by centrifugation at 21,000×g for 20 min at 4° C. The supernatant (cell free extract) was analyzed by SDS-PAGE on 4-15% gradient gels (Bio-Rad) to detect soluble protein levels of the recombinant fusion protein. The level of expression was high (approximately 25-40% of the total soluble protein) for all 3 proteins and similar to that observed for the corresponding pET30 $HIS_6$-tagged (SEQ ID NO: 91) constructs.

The untagged AspC and TyrB proteins were assayed for tryptophan aminotransferase activity using the following protocol. The formation of the co-product of the reaction, glutamate, was measured using the HPLC fluorescence detection method described in Example 18 rather than measuring the formation of the indole-3-pyruvate as described above in Example 1. In this reaction tryptophan reacts stoichiometrically with alpha-ketoglutarate to generate indole-3-pyruvate and glutamate. Glutamate is more stable in aqueous solution than indole-3-pyruvate and thus its measurement may afford a more accurate measure of enzyme activity. The reaction mixture contained, in 1.0 mL, 50 mM Tris-HCl, pH 8.0, 5 mM alpha-ketoglutarate, 0.05 mM pyridoxal phosphate, 5 mM tryptophan and enzyme. All components except the enzyme were mixed together, the enzyme was added to start the reaction and the reaction solution was incubated at 30° C. for 60 min. The reaction was stopped by the addition of 0.15 mL of 20% trichloroacetic acid, the mixture was centrifuged at 21,000 rpm, and the clear supernatant was carefully removed. The results (corrected for background levels of glutamate and for the dilution from the addition of trichloroacetic acid to precipitate the proteins) are shown in Table 3.

TABLE 3

| Aminotransferase gene | µg aminotransferase | [glutamate]; µg/mL |
|---|---|---|
| tyrB | 50 | 310 |
| aspC | 50 | 328 |

This result is surprising as other researchers have observed that the TyrB aminotransferase exhibits higher activity with tryptophan as the substrate than AspC (Hayashi et al (1993) Biochemistry 32:12229-1239). The unexpectedly low level of activity may due to protein instability. However, the level of activity found with the untagged TyrB protein is considerably higher than that seen with the tagged version above (see Table 1). Because tryptophan reacts stoichiometrically with alpha-ketoglutarate to generate indole-3-pyruvate and glutamate in the aminotransferase reaction, the concentration of indole-3-pyruvate formed (as shown in Table 1) and the concentration of glutamate formed (as shown in Table 3) reflect the same activity. However, glutamate is more stable in aqueous solution than indole-3-pyruvate and, thus, its measurement may afford a more accurate measure of enzyme activity. The relative activity (or ratio) of TyrB to AspC using either detection method should yield the same number, and it is clear that the tagged version of TyrB has less activity on tryptophan in comparison to tagged AspC, while the untagged TyrB has nearly the same activity as the untagged AspC.

Example 4

Conversion of Indole-3-lactate to Indole-3-pyruvate

As shown in FIGS. 1 and 3, indole-3-lactic acid can be used to produce indole-3-pyruvate. Conversion between lactic acid and pyruvate is a reversible reaction, as is conversion between indole-3-pyruvate and indole-3-lactate. The oxidation of indole-lactate was typically followed due to the high amount of background at 340 nm from indole-3-pyruvate.

The standard assay mixture contained 100 mM potassium phosphate, pH 8.0, 0.3 mM $NAD^+$, 7 units of lactate dehydrogenase (LDH) (Sigma-L2395, St. Louis, Mo.), and 2 mM substrate in 0.1 mL. The assay was performed in duplicate in a UV-transparent microtiter plate, using a Molecular Devices SpectraMax Plus platereader. Polypeptide and buffer were mixed and pipetted into wells containing the indole-3-lactic acid and $NAD^+$ and the absorbance at 340 nm of each well was read at intervals of 9 seconds after brief mixing. The reaction was held at 25° C. for 5 minutes. The increase in absorbance at 340 nm follows the production of NADH from $NAD^+$. Separate negative controls were performed without $NAD^+$ and without substrate. D-LDH from *Leuconostoc mesenteroides* (Sigma catalog number L2395) appeared to exhibit more activity with the indole-derivative substrates than did L-LDH from *Bacillus stearothermophilus* (Sigma catalog number L5275).

Similar methods were utilized with D-lactic acid and NAD+ or NADH and pyruvate, the natural substrates of D-LDH polypeptides. The $V_{max}$ for the reduction of pyruvate was 100-1000 fold higher than the $V_{max}$ for the oxidation of lactate. The $V_{max}$ for the oxidation reaction of indole-3-lactic with D-LDH was approximately one-fifth of that with lactic acid. The presence of indole-3-pyruvate was also measured by following the change in absorbance at 327 (the enol-borate derivative) using 50 mM sodium borate buffer containing 0.5 mM EDTA and 0.5 mM sodium arsenate. Small, but repeatable, absorbance changes were observed, as compared to the negative controls for both L and D-LDH polypeptides.

Additionally, broad specificity lactate dehydrogenases (enzymes with activity associated with EC 1.1.1.27, EC 1.1.1.28, and/or EC 1.1.2.3) can be cloned and used to make indole-3-pyruvate from indole-3-lactic acid. Sources of broad specificity dehydrogenases include *E. coli, Neisseria gonorrhoeae*, and *Lactobacillus plantarum*.

Alternatively, indole-3-pyruvate can be produced by contacting indole-3-lactate with cellular extracts from *Clostridium sporogenes* which contain an indolelactate dehydrogenase (EC 1.1.1.110); or *Trypanosoma cruzi epimastigotes* cellular extracts which contain p-hydroxyphenylactate dehydrogenase (EC 1.1.1.222) known to have activity on indole-3-pyruvate; or *Pseudomonas acidovorans* or *E. coli* cellular extracts, which contain an imidazol-5-yl lactate dehydrogenase (EC 1.1.1.111); or *Coleus blumei*, which contains a hydroxyphenylpyruvate reductase (EC 1.1.1.237); or *Candida maltosa* which contains a D-aromatic lactate dehydrogenase (EC 1.1.1.222). References describing such activities include, Nowicki et al. (*FEMS Microbiol Lett* 71:119-24, 1992), Jean and DeMoss (*Canadian J. Microbiol.* 14 1968, Coote and Hassall (*Biochem. J.* 111: 237-9, 1969), Cortese et al. (*C. R. Seances Soc. Biol. Fil.* 162 390-5, 1968), Petersen and Alfermann (*Z. Naturforsch. C: Biosci.* 43 501-4, 1988), and Bhatnagar et al. (*J. Gen Microbiol* 135:353-60, 1989). In addition, a lactate oxidase such as the one from *Pseudomonas* sp. (Gu et al. J. Mol. Catalysis B: Enzymatic: 18:299-305, 2002), can be utilized for oxidation of indole-3-lactic to indole-3-pyruvate.

Example 5

Conversion of L-tryptophan to Indole-3-pyruvate Utilizing L-amino acid oxidase

This example describes methods used to convert tryptophan to indole-3-pyruvate via an oxidase (EC 1.4.3.2), as an alternative to using a tryptophan aminotransferase as described in Example 1. L-amino acid oxidase was purified from *Crotalus durissus* (Sigma, St. Louis, Mo., catalog number A-2805). The accession numbers of L-amino acid oxidases for molecular cloning include: CAD21325.1, AAL14831, NP_490275, BAB78253, A38314, CAB71136, JE0266, T08202, S48644, CAC00499, P56742, P81383, O93364, P81382, P81375, S62692, P23623, AAD45200, AAC32267, CAA88452, AP003600, and Z48565.

Reactions were performed in microcentrifuge tubes in a total volume of 1 mL, incubated for 10 minutes while shaking at 37° C. The reaction mix contained 5 mM L-tryptophan, 100 mM sodium phosphate buffer pH 6.6, 0.5 mM sodium arsenate, 0.5 mM EDTA, 25 mM sodium tetraborate, 0.016 mg catalase (83 U, Sigma C-3515), 0.008 mg FAD (Sigma), and 0.005-0.125 Units of L-amino acid oxidase. Negative controls contained all components except tryptophan, and blanks contained all components except the oxidase. Catalase was used to remove the hydrogen peroxide formed during the oxidative deamination. The sodium tetraborate and arsenate were used to stabilize the enol-borate form of indole-3-pyruvate, which shows a maximum absorbance at 327 nm. Indole-3-pyruvate standards were prepared at concentrations of 0.1-1 mM in the reaction mix.

The purchased L-amino acid oxidase had a specific activity of 540 µg indole-3-pyruvate formed per minute per mg protein. This is the same order of magnitude as the specific activity of tryptophan aminotransferase enzymes.

Example 6

Conversion of D-tryptophan to Indole-3-pyruvate Utilizing D-amino acid oxidase

This example describes methods used to convert D-tryptophan to indole-3-pyruvate via an oxidase (EC 1.4.3.3), as an alternative to using L-tryptophan as the starting substrate for the reaction. D-amino acid oxidase was purchased from Bio-Catalytics (Pasadena, Calif., catalog AOD-101).

Reactions were performed in microcentrifuge tubes in a total volume of 1 mL and were incubated for 20 minutes while shaking at 30° C. The reaction mix contained 5 mM L-tryptophan, 50 mM sodium tetraborate buffer pH 8, 0.5 mM sodium arsenate, 0.5 mM EDTA, 25.5 µL tech grade catalase (1000 U, BioCatalytics CAT-101), 0.008 mg FAD (Sigma), and approximately 10 mgs of D-amino acid oxidase crude preparation. The D-amino acid oxidase preparation contained a large amount of insoluble material. Negative controls contained all components except oxidase. Samples were run in duplicate.

The samples were spun to remove debris and the supernatant was diluted 10-fold prior to absorbance measurements at 327 nm. The diluted samples had absorbances of between 0.789-0.926 while the negative controls (undiluted) had OD's of 0.418 and 0.416. As expected, broad specificity D-oxidases can be used to efficiently convert D-tryptophan to indole-3-pyruvate.

Example 7

Converting Indole-3-pyruvate to 2-hydroxy 2-(indol-3-ylmethyl)-4-keto glutaric acid with an Aldolase This example describes methods that can be used to convert indole-3-pyruvate to the 2-hydroxy 2-(indol-3-ylmethyl)-4-keto glutaric acid monatin precursor (MP) using an aldolase (lyase) (FIG. 2). Aldol condensations are reactions that form carbon-carbon bonds between the β-carbon of an aldehyde or ketone and the carbonyl carbon of another aldehyde or ketone. A carbanion is formed on the carbon adjacent to the carbonyl group of one substrate, and serves as a nucleophile attacking the carbonyl carbon of the second substrate (the electrophilic carbon). Most commonly, the electrophilic substrate is an aldehyde, so most aldolases fall into the EC 4.1.2.-category. Quite often, the nucleophilic substrate is pyruvate. It is less common for aldolases to catalyze the condensation between two keto-acids or two aldehydes.

However, aldolases that catalyze the condensation of two carboxylic acids have been identified. For example, EP 1045-029 describes the production of L-4-hydroxy-2-ketoglutaric acid from glyoxylic acid and pyruvate using a *Pseudomonas* culture (EC 4.1.3.16). In addition, 4-hydroxy-4-methyl-2-oxoglutarate aldolase (4-hydroxy-4-methyl-2-oxoglutarate pyruvate lyase, EC 4.1.3.17) can catalyze the condensation of two keto acids. Therefore, similar aldolase polypeptides were used to catalyze the condensation of indole-3-pyruvate with pyruvate. The activity or enantiospecificity of these enzymes can be modified for production of a specific stereoisomer of monatin.

Cloning

4-Hydroxy-4-methyl-2-oxoglutarate pyruvate lyases (e.g., ProA aldolase, EC 4.1.3.17) and 4-hydroxy-2-oxoglutarate glyoxylate-lyases (e.g., KHG aldolase, EC 4.1.3.16) catalyze reactions very similar to the aldolase reaction of FIG. 2. Primers were designed with compatible overhangs for the pET30 Xa/LIC vector (Novagen, Madison, Wis.). The design of these primers is described above in Example 1.

The following primers were designed for pET30 Xa/LIC cloning:

1. *Pseudomonas straminea* (*Pseudomonas ochraceae* NGJI) proA gene (Genbank Accession No.: 12964663 Version: 12964663) and *Comamonas testosteroni* proA gene (SEQ ID NOS: 65-66, nucleic acid sequence and amino acid sequence, respectively)

```
forward
                            (SEQ ID NOS: 55 and 56)
5'-GGTATTGAGGGTCGCATGTACGAACTGGGAGTTGT-3'
and reverse
5'-AGAGGAGAGTTAGAGCCTTAGTCAATATATTTCAGGC-3'.
```

2. *Sinorhizobium meliloti* 1021 SMc00502 gene (homologous to proA, Genbank Accession Nos.: 15074579 and CAC46344, nucleic acid sequence and amino acid sequence, respectively)

forward
                                           (SEQ ID NOS: 61 and 62)
5'-GGTATTGAGGGTCGCATGAGCGTGGTTCACCGGAA-3'
and reverse
5'-AGAGGAGAGTTAGAGCCTCAATCGATATATTTCAGTC-3'.

3. *Sphingomonas* sp. LB126 fldz gene (Genbank Accession No.: 7573247 Version: 7573247, codes for a putative acyl transferase)

forward
                                           (SEQ ID NOS: 57 and 58)
5'-GGTATTGAGGGTCGCATGTCCGGCATCGTTGTCCA-3'
and reverse
5'-AGAGGAGAGTTAGAGCCTCAGACATATTTCAGTCCCA-3'.

4. *Arthrobacter keyseri* pcmE gene (Genbank Accession No.: AF331043 Version: AF331043.1, codes for an oxalocitramalate aldolase)

forward
                                           (SEQ ID NOS: 59 and 60)
5'-GGTATTGAGGGTCGCATGCGACTGAACAACCTCGG-3'
and reverse
5'-AGAGGAGAGTTAGAGCCTCAGTTCTCCACGTATTCCA-3'.

5. *Yersinia pestis* strain CO92 YP00082 gene (Genbank Accession No.: 15978115 Version: 15978115, codes for a possible transferase)

forward
                                           (SEQ ID NOS: 63 and 64)
5'-GGTATTGAGGGTCGCATGAGCCTGGTTAATATGAA-3'
and reverse
5'-AGAGGAGAGTTAGAGCCTTATGACTTTAACGCGTTGA-3'.

6. *Bacillus subtilis* khg gene (Genbank Accession Nos. Z99115.1 GI: 2634478, 126711-127301 and CAB14127.1, nucleic acid sequence and amino acid sequence, respectively)

forward
                                           (SEQ ID NOS: 35 and 36)
5'-GGTATTGAGGGTCGCATGGAGTCCAAAGTCGTTGA-3'
and reverse
5'-AGAGGAGAGTTAGAGCCTTACACTTGGAAAACAGCCT-3'.

7. *E. coli* khg gene (Genbank Accession Nos. .AE000279.1 1331-1972 and AAC74920. 1, nucleic acid and amino acid sequence, respectively)

forward
                                           (SEQ ID NOS: 37 and 38)
5'-GGTATTGAGGGTCGCATGAAAAACTGGAAAACAAG-3'
and reverse
5'-AGAGGAGAGTTAGAGCCTTACAGCTTAGCGCCTTCTA-3'.

8. *S. meliloti* khg gene (Genbank Accession Nos. AL591792.1 GI: 15075850, 65353-64673 and CAC47463.1, nucleic acid and amino acid sequence, respectively)

forward
                                           (SEQ ID NOS: 39 and 40)
5'-GGTATTGAGGGTCGCATGCGAGGGGCATTATTCAA-3'
and reverse
5'-AGAGGAGAGTTAGAGCCTCAGCCCTTGAGCGCGAAG-3'.

Genomic DNA from the organisms described in 1-2 and 6-8, above, was purified using the Qiagen Genomic-tip™ (Valencia, Calif.) protocol. Using similar techniques the genomic DNA from organisms described in 3-5 can be purified.

*Pseudomonas straminea* (ATCC 33636) was grown at 30° C. in Nutrient Broth and hydroxybenzoate medium. *Comamonas testosteroni* (ATCC 49249) was grown at 26° C. in Nutrient Broth and hydroxybenzoate medium. *Sphingomonas* sp. LB 126 (Flemish Institute for Technological Research, VITO, B-2400 Mol, Belgium) is grown according to the method described by Wattiau et al. (*Research in Microbiol.* 152:861-72, 2001). *Arthrobacter keyseri* (Gulf Ecology Division, National Health and Environmental Effects Research Laboratory, U.S. Environmental Protection Agency, Gulf Breeze, Fla. 32561, USA) is grown according to the protocol described by Eaton (*J. Bacteriol.* 183:3689-3703, 2001). *Sinorhizobium meliloti* 1021 (ATCC 51124) was grown at 26° C. in ATCC TY medium and hydroxybenzoate medium. *Yersinia pestis* strain CO92 (ATCC) is grown at 26° C. in ATCC medium 739 Horse blood agar. *Bacillus subtilis* 6051 (ATCC) was grown at 30° C. in Bereto Nutrient Broth (Difco; Detroit, Mich.). *E. coli* genomic DNA was isolated from strain DH10B (Invitrogen) as described in Example 1.

The PCR, cloning, and screening protocols described in Example 1 were used to clone the *C. testosteroni* and the *S. meliloti* proA sequences, as well as the *E. coli, B. subtilis*, and *S. meliloti* khg sequences. The same methods can be used to clone the other sequences described above. For the *C. testosteroni* proA gene, the annealing and extension conditions for PCR were 40-60° C. for 1 minute, 45 seconds (gradient thermocycler) and 72° C. for 2 minutes, 15 seconds.

Positive clones were sequenced using dideoxy chain termination sequencing (Seqwright, Houston, Tex.) with S-tag and T7 terminator primers (Novagen), and internal primers from Integrated DNA Technologies, Inc. (Coralville, Iowa).

Expression and Activity Assays

Plasmid DNA (verified by sequence analysis) was subcloned into expression host BL21(DE3) (Novagen). The cultures were grown in LB medium with 50 mg/L kanamycin, the plasmids isolated using a Qiagen spin plasmid miniprep kit and subsequently analyzed by restriction digest to confirm identity. Induction experiments were done with the BL21 (DE3) constructs grown in LB medium containing 50 mg/L kanamycin at 37° C. Protein expression was induced using 0.1 mM IPTG after the $OD_{600}$ reached approximately 0.6. The cells were grown for 4 hours at 30° C. and harvested by centrifugation. The cells were then lysed using Bugbuster™ reagent (Novagen) and the His-tag recombinant proteins were purified using His-Bind cartridges as described above (Example 1). Purified proteins were desalted on PD-10 disposable columns and eluted in 50 mM Tris-HCl buffer, pH 7.3 with 2 mM $MgCl_2$.

The proteins were analyzed by SDS-PAGE on 4-15% gradient gels to detect soluble protein levels at the predicted MW of the recombinant fusion protein.

The proteins were assayed for activity using indole-3-pyruvate and sodium pyruvate as substrates. The assay mixture contained 100 mM Tris-HCl (pH 7-pH 8.9), 0-8 mM $MgCl_2$, 3 mM potassium phosphate (pH 8), and 6 mM of each substrate in 1 mL. The reaction was started by adding varying amounts of polypeptide (for example from 10 to 100 μg), and was incubated at 25° C.-37° C. for 30 minutes, filtered, and then frozen at −80° C.

Activity Results with proA Gene Products

Both the C. testosteroni proA and S. meliloti SMc00502 gene constructs had high levels of expression when induced with IPTG. The recombinant proteins were highly soluble, as determined by SDS-PAGE analysis of total protein and cellular extract samples. The C. testosteroni gene product was purified to >95% purity. Because the yield of the S. meliloti gene product was very low after affinity purification using a His-Bind cartridge, cellular extract was used for the enzymatic assays.

Both recombinant aldolases catalyzed the formation of MP from indole-3-pyruvate and pyruvate. The presence of both divalent magnesium and potassium phosphate were required for enzymatic activity. No product was apparent when indole-3-pyruvate, pyruvate, or potassium phosphate was absent. A small amount of the product was also formed in the absence of enzyme (typically one order of magnitude less than when enzyme was present).

Using the LC/MS method described in Example 18, the product peak eluted from the reverse phase C18 column slightly later than the indole-3-pyruvate standard, the mass spectrum of this peak showed a collisionally-induced parent ion ([M+H]+) of 292. 1, the parent ion expected for the product MP. The major daughter fragments present in the mass spectrum included those with m/z=158 (1H-indole-3-carbaldehyde carbonium ion), 168 (3-buta-1,3-dienyl-1H-indole carbonium ion), 274 (292-$H_2O$), 256 (292-2 $H_2O$), 238 (292-3 H2O), 228 (292-CH4O3), and 204 (loss of pyruvate). The product also exhibited a UV spectrum characteristic of other indole-containing compounds such as tryptophan, with the $\lambda_{max}$ of 279-280 and a small shoulder at approximately 290 nm.

The amount of MP produced by the C. testosteroni aldolase increased with an increase in reaction temperature from room temperature to 37° C., amount of substrate, and amount of magnesium. The synthetic activity of the enzyme decreased with increasing pH, the maximum product observed was at pH 7. Based on tryptophan standards, the amount of MP produced under a standard assay using 20 μg of purified protein was approximately 10-40 μg per one mL reaction.

Due to the high degree of homology of the S. meliloti and C. testosteroni ProA aldolase coding sequences with the other genes described above, it is expected that all of the recombinant gene products can catalyze this reaction. Moreover, it is expected that aldolases that have threonine (T) at positions 59 and 87, arginine (R) at 119, aspartate (D) at 120, and histidine (H) at 31 and 71, (based on the numbering system of C. testosteroni) will have similar activity. Additional homologs have been sequenced and deposited in NCBI. Their genes could be cloned and the corresponding gene products are expected to have similar activity. Identification numbers, as well as percent identity to the C. testosteroni ProA protein and percent identity to the S. meliloti ProA protein, are provided below as examples of genes and proteins that are expected to have similar aldolase activity:

Aldolase Source: *Bradyrhizobium japonicum* str. USDA 110 (protein blr3842)
    gene: NC_004463.1:4260815.4261498
    protein: GI: 27378953 (NP_770482.1)
    percent identity to C. testosteroni ProA: 63
    percent identity to S. meliloti ProA: 63

Aldolase Source: *Sphingomonas (Pseudomonas) paucimobilis*
    gene: GI: 19918959 (AB073227.1:3738.4424)
    protein: GI: 19918963 (BAB88738.1)
    percent identity to C. testosteroni ProA: 65
    percent identity to S. meliloti ProA: 64

Aldolase Source: *Yersinia pestis* KIM
    gene: AE013606.1 GI: 21956705
    protein: AAM83650.1 GI: 21956715
    percent identity to C. testosteroni ProA: 56
    percent identity to S. meliloti ProA: 57

Aldolase Source: *Ralstonia metallidurans* CH34
    gene: NZ_AAAI02000016.1 GI: 48767334
    protein: ZP_00271743.1 GI: 48767386
    percent identity to C. testosteroni ProA: 60
    percent identity to S. meliloti ProA: 57

Aldolase Source: *Yersinia pseudotuberculosis* IP 32953
    gene: NC_006155.1 GI: 51594359
    protein: YP_068627.1 GI: 51594436
    percent identity to C. testosteroni ProA: 56
    percent identity to S. meliloti ProA: 57

Aldolase Source: *Rhizobium leguminosarum* biovar viciae rhiz23g02-plk_1009_341

(Sanger Institute)

```
gene:
ATGGGCATCGTCGTACAGAACATACCACGGGCGG (SEQ ID NO: 87)

AAGCTGATGTGATCGACAGGCTCGCCAAATCAGG

CGTCGCGACGGTCCACGAAGCCCAGGGGCGCAAA

GGCATGCTCGCCAGCCATATGAGACCAATCTATT

CAGGTGCGCAGATCGCCGGCTCCGCCATTACGAT

CTCCGCACCGCCCGGTGATAACTGGATGATCCAT

GTGGCGATCGAGCAGATCCAGGCCGGCGACATCC

TGGTGCTTTCGCCGACCTCGCCCTGTGACAACGG

TTATTTCGGCGACCTGCTTGCCACCTCGGCGCGG

GCGCGAGGTTGCCGCGGCCTTGTCATCGACGCCG

GTGTCCGCGATATCAGGGATCTGACCCAGATGCA

GTTCCCCGTGTGGTCCAAGGCCGTGTCCGCGCAG

GGGACCGTCAAGGAAACGCTCGGTTCGGTCAACG

TTCCGATCGTCTGCGCTGGCGCCTTCATCGAAGC

CGGCGACATCATCGTCGCCGACGACGACGGGGTG

TGCGTGGTGAAGCTCAACGCGGCCGAGGAGGTTC

TGACTGCTGCCGAGAACCGTGTGGCGAACGAGGA

GGCCAAGCGGCAACGCCTCGCCGCCGGCGAACTC

GGGCTCGATATCTATGACATGCGGTCGAAGCTCC
```

-continued

```
GGGAAAAGGGGCTTAAATATGTATGA
``` protein:
MGIVVQNIPRAEADVIDRLAKSGVATVHEAQGRK (SEQ ID NO: 88)

GMLASHMRPIYSGAQIAGSAITISAPPGDNWMIH

VAIEQIQAGDILVLSPTSPCDNGYFGDLLATSAR

ARGCRGLVIDAGVRDIRDLTQMQFPVWSKAVSAQ

GTVKETLGSVNVPIVCAGAFIEAGDIIVADDDGV

CVVKLNAAEEVLTAAENRVANEEAKRQRLAAGEL

GLDIYDMRSKLREKGLKYVW percent identity to *C. testosteroni* ProA: 58
 percent identity to *S. meliloti* ProA: 61

Aldolase Source: *Novosphingobium aromaticivorans* DSM 12444 (*Sphingomonas aromaticivorans* F199 Contains Same Gene)
 gene: NZ_AAAV02000003.1 GI: 48848843
 protein: ZP_00303270.1 GI: 48849026
 percent identity to *C. testosteroni* ProA: 68
 percent identity to *S. meliloti* ProA: 63

Aldolase Source: *Pseudomonas putida* KT2440
 gene: AE016783.1 GI: 26557027
 protein: AAN68126.1 GI: 24984081
 percent identity to *C. testosteroni* ProA: 57
 percent identity to *S. meliloti* ProA: 60

Aldolase Source: *Magnetospirillum magnetotacticum* MS-1
 gene: NZ_AAAP01003877.1 GI: 23016465
 protein: ZP_00056301.2 GI: 46200890
 percent identity to *C. testosteroni* ProA: 73
 percent identity to *S. meliloti* ProA: 59

Aldolase Source: *Rhodopseudomonas palustris* CGA009
 gene: NC_005296.1 GI: 39933080
 protein: NP_950032.1 GI: 39937756
 percent identity to *C. testosteroni* ProA: 74
 percent identity to *S. meliloti* ProA: 58

Aldolase Source: *Xanthomonas campestris* ATCC-33913
 gene: AE012524.1 GI: 21115292
 protein: AAM43251.1 GI: 21115297
 percent identity to *C. testosteroni* ProA: 63
 percent identity to *S. meliloti* ProA: 64

Aldolase Source: *Xanthomonas axonopodis* citri 306
 gene: AE012066.1 GI: 21110580
 protein: AAM38990.1 GI: 21110581
 percent identity to *C. testosteroni* ProA: 61
 percent identity to *S. meliloti* ProA: 62

Aldolase Source: *Streptomyces avermitilis* MA-4680
 gene: NC_003155.3 GI: 57833846
 protein: NP_822793.1 GI: 29828159
 percent identity to *C. testosteroni* ProA: 49
 percent identity to *S. meliloti* ProA: 56

Activity Results with khg Gene Products

Both the *B. subtilis* and *E. coli* khg gene constructs had high levels of expression of protein when induced with IPTG, while the *S. meliloti* khg had a lower level of expression. The recombinant proteins were highly soluble, as judged by SDS-PAGE analysis of total proteins and cellular extracts. The *B. subtilis* and *E. coli* khg gene products were purified to >95% purity; the yield of the *S. meliloti* gene product was not as high after affinity purification using a His-Bind cartridge.

There is no evidence that magnesium and phosphate are required for activity for this enzyme. However, the literature reports performing the assays in sodium phosphate buffer, and the enzyme reportedly is bifunctional and has activity on phosphorylated substrates such as 2-keto-3-deoxy-6-phosphogluconate (KDPG). The enzymatic assays were performed as described above, and in some instances the phosphate was omitted. The results indicate that the recombinant KHG aldolases produced MP, but were not as active as the ProA aldolases. In some cases the level of MP produced by KHG was almost identical to the amount produced by magnesium and phosphate alone. Phosphate did not appear to increase the KHG activities. The *Bacillus* enzyme had the highest activity, approximately 20-25% higher activity than the magnesium and phosphate alone, as determined by LC/MS/MS (see Example 18). The *Sinorhizobium* enzyme had the least amount of activity, which can be associated with folding and solubility problems noted in the expression. All three enzymes have the active site glutamate (position 43 in *B. subtilis* numbering system) as well as the lysine required for Shiff base formation with pyruvate (position 130); however, the *B. subtilis* enzyme contains a threonine in position 47, an active site residue, rather than arginine. The *B. subtilis* KHG is smaller and appears to be in a cluster distinct from the *S. meliloti* and *E. coli* enzymes, with other enzymes having the active site threonine. The differences in the active site may be the reason for the increased activity of the *B. subtilis* enzyme.

Improvement of Aldolase Activity

Catalytic antibodies can be as efficient as natural aldolases, accept a broad range of substrates, and can be used to catalyze the reaction shown in FIG. 2.

Aldolases can also be improved by directed evolution, for example as previously described for a KDPG aldolase (highly homologous to KHG described above) evolved by DNA shuffling and error-prone PCR to remove the requirement for phosphate and to invert the enantioselectivity. The KDPG aldolase polypeptides are useful in biochemical reactions since they are highly specific for the donor substrate (herein, pyruvate), but are relatively flexible with respect to the acceptor substrate (i.e. indole-3-pyruvate) (Koeller & Wong, Nature 409:232-9, 2001). KHG aldolase has activity for condensation of pyruvate with a number of carboxylic acids and aldehydes. Mammalian versions of the KHG aldolase are thought to have broader enantiospecificity than many bacterial versions, including higher activity on 4-hydroxy 4-methyl 2-oxoglutarate and acceptance of both stereoisomers of 4-hydroxy-2-ketoglutarate. Most bacterial sources appear to have a 10-fold preference for a particular configuration of the fusion product. An exception is the enzyme from the bacterium *Zymomonas mobilis* which shows less substrate selectivity (accepting a broad range of substrates) as well as relaxed substrate sterochemical requirements, similar to the enzymes isolated from mammalian sources such as rat liver (ref: Shelton et al (1996) J Am Chem Soc, 118(9):2117-2125. There are nearly 100 KHG homologs available in genomic databases, and activity has been demonstrated in *Pseudomonas, Paracoccus, Providencia, Sinorhizobium, Morganella, E. coli*, and mammalian tissues. These enzymes can be used as a starting point for tailoring the enantiospecificity that is desired for monatin production.

Aldolases that utilize pyruvate and another substrate that is either a keto acid and/or has a bulky hydrophobic group like indole can be "evolved" to tailor the polypeptide's specificity, speed, and selectivity. In addition to KHG and ProA aldolases demonstrated herein, examples of these enzymes include, but are not limited to: KDPG aldolase and related polypeptides (KDPH); transcarboxybenzalpyruvate hydratase-aldolase from *Nocardioides* st; 4-(2-carboxyphenyl)-2-oxobut-3-enoate aldolase (2'-carboxybenzalpyruvate aldolase) which condenses pyruvate and 2-carboxybenzaldehyde (an aromatic ring-containing substrate); trans-O-hydroxybenzylidenepyruvate hydratase-aldolase from *Pseudomonas putida* and *Sphingomonas aromaticivorans*, which also utilizes pyruvate and an aromatic-containing aldehyde as substrates; 3-hydroxyaspartate aldolase(erythro-3-hydroxy-L-aspartate glyoxylate lyase), which uses 2-oxo acids as the substrates and is thought to be in the organism *Micrococcus denitrificans*; benzoin aldolase(benzaldehyde lyase), which utilizes substrates containing benzyl groups; dihydroneopterin aldolase; L-threo-3-phenylserine benzaldehyde-lyase (phenylserine aldolase) which condenses glycine with benzaldehyde; 4-hydroxy-2-oxovalerate aldolase; 1,2-dihydroxybenzylpyruvate aldolase; and 2-hydroxybenzalpyruvate aldolase.

Using assays similar to those described above, and the detection methods described in Example 18, isocitrate lyase, N-acetyl neuraminic acid synthase, citrate lyase, tryptophanase and certain mutants, beta-tyrosinase and certain mutants, PLP, catalytic aldolase antibodies, tryptophan synthase(s) did not appear to detectably convert indole-3-pyruvate to MP under the conditions tested.

A polypeptide having the desired activity can be selected by screening clones of interest using the following methods. Tryptophan auxotrophs are transformed with vectors carrying the clones of interest on an expression cassette and are grown on a medium containing small amounts of monatin or MP. Since aminotransferases and aldolase reactions are reversible, the cells are able to produce tryptophan from a racemic mixture of monatin. Similarly, organisms (both recombinant and wildtype) can be screened by ability to utilize MP or monatin as a carbon and energy source. One source of target aldolases is expression libraries of various *Pseudomonas* and rhizobacterial strains. Pseudomonads have many unusual catabolic pathways for degradation of aromatic molecules and they also contain many aldolases; whereas the rhizobacteria contain aldolases, are known to grow in the plant rhizosphere, and have many of the genes described for construction of a biosynthetic pathway for monatin.

Example 8

Chemical Synthesis of the Monatin Precursor

Example 7 described a method of using an aldolase to convert indole-3-pyruvate to the 2-hydroxy 2-(indol-3-ylmethyl)-4-keto glutaric acid monatin precursor (MP). This example describes an alternative method of chemically synthesizing MP.

MP can be formed using a typical aldol-type condensation (FIG. 4). Briefly, a typical aldol-type reaction involves the generation of a carbanion of the pyruvate ester using a strong base, such as LDA (lithium diisopropylamide), lithium hexamethyldisilazane or butyl lithium. The carbanion that is generated reacts with the indole-pyruvate to form the coupled product.

Protecting groups that can be used for protecting the indole nitrogen include, but are not limited to: t-butyloxycarbonyl (Boc), and benzyloxycarbonyl (Cbz). Blocking groups for carboxylic acids include, but are not limited to, alkyl esters (for example, methyl, ethyl, benzyl esters). When such protecting groups are used, it is not possible to control the stereochemistry of the product that is formed. However, if R2 and/or R3 are chiral protecting groups (FIG. 4), such as (S)-2-butanol, menthol, or a chiral amine, this can favor the formation of one MP enantiomer over the other.

Example 9

Conversion of Tryptophan or Indole-3-Pyruvate to Monatin

An in vitro process utilizing two enzymes, an aminotransferase and an aldolase, produced monatin from tryptophan and pyruvate. In the first step alpha-ketoglutarate was the acceptor of the amino group from tryptophan in a transamination reaction generating indole-3-pyruvate and glutamate. An aldolase catalyzed the second reaction in which pyruvate was reacted with indole-3-pyruvate, in the presence of $Mg^{2+}$ and phosphate, generating the alpha-keto derivative of monatin (MP), 2-hydroxy-2-(indol-3-ylmethyl)-4-ketoglutaric acid. Transfer of the amino group from the glutamate formed in the first reaction produced the desired product, monatin. Purification and characterization of the product established that the isomer formed was S,S-monatin. Alternative substrates, enzymes, and conditions are described as well as improvements that were made to this process.

Enzymes

The aldolase, 4-hydroxy-4-methyl-2-oxoglutarate pyruvate lyase (ProA aldolase, proA gene) (EC 4.1.3.17) from *Comamonas testosteroni* was cloned, expressed and purified as described in Example 7. The 4-hydroxy-2-oxoglutarate glyoxylate lyases (KHG aldolases) (EC 4.1.3.16) from *B. subtilis, E. coli*, and *S. meliloti* were cloned, expressed and purified as described in Example 7.

The aminotransferases used in conjunction with the aldolases to produce monatin were L-aspartate aminotransferase encoded by the *E. coli* aspC gene, the tyrosine aminotransferase encoded by the *E. coli* tyrB gene, the *S. meliloti* TatA enzyme, the broad substrate aminotransferase encoded by the *L. major* bsat gene, or the glutamic-oxaloacetic transaminase from pig heart (Type IIa). The cloning, expression and purification of the non-mammalian proteins are described in Example 1. Glutamic-oxaloacetic transaminase from pig heart (type IIa) was obtained from Sigma (# G7005).

Method Using ProA aldolase and L-aspartate aminotransferase

The reaction mixture contained 50 mM ammonium acetate, pH 8.0, 4 mM $MgCl_2$, 3 mM potassium phosphate, 0.05 mM pyridoxal phosphate, 100 mM ammonium pyruvate, 50 mM tryptophan, 10 mM alpha-ketoglutarate, 160 mg of recombinant *C. testosteroni* ProA aldolase (unpurified cell extract, ~30% aldolase), 233 mg of recombinant *E. coli* L-aspartate aminotransferase (unpurified cell extract, ~40% aminotransferase) in one liter. All components except the enzymes were mixed together and incubated at 30° C. until the tryptophan dissolved. The enzymes were then added and the reaction solution was incubated at 30° C. with gentle shaking (100 rpm) for 3.5 hours. At 0.5 and 1 hour after the addition of the enzymes aliquots of solid tryptophan (50 mmoles each) were added to the reaction. All of the added tryptophan did not dissolve, but the concentration was maintained at 50 mM or higher. After 3.5 hours, the solid tryptophan was filtered off. Analysis of the reaction mixture by LC/MS using a defined amount of tryptophan as a standard showed that the concentration of tryptophan in the solution was 60.5 mM and the concentration of monatin was 5.81 mM (1.05 g).

The following methods were used to purify the final product. Ninety percent of the clear solution was applied to a column of BioRad AG50W-X8 resin (225 mL; binding capacity of 1.7 meq/mL). The column was washed with water, collecting 300 mL fractions, until the absorbance at 280 nm was <5% of the first flow through fraction. The column was then eluted with 1 M ammonium acetate, pH 8.4, collecting 4 300-mL fractions. All 4 fractions contained monatin and were evaporated to 105 mL using a roto-evaporator with a tepid water bath. A precipitate formed as the volume reduced and was filtered off over the course of the evaporation process.

Analysis of the column fractions by LC/MS showed that 99% of the tryptophan and monatin bound to the column. The precipitate that formed during the evaporation process contained >97% tryptophan and <2% of monatin. The ratio of tryptophan to product in the supernatant was approximately 2:1.

The supernatant (7 ml) was applied to a 100 mL Fast Flow DEAE Sepharose (Amersham Biosciences) column previously converted to the acetate form by washing with 0.5 L 1 M NaOH, 0.2 L water, 1.0 L of 1.0 M ammonium acetate, pH 8.4, and 0.5 L water. The supernatant was loaded at <2 mL/min and the column was washed with water at 3-4 mL/min until the absorbance at 280 nm was ~0. Monatin was eluted with 100 mM ammonium acetate, pH 8.4, collecting 4 100-mL fractions.

Analysis of the fractions showed that the ratio of tryptophan to monatin in the flow through fractions was 85:15 and the ratio in the eluent fractions was 7:93. Assuming the extinction coefficient at 280 nm of monatin is the same as tryptophan, the eluent fractions contained 0.146 mmole of product. Extrapolation to the total 1 L reaction would produce ~2.4 mmoles (~710 mg) of monatin, for a recovery of 68%.

The eluent fractions from the DEAE Sepharose column were evaporated to <20 mL. An aliquot of the product was further purified by application to a $C_8$ preparative reversed-phase column using the same chromatographic conditions as those described in Example 18 for the analytical-scale monatin characterization. Waters Fractionlynx™ software was employed to trigger automated fraction collection of monatin based on detection of the m/z=293 ion. The fraction from the $C_8$ column with the corresponding protonated molecular ion for monatin was collected, evaporated to dryness, and then dissolved in a small volume of water. This fraction was used for characterization of the product.

The resulting product was characterized using the following methods.

UV/Visible Spectroscopy. UV/visible spectroscopic measurements of monatin produced enzymatically were carried out using a Cary 100 Bio UV/visible spectrophotometer. The purified product, dissolved in water, showed an absorption maximum of 280 nm with a shoulder at 288 nm, characteristics typical of indole containing compounds.

LC/MS Analysis. Analyses of mixtures for monatin derived from the in vitro biochemical reactions were carried out as described in Example 18. A typical LC/MS analysis of monatin in an in vitro enzymatic synthetic mixture is illustrated in FIG. 5. The lower panel of FIG. 5 illustrates a selected ion chromatogram for the protonated molecular ion of monatin at m/z=293. This identification of monatin in the mixture was corroborated by the mass spectrum illustrated in FIG. 6. Analysis of the purified product by LC/MS showed a single peak with a molecular ion of 293 and absorbance at 280 nm. The mass spectrum was identical to that shown in FIG. 6.

MS/MS Analysis. LC/MS/MS daughter ion experiments, as described in Example 18, were also performed on monatin. A daughter ion mass spectrum of monatin is illustrated in FIG. 7. Tentative structural assignments of all fragment ions labeled in FIG. 7 were made. These include fragment ions of m/z=275 (293-$H_2O$), 257 (293-(2×$H_2O$)), 230 (275-COOH), 212 (257-COOH), 168 (3-buta-1,3-dienyl-1-indole carbonium ion), 158 (1H-indole-3-carbaldehyde carbonium ion), 144 (3-ethyl-1H-indole carbonium ion), 130 (3-methylene-1H-indole carbonium ion), and 118 (indole carbonium ion). Many of these are the same as those obtained for MP (Example 7), as expected if derived from the indole portion of the molecule. Some are 1 mass unit higher than those seen for MP, due to the presence of an amino group instead of a ketone.

Accurate Mass Measurement of Monatin. FIG. 8 illustrates the mass spectrum obtained for purified monatin employing an Applied Biosystems-Perkin Elmer Q-Star hybrid quadrupole/time-of-flight mass spectrometer. The measured mass for protonated monatin using tryptophan as an internal mass calibration standard was 293.1144. The calculated mass of protonated monatin, based on the elemental composition $C_{14}H_{17}N_2O_5$ is 293.1137. This is a mass measurement error of less than 2 parts per million (ppm), providing conclusive evidence of the elemental composition of monatin produced enzymatically.

NMR Spectroscopy. The NMR experiments were performed on a Varian Inova 500 MHz instrument. The sample of monatin (~3 mg) was dissolved in 0.5 ml of $D_2O$. Initially, the solvent ($D_2O$) was used as the internal reference at 4.78 ppm. Since the peak for water was large, the $^1$H-NMR was run with suppression of the peak for water. Subsequently, due to the broadness of the water peak, the C-2 proton of monatin was used as the reference peak, and set at the published value of 7.192 ppm.

For $^{13}$C-NMR, an initial run of several hundred scans indicated that the sample was too dilute to obtain an adequate $^{13}$C spectrum in the allotted time. Therefore, a heteronuclear multiple quantum coherence (HMQC) experiment was performed, which enabled the correlation of the hydrogens and the carbons to which they were attached, and also providing information on the chemical shifts of the carbons.

A summary of the $^1$H and HMQC data is shown in Tables 4 and 5. By comparison to published values, the NMR data indicated that the enzymatically produced monatin was either (S,S), (R,R), or a mixture of both.

Chiral LC/MS Analysis. To establish that the monatin produced in vitro was one isomer, and not a mixture of the (R,R) and (S,S) enantiomers, chiral LC/MS analyses were carried out using the instrumentation described in Example 18.

Chiral LC separations were made using an Chirobiotic T (Advanced Separations Technology) chiral chromatography column at room temperature. Separation and detection, based on published protocols from the vendor, were optimized for the R-(D) and S-(L) isomers of tryptophan. The LC mobile phase consisted of A) water containing 0.05% (v/v) trifluoroacetic acid; B) Methanol containing 0.05% (v/v) trifluoroacetic acid. The elution was isocratic at 70% A and 30% B. The flow rate was 1.0 mL/min, and PDA absorbance was monitored from 200 nm to 400 nm. The instrumental parameters used for chiral LC/MS analysis of tryptophan and monatin are identical to those described in Example 18 for LC/MS analysis. Collection of mass spectra for the region m/z 150-400 was utilized. Selected ion chromatograms for protonated molecular ions ([M+H]$^+$=205 for both R- and S-tryptophan and [M+H]$^+$=293 for monatin) allowed direct identification of these analytes in the mixtures.

The chromatograms of R- and S-tryptophan and monatin, separated by chiral chromatography and monitored by MS, are shown in FIG. 9. The single peak in the chromatogram of monatin indicates that the compound is one isomer, with a retention time almost identical to S-tryptophan.

TABLE 4

1H NMR data

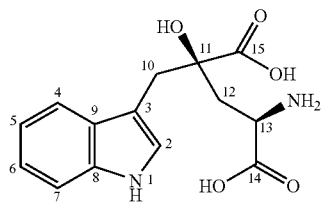

| Atom | Cargill $\delta_H$ | J(HH) Hz | Vleggaar et al.[1] $\delta_H$ | J(HH) Hz | Takeshi et al.[2] $\delta_H$ | J(HH) Hz |
|---|---|---|---|---|---|---|
| 2 | 7.192 (1H, s) | | 7.192 (s) | | 7.18 (s) | |
| 4 | 7.671 (d) | 7.99 | 7.686 (d) | 7.9 | 7.67 (d) | 8.0 |
| 5 | 7.104 (dd) | 7.99 | 7.102 (dd) | 8.0, 8.0 | 7.11 (dd) | 7.5, 7.5 |
| 6 | 7.178 (dd) | * | 7.176 (dd) | 8.0, 8.0 | 7.17 (dd) | 7.5, 7.5 |
| 7 | 7.439 (d) | 7.99 | 7.439 (d) | 8.1 | 7.43 (d) | 8.0 |
| 10a | 3.242 (d) | 14.5 | 3.243 (d) | 14.3 | 3.24 (d) | 14.5 |
| 10b | 3.033 (d) | 14.5 | 3.051 (d) | 14.3 | 3.05 (d) | 14.5 |
| 12 | 2.626 (dd) | 15.5, 1.5 | 2.651 (dd) | 15.3, 1.7 | 2.62 (dd) | 15.5, 1.8 |
|  | 2.015 (dd) | 15.0, 12.0 | 2.006 (dd) | 15.3, 11.7 | 2.01 (dd) | 15.5, 12.0 |
| 13 | 3.571 (dd) | 10.75*, 1.5 | 3.168 (dd) | 11.6, 1.8 | 3.57 (dd) | 12.0, 1.8 |

[1]Vleggaar et al. (J.C.S. Perkin Trans. 1:3095-8, 1992).
[2]Takeshi and Shusuke (JP2002060382, 2002-02-26).

TABLE 5

13C NMR data from HMQC spectrum

| Atom | Cargill $\delta_C$ | Vleggaar et al.[1] $\delta_C$ |
|---|---|---|
| 2 | 126.1 | 126.03 |
| 3 | * | 110.31 |
| 4 | 120.4 | 120.46 |
| 5 | 120.2 | 120.25 |
| 6 | 122.8 | 122.74 |
| 7 | 112.8 | 112.79 |
| 8 | * | 137.06 |
| 9 | * | 129.23 |
| 10a | 36.4 | 36.53 |
| 12 | 39.5 | 39.31 |
| 13 | 54.9 | 54.89 |
| 14 | * | 175.30 |
| 15 | * | 181.18 |

[1]Vleggaar et al. (J. C. S. Perkin Trans. 1: 3095-8, 1992).

Polarimetry. The optical rotation was measured on a Rudolph Autopol III polarimeter. The monatin was prepared as a 14.6 mg/mL solution in water. The expected specific rotation ($[\alpha]_D^{20}$) for S,S monatin (salt form) is −49.6 for a 1 g/mL solution in water (Vleggaar et al). The observed $[\alpha]_D^{20}$ was −28.1 for the purified, enzymatically produced monatin indicating that it was the S,S isomer.

Improvements

The reaction conditions, including reagent and enzyme concentrations, were optimized and yields of 5-10 mg/mL were produced using the following reagent mix: 50 mM ammonium acetate pH 8.3, 2 mM MgCl$_2$, 200 mM pyruvate (sodium or ammonium salt), 5 mM alpha-ketoglutarate (sodium salt), 0.05 mM pyridoxal phosphate, deaerated water to achieve a final volume of 1 mL after the addition of the enzymes, 3 mM potassium phosphate, 50 μg/mL of recombinant ProA aldolase (cell extract; total protein concentration of 167 μg/mL), 1000 μg/mL of L-aspartate aminotransferase encoded by the E. coli aspC gene (cell extract; total protein concentration of 2500 μg/mL), and solid tryptophan to afford a concentration of >60 mM (saturated; some undissolved throughout the reaction). The mixture was incubated at 30° C. for 4 hours with gentle stirring or mixing.

Substitutions

The concentration of alpha-ketoglutarate can be reduced to 1 mM and supplemented with 9 mM aspartate with an equivalent yield of monatin. Alternative amino acid acceptors can be utilized in the first step, such as oxaloacetate.

When recombinant L. major broad substrate aminotransferase was used in place of the E. coli L-aspartate aminotransferase, similar yields of monatin were achieved. However, a second unidentified product (3-10% of the major product) with a molecular mass of 292 was also detected by LC-MS analysis. Monatin concentrations of 0.1-0.5 mg/mL were produced when the E. coli tyrB encoded enzyme, the S. meliloti tatA encoded enzyme or the glutamic-oxaloacetic transaminase from pig heart (type IIa) was added as the aminotransferase. When starting the reaction from indole-3-pyruvate, a reductive amination can be done for the last step with glutamate dehydrogenase and NADH (as in Example 15).

The KHG aldolases from B. subtilis, E. coli, and S. meliloti were also used with the E. coli L-aspartate aminotransferase to produce monatin enzymatically. The following reaction conditions were used: 50 mM NH$_4$—OAc pH 8.3, 2 mM MgCl$_2$, 200 mM pyruvate, 5 mM glutamate, 0.05 mM pyridoxal phosphate, deaerated water to achieve a final volume of 0.5 mL after the addition of the enzymes, 3 mM potassium phosphate, 20 μg/mL of recombinant B. subtilis KHG aldolase (purified), ca. 400 μg/mL of E. coli L-aspartate aminotransferase (AspC) unpurified from cell extract, and 12 mM indole-3-pyruvate. The reactions were incubated at 30° C. for 30 minutes with shaking. The amount of monatin produced using the *B. subtilis* enzyme was 80 ng/mL, and increased with increasing amounts of aldolase. If indole-3-pyruvate and glutamate were replaced by saturating amounts of tryptophan and 5 mM alpha-ketoglutarate, the production of monatin was increased to 360 ng/mL. Reactions were repeated with 30 μg/mL of each of the three KHG enzymes in 50 mM Tris pH 8.3, with saturating amounts of tryptophan, and were allowed to proceed for an hour in order to increase detection. The *Bacillus* enzyme had the highest activity as in Example 7, producing approximately 4000 ng/mL monatin. The *E. coli* KHG produced 3000 ng/mL monatin, and the *S. meliloti* enzyme produced 2300 ng/mL.

Example 10

Conversion of Tryptophan to Monatin Using ProA Aldolase and AspC, TyrB, or HEXAspC Aminotransferases With and Without Amino Terminal HIS$_6$ tags (SEQ ID NO: 91)

The in vitro process utilizing two enzymes to produce monatin from tryptophan, described in Example 9, was further examined using three aminotransferases constructed with and without amino terminal HIS$_6$ tags(SEQ ID NO: 91).

Enzymes

The proA aldolase gene from *Comamonas testosteroni* was cloned and expressed as described in Example 7. The gene product of this gene construct carries the amino terminal HIS$_6$ tag(SEQ ID NO: 91)of the pET30 system.

The aspC and tyrB aminotransferase genes constructed with the pET30 amino terminal HIS$_6$ tag (SEQ ID NO: 91)system were cloned and expressed as described in Example 1. The HEX gene constructed with the pET30 amino terminal HIS$_6$ tag (SEQ ID NO: 91)system was cloned and expressed as described in Example 2. Untagged versions of the three aminotransferase genes were cloned and expressed as described in Example 3.

Gene Expression and Assay of Monatin Production

Using Cell Extracts Containing Aminotransferase Protein

Cell extracts containing the proA, aspC, tyrB, and HEX gene products were prepared from cultures grown in LB medium with 50 mg/L kanamycin. The proteins were induced by the addition of 0.2 mM IPTG after the OD$_{600}$ reached approximately 0.5. The cells were grown for 4 hours at 30° C. after induction and harvested by centrifugation. The washed cells were lysed using Bugbuster™ reagent (Novagen) containing 1 μL/mL benzonase nuclease, 5 μL/mL Calbiochem protease inhibitor cocktail set III and 0.33 μL/10 mL r-Lysozyme following the Novagen recommended protocol. After incubation at 25° C. for 15 min with gentle shaking, the cell debris was pelleted by centrifugation at 21,000×g for 20 min at 4° C. and the supernatant was carefully removed (cell extract).

The protein concentration was estimated using the Pierce BCA Protein Assay Kit in a 96-well plate format. The total assay volume per well was 200 μL. Two hundred μL of working reagent was added to 10 μL protein solution in each well. Bovine serum albumin (Pierce catalog #23209) was utilized for the standard curve determination (0 to 1.0 mg/mL). The absorbance of the assay samples and standards were measured at 562 nm.

The formation of monatin from tryptophan was examined using unpurified enzymes. The level of expression for the two proteins was high in the following example(30 to 40% of the total soluble protein). However, other cell extracts could also be used in which the level of expression is lower, for example from 5 to 30% of the total soluble protein, or higher, for example greater than 40% of the total soluble protein. The reaction mixture contained, in one mL, 100 mM sodium acetate, pH 8.0, 4 mM MgCl$_2$, 3 mM potassium phosphate, 0.05 mM pyridoxal phosphate, 200 mM sodium pyruvate, 50 mM tryptophan, 10 mM alpha-ketoglutarate, 112 μg of recombinant *C. testosteroni* ProA aldolase (unpurified cell extract containing ~30% aldolase (calculated as percent of the total soluble protein)) and either 1000 μg or 10 μg of recombinant aminotransferase(unpurified cell extract containing ~40% aminotransferase (calculated as percent of the total soluble protein)). The tryptophan was added as a solid. All components except the enzymes were mixed together and incubated at 30° C. until the tryptophan dissolved. The enzymes were then added and the reaction solution was incubated at 30° C. with gentle shaking for 1 h. The reaction mixtures were analyzed for monatin formation by LC/M S/MS MRM as described in Example 18. Table 6 lists the activity of the enzymes as the concentration of product formed in the 1 h incubation. These results show that there is no significant difference between the amount of monatin formed from tryptophan when the AspC or HEXAspC aminotransferases are fused with the pET30 amino terminal HIS$_6$ tag (SEQ ID NO: 91) or when they have been expressed as the native proteins. In contrast, the tagged TyrB protein produces less product as compared to the untagged TyrB protein. The untagged TyrB produces approximately 25-75% the level of product observed in the AspC or HEXAspC aminotransferase reaction mixtures, depending on the total amount of aminotransferase enzyme added.

TABLE 6

| (6xHis tags disclosed as SEQ ID NO: 91) | | |
|---|---|---|
| Aminotransferase gene | [Aminotransferase]; μg/mL | [Monatin]; g/L |
| aspC | 300 | 1.085 |
| aspC | 30 | 0.186 |
| tyrB | 300 | 0.751 |
| tyrB | 30 | 0.087 |
| HEX | 300 | 1.514 |
| HEX | 30 | 0.411 |
| HIS$_6$-aspC | 300 | 1.101 |
| HIS$_6$-aspC | 30 | 0.213 |
| HIS$_6$-tyrB | 300 | 0.002 |
| HIS$_6$-tyrB | 30 | 0.001 |
| HIS$_6$-HEX | 300 | 1.581 |
| HIS$_6$-HEX | 30 | 0.487 |
| — | — | ND* |

*below level of detection

When non-optimal media, inducer concentrations, or induction times were utilized the level of expression of AspC or ProA decreased (e.g. to approximately 10-20% of the total soluble protein). In these cases additional amounts of cell extracts were used with equivalent results.

Using Purified Aminotransferase Proteins

The aminotransferases were purified from cell extracts of the tagged pET30 constructs (prepared as described above) using immobilized metal affinity chromatography with His-Bind cartridges following manufacturer's protocols (Novagen, Madison, Wis.). The HIS$_6$-Tag (SEQ ID NO: 91)sequence of the fusion proteins binds to the divalent Ni$^{2+}$ cations immobilized on IDA-based His-Bind resin. The eluent fractions were desalted on PD-10 (Amersham Biosciences, Piscataway, N.J.) columns and eluted in 50 mM Tris-HCl, pH 7.0. The purified proteins were analyzed by SDS-PAGE for purity and the amount of protein in the fractions was determined using the Pierce BCA assay with bovine serum albumin as the standard.

The formation of monatin from tryptophan was examined using purified AspC, HEXAspC, or TyrB aminotransferase and unpurified ProA aldolase. The reaction mixture contained, in 0.5 mL, 50 mM Tris-HCl, pH 8.0, 4 mM MgCl$_2$, 3 mM potassium phosphate, 0.05 mM pyridoxal phosphate, 200 mM sodium pyruvate, ~50 mM tryptophan, 5 mM alpha-ketoglutarate, 165 µg of recombinant C. testosteroni ProA aldolase (unpurified cell extract containing ~30% aldolase (calculated as percent of total soluble protein)) and either 64 µg or 10 µg of purified recombinant E. coli aminotransferase. The tryptophan was added as a solid. All components except the enzymes were mixed together and incubated at 30° C. until the tryptophan dissolved. The enzymes were then added and the reaction solution was incubated at 30° C. with gentle shaking for 2 h. The reaction mixtures were diluted 10-fold and analyzed for monatin formation by LC-MS/MS MRM as described in Example 18. Table 7 lists the activity of the enzymes as the concentration of product formed in the 2 h incubation.

TABLE 7

(6xHis tags disclosed as SEQ ID NO: 91)

| Aminotransferase gene | [Aminotransferase]; µg/ml | [Monatin]; g/L |
|---|---|---|
| HIS$_6$-aspC | 64 | 0.380 |
| HIS$_6$-aspC | 10 | 0.0015 |
| HIS$_6$-tyrB | 10 | 0.0019 |
| HIS$_6$-HEX | 64 | 0.457 |
| HIS$_6$-HEX | 10 | 0.0879 |
| — | — | 0.0032 |

The results of Table 7 show that with limiting quantities of purified aminotransferases and a large excess of the aldolase (unpurified) the HEXAspC aminotransferase reaction produces several-fold more monatin than the AspC aminotransferase reaction (barely measurable vs 0.0879 g/L). With larger aminotransferase concentrations the increase is about 20%. Similar, though, less striking differences were observed with the unpurified enzymes (see Table 6).

The proA aldolase gene from Comamonas testosteroni and the HEX aspartate aminotransferase gene without the HIS$_6$ tag (SEQ ID NO: 91)system were also cloned into a pET23a (Novagen) derivative at the NdeI and XhoI sites of the multiple cloning sequence. Cell extracts of these constructs were prepared from cultures induced with either IPTG or lactose and were used as the source of enzymes for the enzymatic production of monatin. The reactions were carried out in 50 mL using one of three sulfonate buffers (MOPS, 3-(N-morpholio)propanesulfonic acid; HEPES, 4-(2-hydroxyethyl) poperazine-1-sulfonic acid; TAPS, 2-hydroxy-1,1-bis(hydroxymethyl)ethyl)amino)-1-propanesulfonic acid) at a pH range of 7.5 to 8.9. The reactions contained 50 mM buffer, 2 mM MgCl$_2$, 200 mM pyruvate, 5 mM glutamate, 0.05 mM pyridoxal phosphate, deaerated water to achieve a final volume of 50 mL after the addition of the enzymes, 3 mM potassium phosphate, 194 µg/mL of ProA aldolase cell extract (containing ~50 µg/mL aldolase) and either 281 µg/mL or 2810 µg/mL of HEXAspC aminotransferase cell extract (containing ~50 µg/mL or ~500 µg/mL aminotransferase). Solid tryptophan (0.5 g) was added to the reaction mixtures just before the addition of the enzymes and at time intervals after the reactions were initiated. The reactions were stirred at room temperature and aliquots were withdrawn for analysis by LC-MS as described above. Under these conditions, the pH optimum for monatin production was between 8.2 and 8.5. The enzymes continued to produce monatin for several days after the reactions were initiated and produced up to 6 g/L of product.

Example 11

This example describes methods that were used to clone and analyze the KHG aldolase from Zymomonas mobilis (ATCC 29191). This enzyme was used in combination with an aminotransferase to produce monatin from tryptophan.

Cloning

The khg gene from Z. mobilis (ATCC 29191) was cloned in a similar fashion to that described in Example 2. The genomic DNA was isolated using the method of Mekalanos J J, Duplication and amplification of toxin genes in Vibrio cholerae, Cell 35:253-263 (1983).

The following primers were designed for cloning the Z. mobilis khg gene into pET30a and pET28 vectors (Novagen, Madison, Wis.)

N term:
(SEQ ID NO: 81)
5'-GGCCGGCATATGCGTGATATCGATTCCGTAAT-3';

C term:
(SEQ ID NO: 82)
5'-GGAATTCTCGAGTTAGGCAACAGCAGCGCG-3'.

The following PCR protocol was used for gene amplification: In a 50 µL reaction, 200 ng DNA template, 1.6 µM of each primer, 0.4 mM each dNTP, 0.5 U pfuUltra HF Polymerase (Stratagene), 2.8 U Expand High Fidelity™ Polymerase (Roche Molecular Biochemicals, Indianapolis, Ind.), and 1× Expand™ buffer with MgCl$_2$ were added. The thermocycler program utilized a hot start of 94° C. for 3 minutes; followed by8 cycles of a denaturing step at 94° C. (30 sec), an annealing step at 53° C. (30 sec), and an extension step at 72° C. (1 min 30 sec); 20 cycles of a denaturing step at 94° C. (30 sec), an annealing step at 59° C. (30 sec), and an extension step at 72° C. (1 min 30 sec); and finally a finishing step at 72° C. (7 min). The amplified DNA was purified from a 1% agarose gel using a Qiagen QIAquick® Gel Extraction Kit (Valencia, Calif.). The purified DNA and purified plasmid DNAs (purified using a Qiagen QIAprep® Spin Miniprep Kit) were digested with the NdeI and XhoI according to the manufacturer's directions (NEB; Beverly, Mass.). Digestion of the pET30a vector with NdeI removes the amino terminal HIS$_6$-tag (SEQ ID NO: 91)region. The digested DNA was purified from a 1% agarose gel using a Qiagen QIAquick® Gel Extraction Kit (Valencia, CA.). The purified DNA product was quantified by measuring the absorbance at 260 nm, and ligated using a Rapid DNA Ligation Kit (Roche). Transformation of the ligation reactions into electrocompetent DH10B was performed under standard conditions using a 0.2 cm cuvette and a Bio-Rad Gene Pulser II system as described in the Bio-Rad electroporation manual. Clones containing the khg gene were identified by restriction analysis and confirmed by DNA sequencing. SEQ ID NOS 83 and 84 show nucleotide and the corresponding amino acid sequences of the khg gene and gene product.

Gene Expression and Assays

Plasmid DNA (verified by sequence analysis) was transformed into expression host BL21(DE3) according to manufacturer's protocols (Novagen). The cultures were grown in LB medium with 50 mg/L kanamycin. Induction experiments were carried out with the BL21(DE3) construct grown in LB medium containing 50 mg/L kanamycin at 37° C. Protein expression was induced using 0.2 mM IPTG after the OD$_{600}$ reached approximately 0.6. The cells were grown for 4 hours at 30° C. and harvested by centrifugation. The cells were then lysed using Bugbuster™ reagent (Novagen) containing 1 μL/mL benzonase nuclease, and 5 μL/mL Calbiochem protease inhibitor cocktail set III following the Novagen recommended protocol. The supernatant (cell free extract) was analyzed by SDS-PAGE on 4-15% gradient gels (Bio-Rad) to detect soluble protein levels of the recombinant fusion protein. The Z. mobolis aldolase was expressed efficiently in E. coli and accounted for approximately 30% of the soluble protein as judged on a SDS polyacrylamide gel.

The formation of monatin from tryptophan was examined using unpurified enzymes. The reaction mixtures contained, in one mL, 100 mM sodium acetate, pH 8.0, 4 mM MgCl$_2$, 3 mM potassium phosphate, 0.05 mM pyridoxal phosphate, 100 mM sodium pyruvate, 50 mM tryptophan, 10 mM alpha-ketoglutarate, 239 μg of recombinant HEXAspC aminotransferase (unpurified cell extract containing ~30-40% aldolase (calculated as percent of the total soluble protein)) and either recombinant Z. mobilis khg aldolase (10 or 100 μg of unpurified cell extract containing ~30% aldolase (calculated as percent of the total soluble protein)) or ProA aldolase (11.2 or 112 μg of unpurified cell extract containing 30% aldolase (calculated as percent of the total soluble protein)). The tryptophan was added as a solid. All components except the enzymes were mixed together and incubated at 30° C. until the tryptophan dissolved. The enzymes were then added and the reaction solution was incubated at 30° C. with gentle shaking for 1 h or 22 h. The reaction mixtures were diluted 10-fold and analyzed for monatin formation by LC/MS/MS MRM as described in Example 18. Table 8 lists the activity of the enzymes as the concentration of product formed in the incubations.

TABLE 8

| Aldolase gene | μg aldolase | μg aminotransferase | Incubation time (h) | [Monatin]; μg/mL |
|---|---|---|---|---|
| Z. mobilis khg | 10 | 239 | 1 | 0.730 |
| Z. mobilis khg | 10 | 239 | 24 | 18.150 |
| Z. mobilis khg | 100 | 239 | 1 | 0.800 |
| Z. mobilis khg | 100 | 239 | 24 | 18.630 |
| Z. mobilis khg | 0 | 239 | 1 | nd |
| Z. mobilis khg | 0 | 239 | 24 | <0.2 |
| Z. mobilis khg | 0 | 0 | 1 | 0.980 |
| Z. mobilis khg | 0 | 0 | 24 | 16.990 |
| C. testosteroni proA | 11.2 | 239 | 1 | 214 |
| C. testosteroni proA | 11.2 | 239 | 24 | 1464 |
| C. testosteroni proA | 112 | 239 | 1 | 746 |
| C. testosteroni proA | 112 | 239 | 24 | 1160 |
| C. testosteroni proA | 0 | 239 | 1 | <0.2 |
| C. testosteroni proA | 0 | 239 | 24 | 1.790 |
| C. testosteroni proA | 0 | 0 | 1 | 0.990 |
| C. testosteroni proA | 0 | 0 | 24 | 17.470 |

The results listed in Table 8 show that the Z. mobilis KHG aldolase is catalyzing the formation of monatin, though at low levels compared to the reactions in which the ProA aldolase is present. As can be seen by comparison of the results in rows 2 and 4, when a higher concentration of the KHG aldolase was added to the reaction, more monatin was formed. Two peaks with the monatin MS/MS signature were observed in the LC/MS/MS chromatograms from the reactions in which the Z. mobilis KHG aldolase was present, suggesting that more than one isomer of monatin was formed by this enzyme. The results shown in Table 8 reflect the sum of these two peaks.

The 24 hour samples from the Z. mobilis assay, when analyzed using chiral techniques, showed that the majority of the sample was S,S-monatin. There was, however a small amount of R,S-monatin indicating that the Z. mobilis aldolase is capable of making the R-monatin precursor (R-MP) stereoisomer.

The Z. mobilis KHG was further characterized by comparison to the E. coli homolog described in Example 7, as well as with the ProA aldolase. The following were added per 1 mL of reaction mixture: approximately 60 μg aldolase (supplied in cellular extracts), 4 mM MgCl$_2$, 50 mM D-tryptophan, 0.5 mg BioCatalytics D-aminotransferase (AT-103), 100 mM sodium pyruvate, 100 mM potassium phosphate buffer pH 7.5 or 100 mM sodium acetate buffer pH 8, 0.05 mM PLP, 3 mM potassium phosphate (only to the acetate reactions), and 10 mM α-ketoglutarate. Experiments were run in duplicate, with negative controls in which no aldolase was added. Samples were incubated overnight (20 hours) at 30° C. with gentle shaking and filtered prior to LC/MS/MS analysis and FDAA derivitization. The actual pH of the sodium acetate samples was approximately 5, while the final pH for the phosphate buffered samples was approximately 7. None of the aldolases appeared to have significant activity at pH 5, the sample containing ProA aldolase was slightly above the negative control but probably not above experimental error. In potassium phosphate, the ProA aldolase produced 73.4 ppm monatin with a ratio of R,R:S,R of 1.7:1. The KHG aldolases produced 0.03-0.6 ppm monatin, with approximate ratios of 2:1-4:1 for R,R:S,R production.

Example 12

Production of S,S Monatin Using Another Aspartate Aminotransferase from E. coli

A putative PLP-dependent aminotransferase having homology to both aspartate and aromatic aminotransferases was cloned from E. coli MG1655 and the recombinant protein was tested for activity in producing S,S-monatin. Primers were designed based on the yfdZ gene sequence deposited in NCBI as GI: 48994873 bases 2496317-2495079, coding for protein GI: 1788722 (protein ID AAC75438.1).

```
5' primer:
TGA CCC TCT AGA TAA GAA GGA GAT      (SEQ ID NO: 85)

ATA CAT ATG GCT GAC ACT CGC CCT

GAA C

3' primer:
TTC TCA AGC TTT TAT TCC GCG TTT      (SEQ ID NO: 86)

TCG TGA ATA TGT TTG
```

Genomic DNA from MG1655 was prepared using standard techniques and 100 ng was used in a 100 μL PCR reaction which also contained 1× rTth buffer, 1 mM magnesium acetate, 0.3 mM each dNTP, 0.75 μM of each primer, 0.5 μL Pfu Polymerase (Stratagene), and 4 Units rTth Polymerase (Applied Biosystems). Eight rounds of PCR utilized a 56° C. annealing temperature followed by 22 rounds of PCR using a 60° C. annealing temperature. The extension step was done at 68° C. for two minutes and 15 seconds. The PCR product was gel purified using a Qiagen QIAquick Gel Extraction Kit (Valencia, Calif.) and eluted in 50 μL EB buffer. The purified PCR product and pTRC99a (Pharmacia Biotech) vector were digested overnight at 37° C. with Xba and HindIII in 1× NEB buffer 2 plus BSA. The digestion product was purified using a Qiagen QIAquick® PCR Purification Kit and eluted in 32 µL 0.5×EB. Ligations were performed using a Quick Ligation Kit (NEB) and a 6:1 insert:vector ratio. The ligation reaction was purified using a PCR Purification Kit and electroporated into DH10B competent cells. Two µL were plated on LB plates containing 100 µg/mL ampicillin. Colonies were screened by PCR using primers derived from the pTRC99a vector. Miniprep DNA was sequenced to confirm correct insertion into the vector.

Cells were grown in LB medium containing ampicillin to an OD of 0.4 and induced with 1 mM IPTG for 3 hours at 37° C. Cellular extracts were produced using BugBuster™ (Novagen) according to manufacturer's protocols, and protein concentration was determined using a Pierce BCA assay with 0-2 mg/mL BSA standards. Expression was verified by SDS-PAGE analysis of soluble protein and it was estimated that the putative aminotransferase (YfdZ) comprised approximately 10% of the soluble protein.

The yfdz gene product was assayed in both 100 mM sodium acetate and 50 mM potassium phosphate buffers (pH 7.5) for production of monatin and compared with the HEXAspC protein prepared as described in Example 2. Fifty µg of unpurified aminotransferase was assayed in each buffer with 20 mM L-tryptophan, 4 mM MgCl$_2$, 3 mM potassium phosphate (for acetate buffer only), 0.05 mM PLP, 10 mM α-ketoglutarate, 100 mM sodium pyruvate, and 50 µg ProA aldolase (described in Example 7) provided as a cellular extract. The pH of the acetate samples had to be adjusted from 6 to 7.5 prior to addition of enzymes. The 1 mL samples (run in duplicate) were incubated with gentle shaking at 30° C. for 1 hour. Negative controls were also done in each buffer and did not contain any aminotransferase other than what is present in the cellular extracts of the ProA aldolase. Samples were filtered and analyzed by LC/MS/MS (MRM) as described in Example 18. After subtraction of background amounts of monatin produced (between 410-469 ng/mL monatin), the HEXAspC aminotransferase was found to produce 1285 ng/mL monatin in phosphate buffer, while the YfdZ protein produced 426 ng/mL monatin. In sodium acetate buffer, the HEXAspC aminotransferase produced 815 ng/mL monatin while the putative aminotransferase produced 446 ng/mL. The results confirm that the yfdz gene product is in fact an aminotransferase that behaves similarly to the aspartate aminotransferase described in Example 1, with activity towards both tryptophan and monatin.

Example 13

Comparison of Monatin Production from indole-3-pyruvate Using a Commercially Available Transaminase Library A transaminase library was purchased from BioCatalytics (Pasadena, Calif.) and the enzymes were tested for production of monatin in coupled reactions using the ProA aldolase from *C. testosteroni*. The library consisted of: AT-101, a broad range L-aminotransferase; AT-102, a branched chain L-transaminase (i.e., a branched-chain aminotransferase (BCAT, EC 2.6.1.42)); AT-103, a broad range D-transaminase; AT-104, a branched chain L-transaminase (i.e., a branched-chain aminotransferase (BCAT, EC 2.6.1.42)); AT-105, lysine-6-aminotransferase; and AT-106, a broad range L-transaminase. In reactions with AT-103, D-glutamate was used as the amino acid donor. For reactions with AT-105, L-lysine was used as the amino donor. All other reactions utilized L-glutamate as the co-substrate. Enzymes and additional components/substrates were added directly to the reaction buffer provided in the kit, which contained 100 mM potassium phosphate buffer pH 7.5, 100 mM amino donor, and 0.1 mM PLP. To one mL of reaction buffer were added: 4 mg indole-3-pyruvate, 20 mg pyruvate, approximately 50 µg ProA provided in a cellular extract, 1 µL 2 M MgCl$_2$, and 2 mg of aminotransferase enzyme to be tested. All reactions were performed in duplicate, and a negative control reaction was done with no additional aminotransferase added. Background production of monatin is due to native *E. coli* aminotransferases present in the cellular extract of the recombinant ProA enzyme. The reactions were incubated overnight at 30° C. with gentle shaking (100 rpm). The samples were filtered and submitted for reverse phase LC/MS/MS analysis as described in Example 18. The results are presented in Table 8 below:

| Enzyme | µg/mL monatin produced |
|---|---|
| AT-101 | 173.05 |
| AT-102 | 122.05 |
| AT-103 | 369.7 |
| AT-104 | 133.05 |
| AT-105 | 15.2 |
| AT-106 | 78.35 |
| negative | 73.25 |

AT-101, AT-102, AT-103, and AT-104 aminotransferases clearly produced more monatin than the negative control. AT-105 produced less monatin than the negative control, presumably because lysine was utilized as the amino donor, which is not suitable for native *E. coli* aminotransferases in the cellular extract. Similarly, one would expect the background to be lower for the reactions with AT-103 which were provided D-glutamate. The results were further analyzed to determine ratios of S,R/R,S versus R,R/S,S monatin, on the basis of the peak areas of the two stereoisomer pools that resolve during the chromatographic separation. Of the total monatin produced, the negative control contained approximately 99.7% R,R/S,S monatin. AT-102 showed the next highest specificity (89% RR/SS peak) followed by AT-101 and AT-104 (~80%). The reactions utilizing the broad specificity D-aminotransferase, AT-103, produced 69% R,R/S,S monatin in comparison to the mixed isomers. This enzyme is homologous to the *Bacillus subtilis* DAT enzyme described in Example 1, which is known to have a broad specificity for D-amino acids and was shown in Example 1 to accept D-tryptophan as a substrate. Chiral analysis was performed using the methodology described in Example 18, which verified that the D-aminotransferase was making R,R monatin as expected. Further experimentation with S,S monatin or R,R monatin as a substrate verified that the BioCatalytics enzyme is highly selective for the D-configuration, as expected (results described in Example 15).

To decrease the amount of S,S monatin or R,S monatin produced as byproducts in coupled reactions with AT-103 (the broad range D-transaminase) and the ProA aldolase, the aldolase was purified using His-Bind cartridges, as described in Example 1. The purified enzyme should not contain wildtype aminotransferase activities that can be present in cellular extracts. The His-Bind eluent was desalted to remove imidazole using PD-10 columns (G25 Sephadex, Amersham-Pharmacia) and was eluted in 50 mM Tris-Cl, pH 7. Experiments were carried out in duplicate in a volume of 1 mL and contained 100 mM Tris-Cl buffer, pH 7.8, 50 µg ProA aldolase, 4 mg indole-3-pyruvate, 1 or 2 mg D-aminotransferase, 200 mM sodium pyruvate, 2 mM MgCl$_2$, 3 mM potassium phosphate, 0.1 mM PLP, and 14.7 mg of D-glutamate. The tubes were incubated at 30° C. with gentle shaking. Two hour time points were taken and frozen immediately at −20° C. The pH was adjusted at two hours from 5 to between 7-8 using NaOH, and the assays were incubated overnight. Samples were filtered and analyzed for monatin as described in Example 18. The two hour samples did not have detectable amounts of monatin, probably due to the low pH. The overnight samples contained approximately 190 ng/mL monatin when 1 mg of D-aminotransferase was used, and approximately 84% was R,R monatin and 16% was S,R monatin. When 2 mg of D-aminotransferase were used, 540 ng/mL monatin was produced, approximately 71% was R,R monatin.

Similar experiments were conducted using Biocatalytics Aminotransferase buffer, which contained 100 mM potassium phosphate pH 7.5, 0.1 mM PLP, and 100 mM glutamate. Solid indole-pyruvate and D-aminotransferase were added as above. ProA aldolase (50 µg), MgCl$_2$, and 50 mM pyruvate were added from stock solutions. The assays were treated as above, although no pH adjustment was required in this case. A negative control was done with just the BioCatalytics supplied enzyme and buffer, which did not produce any monatin. The experimental results are shown in Table 9.

TABLE 9

Production of Monatin from Indole-3-Pyruvate in Phosphate Buffer

| Mg D-aminotransferase | time (hrs) | Total monatin (ng/mL) | % R, R |
| --- | --- | --- | --- |
| 0 | 2 | 0 | n/a |
| 1 | 2 | 6780 | not determined |
| 2 | 2 | 13170 | 55% |
| 0 | 16 | 0 | n/a |
| 1 | 16 | 15000 | not determined |
| 2 | 16 | 28930 | 51% |

The production of monatin in phosphate buffer is clearly higher than that in Tris buffered systems.

To compare activities of the cloned B. subtilis DAT from Example 1 with the BioCatalytics enzyme additional assays were done. The B. subtilis dat gene was also subcloned to remove the His-6 tag (SEQ ID NO:91), as described for the AspC and HEXAspC aminotransferases in Example 1. Untagged and tagged enzyme were produced in BL21 (DE3), as described in Example 1. Cellular extracts were made and total protein assays were done to estimate protein concentration as described previously. Duplicate one mL reactions were done which contained: 500 µg D-aminotransferase, 50 µg ProA aldolase, 100 mM potassium phosphate pH 7.5, 3 mM MgCl$_2$, 4 mg indole-3-pyruvate, 200 mM sodium pyruvate, 7.35 mg (50 mM) D-glutamate, and 0.1 mM PLP. Samples were incubated at 30° C. for 1 hr, 2 hr, and overnight, and were filtered for LC/MS/MS analysis. The samples contained only the S,R and R,R stereoisomers of monatin, as determined by the FDAA derivitization protocol described in Example 18. The results are summarized in Table 10 below. The % RR was determined by peak areas that were separated by reverse phase chromatography, and the composition of the overnight samples was further verfied by the FDAA dervitization technique.

TABLE 10

Comparison of D-aminotransferase enzymes

| Enzyme | time (hr) | Monatin (ppb) | % RR Monatin |
| --- | --- | --- | --- |
| B. sub DAT-HIS | 1 | 512 | not determined |
| B. sub DAT untagged | 1 | 1056 | not determined |
| BioCatalytics AT-103 | 1 | 2353 | not determined |
| B. sub DAT-HIS | 2 | 894 | ~80-90% |
| B. sub DAT untagged | 2 | 1913 | ~80% |
| BioCatalytics AT-103 | 2 | 6887 | 92.5% |
| B. sub DAT-HIS | 16 | 3014 | 31 |
| B. sub DAT untagged | 16 | 5612 | 33 |
| BioCatalytics AT-103 | 16 | 16131 | 66 |

The removal of the HIS-6 tag (SEQ ID NO: 91) appears to have improved the activity of the B. subtilis D-aminotransferase; however, the BioCatalytics D-aminotransferase homolog clearly had the highest activity. It also showed more substrate specificity for the R-MP. Increased incubation times appear to reduce the enantiomeric excess of R,R monatin that is produced.

Other homologous D-amino acid aminotransferases from Bacillus species have been characterized. The enzyme from Bacillus sp. YM-1 was found to have similar substrate specificity to the B. subtilis enzyme, and therefore it is expected that this enzyme would work for production of monatin. Additionally, the B. YM-1 and B. subtilis have been shown to be more specific enzymes, and do not have as broad of substrate specificity as homologs from B. sphaericus and other species. Therefore, it is expected that all of the Bacillus homologs will be active in the enzymatic pathway to monatin. See K. Yonaha, H. Misono, T. Yamamoto, and K. Soda, JBC, 250: 6983-6989 (1975); K. Tanizawa, Y. Masu, S. Asano, H. Tanaka, and K. Soda, JBC, 264: 2445-2449 (1989). AT-103, one homologous enzyme tested (above), was shown to catalyze the production of monatin. Many genes are known that code for D-amino acid aminotransferases in Bacillus species, including B. anthracis, B. cereus, B. halodurans, B. licheniformis, B. sphaericus, B. stearothermophilus, B. subtilis, B. thuringiensis, B. YM-1/YM-2, Geobacillus sp., thermophilic sp., and Oceanobacillus sp.

Example 14

Production of Monatin Using Commercially Available Dehydrogenase Enzymes

Production of monatin from indole-3-pyruvate and pyruvate, using BioCatalytics amino acid dehydrogenase enzymes coupled with the C. testosteroni ProA aldolase, was assayed under the following conditions: 6-7 mg/ml dehydrogenase enzyme, 5 mg NADH or NADPH, 50 µg aldolase (unpurified, see Example 7), 3 mM potassium phosphate buffer, 2 mM MgCl$_2$, 4 mg indole-3-pyruvate, and 20 mg pyruvate were added to one mL of AADH reaction buffer (100 mM bicarbonate, pH 9.5, 200 mM NH$_4$Cl). Negative controls contained no amino acid dehydrogenase enzyme. Samples were incubated at 30° C. at 100 rpm overnight. Experiments were performed in duplicate. The dehydrogenases tested were AADH-110, AADH-111, AADH-112, and AADH-113. AADH-110 and 111 have been defined as broad specificity enzymes, while 112 and 113 are glutamate dehydrogenases. AADH-110 produced the most monatin (as measured by LC/MS/MS) in comparison to the negative controls, approximately 0.36 µg/mL. The NADH-utilizing glutamate dehydrogenase, AADH-112, showed higher activity than the NADPH utilizing glutamate dehydrogenase (AADH-113).

AADH-111 did not appear to produce more monatin than the negative control under the conditions assayed.

Example 15

Interconversion Between MP and Monatin

The amination of MP to form monatin can be catalyzed by aminotransferases, or by dehydrogenases that require a reducing cofactor such as NADH or NADPH. See Examples 1 and 9, 10, 12-14. These reactions are reversible and can be measured in either direction. The directionality, when using a dehydrogenase enzyme, can be largely controlled by the concentration of ammonium salts.

Dehydrogenase activity. The oxidative deamination of monatin was monitored by following the increase in absorbance at 340 nm as NAD(P)+ was converted to the more chromophoric NAD(P)H. Monatin was enzymatically produced and purified as described in Example 9.

A typical assay mixture contained 50 mM Tris-HCl, pH 8.0 to 8.9, 0.33 mM $NAD^+$ or $NADP^+$, 2 to 22 units of glutamate dehydrogenase (Sigma), and 10-15 mM substrate in 0.2 mL. The assay was performed in duplicate in a UV-transparent microtiter plate, on a Molecular Devices SpectraMax Plus platereader. A mix of the enzyme, buffer, and $NAD(P)^+$ were pipetted into wells containing the substrate and the increase in absorbance at 340 nm was monitored at 10 second intervals after brief mixing. The reaction was incubated at 25° C. for 10 minutes. Negative controls were carried out without the addition of substrate, and glutamate was utilized as a positive control. The type III glutamate dehydrogenase from bovine liver (Sigma # G-7882) catalyzed the conversion of the monatin to MP at a rate of conversion approximately one-hundredth the rate of the conversion of glutamate to alpha-ketoglutarate. Attempts to produce monatin from indole-3-pyruvate utilizing glutamate dehydrogenases resulted in production of detectable amounts of tryptophan, indicating that glutamate dehydrogenases, or mutants thereof, could potentially be utilized for deamination of tryptophan rather than using an oxidase or an aminotransferase for this step in the pathway.

Transamination activity. Monatin aminotransferase assays were conducted with the aspartate aminotransferase ($HIS_6$-AspC; 6xHis tag disclosed as SEQ ID NO: 91) from *E. coli*, the tyrosine aminotransferase ($HIS_6$-TyrB; 6xHis tag disclosed as SEQ ID NO: 91) from *E. coli*, the broad substrate aminotransferase ($HIS_6$-BSAT; 6xtag disclosed as SEQ ID NO: 91) from *L. major*, and the two commercially available porcine glutamate-oxaloacetate aminotransferases described in Example 1. Both oxaloacetate and alpha-ketoglutarate were tested as the amino acceptor. The assay mixture contained (in 0.5 mL) 50 mM Tris-HCl, pH 8.0, 0.05 mM PLP, 5 mM amino acceptor, 5 mM monatin, and 25 μg of aminotransferase. The assays were incubated at 30° C. for 30 minutes, and the reactions were stopped by addition of 0.5 mL isopropyl alcohol. The loss of monatin was monitored by LC/MS or LC/MS/MS (Example 18). The highest amount of activity was noted with *L. major* $HIS_6$-BSAT (6xHis tag disclosed as SEQ ID NO: 91) with oxaloacetate as the amino acceptor, followed by the same enzyme with alpha-ketoglutarate as the amino acceptor. The relative activity with oxaloacetate was: $HIS_6$-BSAT (6xHis tag disclosed as SEQ ID NO: 91) >$HIS_6$-AspC (6xHis tag disclosed as SEQ ID NO: 91) >porcine type IIa >porcine type I=$HIS_6$-TyrB (6xHis tag disclosed as SEQ ID NO: 91). The relative activity with alpha-ketoglutarate was: $HIS_6$-BSAT (6xHis tag disclosed as SEQ ID NO: 91)>$HIS_6$-AspC (6xHis tag disclosed as SEQ ID NO: 91)>porcine type I>porcine type IIa>$HIS_6$-TyrB (6xHis tag disclosed as SEQ ID NO: 91).

Using assays similar to those described above, and the detection methods described in Example 18, two enzymes, *S. meliloti* TatA and *R. sphaeroides* TatA, did not appear to detectably convert monatin to MP under the conditions tested. This lack of detectable activity, however, may be due to the fact that MP is sometimes difficult to detect because it is unstable in an aqueous solution. In reactions using approximately 50 μg each of purified ProA aldolase and purified *S. meliloti* aminotransferase (under conditions similar to Example 9), tryptophan and pyruvate were converted to 6 ppm monatin in two hours, and 40 ppm monatin in overnight reactions. The *R. sphaeroides* tryptophan aminotransferase produced approximately 10-fold more monatin, indicating a higher activity in converting MP to monatin.

The aminotransferase activity and substrate specificity of the untagged TyrB and AspC proteins were also measured by following the formation of the co-product glutamate using the protocol described in Example 3 in which S,S-monatin (5 mM) was added as the substrate instead of tryptophan. In this aminotransferase reaction S,S-monatin reacts stoichiometrically with the amino acceptor alpha-ketoglutarate to form MP and glutamate. Thus, if 1 μmole of glutamate is formed, 1 μmole of MP should also be formed. The results are listed in Table 11.

TABLE 11

| Aminotransferase gene | μg protein | [glutamate]; μg/mL |
|---|---|---|
| tyrB | 50 | 211.8 |
| aspC | 50 | 54.3 |

Comparison of these results with those described in Example 3 indicate that the AspC has a 6-fold higher substrate preference for tryptophan over S,S-monatin (328.2 μg/mL/54.3 μg/mL). TyrB, on the other hand, only shows 1.5-fold preference for tryptophan (310.1 μg/mL/211.8 μg/mL) and shows substantially more activity than the AspC protein when monatin is the substrate.

Conversion of Monatin to MP Using Commercially Available Dehydrogenases

Several amino acid dehydrogenases from BioCatalytics (AADH-101-110) were assayed for conversion of monatin to MP. Assays were performed in 100 mM sodium bicarbonate buffer, pH 10.0, 10-20 mM $NAD^+$, 20-200 mM monatin prepared as described in Example 9, and 20 mg/ml enzyme. Reactions were incubated at 30-45° C. for 2 hours, and then 30° C. for 16 hours. The reaction progress was monitored by following absorbance changes at 340 nm due to production of NADH. Negative controls were done in which enzyme was absent, or AADH-101 was present but either $NAD^+$ or monatin were omitted. Positive controls were done using AADH-101 with valine as the substrate. Although low (~1-4%) in comparison to the positive controls, AADH-102 (an aromatic L-amino acid dehydrogenase) and AADH-110 (a broad specificity branched chain L-amino acid dehydrogenase; EC 1.4.1.9) appeared to have some activity on S,S-monatin and could potentially be evolved to improve activity in a biocatalytic process. The reductive amination reaction, which is what is needed production of monatin from MP, is typically a much faster reaction than the oxidative deamination reaction that was measured here. MP was not detectable by LC/MS; however, it has been found to be unstable and difficult to assay.

Conversion of Monatin and α-KG to MP and Glutamate Using Commercially Available Aminotransferases AT-101, AT-102, AT-103, and AT-104 were purchased from BioCatalytics (Pasadena, Calif.). AT-101 is a broad range L-transaminase, AT-102 is a branched-chain aminotransferase (EC 2.6.1.42), AT-103 is a broad range D-aminotransferase, and AT-104 is a branched-chain aminotransferase (EC 2.6.1.42). These enzymes all were active in production of monatin from indole-pyruvate and pyruvate when coupled with aldolase enzyme (see Example 13). The enzymes were tested for activity on S,S and R,R monatin that was produced chemically. Reactions were performed in a total volume of 0.5 mL, and run in duplicate. The assay contained 50 mM Tris pH 7.8, 0.08 mM PLP, 10 mM α-ketoglutarate (α-KG), 5 mM monatin, and 1 mg/ml aminotransferase enzyme. Negative controls did not contain aminotransferase enzyme. The samples were incubated for 2 hrs at 30° C. at 100 rpm shaking. Samples were filtered and LC/MS/MS analysis was run to ascertain glutamate levels (as described in Example 18). Glutamate levels should correlate stoichiometrically with MP production. The negative controls contain some background levels of glutamate from the cell extracts of the aldolase, as well as glutamate production from native $E.$ $coli$ aminotranferases. When R,R was used as the reaction substrate, the only significant glutamate produced in comparison to the negative control was by the D-transaminase (AT-103), approximately 1.1 μg/ml was detected. AT-101 and AT-104 produced slightly more glutamate than the negative controls. The D-transaminase enzyme showed no detectable activity on S,S-monatin. The aminotransferases are enantioselective for the chiral carbon that contains the amino moiety, as expected. All of the L-aminotransferases showed activity on S,S-monatin. AT-101 produced 75 μg/ml glutamate, AT-102 produced 102 μg/ml glutamate, and AT-104 produced 64 μg/ml glutamate.

Similar reactions using 25 mM R,R-monatin, 100 mM potassium phosphate, pH 7.5, 0.08 mM PLP, 50 mM α-ketoglutarate, and 4 mg/mL AT-103 enzyme produced 0.145, 0.268, 0.391, and 0.593 mM glutamate (determined by the LC-post column fluorescence method described in Example 18) at 1, 2, 3, and 19 hrs incubation at 30° C. Phosphate appears to have increased the D-aminotransferase activity when compared to Tris-Cl buffer. In parallel experiments using 1 mg/mL AspC and S,S-monatin as a substrate, 0.11-0.18 mM glutamate was formed during the incubation time. Increasing the AspC concentration to 2 mg/ml increased glutamate concentrations to 1.2 mM in a 4 hour reaction.

Example 16

Production of Monatin from Tryptophan and C3 Sources Other Than Pyruvate

As described above in Example 9, indole-3-pyruvate or tryptophan can be converted to monatin using pyruvate as the C3 molecule. However, in some circumstances, pyruvate may not be a desirable raw material. For example, pyruvate may be more expensive than other C3 carbon sources, or may have adverse effects on fermentations if added to the medium. Alanine can be transaminated by many PLP-enzymes to produce pyruvate.

Tryptophanase-like enzymes perform beta-elimination reactions at faster rates than other PLP enzymes such as aminotransferases. Enzymes from this class (4.1.99.-) can produce ammonia and pyruvate from amino acids such as L-serine, L-cysteine, and derivatives of serine and cysteine with good leaving groups such as O-methyl-L-serine, O-benzyl-L-serine, S-methylcysteine, S-benzylcysteine, S-alkyl-L-cysteine, O-acyl-L-serine, 3-chloro-L-alanine.

Processes to produce monatin using EC 4.1.99.-polypeptides can be improved by mutating the β-tyrosinase (TPL) or tryptophanase according to the method of Mouratou et al. ($J.$ $Biol.$ $Chem$ 274:1320-5, 1999). Mouratou et al. describe the ability to covert the β-tyrosinase into a dicarboxylic amino acid β-lyase, which has not been reported to occur in nature. The change in specificity was accomplished by converting valine (V) 283 to arginine (R) and arginine (R) 100 to threonine (T). These amino acid changes allow for the lyase to accept a dicarboxylic amino acid for the hydrolytic deamination reaction (such as aspartate). Aspartate, therefore, can also be used as a source of pyruvate for subsequent aldol condensation reactions.

Additionally, cells or enzymatic reactors can be supplied with lactate and an enzyme that converts lactate to pyruvate. Examples of enzymes capable of catalyzing this reaction include lactate dehydrogenase and lactate oxidase.

Isolation of Genomic DNA

Tryptophanase polypeptides have previously been reported in, for example, Mouratou et al. ($JBC$ 274:1320-5, 1999). To isolate genes that encode tryptophanase polypeptides, genomic DNA from $E.$ $coli$ DH10B was used as a template for PCR as described in Example 1.

The gene for tyrosine-phenol lyase was isolated from $C.$ $freundii$ (ATCC catalog number 8090, Designation ATCC 13316; NCTC 9750) and grown on Nutrient agar (Difco 0001) and nutrient broth (Difco 0003) at 37° C. to an OD of 2.0. The genomic DNA was purified using a Qiagen Genomic-tip™ 100/G kit.

PCR Amplification of Coding Sequences

Primers were designed with compatible overhangs for the pET 30 Xa/LIC vector (Novagen, Madison, Wis.) as described above in Example 1.

$E.$ $coli$ tna (SEQ ID NO: 41). N-terminal primer for pET30 Xa/LIC cloning: 5'-GGT ATT GAG GGT CGC ATG GAA AAC TTT AAA CAT CT-3' (SEQ ID NO: 43). C-terminal primer for pET30 Xa/LIC cloning: 5'-AGA GGA GAG TTA GAG CCT TAA ACT TCT TTA AGT TTT G-3' (SEQ ID NO: 44).

$C.$ $freundii$ tpl (SEQ ID NO: 42). N-terminal primer for pET30 Xa/LIC cloning: 5'-GGT ATT GAG GGT CGC ATGAATTATCCGGCAGAACC-3' (SEQ ID NO: 45). C-terminal primer for pET 30 Xa/LIC cloning: 5'-AGA GGA GAG TTA GAG CCTTAGATGTAATCAAAGCGTG-3' (SEQ ID NO: 46).

The Eppendorf Mastercycler™ Gradient 5331 Thermal Cycler was used for all PCR reactions. In 50 [L was added 0.5 μg template (genomic DNA), 1.0 μM of each primer, 0.4 mM each dNTP, 3.5 U Expand High Fidelity Polymerase (Roche), 1× Expand buffer with Mg, and 5% DMSO (final concentration). The thermocycler PCR program used was as follows: 96° C. hot start (5 minutes), 94° C.-30 seconds, 40-60° C.-1 minute 45 seconds, 72° C.-2 minutes 15 seconds; 30 repetitions. The final polymerization step was for 7 minutes, and the samples were then stored at 4° C.

Cloning

Cloning and positive clone identification procedures detailed above in Example 1 were used to identify the appropriate clones.

Gene Expression and Activity Assays

Plasmid DNA (verified by sequence analysis) was subcloned into the expression host BL21(DE3) (Novagen). The cultures were grown in LB medium with 30 mg/L kanamycin, the plasmids were isolated using a Qiagen miniprep kit, and analyzed by restriction digest to confirm identity.

Induction experiments were done with the BL21(DE3) expression host, the constructs were grown in LB medium containing 50 mg/L kanamycin at 37° C. Protein expression was induced using 0.1 mM IPTG after the $OD_{600}$ of the culture reached approximately 0.6. The cells were grown for 4 hours at 30° C. and harvested by centrifugation. The cells were then lysed in 5 mL/g wet cell weight BugBuster™ (Novagen) reagent containing 5 μL/mL protease inhibitor cocktail set #III (Calbiochem) and 1 μL/mL benzonase nuclease (Novagen), and the His-tagged recombinant proteins were purified using the His-Bind cartridges as described above in Example 1. Purified proteins were desalted on a PD-10 (G25 Sephadex, Amersham Biosciences) column and eluted in 100 mM Tris-Cl buffer, pH 8.0. The proteins were analyzed by SDS-PAGE on 4-15% gradient gels to check for soluble protein levels at the predicted MW of the recombinant fusion protein.

Mutagenesis

Some members of polypeptide class 4.1.99.-(tryptophanase and β-tyrosinase) will perform the beta-lyase reaction with aspartate or similar amino acids without any modification. However, some members of the class may need to be mutagenized to allow for the use of the substrates and/or the creation of the product. Moreover, in some cases polypeptides that can perform the conversion can be further optimized by mutagenesis.

Site directed mutagenesis was performed based on 3D structure analysis of PLP-binding polypeptides. Two examples for changing the substrate specificity of the polypeptides are shown below.

Mutagenesis of Tryptophanase: Example 16A

The mutagenesis protocol provided below introduced two point mutations in the amino acid sequence. The first point mutation changed arginine (R) at position 103 to threonine (T) and the second point mutation changed valine (V) at position 299 to arginine (R) (numbering system for E. coli mature protein). Mutagenesis experiments were performed by ATG Laboratories (Eden Prairie, Minn.). Mutations were introduced sequentially by PCR of gene fragments and reassembly of the fragments was accomplished by PCR as well. Primers for converting arginine (R)103 to threonine (T):

```
                                            (SEQ ID NO: 47)
5'-CCAGGGCACCGGCGCAGAGCAAATCTATATT-3'
and (SEQ ID NO: 48)
5'-TGCGCCGGTGCCCTGGTGAGTCGGAATGGT-3'.
```

Primers for converting valine (V)299 to arginine (R):

```
                                            (SEQ ID NO: 49)
5'-TCCTGCACGCGGCAAAGGGTTCTGCACTCGGT-3'
and (SEQ ID NO: 50)
5'-CTTTGCCGCGTGCAGGAAGGCTTCCCGACA-3'.
```

Mutants were screened by restriction digest with Xba I/HindIII and SphI, and verified by sequencing.

Mutagenesis of Tyrosine Phenol Lyase (β-tyrosinase): Example 16B

Two point mutations were made to the tyrosine phenol lyase amino acid sequence. These mutations converted arginine (R) at position 100 to threonine (T) and valine (V) at position 283 to arginine (R) (in C. freundii mature protein sequence).

Primers for the R100T conversion were:

```
                                            (SEQ ID NO: 51)
5'-AGGGGACCGGCGCAGAAAACCTGTTATCG-3'
and (SEQ ID NO: 52)
5'-TCTGCGCCGGTCCCCTGGTGAGTCGGAACAAT-3'.
```

Primers for the V283R conversion were:

```
                                            (SEQ ID NO: 53)
5'-GTTAGTCCGCGTCTACGAAGGGATGCCAT-3'
and (SEQ ID NO: 54)
5'-GTAGACGCGGACTAACTCTTTGGCAGAAG-3'.
```

The methods described above were used, and the clones were screened by KpnI/SacI digestion, and BstXI digestion. The sequences were verified by dideoxy chain termination sequencing. Recombinant protein was produced as described above for the wildtype enzymes.

The reaction mixture consisted of 50 mM Tris-Cl pH 8.3, 2 mM $MgCl_2$, 200 mM C3 carbon source, 5 mM alpha-ketoglutarate, sodium salt, 0.05 mM pyridoxal phosphate, deaerated water to achieve a final volume of 0.5 mL after the addition of the enzymes, 3 mM potassium phosphate pH 7.5, 25 μg of crude recombinant C. testosteroni ProA aldolase as prepared in Example 7, 500 μg of crude L-aspartate aminotransferase (AspC) as prepared in Example 1, and solid tryptophan to afford a concentration of >60 mM (saturated; some undissolved throughout the reaction). The reaction mix was incubated at 30° C. for 30 minutes with mixing. Serine, alanine, and aspartate were supplied as 3-carbon sources. Assays were performed with and without secondary PLP enzymes (purified) capable of performing beta-elimination and beta-lyase reactions (tryptophanase (TNA), double mutant tryptophanase, β-tyrosinase (TPL)). The results of the LC/MS analyses of the reaction mixtures are shown in Table 12:

TABLE 12

Production of Monatin utilizing alternative C3-carbon sources

| C3-carbon source | Additional PLP Enzyme | Relative Activity |
|---|---|---|
| none | None | 0% |
| pyruvate | None | 100% |
| serine | None | 3% |
| serine | 11 μg wildtype TNA (1 U) | 5.1% |
| serine | 80 μg double mutant TNA | 4.6% |
| alanine | None | 32% |
| alanine | 11 μg wildtype TNA | 41.7% |
| alanine | 80 μg mutant TNA | 43.9% |
| aspartate | 110 μg wildtype TNA (10 U) | 7.7% |
| aspartate | 5 U wildtype TPL (crude) | 5.1% |
| aspartate | 80 μg mutant TNA | 3.3% |

The monatin produced from alanine and serine as 3-carbon sources was verified by LC/MS/MS daughter scan analysis, and was identical to the characterized monatin produced in Example 9. Alanine was the best alternative tested, and was transaminated by the AspC enzyme. The amount of monatin produced was increased by addition of the tryptophanase, which has a transamination secondary activity. The amount of monatin produced with serine as a carbon source nearly doubled with the addition of the tryptophanase enzymes, even though only one-fifth of the amount of tryptophanase was added in comparison to the aminotransferase. AspC is capable of some amount of beta-elimination activity alone. The results with aspartate indicate that the tryptophanase activity on aspartate does not increase with the same site-directed mutations as previously suggested for β-tyrosinase. It is expected that the mutant β-tyrosinase will have higher activity for production of monatin.

Example 17

Chemical Synthesis of Monatin

The addition of alanine to indole-3-pyruvic acid produces monatin, and this reaction can be performed synthetically with a Grignard or organolithium reagent.

For example, to 3-chloro- or 3-bromo-alanine which has been appropriately blocked at the carboxyl and amino groups, is added magnesium under anhydrous conditions. Indole-3-pyruvate (appropriately blocked) is then added to form the coupled product followed by removal of the protecting groups to form monatin. Protecting groups that are particularly useful include THP (tetrahydropyranyl ether) which is easily attached and removed.

Example 18

Detection of Monatin, MP, Tryptophan, and Glutamic Acid

This example describes methods used to detect the presence of monatin, or its precursor 2-hydroxy 2-(indol-3-ylmethyl)-4-keto glutaric acid, as well tryptophan and glutamic acid. It also describes a method for the separation and detection of the four stereoisomers of monatin.

LC/MS Analysis of Monatin, MP, and Tryptophan

Analyses of mixtures for monatin, MP, and/or tryptophan derived from in vitro or in vivo biochemical reactions were performed using a Waters/Micromass liquid chromatography-tandem mass spectrometry (LC/MS/MS) instrument including a Waters 2795 liquid chromatograph with a Waters 996 Photo-Diode Array (PDA) absorbance monitor placed in series between the chromatograph and a Micromass Quattro Ultima triple quadrupole mass spectrometer. LC separations were made using an Xterra MS $C_8$ reversed-phase chromatography column, 2.1 mm×250 mm, or a Supelco Discovery $C_{18}$ reversed phase chromatography column, 2.1 mm×150 mm at room temperature or at 40° C. The LC mobile phase consisted of A) water containing 0.05% (v/v) trifluoroacetic acid and B) methanol containing 0.05% (v/v) trifluoroacetic acid.

The gradient elution was linear from 5% B to 35% B, 0-4 min, linear from 35% B to 60% B, 4-6.5 min, linear from 60% B to 90% B, 6.5-7 min, isocratic at 90% B 7-11 min, linear from 90% B to 95% B, 11-12 min, linear from 95% B to 5% B, 12-13 min, with a 5 min re-equilibration period between runs. The flow rate was 0.25 mL/min, and PDA absorbance was monitored from 200 nm to 400 nm. All parameters of the ESI-MS were optimized and selected based on generation of protonated molecular ions ([M+H]$^+$) of the analytes of interest, and production of characteristic fragment ions.

The following instrumental parameters were used for LC/MS analysis of monatin: Capillary: 3.5 kV; Cone: 40 V; Hex 1:20 V; Aperture: 0 V; Hex 2:0 V; Source temperature: 100° C.; Desolvation temperature: 350° C.; Desolvation gas: 500 L/h; Cone gas: 50 L/h; Low mass resolution (Q1): 15.0; High mass resolution (Q1): 15.0; Ion energy: 0.2; Entrance: 50V; Collision Energy: 2; Exit: 50V; Low mass resolution (Q2): 15; High mass resolution (Q2): 15; Ion energy (Q2): 3.5; Multiplier: 650. Uncertainties for reported mass/charge ratios (m/z) and molecular masses are ±0.01%. Initial detection of the alpha-keto acid form of monatin (MP) and monatin in the mixtures was accomplished by LC/MS monitoring with collection of mass spectra for the region m/z 150-400. Selected ion chromatograms for protonated molecular ions ([M+H]$^+$=292 for MP, [M+H]$^+$=293 for monatin, [M+H]$^+$=205 for tryptophan) allowed direct identification of these analytes in the mixtures. Subsequent methods for monatin and MP detection used multiple reaction monitoring (MRM) LC/MS/MS methodology (see below).

LC/MS/MS Analysis for Monatin

LC/MS/MS daughter ion experiments were performed on monatin as follows. A daughter ion analysis involves transmission of the parent ion (e.g., m/z=293 for monatin) of interest from the first mass analyzer (Q1) into the collision cell of the mass spectrometer, where argon is introduced and chemically dissociates the parent into fragment (daughter) ions. These fragment ions are then detected with the second mass analyzer (Q2), and can be used to corroborate the structural assignment of the parent. Tryptophan was characterized and quantified in the same way via transmission and fragmentation of m/z=205.

The following instrumental parameters were used for LC/MS/MS analysis of monatin: Capillary: 3.5 kV; Cone: 40 V; Hex 1:20 V; Aperture: 0 V; Hex 2:0 V; Source temperature: 100° C.; Desolvation temperature: 350° C.; Desolvation gas: 500 L/h; Cone gas: 50 L/h; Low mass resolution (Q1): 13.0; High mass resolution (Q1): 13.0; Ion energy: 0.2; Entrance: −5 V; Collision Energy: 14; Exit: 1V; Low mass resolution (Q2): 15; High mass resolution (Q2): 15; Ion energy (Q2): 3.5; Multiplier: 650.

LC/MS/MS Multiple Reaction Monitoring

To increase the sensitivity and selectivity of monatin detection, an LC/MS/MS method employing MRM measurements has been developed. LC separations were performed as described in previous sections. Instrumental parameters for ESI-MS/MS were set up as described in the previous section, except that low and high mass resolution settings for Q1 and Q2 are set to 12.0 to maximize sensitivity. Five monatin-specific parent-to daughter transitions are used to specifically detect monatin in in vitro and in vivo reactions. The transitions are 293.1 to 158.3, 293.1 to 168.2, 293.1 to 211.2, 293.1 to 230.2, and 293.1 to 257.2.

High-Throughput Determination of Monatin, Tryptophan, and Glutamic Acid (Glutamate)

High-throughput analyses (<5 min/sample) of mixtures for monatin, tryptophan, and/or glutamic acid derived from in vitro or in vivo reactions were carried out using instrumentation described above, and the same MS parameters as described for LC/MS/MS Multiple Reaction Monitoring. LC separations were made using a 4.6 mm×50 mm Advanced Separation Technologies Chirobiotic T column at room temperature. The LC mobile phase consisted of A) water containing 0.25% acetic acid; B) Methanol containing 0.25% acetic acid. The isocratic elution was at 50% B, 0-5 min. The flow rate was 0.6 mL/min. All parameters of the ESI-MS/MS system were optimized and selected based on optimal in-source generation of the protonated molecular ions of tryptophan and monatin and the internal standard $^2H_5$-tryptophan or $^2H_3$-glutamic acid, as well as collision-induced production of analyte-specific fragment ions for multiple reaction monitoring (MRM) experiments (204.7 to 146.4 for tryptophan, 209.7 to 151.4 for $^2H_5$-tryptophan, 147.6 to 102.4 for glutamic acid, 150.6 to 105.4 for $^2H_3$-glutamic acid, monatin-specific transitions listed in the previous section).

Accurate Mass Measurement of Monatin.

High resolution MS analysis was carried out using an Applied Biosystems-Perkin Elmer Q-Star hybrid quadrupole/time-of-flight mass spectrometer. The measured mass for protonated monatin used tryptophan as an internal mass calibration standard. The calculated mass of protonated monatin, based on the elemental composition $C_{14}H_{17}N_2O_5$ is 293.1137. Monatin produced using the biocatalytic process described in Example 9 showed a measured mass of 293.1144. This is a mass measurement error of less than 2 parts per million (ppm), providing conclusive evidence of the elemental composition of monatin produced enzymatically.

Chiral LC/MS/MS (MRM) Measurement of Monatin

Determination of the stereoisomer distribution of monatin in in vitro and in vivo reactions was accomplished by derivitization with 1-fluoro-2-4-dinitrophenyl-5-L-alanine amide (FDAA), followed by reversed-phase LC/MS/MS MRM measurement.

Derivitization of Monatin with FDAA

To 50 μL of sample or standard was added 200 μL of a 1% solution of FDAA in acetone. Forty μL of 1.0 M Sodium bicarbonate was added, and the mixture incubated for 1 h at 40° C. with occasional mixing. The sample was removed and cooled, and neutralized with 20 μL of 2.0 M HCl (more HCl may be required to effect neutralization of a buffered biological mixture). After degassing is complete, samples were ready for analysis by LC/MS/MS.

LC/MS/MS Multiple Reaction Monitoring for the Determination of the Stereoisomer Distribution of Monatin in In Vitro and In Vivo Reactions.

Analyses were performed using the LC/MS/MS instrumentation described in previous sections. LC separations capable of separating all four stereoisomers of monatin (specifically FDAA-monatin) were performed on a Phenomenex Luna (5 μm) C18 reversed phase chromatography column at 40° C. The LC mobile phase consisted of A) water containing 0.05% (mass/volume) ammonium acetate and B) acetonitrile. The gradient elution was linear from 2% B to 34% B, 0-33 min, linear from 34% B to 90% B, 33-34 min, isocratic at 90% B 34-44 min, and linear from 90% B to 2% B, 44-46 min, with a 16 min re-equilibration period between runs. The flow rate was 0.25 mL/min, and PDA absorbance was monitored from 200 nm to 400 nm. All parameters of the ESI-MS were optimized and selected based on generation of protonated molecular ions ([M+H]$^+$) of FDAA-monatin, and production of characteristic fragment ions.

The following instrumental parameters were used for LC/MS analysis of monatin in the negative ion ESI/MS mode: Capillary: 2.0 kV; Cone: 25 V; Hex 1:10 V; Aperture: 0 V; Hex 2:0 V; Source temperature: 100° C.; Desolvation temperature: 350° C.; Desolvation gas: 500 L/h; Cone gas: 50 L/h; Low mass resolution (Q1): 12.0; High mass resolution (Q1): 12.0; Ion energy: 0.2; Entrance: −5V; Collision Energy: 20; Exit: 1V; Low mass resolution (Q2): 12; High mass resolution (Q2): 12; Ion energy (Q2): 3.0; Multiplier: 650. Three FDAA-monatin-specific parent-to daughter transitions are used to specifically detect FDAA-monatin in in vitro and in vivo reactions. The transitions are 543.6 to 268.2, 543.6 to 499.2, and 543.6 to 525.2. Identification of FDAA-monatin stereoisomers is based on chromatographic retention time as compared to purified monatin stereoisomers, and mass spectral data.

Liquid Chromatography-Post Column Fluorescence Detection of Amino Acids Including Glutamate Liquid chromatography with post-column fluorescence detection for the determination of glutamic acid in in vitro and in vivo reactions was performed on a Waters 2690 LC system or equivalent combined with a Waters 474 scanning fluorescence detector, and a Waters post-column reaction module. LC separations were performed on, an Interaction-Sodium loaded ion exchange column at 60° C. Mobile phase A was Pickering Na 328 buffer (Pickering Laboratories, Inc.; Mountain View, Calif.). Mobile phase B was Pickering Na 740 buffer. The gradient elution was from 0% B to 100% B, 0-20 min, isocratic at 100% B, 20-30 min, and linear from 100% B to 0% B, 30-31 min, with a 20 min re-equilibration period between runs. The flow rate for the mobile phase was 0.5 mL/min. The flow rate for the OPA post-column derivitization solution was 0.5 mL/min. The fluorescence detector settings were EX 338 nm and Em 425 nm. Norleucine was employed as an internal standard for the analysis. Identification of amino acids was based on chromatographic retention time data for purified standards.

Example 19

Production of Monatin in Bacteria

This example describes methods used to produce monatin in *E. coli* cells. One skilled in the art will understand that similar methods can be used to produce monatin in other bacterial cells. In addition, vectors containing other genes in the monatin synthesis pathway (FIG. 2) can be used.

Trp-1+glucose medium, a minimal medium that has been used for increased production of tryptophan in *E. coli* cells (Zeman et al. *Folia Microbiol.* 35:200-4, 1990), was prepared as follows. To 700 mL nanopure water the following reagents were added: 2 g $(NH_4)_2SO_4$, 13.6 g $KH_2PO_4$, 0.2 g $MgSO_4.7H_2O$, 0.01 g $CaCl_2.2H_2O$, and 0.5 mg $FeSO_4.7H_2O$. The pH was adjusted to 7.0, the volume was increased to 850 mL, and the medium was autoclaved. A 50% glucose solution was prepared separately, and sterile-filtered. Forty mL was added to the base medium (850 mL) for a 1 L final volume.

A 10 g/L L-tryptophan solution was prepared in 0.1 M sodium phosphate pH 7, and sterile-filtered. One-tenth volume was typically added to cultures as specified below. A 10% sodium pyruvate solution was also prepared and sterile-filtered. A 10 mL aliquot was typically used per liter of culture. Stocks of ampicillin (100 mg/mL), kanamycin (25 mg/mL) and IPTG (840 mM) were prepared, sterile-filtered, and stored at −20° C. before use. Tween 20 (polyoxyethylene 20-Sorbitan monolaurate) was utilized at a 0.2% (vol/vol) final concentration. Ampicillin was used at non-lethal concentrations, typically 1-10 μg/mL final concentration.

Fresh plates of *E. coli* BL21(DE3)::*C. testosteroni* proAl-pET 30 Xa/LIC (described in Example 7) were prepared on LB medium containing 50 μg/mL kanamycin. Overnight cultures (5 mL) were inoculated from a single colony and grown at 30° C. in LB medium with kanamycin. Typically a 1 to 50 inoculum was used for induction in trp-1+glucose medium. Fresh antibiotic was added to a final concentration of 50 mg/L. Shake flasks were grown at 37° C. prior to induction.

Cells were sampled every hour until an $OD_{600}$ of 0.35-0.8 was obtained. Cells were then induced with 0.1 mM IPTG, and the temperature reduced to 34° C. Samples (1 ml) were collected prior to induction (zero time point) and centrifuged at 5000×g. The supernatant was frozen at −20° C. for LC/MS analysis. Four hours post-induction, another 1 mL sample was collected, and centrifuged to separate the broth from the cell pellet. Tryptophan, sodium pyruvate, ampicillin, and Tween were added as described above.

The cells were grown for 48 hours post-induction, and another 1 mL sample was taken and prepared as above. At 48 hours, another aliquot of tryptophan and pyruvate were added. The entire culture volume was centrifuged after approximately 70 hours of growth (post-induction), for 20 minutes at 4° C. and 3500 rpm. The supernatant was decanted and both the broth and the cells were frozen at −80° C. The broth fractions were filtered and analyzed by LC/MS. The heights and areas of the [M+H]$^+$=293 peaks were monitored as described in Example 18. The background level of the medium was subtracted. The data was also normalized for cell growth by plotting the height of the [M+H]$^+$=293 peak divided by the optical density of the culture at 600 mn.

Higher levels of monatin were produced when pyruvate, ampicillin, and Tween were added 4 hours post induction rather than at induction. Other additives such as PLP, additional phosphate, or additional $MgCl_2$ did not increase the production of monatin. Higher titers of monatin were obtained when tryptophan was utilized instead of indole-3-pyruvate, and when the tryptophan was added post-induction rather than at inoculation, or at induction. Prior to induction, and 4 hours post-induction (at time of substrate addition), there was typically no detectable level of monatin in the fermentation broth or cellular extracts. Negative controls were done utilizing cells with pET30a vector only, as well as cultures where tryptophan and pyruvate were not added. A parent MS scan demonstrated that the compound with (m+1)/z=293 was not derived from larger molecules, and daughter scans (performed as in Example 18) were similar to monatin made in vitro.

The effect of Tween was studied by utilizing 0, 0.2% (vol/vol), and 0.6% final concentrations of Tween-20. The highest amount of monatin produced by shake flasks was at 0.2% Tween. The ampicillin concentration was varied between 0 and 10 µg/mL. The amount of monatin in the cellular broth increased rapidly (2.5×) between 0 and 1 µg/mL, and increased 1.3× when the ampicillin concentration was increased from 1 to 10 µg/mL.

A time course experiment showing typical results is shown in FIG. 10. The amount of monatin secreted into the cell broth increased, even when the values are normalized for cell growth. By using the molar extinction coefficient of tryptophan, the amount of monatin in the broth was estimated to be less than 10 µg/mL. The same experiment was repeated with the cells containing vector without proA insert. Many of the numbers were negative, indicating the peak height at m/z=293 was less in these cultures than in the medium alone (FIG. 10). The numbers were consistently lower when tryptophan and pyruvate were absent, demonstrating that monatin production is a result of an enzymatic reaction catalyzed by the aldolase enzyme.

The in vivo production of monatin in bacterial cells was repeated in 800 mL shake flask experiments and in fermentors. A 250 mL sample of monatin (in cell-free broth) was purified by anion exchange chromatography and preparative reverse-phase liquid chromatography. This sample was evaporated, and submitted for high resolution mass analysis (described in Example 9). The high resolution MS indicated that the metabolite being produced is monatin.

In vitro assays indicate that aminotransferase needs to be present at higher levels than aldolase (see Example 9), therefore the aspartate aminotransferase from E. coli was overexpressed in combination with the aldolase gene to increase the amount of monatin produced. Primers were designed to introduce C. testosteroni proA into an operon with aspC/pET30 Xa/LIC, as follows: 5' primer: ACTCGGATCCGAAG-GAGATATACATATGTACGAACTGGGACT (SEQ ID NO: 67) and 3' primer: CGGCTGTCGACCGTTAGT-CAATATATTTCAGGC (SEQ ID NO: 68). The 5' primer contains a BamHI site, the 3' primer contains a SalI site for cloning. PCR was performed as described in Example 7, and gel purified. The aspC/pET30 Xa/LIC construct was digested with BamHI and SalI, as was the PCR product. The digests were purified using a Qiagen spin column. The proA PCR product was ligated to the vector using the Roche Rapid DNA Ligation kit (Indianapolis, Ind.) according to manufacturer's instructions. Chemical transformations were done using Novablues Singles (Novagen) as described in Example 1. Colonies were grown up in LB medium containing 50 mg/L kanamycin and plasmid DNA was purified using the Qiagen spin miniprep kit. Clones were screened by restriction digest analysis and sequence was confirmed by Seqwright (Houston, Tex.). Constructs were subcloned into BLR(DE3), BLR (DE3)pLysS, BL21(DE3) and BL21(DE3)pLysS (Novagen). The proA/pET30 Xa/LIC construct was also transformed into BL21(DE3)pLysS.

Initial comparisons of BLR(DE3) shake flask samples under the standard conditions described above demonstrated that the addition of the second gene (aspC) improved the amount of monatin produced by seven-fold. To hasten growth, BL21(DE3)-derived host strains were used. The proA clones and the two gene operon clones were induced in Trp-1 medium as above, the pLysS hosts had chloramphenicol (34 mg/L) added to the medium as well. Shake flask experiments were performed with and without the addition of 0.2% Tween-20 and 1 mg/L ampicillin. The amount of monatin in the broth was calculated using in vitro produced purified monatin as a standard. SRM analyses were performed as described in Example 18. Cells were sampled at zero, 4 hours, 24 hours, 48 hours, 72 hours, and 96 hours of growth.

The results are shown in Table 13 for the maximum amounts produced in the culture broths. In most instances, the two gene construct gave higher values than the ProA construct alone. The pLysS strains, which should have leakier cell envelopes, had higher levels of monatin secreted, even though these strains typically grow at a slower rate. The additions of Tween and ampicillin were beneficial.

TABLE 13

Amount of Monatin Produced by E. coli Bacteria

| Construct | Host | Tween + Amp | µg/mL Monatin | time |
|---|---|---|---|---|
| proA | BL21(DE3) | − | 0.41 | 72 hr |
| proA | BL21(DE3) | + | 1.58 | 48 hr |
| proA | BL21(DE3)pLysS | − | 1.04 | 48 hr |
| proA | BL21(DE3)pLysS | + | 1.60 | 48 hr |
| aspC:proA | BL21(DE3) | − | 0.09 | 48 hr |
| aspC:proA | BL21(DE3) | + | 0.58 | 48 hr |
| aspC:proA | BL21(DE3)pLysS | − | 1.39 | 48 hr |
| aspC:proA | BL21(DE3)pLysS | + | 6.68 | 48 hr |

Example 20

Production of Monatin in Yeast

This example describes methods used to produce monatin in eukaryotic cells. One skilled in the art will understand that similar methods can be used to produce monatin in any cell of interest. In addition, other genes can be used (e.g., those listed in FIG. 2) in addition to, or alternatively to those described in this example.

The pESC Yeast Epitope Tagging Vector System (Stratagene, La Jolla, Calif.) was used to clone and express the *E. coli* aspC and *C. testosteroni* proA genes into *Saccharomyces cerevisiae*. The pESC vectors contain both the GAL1 and the GAL10 promoters on opposite strands, with two distinct multiple cloning sites, allowing for expression of two genes at the same time. The pESC-His vector also contains the His3 gene for complementation of histidine auxotrophy in the host (YPH500). The GAL1 and GAL10 promoters are repressed by glucose and induced by galactose; a Kozak sequence is utilized for optimal expression in yeast. The pESC plasmids are shuttle vectors, allowing the initial construct to be made in *E. coli* (with the bla gene for selection); however, no bacterial ribosome binding sites are present in the multiple cloning sites.

The following primers were designed for cloning into pESC-His (restriction sites are underlined, Kozak sequence is in bold): aspC (BamHI/SalI), GAL1:

```
                                            (SEQ ID NO: 69)
5'-CGCGGATCCATAATGGTTGAGAACATTACCG-3'
and (SEQ ID NO: 70)
5'-ACGCGTCGACTTACAGCACTGCCACAATCG-3'.
``` proA (EcoRI/NotI), GAL10:

```
                                            (SEQ ID NO: 71)
5'-CCGGAATTCATAATGGTCGAACTGGGAGTTGT-3'
and (SEQ ID NO: 72)
5'-GAATGCGGCCGCTTAGTCAATATATTTCAGGCC-3'.
```

The second codon for both mature proteins was changed from an aromatic amino acid to valine due to the introduction of the Kozak sequence. The genes of interest were amplified using pET30 Xa/LIC miniprep DNA from the clones described in Examples 1 and Example 7 as template. PCR was performed using an Eppendorf Master cycler gradient thermocycler and the following protocol for a 50 µL reaction: 1.0 µL template, 1.0 µM of each primer, 0.4 mM each dNTP, 3.5 U Expand High Fidelity Polymerase (Roche, Indianapolis, Ind.), and 1× Expand™ buffer with Mg. The thermocycler program used consisted of a hot start at 94° C. for 5 minutes, followed by 29 repetitions of the following steps: 94° C. for 30 seconds, 50° C. for 1 minute 45 seconds, and 72° C. for 2 minutes 15 seconds. After the 29 repetitions the sample was maintained at 72° C. for 10 minutes and then stored at 4° C. The PCR products were purified by separation on a 1% TAE-agarose gel followed by recovery using a QIAquick Gel Extraction Kit (Qiagen, Valencia, Calif.).

The pESC-His vector DNA (2.7 µg) was digested with BamHI/SalI and gel-purified as above. The aspC PCR product was digested with BamHI/SalI and purified with a QIAquick PCR Purification Column. Ligations were performed with the Roche Rapid DNA Ligation Kit following the manufacturer's protocols. Desalted ligations were electroporated into 40 µl Electromax DH10B competent cells (Invitrogen) in a 0.2 cm Biorad disposable cuvette using a Biorad Gene Pulser II with pulse controller plus, according to the manufacturer's instructions. After 1 hour of recovery in 1 mL of SOC medium, the transformants were plated on LB medium containing 100 µg/mL ampicillin. Plasmid DNA preparations for clones were done using QIAprep Spin Miniprep Kits. Plasmid DNA was screened by restriction digest, and sequenced (Seqwright) for verification using primers designed for the vector.

The aspC/pESC-His clone was digested with EcoRI and NotI, as was the proA PCR product. DNA was purified as above, and ligated as above. The two gene construct was transformed into DH10B cells and screened by restriction digest and DNA sequencing.

The construct was transformed into *S. cerevisiae* strain YPH500 using the S.c. EasyComp™ Transformation Kit (Invitrogen). Transformation reactions were plated on SC-His minimal medium (Invitrogen pYES2 manual) containing 2% glucose. Individual yeast colonies were screened for the presence of the proA and aspC genes by colony PCR using the PCR primers above. Pelleted cells (2 µl) were suspended in 20µL of Y-Lysis Buffer (Zymo Research) containing 1 µl of zymolase and heated at 37° C. for 10 minutes. Four µL of this suspension was then used in a 50 µL PCR reaction using the PCR reaction mixture and program described above.

Five mL cultures were grown overnight on SC-His +glucose at 30° C. and 225 rpm. The cells were gradually adjusted to growth on raffinose in order to minimize the lag period prior to induction with galactose. After approximately 12 hours of growth, absorbance measurements at 600 nm were taken, and an appropriate volume of cells was spun down and resuspended to give an OD of 0.4 in the fresh SC-His medium. The following carbon sources were used sequentially: 1% raffinose+1% glucose, 0.5% glucose+1.5% raffinose, 2% raffinose, and finally 1% raffinose+2% galactose for induction.

After approximately 16 hours of growth in induction medium, the 50 mL cultures were divided into duplicate 25 mL cultures, and the following were added to only one of the duplicates: (final concentrations) 1 g/L L-tryptophan, 5 mM sodium phosphate pH 7.1, 1 g/L sodium pyruvate, 1 mM $MgCl_2$. Samples of broths and cell pellets from the non-induction medium, and from the 16 hour cultures prior to addition of substrates for the monatin pathway, were saved as negative controls. In addition, constructs containing only a functional aspC gene (and a truncated proA gene) were utilized as another negative control. The cells were allowed to grow for a total of 69 hours post-induction. Occasionally the yeast cells were induced at a lower OD, and only grown for 4 hours prior to addition of tryptophan and pyruvate. However, these monatin substrates appear to inhibit growth and the addition at higher OD was more effective.

The cell pellets from the cultures were lysed with 5 mL of YeastBuster™+50 µl THP (Novagen) per gram (wet weight) of cells following manufacturer's protocols, with the addition of protease inhibitors and benzonase nuclease as described in previous examples. The culture broth and cell extracts were filtered and analyzed by SRM as described in Example 18. Using this method, no monatin was detected in the broth samples, indicating that the cells could not secrete monatin under these conditions. The proton motive force may be insufficient under these conditions or the general amino acid transporters may be saturated with tryptophan. Protein expression was not at a level that allowed for detection of changes using SDS-PAGE.

Monatin was detectable (approximately 60 ng/mL) transiently in cell extracts of the culture with two functional genes, when tryptophan and pyruvate were added to the medium. Monatin was not detected in any of the negative control cell extracts. In vitro assays for monatin were performed in duplicate with 4.4 mg/mL of total protein (about double what is typically used for *E. coli* cell extracts) using the optimized assay described in Example 9. Other assays were performed with the addition of either 32 μg/mL *C. testosteroni* ProA aldolase or 400 μg/mL AspC aminotransferase, to determine which enzyme was limiting in the cell extract. Negative controls were performed with no addition of enzyme, or the addition of only AspC aminotransferase (the aldol condensation can occur to some extent without enzyme). Positive controls were performed with partially pure enzymes (30-40%), using 16 μg/mL aldolase and 400 μg/mL aminotransferase.

In vitro results were analyzed by SRM. The analysis of cell extracts showed that tryptophan was effectively transported into the cells when it was added to the medium post-induction, resulting in tryptophan levels two orders of magnitude higher than those in which no additional tryptophan was added. The results for in vitro monatin analysis are shown in Table 14 (numbers indicate ng/mL).

TABLE 14

Monatin production with yeast cell extracts.

| | aspC construct | +aldolase | +AspC | two-gene construct | +aldolase | +AspC |
|---|---|---|---|---|---|---|
| repressed (glucose medium) | 0 | 888.3 | 173.5 | 0 | 465.2 | 829 |
| 24 hr induced | 0 | 2832.8 | 642.4 | 0 | 1375.6 | 9146.6 |
| 69 hr induced | 0 | 4937.3 | 340.3 | 71.9 | 1652.8 | 23693.5 |
| 69 hr + subs. | 0 | 556.9 | 659.1 | 21.9 | 755.6 | 16688.2 |
| +control (purified enzymes) | 21853 | | | 21853 | | |
| −control (no enzymes) | 0 | | 254.3 | 0 | | 254.3 |

Positive results were obtained with the full two-gene construct cell extracts with and without substrate added to the growth medium. These results, in comparison to the positive controls, indicate that the enzymes were expressed at levels of close to 1% of the total protein in yeast. The amount of monatin produced when the cell extract of the aspC construct (with truncated ProA) was assayed with aldolase was significantly greater than when cell extracts were assayed alone, and indicates that the recombinant AspC aminotransferase comprises approximately 1-2% of the yeast total protein. The cell extracts of uninduced cultures had a small amount of activity when assayed with aldolase due to the presence of native aminotransferases in the cells. When assayed with AspC aminotransferase, the activity of the extracts from uninduced cells increased to the amount of monatin produced by the negative control with AspC (ca. 200 ng/ml). In contrast, the activity observed when assaying the two gene construct cell extract increases more when aminotransferase is supplemented than when aldolase is added. Since both genes should be expressed at the same level, this indicates that the amount of monatin produced is maximized when the level of aminotransferase is higher than that of aldolase, in agreement with results shown in Example 9.

The addition of pyruvate and tryptophan not only inhibits cellular growth, but apparently inhibits protein expression as well. The addition of the pESC-Trp plasmid can be used to correct for tryptophan auxotrophy of the YPH500 host cells, to provide a means of supplying tryptophan with fewer effects on growth, expression, and secretion.

Example 21

Improvement of Enzymatic Processes Using Coupled Reactions

In theory, if no side reactions or degradation of substrates or intermediates occurs, the maximum amount of product formed from the enzymatic reaction illustrated in FIG. 1 is directly proportional to the equilibrium constants of each reaction and the concentrations of tryptophan and pyruvate. Tryptophan is not a highly soluble substrate and concentrations of pyruvate greater than 200 mM appear to have a negative effect on the yield (see Example 9).

Ideally, the concentration of monatin is maximized with respect to substrates in order to decrease the cost of separation. Physical separations can be performed such that the monatin is removed from the reaction mixture, preventing the reverse reactions from occurring. The raw materials and catalysts can then be regenerated. Due to the similarity of monatin in size, charge, and hydrophobicity to several of the reagents and intermediates, physical separations will be difficult unless there is a high amount of affinity for monatin (such as an affinity chromatography technique). However, the monatin reactions can be coupled to other reactions such that the equilibrium of the system is shifted toward monatin production. The following are examples of processes for improving the yield of monatin obtained from tryptophan or indole-3-pyruvate.

Coupled Reactions Using Oxaloacetate Decarboxylase (EC 4.1.1.3)

FIG. 11 is an illustration of the pathway to produce monatin in which oxaloacetate decarboxylase is added to remove the co-product oxaloacetate formed during the conversion of MP to monatin. Tryptophan oxidase and catalase are utilized to drive the reaction in the direction of indole-3-pyruvate production. Catalase is used in excess such that hydrogen peroxide is not available to react in the reverse direction or to damage the enzymes or intermediates. Oxygen is regenerated during the catalase reaction. Alternatively, indole-3-pyruvate can be used as the initial substrate.

In this pathway, aspartate is used as the amino donor for the amination of MP in a reaction catalyzed by aspartate aminotransferase. Ideally, an aminotransferase that has a low specificity for the tryptophan/indole-3-pyruvate reaction in comparison to the MP/monatin reaction is used so that the aspartate does not act as an amino donor to reaminate the indole-3-pyruvate. Oxaloacetate decarboxylase (from *Pseudomonas* sp.) can be added to convert the oxaloacetate to pyruvate and carbon dioxide. Since $CO_2$ is volatile it is not available for reaction with the enzymes, thus decreasing or even preventing the reverse reactions. The pyruvate produced in this step can also serve as a substrate in the aldol condensation reaction to form MP. Other decarboxylase enzymes can be used; homologs are known to exist in *Actinobacillus actinomycetemcomitans, Aquifex aeolicus, Archaeoglobusfulgidus, Azotobacter vinelandii, Bacteroides fragilis,* several *Bordetella* species, *Campylobacterjejuni, Chlorobium tepidum, Chloroflexus aurantiacus, Enterococcus faecalis, Fusobacterium nucleatum, Klebsiella pneumoniae, Legionella pneumophila, Magnetococcus* MC-1, *Mannheimia haemolytica, Methylobacillus flagellatus* KT, *Pasteurella multocida* Pm70, *Petrotoga miotherma, Porphyromonas gingivalis,* several *Pseudomonas* species, several *Pyrococcus* species, *Rhodococcus,* several *Salmonella* species, several *Streptococcus* species, *Thermochromatium tepidum, Thermotoga maritima, Treponema pallidum,* and several *Vibrio* species.

Tryptophan aminotransferase assays were performed with the HIS$_6$-tagged (SEQ ID NO: 91) aspartate aminotransferase (AspC) from *E. coli,* the HIS$_6$-tagged (SEQ ID NO: 91) tyrosine aminotransferase (TyrB) from *E. coli,* the HIS$_6$-tagged (SEQ ID NO: 91) broad substrate aminotransferase (BSAT) from *L. major,* and the two commercially available porcine glutamate-oxaloacetate aminotransferases as described in Example 1. Both oxaloacetate and alpha-ketoglutarate were tested as amino acceptors. The ratio of activity using monatin (Example 15) versus activity using tryptophan was compared to determine which enzyme had the highest specificity for the monatin aminotransferase reaction. These results indicated that the enzyme with the highest specificity for the monatin reaction verses the tryptophan reaction is the Porcine type II-A glutamate-oxaloacetate aminotransferase, GOAT (Sigma # G7005). This specificity was independent of which amino acceptor was utilized. Therefore, this enzyme was used in the coupled reactions with oxaloacetate decarboxylase.

A typical reaction starting from indole-3-pyruvate contained (final concentrations) 50 mM Tris-Cl pH 7.3, 6 mM indole-3-pyruvate, 6 mM sodium pyruvate, 6 mM aspartate, 0.05 mM PLP, 3 mM potassium phosphate, 3 mM MgCl$_2$, 25 µg/mL aminotransferase, 50 µg/mL *C. testosteroni* ProA aldolase, and 3 Units/mL of decarboxylase (Sigma # O4878). The reaction mixtures were incubated for 1 hour at 26° C. In some cases, the decarboxylase was omitted or the aspartate was substituted with alpha-ketoglutarate (as negative controls). The aminotransferase enzymes described above were also tested in place of the GOAT to confirm earlier specificity experiments. Samples were filtered and analyzed by LC/MS as described in Example 18. The results demonstrate that the GOAT enzyme produced the highest amount of monatin per mg of protein, with the least amount of tryptophan produced as a byproduct. In addition, there was a 2-3 fold increase in product formation when the decarboxylase enzyme was added. The *E. coli* AspC enzyme also produced greater amounts of monatin in comparison to the other aminotransferases.

Monatin production was increased by: 1) periodically adding 2 mM additions of indole-pyruvate, pyruvate, and aspartate (every half hour to hour), 2) performing the reactions in an anaerobic environment or with degassed buffers, 3) allowing the reactions to proceed for several hours, and 4) using freshly prepared decarboxylase that has not been freeze-thawed multiple times. The decarboxylase was inhibited by concentrations of pyruvate greater than 12 mM. At concentrations of indole-3-pyruvate higher than 4 mM, side reactions with indole-3-pyruvate were hastened. The amount of indole-3-pyruvate used in the reaction could be increased if the amount of aldolase was also increased. High levels of phosphate (50 mM) and aspartate (50 mM) were inhibitory to the decarboxylase enzyme reaction. The amount of decarboxylase enzyme added could be reduced to 0.5 U/mL with no decrease in monatin production in a one hour reaction. The amount of monatin produced increased when the temperature was increased from 26° C. to 30° C. and from 30° C. to 37° C. However, at 37° C. the side reactions of indole-3-pyruvate were also hastened. The amount of monatin produced increased with increasing pH from 7 to 7.3 and was relatively stable from pH 7.3-8.3.

A typical reaction starting with tryptophan included (final concentrations) 50 mM Tris-Cl pH 7.3, 20 mM tryptophan, 6 mM aspartate, 6 mM sodium pyruvate, 0.05 mM PLP, 3 mM potassium phosphate, 3 mM MgCl$_2$, 25 µg/mL aminotransferase, 50 µg/mL *C. testosteroni* ProA aldolase, 4 Units/mL of decarboxylase, 5-200 mU/mL L-amino acid oxidase (Sigma # A-2805), 168 U/mL catalase (Sigma # C-3515), and 0.008 mg FAD. Reactions were carried out for 30 minutes at 30° C. Improvement was observed with the addition of decarboxylase. The greatest amount of monatin was produced when 50 mU/mL of oxidase was used. Improvements were similar to those observed when indole-3-pyruvate was used as the substrate. In addition, the amount of monatin produced increased when 1) the tryptophan level was low (i.e., tryptophan concentrations below the K$_m$ of the aminotransferase enzyme and therefore less competitive with MP in the active site of the aminotransferase), and 2) the ratio of oxidase to aldolase and aminotransferase was maintained at a level such that indole-3-pyruvate could not accumulate.

Whether starting with either indole-3-pyruvate or tryptophan, the amount of monatin produced in assays with incubation times of 1-2 hours increased when 2-4 times the amounts of all the enzymes were used while maintaining the same enzyme ratio. Using either substrate, concentrations of approximately 1 mg/mL of monatin were achieved. The amount of tryptophan produced if starting from indole-pyruvate was typically less than 20% of the amount of product, showing the benefit of utilizing coupled reactions. With further optimization and control of the concentrations of intermediates and side reactions, the productivity and yield can be improved further.

In place of oxaloacetate, alpha-ketoglutarate can be utilized as the amino acceptor, with the enzyme 2-oxoglutarate decarboxylase (EC 4.1.1.71). In this case, succinate semialdehyde and carbon dioxide are produced. This reaction scheme is expected to also prevent the reverse reactions from occurring, but does not have the benefit of providing pyruvate as a byproduct. Numerous gene sequences are published that encode this enzyme.

Coupled Reactions Using Lysine Epsilon Aminotransferase (EC 2.6.1.36)

Lysine epsilon aminotransferase (L-Lysine 6-transaminase) is found in several organisms, including *Rhodococcus, Mycobacterium, Streptomyces, Nocardia, Flavobacterium, Candida utilis,* and *Streptomyces*. It is utilized by organisms as the first step in the production of some beta-lactam antibiotics (Rius and Demain, *J. Microbiol. Biotech.,* 7:95-100, 1997). This enzyme converts lysine to L-2-aminoadipate 6-semialdehyde (allysine), by a PLP-mediated transamination of the C-6 of lysine when alpha-ketoglutarate is the amino acceptor. Allysine is unstable and spontaneously undergoes an intramolecular dehydration to form 1-piperideine 6-carboxylate, a cyclic molecule. This effectively inhibits any reverse reaction from occurring. The reaction scheme is depicted in FIG. 12. Alternatively, lysine-pyruvate 6-transaminase (EC 2.6.1.71), can also be used.

A typical reaction contained in 1 mL: 50 mM Tris-HCl pH 7.3, 20 mM indole-3-pyruvate, 0.05 mM PLP, 6 mM potassium phosphate pH 8, 2-50 mM sodium pyruvate, 1.5 mM $MgCl_2$, 50 mM lysine, 100 μg aminotransferase (lysine epsilon aminotransferase LAT-101, BioCatalytics Pasadena, Calif.), and 200 μg *C. testosteroni* ProA aldolase. The amount of monatin produced increased with increasing concentrations of pyruvate. The maximum amount using these reaction conditions (at 50 mM pyruvate) was 10-fold less than what was observed with coupled reactions with oxaloacetate decarboxylase (approximately 0.1 mg/mL).

In the LC/MS analysis of the reaction mixtures, a peak with $[M+H]^+=293$ eluted at the expected time for monatin and the mass spectrum contained several of the same fragments observed with other enzymatic processes. A second peak with the correct mass to charge ratio (293) eluted slightly earlier than what is typically observed for the S,S-monatin produced in Example 9, suggestiong the presence of another isomer of monatin. Very little tryptophan was produced by this enzyme. However, this enzyme may be able to use pyruvate as a substrate (producing alanine as a byproduct). Also, the enzyme is known to be unstable. Improvements can be made by performing directed evolution experiments to increase stability, reduce the activity with pyruvate, and increase the activity with MP. These reactions can also be coupled to L-amino acid oxidase/catalase as described above.

An analogous process to that shown in FIG. 12 utilizes ornithine δ-aminotransferase (EC 2.6.1.13) in place of lysine epsilon aminotransferase, and ornithine serves as the amino donor in this case. The alpha-keto product, L-glutamic acid semialdehyde, spontaneously cyclizes to form $\Delta^1$-pyrroline-5-carboxylate. Alternative reaction schemes using these types of enzymes are described elsewhere for production of non-proteinogenic amino acid preparation (T. Li, A. B. Kootstra, I. G. Fotheringham, *Organic Process Research & Development*, 6: 533-538 (2002)). These schemes require the addition of another aminotransferase with higher activity for the amino acid of interest (such as HEXAspC for monatin) and glutamate.

Other Coupled Reactions

Another coupling reaction that can improve monatin yield from tryptophan or indole-pyruvate is shown in FIG. 13. Formate dehydrogenase (EC 1.2.1.2 or 1.2.1.43) is a common enzyme. Some formate dehydrogenases require NADH while others can utilize NADPH. Glutamate dehydrogenase was shown to catalyze the interconversion between MP and monatin in previous examples, using ammonium based buffers. The presence of ammonium formate and formate dehydrogenase is an efficient system for regeneration of cofactors, and the production of carbon dioxide is an efficient way to decrease the rate of the reverse reactions (Bommarius et al., *Biocatalysis* 10:37, 1994 and Galkin et al. *Appl. Environ. Microbiol.* 63:4651-6, 1997). In addition, large amounts of ammonium formate can be dissolved in the reaction buffer. The yield of monatin produced by glutamate dehydrogenase reactions (or similar reductive aminations) could be improved by the addition of formate dehydrogenase and ammonium formate.

Suitable enzymes to catalyze similar reductive aminations were demonstrated in Examples 14 and 15. These included broad specificity branched chain dehydrogenases (EC 1.4.1.9) as well as an aromatic (phenylalanine) dehydrogenase (EC 1.4.1.20). It is expected that broad specificity D-amino acid dehydrogenases (1.4.99.1) can also be utilized to catalyze this reaction.

Other processes can be used to drive the equilibrium toward monatin production. For instance, if aminopropane serves as the amino acid donor in the conversion of MP to monatin in a reaction catalyzed by an omega-amino acid aminotransferase (EC 2.6.1.18) such as those described by in U.S. Pat. Nos. 5,360,724 and 5,300,437, one of the resulting products would be acetone, a more volatile product than the substrate, aminopropane. The temperature could be raised periodically for short periods to selectively volatilize the acetone, thereby alleviating equilibrium. Acetone has a boiling point of 47° C., a temperature not likely to degrade the intermediates if used for short periods of time. Most aminotransferases that can utilize alpha-ketoglutarate as an amino acceptor also have activity on MP. Similarly, if a glyoxylate/aromatic acid aminotransferase (EC 2.6.1.60) is used with glycine as the amino donor, glyoxylate is produced. This product is unstable and has a lower boiling point than that of glycine.

Example 22

Recombinant Expression

With publicly available enzyme cDNA and amino acid sequences, and the enzymes and sequences disclosed herein, such as SEQ ID NOS: 11 and 12, as well as variants, polymorphisms, mutants, fragments and fusions thereof, the expression and purification of any protein, such as an enzyme, by standard laboratory techniques is enabled. One skilled in the art will understand that enzymes and fragments thereof can be produced recombinantly in any cell or organism of interest, and purified prior to use, for example prior to production of SEQ ID NO: 12 and derivatives thereof.

Methods for producing recombinant proteins are well known in the art. Therefore, the scope of this disclosure includes recombinant expression of any protein or fragment thereof, such as an enzyme. For example, see U.S. Pat. No. 5,342,764 to Johnson et al.; U.S. Pat. No. 5,846,819 to Pausch et al.; U.S. Pat. No. 5,876,969 to Fleer et al. and Sambrook et al. (*Molecular Cloning: A Laboratory Manual*, Cold Spring Harbor, N.Y., 1989, Ch. 17).

Briefly, partial, full-length, or variant cDNA sequences, which encode for a protein or peptide, can be ligated into an expression vector, such as a bacterial or eukaryotic expression vector. Proteins and/or peptides can be produced by placing a promoter upstream of the cDNA sequence. Examples of promoters include, but are not limited to lac, trp, tac, trc, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

Vectors suitable for the production of intact native proteins include pKC30 (Shimatake and Rosenberg, 1981, *Nature* 292:128), pKK177-3 (Amann and Brosius, 1985, *Gene* 40:183) and pET-3 (Studier and Moffatt, 1986, *J. Mol. Biol.* 189:113). A DNA sequence can be transferred to other cloning vehicles, such as other plasmids, bacteriophages, cosmids, animal viruses and yeast artificial chromosomes (YACs) (Burke et al., 1987, *Science* 236:806-12). These vectors can be introduced into a variety of hosts including somatic cells, and simple or complex organisms, such as bacteria, fingi (Timberlake and Marshall, 1989, *Science* 244: 1313-7), invertebrates, plants (Gasser and Fraley, 1989, *Science* 244:1293), and mammals (Pursel et al., 1989, *Science*

244:1281-8), which are rendered transgenic by the introduction of the heterologous cDNA.

For expression in mammalian cells, a cDNA sequence can be ligated to heterologous promoters, such as the simian virus SV40, promoter in the pSV2 vector (Mulligan and Berg, 1981, *Proc. Natl. Acad. Sci. USA* 78:2072-6), and introduced into cells, such as monkey COS-1 cells (Gluzman, 1981, Cell 23:175-82), to achieve transient or long-term expression. The stable integration of the chimeric gene construct can be maintained in mammalian cells by biochemical selection, such as neomycin (Southern and Berg, 1982, *J. Mol. Appl. Genet.* 1:327-41) and mycophoenolic acid (Mulligan and Berg, 1981, *Proc. Natl. Acad. Sci. USA* 78:2072-6).

The transfer of DNA into eukaryotic, such as human or other mammalian cells, is a conventional technique. The vectors are introduced into the recipient cells as pure DNA (transfection) by, for example, precipitation with calcium phosphate (Graham and vander Eb, 1973, *Virology* 52:466) strontium phosphate (Brash et al., 1987, *Mol. Cell Biol.* 7:2013), electroporation (Neumann et al., 1982, *EMBO J.* 1:841), lipofection (Felgner et al., 1987, *Proc. Natl. Acad. Sci USA* 84:7413), DEAE dextran (McCuthan et al., 1968, *J. Natl. Cancer Inst.* 41:351), microinjection (Mueller et al., 1978, *Cell* 15:579), protoplast fusion (Schafner, 1980, *Proc. Natl. Acad. Sci. USA* 77:2163-7), or pellet guns (Klein et al., 1987, *Nature* 327:70). Alternatively, the cDNA can be introduced by infection with virus vectors, for example retroviruses (Bernstein et al., 1985, *Gen. Engrg.* 7:235) such as adenoviruses (Ahmad et al., 1986, *J. Virol.* 57:267) or Herpes (Spaete et al., 1982, *Cell* 30:295).

In view of the many possible embodiments to which the principles of our disclosure may be applied, it should be recognized that the illustrated embodiments are only particular examples of the disclosure and should not be taken as a limitation on the scope of the disclosure. Rather, the scope of the disclosure is in accord with the following claims. We therefore claim as our invention all that comes within the scope and spirit of these claims.

We claim:

1. A method for producing 2-hydroxy 2-(indol-3-ylmethyl)-4-keto glutaric acid comprising
contacting indole-3-pyruvate with a polypeptide chosen from KHG aldolase (4-hydroxy-2-oxoglutarate glyoxylate-lyase, EC 4.1.3.16) and ProA aldolase (4-hydroxy-4-methyl-2-oxoglutarate pyruvate-lyase, EC 4.1.3.17) under conditions in which 2-hydroxy 2-(indol-3-ylmethyl)-4-keto glutaric acid is produced.

2. A method of producing monatin or salt thereof, comprising, under conditions in which monatin is produced,
   (a) providing tryptophan or salt thereof, indole-3-lactic acid or salt thereof, a compound from which tryptophan, indole-3-lactic acid or a combination thereof can be produced in one or more steps, or a combination thereof;
   (b) contacting tryptophan or salt thereof, indole-3-lactic acid or salt thereof, or combinations thereof with a first polypeptide that facilitates converting tryptophan or salt thereof, indole-3-lactic acid or salt thereof, or a combination thereof to indole-3-pyruvate or salt thereof, wherein, when the first polypeptide facilitates converting tryptophan or salt thereof to indole-3-pyruvate or salt thereof, the first polypeptide is chosen from tryptophan aminotransferase (EC 2.6.1.27), tyrosine (aromatic) aminotransferase (EC 2.6.1.5), tryptophan dehydrogenase (EC 1.4.1.19), glutamate dehydrogenase (EC 1.4.1.2, 1.4.1.3, 1.4.1.4), phenylalanine dehydrogenase (EC 1.4.1.20), tryptophan-phenylpyruvate transaminase (EC 2.6.1.28), aspartate aminotransferase (EC 2.6.1.1), L-amino acid oxidase (EC 1.4.3.2), D-amino acid dehydrogenase (EC 1.4.99.1), D-amino acid oxidase (EC 1.4.3.3), D-amino acid (D-alanine) aminotransferase (EC 2.6.1.21), or a combination thereof, wherein, when the first polypeptide facilitates converting indole-3-lactic acid or salt thereof to indole-3-pyruvate of salt thereof, the first polypeptide is chosen from indolelactate dehydrogenase (EC 1.1.1.110), R-4-hydroxyphenyllactate dehydrogenase (EC 1.1.1.222), 3-(4)-hydroxyphenylpyruvate reductase (EC 1.1.1.237), lactate dehydrogenase (EC 1.1.1.27, 1.1.1.28, 1.1.2.3), (3-imidazol-5-yl) lactate dehydrogenase (EC 1.1.1.111), lactate oxidase (EC 1.1.3.-), and a combination thereof
   (c) contacting said indole-3-pyruvate or salt thereof with a second polypeptide that facilitates converting indole-3-pyruvate or salt thereof and a C3 carbon source to 2-hydroxy 2-(indol-3ylmethyl)-4-keto glutaric acid or salt thereof, wherein said second polypeptide is chosen from 4-hydroxy-2-oxoglutarate glyoxylate-lyase (EC 4.1.3.16) and 4-hydroxy-4-methyl-2-oxoglutarate pyruvate-lyase (EC 4.1.3.17); and
   (d) contacting said 2-hydroxy 2-(indol-3ylmethyl)-4-keto glutaric acid or salt thereof with a third polypeptide that facilitates converting 2-hydroxy 2-(indol-3ylmethyl)-4-keto glutaric acid or salt thereof to monatin or salt thereof, wherein said third polypeptide is chosen from tryptophan aminotransferase (EC 2.6.1.27), tyrosine (aromatic) aminotransferase (EC 2.6.1.5), tryptophan dehydrogenase (EC 1.4.1.19), aspartate aminotransferase (EC 2.6.1.1), glutamate dehydrogenase (EC 1.4.1.2-4), phenylalanine dehydrogenase (EC 1.4.1.20), D-amino acid dehydrogenase (EC 1.4.99.1), D-amino acid (D-alanine) aminotransferase (EC 2.6.1.21), D-methionine-pyruvate aminotransferase (EC 2.6.1.41), and combinations thereof,
thereby producing monatin or salt thereof.

3. The method of claim 2, wherein at least one of said first, second or third polypeptide is chosen from purified polypeptides, polypeptides expressed from exogenous, recombinant or isolated nucleic acid, chemically synthesized polypeptides, and polypeptides in recombinant cells or recombinant cell extracts, and combinations thereof.

4. The method of claim 2, wherein at least one of said polypeptides is provided in an unpurified cell extract.

5. The method of claim 4, wherein the unpurified cell extract comprises a total soluble protein content, and wherein at least about 30% of the total soluble protein content is recombinant polypeptide.

6. The method of claim 1, wherein the polypeptide is expressed from an exogenous, recombinant or isolated nucleic acid inside a cell, and wherein tryptophan or salt thereof is converted to monatin or salt thereof inside the cell.

7. The method of claim 2 wherein the method is performed in a single biocatalytic reactor.

8. The method of claim 7, further comprising providing an amino donor chosen from alanine, lysine, serine, glutamate, aspartate, cysteine, tryptophan, phenylalanine, glycine, aminopropane, methionine, tyrosine, ammonium formate, ammonium pyruvate, and a combination thereof in step(d).

9. The method of claim 7, wherein said C3 carbon source is pyruvate.

10. The method of claim 2 further comprising purifying said monatin or salt thereof.

11. The method of claim 2 where at least about 0.1 mg/mL of monatin or salt thereof is produced.

12. The method of claim 2, further comprising providing an amino acceptor chosen from pyruvate, oxaloacetate, alpha-ketoglutarate, allysine, phenylpyruvate, 3(4-hydroxyphenyl)pyruvate, glyoxylate, acetone, 4-methylthio-2-oxobutanoate, 2-hydroxy 2-(indol-3ylmethyl)-4-keto glutaric acid and a combination thereof in step (b).

13. The method of claim 2 wherein the C3 carbon source is chosen from pyruvate, alanine, serine, cysteine, aspartate, lactate, oxaloacetate, phosphoenolpyruvate, O-methyl-L-serine, O-benzyl-L-serine, S-methylcysteine, S-benzylcysteine, S-alkyl-L-cysteine, O-acyl-L-serine, and 3-chloro-L-alanine and a combination thereof.

14. The method of claim 13 wherein the pyruvate is produced by combining: (i) alanine with a polypeptide that performs transamination of alanine; (ii) serine with a polypeptide that performs beta-elimination of serine; (iii) cysteine with a polypeptide that preforms beta-elimination of cysteine; (iv) aspartate with a polypeptide that performs beta-lyase reactions with a dicarboxylic amino acid; (v) lactate with a lactate oxidase (EC 1.1.3.-); (vi) lactate dehydrogenase (EC 1.1.1.27, 1.1.1.28, 1.1.2.3);(vii) oxaloacetate with an oxaloacetate decarboxylase or (viii) a combination thereof.

15. The method of claim 13, wherein the pyruvate is produced by one or more polypeptides that perform beta-lyase reactions, wherein the one or more polypeptides are chosen from EC 4.1.99- polypeptides, β-tyrosinases, tryptophanases and a combination thereof.

16. The method of claim 2 wherein the first polypeptide, third polypeptide or both is/are chosen from an amino acid sequence shown in SEQ ID NOs: 2, 4, 6, 8, 10, 12, 14, 32, 96 and 97.

17. The method of claim 2 wherein the second polypeptide is an amino acid sequence chosen from SEQ ID NOs:66, 94 and 95.

18. A method of producing monatin or salt thereof, comprising, under conditions in which monatin is produced,
(a) providing tryptophan or salt thereof, a compound from which tryptophan can be produced in one or more steps, or a combination thereof;
(b) contacting tryptophan or salt thereof with a first polypeptide that facilitates converting tryptophan or salt thereof to indole-3 -pyruvate or salt thereof, wherein said first polypeptide is chosen from tryptophan aminotransferase (EC 2.6.1.27), tyrosine (aromatic) aminotransferase (EC 2.6.1.5), tryptophan dehydrogenase (EC 1.4.1.19), glutamate dehydrogenase (EC 1.4.1.2, 1.4.1.3, 1.4.1.4), phenylalanine dehydrogenase (EC 1.4.1.20), tryptophan-phenylpyruvate transaminase (EC 2.6.1.28), aspartate aminotransferase (EC 2.6.1.1), L-amino acid oxidase (EC 1.4.3.2), D-amino acid dehydrogenase (EC 1.4.99.1), D-amino acid oxidase (EC 1.4.3.3), D-amino acid (D-alanine) aminotransferase (EC 2.6.1.21), and a combination thereof;
(c) contacting said indole-3-pyruvate or salt thereof with a second polypeptide that facilitates converting indole-3-pyruvate or salt thereof and a C3 carbon source to 2-hydroxy 2-(indol-3ylmethyl)-4-keto glutaric acid or salt thereof, wherein said second polypeptide is chosen from 4-hydroxy-2-oxoglutarate glyoxylate-lyase (EC 4.1.3.1 6) and 4-hydroxy-4-methyl-2-oxoglutarate pyruvate-lyase (EC 4.1.3.17); and
(d) contacting said 2-hydroxy 2-(indol-3ylmethyl)-4-keto glutaric acid or salt thereof with a third polypeptide that facilitates converting 2-hydroxy 2-(indol-3ylmethyl)-4-keto glutaric acid or salt thereof to monatin or salt thereof, wherein said third polypeptide is chosen from tryptophan aminotransferase (EC 2.6.1.27), tyrosine (aromatic) aminotransferase (EC 2.6.1.5), tryptophan dehydrogenase (EC 1.4.1.19), aspartate aminotransferase (EC 2.6.1.1), glutamate dehydrogenase (EC 1.4.1.2-4), phenylalanine dehydrogenase (EC 1.4.1.20), D-amino acid dehydrogenase (EC1.4.99.1), D-amino acid (D-alanine) aminotransferase (EC 2.6.1.21), D-methionine-pyruvate aminotransferase (EC 2.6.1.41), and combinations thereof,
thereby producing monatin or salt thereof.

19. The method of claim 18, wherein at least one of said first, second or third polypeptide is chosen from purified polypeptides, polypeptides expressed from exogenous, recombinant or isolated nucleic acid, chemically synthesized polypeptides, and polypeptides in recombinant cells or recombinant cell extracts, and combinations thereof.

20. The method of claim 19, wherein at least one of said polypeptides is provided in an unpurified cell extract.

21. The method of claim 20, wherein the unpurified cell extract comprises a total soluble protein content, and wherein at least about 3000 of the total soluble protein content is recombinant polypeptide.

22. The method of claim 19, wherein the method is performed in a single biocatalytic reactor.

23. The method of claim 19 further comprising purifying said monatin or salt thereof.

24. The method of claim 19, where at least about 0.1 mg/mL of monatin or salt thereof is produced.

25. The method of claim 19, wherein the C3 carbon source is chosen from pyruvate, alanine, serine, cysteine, aspartate, lactate, oxaloacetate, phosphoenolpyruvate, O-methyl-L-serine, O-benzyl-L-serine, S-methylcysteine, S-benzylcysteine, S-alkyl-L-cysteine, O-acyl-L-serine, and 3 -chloro-L-alanine and a combination thereof.

26. The method of claim 19, further comprising providing an amino acceptor chosen from pyruvate, oxaloacetate, alpha-ketoglutarate, allysine, phenylpyruvate, 3 -(4-hydroxyphenyl) pyruvate, glyoxylate, acetone, 4-methylthio-2-oxobutanoate, 2-hydroxy 2-(indol-3ylmethyl)-4-keto glutaric acid and a combination thereof in step (b).

27. The method of claim 19, wherein the C3 carbon source is chosen from pyruvate, alanine, serine, cysteine, asparatate, lactate, oxaloacetate, exogenous, recombinant or isolated nucleic acid, chemically synthesized polypeptides, and polypeptides in recombinant cells or recombinant cell extracts, and combinations thereof.

28. The method of claim 27, wherein the pyruvate is produced by combining: (i) alanine with a polypeptide that performs transamination of alanine; (ii) serine with a polypeptide that performs beta-elimination of serine; (iii) cysteine with a polypeptide that performs beta-elimination of cysteine; (iv) aspartate with a polypeptide that performs beta-lyase reactions with a dicarboxylic amino acid; (v) lactate with a lactate oxidase (EC 1.1.3.-); (vi) lactate with a lactate dehydrogenase (EC 1.1.1.27, 1.1.1.28, 1.1.2.3); (vii) oxaloacetate with an oxaloacetate decarboxylase or (viii) a combination thereof.

29. The method of claim 27, wherein the pyruvate is produced by one or more polypeptides that perform beta-lyase reactions, wherein the one or more polypeptides are chosen from EC 4.1.99- polypeptides, β-tyrosinases, tryptophanases and a combination thereof.

30. The method of claim 19, further comprising providing an amino donor chosen from alanine, lysine, serine, glutamate, aspartate, cysteine, tryptophan, phenylalanine, glycine, aminopropane, methionine, tyrosine, ammonium formate, ammonium pyruvate, and a combination thereof in step of(d).

31. The method of claim 19, wherein said C3 carbon source is pyruvate.

32. The method of claim 18, wherein the first polypeptide, third polypeptide or both is/are chosen from an amino acid sequence shown in SEQ ID NOs: 2, 4, 6, 8, 10, 12, 14, 32, 96 and 97

33. The method of claim 18, wherein the second polypeptide is an amino acid sequence chosen from SEQ ID NOs: 66, 94 and 95.

34. A method of producing monatin or salt thereof, comprising:
(a) providing tryptophan or salt thereof, indole-3-lactic acid or salt thereof, a compound from which tryptophan, indole-3-lactic acid or a combination thereof can be produced in one or more steps, or a combination thereof;
(b) contacting the tryptophan or salt thereof, indole-3-lactic acid or salt thereof, or combinations thereof with a first polypeptide that facilitates converting tryptophan or salt thereof, indole-3-lactic acid or salt thereof, or a combination thereof to indole-3-pyruvate or salt thereof, wherein said first polypeptide is chosen from tryptophan aminotransferase (EC 2.6.1.27), tyrosine (aromatic) aminotransferase (EC 2.6.1.5), tryptophan dehydrogenase (EC 1.4.1.19), glutamate dehydrogenase (EC 1.4.1.2, 1.4.1.3, 1.4.1.4), phenylalanine dehydrogenase (EC 1.4.1.20), tryptophan-phenylpyruvate transaminase (EC 2.6.1.28), aspartate aminotransferase (EC 2.6.1.1), L-amino acid oxidase (EC 1.4.3.2), D-amino acid dehydrogenase (EC 1.4.99.1), D-amino acid oxidase (EC 1.4.3.3), D-amino acid (D-alanine) aminotransferase (EC 2.6.1.21), and combinations thereof;

(c) chemically reacting said indole-3-pyruvate or salt thereof and a C3 carbon source under conditions in which an aldol condensation occurs to produce 2-hydroxy 2-(indol-3ylmethyl)-4-keto glutaric acid or salt thereof;

(d) purifying said 2-hydroxy 2-(indol-3ylmethyl)-4-keto glutaric acid or salt thereof; and (e) contacting said purified 2-hydroxy 2-(indol-3ylmethyl)-4-keto glutaric acid or salt thereof with a second polypeptide that facilitates converting 2-hydroxy 2-(indol-3ylmethyl)-4-keto glutaric acid or salt thereof to monatin or salt thereof, wherein said third polypeptide is chosen from tryptophan aminotransferase (EC 2.6.1.27), tyrosine (aromatic) aminotransferase (EC 2.6.1.5), tryptophan dehydrogenase (EC 1.4.1.19), aspartate aminotransferase (EC 2.6.1.1), glutamate dehydrogenase (EC 1.4.1.2-4), phenylalanine dehydrogenase (EC 1.4.1.20), D-amino acid dehydrogenase (EC1.4.99.1), D-amino acid (D-alanine) aminotransferase (EC 2.6.1.21), D-methionine-pyruvate aminotransferase (2.6.1.41), and combinations thereof, thereby producing monatin or salt thereof.

35. The method of claim 34, wherein at least one of said first or second polypeptide is chosen from purified polypeptides, polypeptides expressed from exogenous, recombinant or isolated nucleic acid, chemically synthesized polypeptides, and polypeptides in recombinant cells or recombinant cell extracts, and combinations thereof.

36. The method of claim 34, wherein the reacting step in step (c) is performed in the presence of a strong base chosen from lithium diisopropylamide, lithium hexamethyldisilazane and butyl lithium.

37. The method of claim 34, further comprising purifying said monatin or salt thereof.

38. The method of claim 34, where at least about 0.1 mg/mL of monatin or salt thereof is produced.

39. The method of claim 34, wherein said C3 carbon source is pyruvate.

40. The method of claim 34, further comprising providing an amino donor chosen from alanine, lysine, seine, glutamate, aspartate, cysteine, tryptophan, phenylalanine, glycine, aminopropane, methionine, tyrosine, ammonium formate, ammonium pyruvate, and a combination thereof in step (e).

41. The method of claim 34, further comprising purifying said indole-3-pyruvate or salt thereof prior to said reacting in step (c).

42. A method of producing monatin or salt thereof, comprising:
   (a) providing tryptophan or salt thereof, a compound from which tryptophan can be produced in one or more steps, or a combination thereof;
   (b) contacting the tryptophan or salt thereof with a first polypeptide that facilitates converting tryptophan to indole-3-pyruvate or salt thereof, wherein said first polypeptide is chosen from an AspC aminotransferase (EC 2.6.1.1) and a D-alanine aminotransferase (EC 2.6.1.21);
   (c) contacting said indole-3-pyruvate or salt thereof with a second polypeptide that facilitates converting indole-3-pyruvate or salt thereof and a C3 carbon source to 2-hydroxy 2-(indol-3ylmethyl)-4-keto glutaric acid or salt thereof, wherein said second polypeptide is a ProA aldolase (EC 4.1.3.17); and
   (d) contacting said 2-hydroxy 2-(indol-3ylmethyl)-4-keto glutaric acid or salt thereof with a third polypeptide that facilitates converting 2-hydroxy 2-(indol-3ylmethyl)-4-keto glutaric acid or salt thereof to monatin or salt thereof, wherein said third polypeptide is chosen from an AspC aminotransferase (EC 2.6.1.1) and a D-alanine aminotransferase (EC 2.6.1.21),
thereby producing monatin or salt thereof.

43. The method of claim 42, wherein at least one of said first, second or third polypeptide is chosen from purified polypeptides, polypeptides expressed from exogenous, recombinant or isolated nucleic acid, chemically synthesized polypeptides, and polypeptides in recombinant cells or recombinant cell extracts, and combinations thereof.

44. The method of claim 43, further comprising purifying said monatin or salt thereof.

45. The method of claim 18, wherein the first polypeptide, third polypeptide or both is/are chosen from an amino acid sequence shown in SEQ ID NOs: 2, 4, 6, 8, 10, 12, 14, 32, 96 and 97.

* * * * *

UNITED STATES PATENT AND TRADEMARK OFFICE
CERTIFICATE OF CORRECTION

PATENT NO. : 7,572,607 B2
APPLICATION NO. : 11/114922
DATED : August 11, 2009
INVENTOR(S) : Paula M. Hicks et al.

It is certified that error appears in the above-identified patent and that said Letters Patent is hereby corrected as shown below:

In column 38, line 62, delete "DNAn" and insert -- DNA --, therefor.

In column 63, line 66, delete "verfied" and insert -- verified --, therefor.

In column 63, line 66-67, delete "dervitization" and insert -- derivitization --, therefor.

In column 84, line 65, delete "fingi" and insert -- fungi --, therefor.

In column 89, line 29, delete "419" and insert -- 304 --, therefor.

In column 93, line 18, delete "419" and insert -- 304 --, therefor.

In column 97, line 14, delete "Gln" and insert -- Gly --, therefor.

In column 97, line 24, delete "Gln" and insert -- Gly --, therefor.

In column 99, line 5, delete "Gln" and insert -- Gly --, therefor.

In column 99, line 11, delete "Glu" and insert -- Gly --, therefor.

In column 147, line 52, in Claim 2, after "thereof" insert -- ; --.

In column 147, lines 58-59, in Claim 2, delete "(EC 4.1.3.1 6)" and insert -- (EC 4.1.3.16) --, therefor.

In column 148, line 30, in Claim 6, delete "claim 1," and insert -- claim 2, --, therefor.

In column 148, line 34, in Claim 7, after "claim 2" insert -- , --.

In column 148, line 44, in Claim 10, after "claim 2" insert -- , --.

In column 148, line 46, in Claim 11, after "claim 2" insert -- , --.

In column 148, line 50, in Claim 12, delete "3(4-hydroxyphenyl)" and insert -- 3-(4-hydroxyphenyl) --, therefor.

In column 148, line 64, in Claim 14, delete "preforms" and insert -- performs --, therefor.

In column 148, line 67, in Claim 14, insert -- with a lactate -- before "dehydrogenase".

In column 149, line 9, in Claim 16, after "claim 2" insert -- , --.

In column 149, line 13, in Claim 17, after "claim 2" insert -- , --.

In column 149, lines 41-42, in Claim 18, delete "(EC 4.1.3.1 6)" and insert -- (EC 4.1.3.16) --, therefor.

In column 150, line 3, in Claim 21, delete "3000" and insert -- 30% --, therefor.

In column 150, lines 5-6, in Claim 22, delete "The method of claim 19, wherein the method is performed in a single biocatalytic reactor." and insert -- The method of claim 19, wherein the polypeptide is expressed from an exogenous, recombinant or isolated nucleic acid inside a cell, and wherein tryptophan is converted to monatin or salt thereof inside the cell. --, therefor.

In column 150, lines 7-8, in Claim 23, delete "The method of claim 19 further comprising purifying said monatin or salt thereof." and insert -- The method of claim 19, wherein the method is performed in a single biocatalytic reactor. --, therefor.

In column 150, lines 9-10, in Claim 24, delete "The method of claim 19, where at least about 0.1 mg/mL of monatin or salt thereof is produced." and insert -- The method of claim 19, further comprising purifying said monatin or salt thereof. --, therefor.

In column 150, lines 11-16, in Claim 25, delete "The method of claim 19, wherein the C3 carbon source is chosen from pyruvate, alanine, serine, cysteine, aspartate, lactate, oxaloacetate, phosphoenolpyruvate, O-methyl-L-serine, O-benzyl-L-serine, S-methylcysteine, S-benzylcysteine, S-alkyl-L-cysteine, O-acyl-L-serine, and 3 -chloro-L-alanine and a combination thereof." and insert -- The method of claim 19, where at least about 0.1 mg/mL of monatin or salt thereof is produced. --, therefor.

In column 150, lines 23-28, in Claim 27, delete "The method of claim 19, wherein the C3 carbon source is chosen from pyruvate, alanine, serine, cysteine, asparatate, lactate, oxaloacetate, exogenous, recombinant or isolated nucleic acid, chemically synthesized polypeptides, and polypeptides in recombinant cells or recombinant cell extracts, and combinations thereof." and insert -- The method of claim 19, wherein the C3 carbon source is chosen from pyruvate, alanine, serine, cysteine, aspartate, lactate, oxaloacetate, phosphoenolpyruvate, O-methyl-L-serine, O-benzyl-L-serine, S-methylcysteine, S-benzylcysteine, S-alkyl-L-cysteine, O-acyl-L-serine, and 3-chloro-L-alanine and a combination thereof. --, therefor.

CERTIFICATE OF CORRECTION (continued)
U.S. Pat. No. 7,572,607 B2

In column 151, line 29, in Claim 34, delete "trvptophan" and insert -- tryptophan --, therefor.

In column 152, line 4, in Claim 40, delete "seine" and insert -- serine --, therefor.

In column 152, lines 45-48, in Claim 45, delete "The method of claim 18, wherein the first polypeptide, third polypeptide or both is/are chosen from an amino acid sequence shown in SEQ ID NOs: 2, 4, 6, 8, 10, 12, 14, 32, 96 and 97." and insert -- The method of claim 42, wherein said AspC aminotransferase has the sequence shown in SEQ ID NO: 97, wherein said D-alanine aminotransferase has the sequence shown in SEQ ID NO: 96, wherein said ProA aldolase has the sequence shown in SEQ ID NO:66. --, therefor.

Signed and Sealed this

Sixteenth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,572,607 B2  Page 1 of 1
APPLICATION NO. : 11/114922
DATED : August 11, 2009
INVENTOR(S) : Hicks et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 618 days.

Signed and Sealed this

Seventh Day of September, 2010

David J. Kappos
*Director of the United States Patent and Trademark Office*

SEQUENCE LISTING

```
<160> NUMBER OF SEQ ID NOS: 91

<210> SEQ ID NO 1
<211> LENGTH: 1170
<212> TYPE: DNA
<213> ORGANISM: Sinorhizobium meliloti

<400> SEQUENCE: 1
atgttcgacg ccctcgcccg ccaagccgac gatcccttgc ttttcctgat cggcctgttc      60
aggaaggatg agcgccccgg aaaggtcgat ctcggcgtag gagtctatcg cgacgagacc     120
ggacgcacgc cgatcttccg ggccgtcaag gcggcggaaa agcggcttct cgaaacacag     180
gacagcaagg cctatatcgg ccccgaaggg gacctcgtct ttctcgatcg gctctgggaa     240
ctcgtcggcg gcgacacgat cgagcggagc catgttgcgg gcgtccagac gcccggcggc     300
tccggcgcgc tccgtttggc ggcggacctc atcgcccgca tgggcggccg aggcatctgg     360
ctcgggctgc cgagctggcc gaaccacgcg ccgatcttca aggcggccgg gctcgatatc     420
gccacctacg acttcttcga cattccgtcg cagtcggtca tcttcgataa tctggtgagc     480
gcgctggaag gcgccgcatc cggcgatgcg gtgctgctgc atgcaagctg ccacaacccg     540
accggcggcg tcctgagcga agcacaatgg atggagatcg ccgcgctggt ggccgagcgc     600
ggcctgctgc cgctcgtcga tctcgcctat caggggttcg gccgcggcct cgaccaggat     660
gtcgcgggcc tccggcatct tctcggcgtg gtcccggaag cgctcgtcgc ggtttcctgc     720
tcgaagtcct tcgggcttta tcgcgagcgc gcgggcgcga tcttcgcgcg gaccagctcg     780
actgcctcgg cggacagggt gcgctcaaac ctcgcgggcc tcgcacgcac cagctattcc     840
atgccgccgg atcacggcgc agccgtcgtg cggacgatcg ttgacgaccc ggaactcagg     900
cgcgactgga cggaggagct cgagacgatg cggctcagga tgacgggcct ccggcggtcg     960
cttgccgagg gactccgcac ccgctggcag agcctcggcg cagtcgccga tcaggagggc    1020
atgttctcca tgctgccgct ttccgaagcg gaggttatgc ggctcaggac cgagcacggc    1080
atctatatgc cggcatccgg ccgcatcaac atcgccgggc tgaagacggc ggaagccgcc    1140
gagattgccg gcaagttcac cagtctctga                                     1170

<210> SEQ ID NO 2
```

```
<211> LENGTH: 389
<212> TYPE: PRT
<213> ORGANISM: Sinorhizobium meliloti

<400> SEQUENCE: 2

Met Phe Asp Ala Leu Ala Arg Gln Ala Asp Pro Leu Leu Phe Leu
  1               5                  10                  15

Ile Gly Leu Phe Arg Lys Asp Glu Arg Pro Gly Lys Val Asp Leu Gly
                 20                  25                  30

Val Gly Val Tyr Arg Asp Glu Thr Gly Arg Thr Pro Ile Phe Arg Ala
             35                  40                  45

Val Lys Ala Ala Glu Lys Arg Leu Leu Glu Thr Gln Asp Ser Lys Ala
 50                  55                  60

Tyr Ile Gly Pro Glu Gly Asp Leu Val Phe Leu Asp Arg Leu Trp Glu
 65                  70                  75                  80

Leu Val Gly Gly Asp Thr Ile Glu Arg Ser His Val Ala Gly Val Gln
                 85                  90                  95

Thr Pro Gly Gly Ser Gly Ala Leu Arg Leu Ala Ala Asp Leu Ile Ala
            100                 105                 110

Arg Met Gly Gly Arg Gly Ile Trp Leu Gly Leu Pro Ser Trp Pro Asn
            115                 120                 125

His Ala Pro Ile Phe Lys Ala Ala Gly Leu Asp Ile Ala Thr Tyr Asp
        130                 135                 140

Phe Phe Asp Ile Pro Ser Gln Ser Val Ile Phe Asp Asn Leu Val Ser
145                 150                 155                 160

Ala Leu Glu Gly Ala Ala Ser Gly Asp Ala Val Leu Leu His Ala Ser
                165                 170                 175

Cys His Asn Pro Thr Gly Gly Val Leu Ser Glu Ala Gln Trp Met Glu
            180                 185                 190

Ile Ala Ala Leu Val Ala Glu Arg Gly Leu Leu Pro Leu Val Asp Leu
        195                 200                 205

Ala Tyr Gln Gly Phe Gly Arg Gly Leu Asp Gln Asp Val Ala Gly Leu
    210                 215                 220

Arg His Leu Leu Gly Val Val Pro Glu Ala Leu Val Ala Val Ser Cys
225                 230                 235                 240

Ser Lys Ser Phe Gly Leu Tyr Arg Glu Arg Ala Gly Ala Ile Phe Ala
                245                 250                 255

Arg Thr Ser Ser Thr Ala Ser Ala Asp Arg Val Arg Ser Asn Leu Ala
            260                 265                 270

Gly Leu Ala Arg Thr Ser Tyr Ser Met Pro Pro Asp His Gly Ala Ala
        275                 280                 285

Val Val Arg Thr Ile Leu Asp Asp Pro Glu Leu Arg Arg Asp Trp Thr
    290                 295                 300

Glu Glu Leu Glu Thr Met Arg Leu Arg Met Thr Gly Leu Arg Arg Ser
305                 310                 315                 320

Leu Ala Glu Gly Leu Arg Thr Arg Trp Gln Ser Leu Gly Ala Val Ala
                325                 330                 335

Asp Gln Glu Gly Met Phe Ser Met Leu Pro Leu Ser Glu Ala Glu Val
            340                 345                 350

Met Arg Leu Arg Thr Glu His Gly Ile Tyr Met Pro Ala Ser Gly Arg
        355                 360                 365

Ile Asn Ile Ala Gly Leu Lys Thr Ala Glu Ala Ala Glu Ile Ala Gly
    370                 375                 380

Lys Phe Thr Ser Leu
```

<210> SEQ ID NO 3
<211> LENGTH: 1260
<212> TYPE: DNA
<213> ORGANISM: Rhodobacter sphaeroides

<400> SEQUENCE: 3

```
atgcgctcta cgacggctcc tggtccgagt ggggcatgta tgacgatctc aaggtcgcga      60
aaggatgacg aaggaatgct gaccgccctg aagccgcagc ccgcggacaa gatcctgcaa     120
ctgatccaga tgttccgcga ggatgcgcgc gcggacaaga tcgatctggg cgtgggcgtc     180
tacaaggacc cgaccgggct caccccggtc atgcgggccg tgaaggcggc cgagaagcgg     240
ctctgggagg tcgagaccac caagacctac accggccttg ccgacgagcc ggcctacaat     300
gccgcgatgg cgaagctgat cctcgcgggc gcggtcccgg ccgaccgggt ggcctcggtc     360
gccaccccg gcggcacggg cgcggtgcgt caggcgctcg agctgatccg catggcctcg     420
cccgaggcca ccgtctggat ctcgaacccg acctggccga accatctgtc gatcgtgaaa     480
tatctcggca tcccgatgcg ggaataccgc tatttcgacg ccgagaccgg cgccgtcgat     540
gccgagggca tgatggagga tctggcccag gtgaaggcgg cgacgtggt gctgctgcac     600
ggctgctgcc acaacccgac cggcgccaac ccgaacccgg tgcagtggct ggccatctgc     660
gagagcctgg cccggacagg cgcggtgccg ctgatcgacc tcgcctatca gggcttcggc     720
gacgggctcg agatggatgc ggcggcgacg cggcttctgg ccaccagact gcccgaggtg     780
ctgatcgcgg cctcctgctc gaagaacttc ggcatctacc gcgagcgcac gggcatcctg     840
atcgccatcg gcgaggcggc gggccggggc acggtgcagg ccaacctcaa cttcctgaac     900
cggcagaact actccttccc gccggaccat ggcgcgcggc tcgtgaccat gatcctcgag     960
gacgagacgc tgagcgccga ctggaaggcg gaactcgagg aggtgcggct caacatgctg    1020
acactgcgcc gccagcttgc cgatgcgctg caggccgaga ccggctcgaa ccgcttcggc    1080
ttcgtggccg agcatcgcgg catgttctcg cgcctcggga tcacgcccgc cgaggtggag    1140
cggctgcgga ccgagcacgg ggtctacatg gtgggcgatt cgcggctgaa catcgcgggg    1200
ctgaaccgga cgaccgtgcc ggtgctggcg cgcgcggtgg ccaaggtgct gcgcggctga    1260
```

<210> SEQ ID NO 4
<211> LENGTH: 419
<212> TYPE: PRT
<213> ORGANISM: Rhodobacter sphaeroides

<400> SEQUENCE: 4

Met Arg Ser Thr Thr Ala Pro Gly Pro Ser Gly Ala Cys Met Thr Ile
1               5                   10                  15

Ser Arg Ser Arg Lys Asp Asp Glu Gly Met Leu Thr Ala Leu Lys Pro
            20                  25                  30

Gln Pro Ala Asp Lys Ile Leu Gln Leu Ile Gln Met Phe Arg Glu Asp
        35                  40                  45

Ala Arg Ala Asp Lys Ile Asp Leu Gly Val Gly Val Tyr Lys Asp Pro
    50                  55                  60

Thr Gly Leu Thr Pro Val Met Arg Ala Val Lys Ala Ala Glu Lys Arg
65                  70                  75                  80

Leu Trp Glu Val Glu Thr Thr Lys Thr Tyr Thr Gly Leu Ala Asp Glu
                85                  90                  95

Pro Ala Tyr Asn Ala Ala Met Ala Lys Leu Ile Leu Ala Gly Ala Val

```
            100                 105                 110
Pro Ala Asp Arg Val Ala Ser Val Ala Thr Pro Gly Gly Thr Gly Ala
        115                 120                 125

Val Arg Gln Ala Leu Glu Leu Ile Arg Met Ala Ser Pro Glu Ala Thr
    130                 135                 140

Val Trp Ile Ser Asn Pro Thr Trp Pro Asn His Leu Ser Ile Val Lys
145                 150                 155                 160

Tyr Leu Gly Ile Pro Met Arg Glu Tyr Arg Tyr Phe Asp Ala Glu Thr
                165                 170                 175

Gly Ala Val Asp Ala Glu Gly Met Met Glu Asp Leu Ala Gln Val Lys
            180                 185                 190

Ala Gly Asp Val Val Leu Leu His Gly Cys Cys His Asn Pro Thr Gly
        195                 200                 205

Ala Asn Pro Asn Pro Val Gln Trp Leu Ala Ile Cys Glu Ser Leu Ala
    210                 215                 220

Arg Thr Gly Ala Val Pro Leu Ile Asp Leu Ala Tyr Gln Gly Phe Gly
225                 230                 235                 240

Asp Gly Leu Glu Met Asp Ala Ala Ala Thr Arg Leu Leu Ala Thr Arg
                245                 250                 255

Leu Pro Glu Val Leu Ile Ala Ala Ser Cys Ser Lys Asn Phe Gly Ile
            260                 265                 270

Tyr Arg Glu Arg Thr Gly Ile Leu Ile Ala Ile Gly Glu Ala Ala Gly
        275                 280                 285

Arg Gly Thr Val Gln Ala Asn Leu Asn Phe Leu Asn Arg Gln Asn Tyr
    290                 295                 300

Ser Phe Pro Pro Asp His Gly Ala Arg Leu Val Thr Met Ile Leu Glu
305                 310                 315                 320

Asp Glu Thr Leu Ser Ala Asp Trp Lys Ala Glu Leu Glu Glu Val Arg
                325                 330                 335

Leu Asn Met Leu Thr Leu Arg Arg Gln Leu Ala Asp Ala Leu Gln Ala
            340                 345                 350

Glu Thr Gly Ser Asn Arg Phe Gly Phe Val Ala Glu His Arg Gly Met
        355                 360                 365

Phe Ser Arg Leu Gly Ile Thr Pro Ala Glu Val Glu Arg Leu Arg Thr
    370                 375                 380

Glu His Gly Val Tyr Met Val Gly Asp Ser Arg Leu Asn Ile Ala Gly
385                 390                 395                 400

Leu Asn Arg Thr Thr Val Pro Leu Ala Arg Ala Val Ala Lys Val
                405                 410                 415

Leu Arg Gly

<210> SEQ ID NO 5
<211> LENGTH: 1260
<212> TYPE: DNA
<213> ORGANISM: Rhodobacter sphaeroides

<400> SEQUENCE: 5
atgcgctcta cgacggctcc tggtccgagt ggggcatgta tgacgatctc aaggtcgcga      60
aaggatgacg aaggaatgct gaccgccctg aagccgcagc ccgcggacaa gatcctgcaa     120
ctgatccaga tgttccgcga ggatgcgcgc gcggacaaga tcgatctggg cgtgggcgtc     180
tacaaggacc cgaccgggct caccccggtc atgcgggccg tgaaggccgc cgagaagcgg     240
ctctggggag tcgagaccac caagacctac accggccttg ccggcgagcc cgcctacaat     300
```

```
gccgcgatgg cgaagctgat cctcgcaggc gcggtcccgg ccgaccgggt ggcctcggtc    360 gccaccccg gcggcacggg cgcggtgcgt caggcgctcg agctgatccg catggcctcg    420
cccgaggcca ctgtctggat ctcgaacccg acctggccga accatctgtc gatcgtgaaa    480
tatctcggca tcccgatgcg ggaataccgc tatttcgacg ccgagaccgg cgccgtcgat    540
gccgagggct tgatggagga tctggcccag gtgaaggcgg cgacgtggt gctgctgcac     600 ggctgctgcc acaacccgac cggcgccaac ccgaacccgg tgcagtggct ggccgtctgc    660
gagagcctgg cccggacagg cgcggtgccg ctgatcgacc tcgcctatca gggcttcggc    720
gacgggctcg agatggatgc ggcggcgacg cggcttctgg ccaccagact gcccgaggtg    780
ctgatcgcgg cctcctgctc gaagaacttc ggcatctacc gcgagcgaac gggcatcctg    840
atcgccatcg gcgaggcggc gggccggggc acggtgcagg ccaacctcaa cttcctgaac    900
cggcagaact actccttccc gccggaccat ggcgcgcggc tcgtgaccat gatcctcgag    960
gacgagacgc tgagcgccga ctggaaggcg gaactcgagg aggtgcggct caacatgctg   1020
acgctgcgcc gccagcttgc cgatgcgctg caggccgaga ccggctcgaa ccgcttcggc   1080
ttcgtggccg agcatcgcgg catgttctcg cgcctcggga tcacgcccgc cgaggtggag   1140
cggctgcgga ccgagcacgg ggtctacatg gtgggcgatt cgcggctgaa catcgcgggg   1200
ctgaaccgga cgaccgtgcc ggtgctggcg cgcgcggtgg ccaaggtgct gcgcggctga   1260
```

<210> SEQ ID NO 6
<211> LENGTH: 419
<212> TYPE: PRT
<213> ORGANISM: Rhodobacter sphaeroides

<400> SEQUENCE: 6

```
Met Arg Ser Thr Thr Ala Pro Gly Pro Ser Gly Ala Cys Met Thr Ile
 1               5                  10                  15

Ser Arg Ser Arg Lys Asp Asp Glu Gly Met Leu Thr Ala Leu Lys Pro
            20                  25                  30

Gln Pro Ala Asp Lys Ile Leu Gln Leu Ile Gln Met Phe Arg Glu Asp
        35                  40                  45

Ala Arg Ala Asp Lys Ile Asp Leu Gly Val Gly Val Tyr Lys Asp Pro
    50                  55                  60

Thr Gly Leu Thr Pro Val Met Arg Ala Val Lys Ala Ala Glu Lys Arg
65                  70                  75                  80

Leu Trp Glu Val Glu Thr Thr Lys Thr Tyr Thr Gly Leu Ala Gly Glu
                85                  90                  95

Pro Ala Tyr Asn Ala Ala Met Ala Lys Leu Ile Leu Ala Gly Ala Val
            100                 105                 110

Pro Ala Asp Arg Val Ala Ser Val Ala Thr Pro Gly Gly Thr Gly Ala
        115                 120                 125

Val Arg Gln Ala Leu Glu Leu Ile Arg Met Ala Ser Pro Glu Ala Thr
    130                 135                 140

Val Trp Ile Ser Asn Pro Thr Trp Pro Asn His Leu Ser Ile Val Lys
145                 150                 155                 160

Tyr Leu Gly Ile Pro Met Arg Glu Tyr Arg Tyr Phe Asp Ala Glu Thr
                165                 170                 175

Gly Ala Val Asp Ala Glu Gly Leu Met Glu Asp Leu Ala Gln Val Lys
            180                 185                 190

Ala Gly Asp Val Val Leu Leu His Gly Cys Cys His Asn Pro Thr Gly
        195                 200                 205
```

-continued

```
Ala Asn Pro Asn Pro Val Gln Trp Leu Ala Val Cys Glu Ser Leu Ala
    210                 215                 220
Arg Thr Gly Ala Val Pro Leu Ile Asp Leu Ala Tyr Gln Gly Phe Gly
225                 230                 235                 240
Asp Gly Leu Glu Met Asp Ala Ala Ala Thr Arg Leu Leu Ala Thr Arg
                245                 250                 255
Leu Pro Glu Val Leu Ile Ala Ala Ser Cys Ser Lys Asn Phe Gly Ile
            260                 265                 270
Tyr Arg Glu Arg Thr Gly Ile Leu Ile Ala Ile Gly Glu Ala Ala Gly
        275                 280                 285
Arg Gly Thr Val Gln Ala Asn Leu Asn Phe Leu Asn Arg Gln Asn Tyr
    290                 295                 300
Ser Phe Pro Pro Asp His Gly Ala Arg Leu Val Thr Met Ile Leu Glu
305                 310                 315                 320
Asp Glu Thr Leu Ser Ala Asp Trp Lys Ala Glu Leu Glu Glu Val Arg
                325                 330                 335
Leu Asn Met Leu Thr Leu Arg Arg Gln Leu Ala Asp Ala Leu Gln Ala
            340                 345                 350
Glu Thr Gly Ser Asn Arg Phe Gly Phe Val Ala Glu His Arg Gly Met
        355                 360                 365
Phe Ser Arg Leu Gly Ile Thr Pro Ala Glu Val Glu Arg Leu Arg Thr
370                 375                 380
Glu His Gly Val Tyr Met Val Gly Asp Ser Arg Leu Asn Ile Ala Gly
385                 390                 395                 400
Leu Asn Arg Thr Thr Val Pro Val Leu Ala Arg Ala Val Ala Lys Val
                405                 410                 415
Leu Arg Gly
```

<210> SEQ ID NO 7
<211> LENGTH: 1239
<212> TYPE: DNA
<213> ORGANISM: Leishmania major

<400> SEQUENCE: 7

| | | |
|---|---|---|
| atgtccatgc aggcggccat gaccacggcg gagcgctggc agaagattca ggcacaagct | 60 |
| cccgatgtca tcttcgatct cgcaaaacgc gccgccgctg ccaagggccc caaggccaac | 120 |
| ctcgtcattg gtgcctaccg cgacgagcag ggccgtccct atccgctacg cgtggtccgc | 180 |
| aaggctgagc agcttctctt ggacatgaat ctcgactacg agtacctacc catctcgggc | 240 |
| taccagccct tcatcgatga ggcggtaaag attatctacg gcaataccgt cgagctggag | 300 |
| aacctggttg cggtgcagac gctgagcggg accggtgctg tctctctcgg ggcgaagctg | 360 |
| ctgactcgcg tcttcgacgc tgagacgacg cccatctacc tttccgaccc cacgtggccc | 420 |
| aaccactacg gcgtcgtgaa ggctgctggc tggaagaaca tctgcacgta cgcctactac | 480 |
| gaccccaaga cggtcagcct gaatttcgag ggcatgaaga agacattct ggcggcgccg | 540 |
| gacggctccg tgttcattct gcaccagtgc gcgcacaacc ccaccggcgt ggacccgtcg | 600 |
| caggagcagt ggaacgagat cgcgtcactg atgctggcca agcaccatca ggtgttcttc | 660 |
| gactccgcct accaaggcta tgcgagcggc agcctcgaca cggacgcgta tgctgccccgc | 720 |
| ctgtttgccc gccgcggcat cgaggtactg ctggcgcagt cgttctccaa gaacatgggc | 780 |
| ttgtacagcg agcgtgcagg cacgctgtcg ctgctcctca aggacaagac gaagcgcgcg | 840 |
| gatgtaaaga gcgtgatgga ttcgctgatc cgtgaggagt acacgtgccc ccagcccac | 900 |

-continued

```
ggtgcccgct tagcccacct aatcctgagc aacaacgaac tgcgaaagga gtgggaggca      960
gagctatcag ccatggcaga gcgcatccgt acgatgcgcc gcaccgtgta cgacgagctc     1020
ctgcgcctgc agacgcccgg gagctgggaa catgtcatta accagattgg catgttttcc     1080
ttcctcgggc tgtcaaaggc gcagtgcgaa tactgccaaa accacaacat cttcatcaca     1140
gtgtcgggcc gcgctaacat ggcaggtctg acgcatgaga cggcgctgat gctagcacag     1200
acgatcaacg atgctgtgcg caatgtgaat cgtgagtga                            1239
```

<210> SEQ ID NO 8
<211> LENGTH: 412
<212> TYPE: PRT
<213> ORGANISM: Leishmania major

<400> SEQUENCE: 8

```
Met Ser Met Gln Ala Ala Met Thr Thr Ala Glu Arg Trp Gln Lys Ile
  1               5                  10                  15

Gln Ala Gln Ala Pro Asp Val Ile Phe Asp Leu Ala Lys Arg Ala Ala
             20                  25                  30

Ala Ala Lys Gly Pro Lys Ala Asn Leu Val Ile Gly Ala Tyr Arg Asp
         35                  40                  45

Glu Gln Gly Arg Pro Tyr Pro Leu Arg Val Val Arg Lys Ala Glu Gln
     50                  55                  60

Leu Leu Leu Asp Met Asn Leu Asp Tyr Glu Tyr Leu Pro Ile Ser Gly
 65                  70                  75                  80

Tyr Gln Pro Phe Ile Asp Glu Ala Val Lys Ile Ile Tyr Gly Asn Thr
                 85                  90                  95

Val Glu Leu Glu Asn Leu Val Ala Val Gln Thr Leu Ser Gly Thr Gly
            100                 105                 110

Ala Val Ser Leu Gly Ala Lys Leu Leu Thr Arg Val Phe Asp Ala Glu
        115                 120                 125

Thr Thr Pro Ile Tyr Leu Ser Asp Pro Thr Trp Pro Asn His Tyr Gly
    130                 135                 140

Val Val Lys Ala Ala Gly Trp Lys Asn Ile Cys Thr Tyr Ala Tyr Tyr
145                 150                 155                 160

Asp Pro Lys Thr Val Ser Leu Asn Phe Glu Gly Met Lys Lys Asp Ile
                165                 170                 175

Leu Ala Ala Pro Asp Gly Ser Val Phe Ile Leu His Gln Cys Ala His
            180                 185                 190

Asn Pro Thr Gly Val Asp Pro Ser Gln Glu Gln Trp Asn Glu Ile Ala
        195                 200                 205

Ser Leu Met Leu Ala Lys His His Gln Val Phe Phe Asp Ser Ala Tyr
    210                 215                 220

Gln Gly Tyr Ala Ser Gly Ser Leu Asp Thr Asp Ala Tyr Ala Ala Arg
225                 230                 235                 240

Leu Phe Ala Arg Arg Gly Ile Glu Val Leu Leu Ala Gln Ser Phe Ser
                245                 250                 255

Lys Asn Met Gly Leu Tyr Ser Glu Arg Ala Gly Thr Leu Ser Leu Leu
            260                 265                 270

Leu Lys Asp Lys Thr Lys Arg Ala Asp Val Lys Ser Val Met Asp Ser
        275                 280                 285

Leu Ile Arg Glu Glu Tyr Thr Cys Pro Pro Ala His Gly Ala Arg Leu
    290                 295                 300

Ala His Leu Ile Leu Ser Asn Asn Glu Leu Arg Lys Glu Trp Glu Ala
305                 310                 315                 320
```

Glu Leu Ser Ala Met Ala Glu Arg Ile Arg Thr Met Arg Arg Thr Val
                325                 330                 335

Tyr Asp Glu Leu Leu Arg Leu Gln Thr Pro Gly Ser Trp Glu His Val
            340                 345                 350

Ile Asn Gln Ile Gly Met Phe Ser Phe Leu Gly Leu Ser Lys Ala Gln
        355                 360                 365

Cys Glu Tyr Cys Gln Asn His Asn Ile Phe Ile Thr Val Ser Gly Arg
    370                 375                 380

Ala Asn Met Ala Gly Leu Thr His Glu Thr Ala Leu Met Leu Ala Gln
385                 390                 395                 400

Thr Ile Asn Asp Ala Val Arg Asn Val Asn Arg Glu
                405                 410

<210> SEQ ID NO 9
<211> LENGTH: 1182
<212> TYPE: DNA
<213> ORGANISM: Bacillus subtilis

<400> SEQUENCE: 9

```
atggaacatt tgctgaatcc gaaagcaaga gagatcgaaa tttcaggaat acgcaaattc        60
tcgaatcttg tagcccaaca cgaagacgtc atttcactta caatcggcca gcctgatttt       120
ttcacaccgc atcatgtgaa agctgccgca aaaaaagcca ttgatgaaaa cgtgacgtca       180
tatactccga atgccggcta cctggagctg agacaagctg tgcagcttta tatgaagaaa       240
aaagcggatt caactatga tgctgaatct gaaattatca tcacaacagg cgcaagccaa        300
gccattgatg ctgcattccg gacgatttta tctcccggtg atgaagtcat tatgccaggg       360
cctatttatc cgggctatga acctattatc aatttgtgcg gggccaagcc tgtcattgtt       420
gatactacgt cacacggctt aagcttacc gcccggctga ttgaagatgc tctgacaccc        480
aacaccaagt gtgtcgtgct tccttatccg tcaaacccta ccggcgtgac tttatctgaa       540
gaagaactga aaagcatcgc agctctctta aaaggcagaa atgtcttcgt attgtctgat       600
gaaatataca gtgaattaac atatgacaga ccgcattact ccatcgcaac ctatttgcgg       660
gatcaaacga ttgtcattaa cgggttgtca aaatcacaca gcatgaccgg ttggagaatt       720
ggatttttat ttgcaccgaa agacattgca agcacattt taaaggttca tcaatacaat       780
gtgtcgtgcg cctcatccat ttctcaaaaa gccgcgcttg aagctgtcac aaacggcttt       840
gacgatgcat tgattatgag agaacaatac aaaaaacgtc tggactatgt ttatgaccgt       900
cttgtttcca tgggacttga cgtagttaaa ccgtccggtg cgttttatat cttcccttct       960
attaaatcat ttggaatgac ttcatttgat tttagtatgg ctcttttgga agacgctggc      1020
gtggcactcg tgccgggcag ctcgttctca acatatggtg aaggatatgt aaggctgtct      1080
tttgcatgct caatggacac gctgagagaa ggcctagacc gtttagaatt atttgtatta      1140
aaaaaacgtg aagcaatgca gacgataaac aacggcgttt aa                        1182
```

<210> SEQ ID NO 10
<211> LENGTH: 393
<212> TYPE: PRT
<213> ORGANISM: Bacillus subtilis

<400> SEQUENCE: 10

Met Glu His Leu Leu Asn Pro Lys Ala Arg Glu Ile Glu Ile Ser Gly
1               5                   10                  15

Ile Arg Lys Phe Ser Asn Leu Val Ala Gln His Glu Asp Val Ile Ser

```
                20                  25                  30
Leu Thr Ile Gly Gln Pro Asp Phe Phe Thr Pro His His Val Lys Ala
         35                  40                  45
Ala Ala Lys Lys Ala Ile Asp Glu Asn Val Thr Ser Tyr Thr Pro Asn
 50                  55                  60
Ala Gly Tyr Leu Glu Leu Arg Gln Ala Val Gln Leu Tyr Met Lys Lys
 65                  70                  75                  80
Lys Ala Asp Phe Asn Tyr Asp Ala Glu Ser Glu Ile Ile Thr Thr
                 85                  90                  95
Gly Ala Ser Gln Ala Ile Asp Ala Ala Phe Arg Thr Ile Leu Ser Pro
                100                 105                 110
Gly Asp Glu Val Ile Met Pro Gly Pro Ile Tyr Pro Gly Tyr Glu Pro
                115                 120                 125
Ile Ile Asn Leu Cys Gly Ala Lys Pro Val Ile Val Asp Thr Thr Ser
                130                 135                 140
His Gly Phe Lys Leu Thr Ala Arg Leu Ile Glu Asp Ala Leu Thr Pro
145                 150                 155                 160
Asn Thr Lys Cys Val Val Leu Pro Tyr Pro Ser Asn Pro Thr Gly Val
                165                 170                 175
Thr Leu Ser Glu Glu Glu Leu Lys Ser Ile Ala Ala Leu Leu Lys Gly
                180                 185                 190
Arg Asn Val Phe Val Leu Ser Asp Glu Ile Tyr Ser Glu Leu Thr Tyr
                195                 200                 205
Asp Arg Pro His Tyr Ser Ile Ala Thr Tyr Leu Arg Asp Gln Thr Ile
                210                 215                 220
Val Ile Asn Gly Leu Ser Lys Ser His Ser Met Thr Gly Trp Arg Ile
225                 230                 235                 240
Gly Phe Leu Phe Ala Pro Lys Asp Ile Ala Lys His Ile Leu Lys Val
                245                 250                 255
His Gln Tyr Asn Val Ser Cys Ala Ser Ser Ile Ser Gln Lys Ala Ala
                260                 265                 270
Leu Glu Ala Val Thr Asn Gly Phe Asp Asp Ala Leu Ile Met Arg Glu
                275                 280                 285
Gln Tyr Lys Lys Arg Leu Asp Tyr Val Tyr Asp Arg Leu Val Ser Met
                290                 295                 300
Gly Leu Asp Val Val Lys Pro Ser Gly Ala Phe Tyr Ile Phe Pro Ser
305                 310                 315                 320
Ile Lys Ser Phe Gly Met Thr Ser Phe Asp Ser Met Ala Leu Leu
                325                 330                 335
Glu Asp Ala Gly Val Ala Leu Val Pro Gly Ser Ser Phe Ser Thr Tyr
                340                 345                 350
Gly Glu Gly Tyr Val Arg Leu Ser Phe Ala Cys Ser Met Asp Thr Leu
                355                 360                 365
Arg Glu Gly Leu Asp Arg Leu Glu Leu Phe Val Leu Lys Lys Arg Glu
                370                 375                 380
Ala Met Gln Thr Ile Asn Asn Gly Val
385                 390

<210> SEQ ID NO 11
<211> LENGTH: 1176
<212> TYPE: DNA
<213> ORGANISM: Lactobacillus amylovorus

<400> SEQUENCE: 11
```

-continued

```
atgccagaat tagctaatga tttaggatta agcaaaaaga tcactgatgt aaaagcttca      60
ggaattagaa tctttgataa caaagtttca gctattcctg gcattatcaa attgactttg     120
ggtgaaccag atatgaatac tcctgagcat gttaagcaag cggctattaa gaatattgca     180
gataatgatt cacactatgc tccacaaaag ggaaagcttg aattaagaaa agctatcagt     240
aaatatttga aaaagattac tggaattgaa tatgatccag aaacagaaat cgtagtaaca     300
gttggtgcaa ctgaagcaat taacgctacc ttgtttgcta ttactaatcc gggtgacaag     360
gttgcaattc ctacgccagt cttttctcta tattggcccg tggctacact tgctgatgcc     420
gattatgttt tgatgaatac tgcagaagat ggttttaagt taacacctaa gaagttagaa     480
gaaactatca agaaaatcc aacaattaaa gcagtaattt tgaattatcc aactaaccca      540
actggtgttg aatatagcga agatgaaatt aaagctttgg ctaaggtaat taagataat      600
catctgtacg taattaccga tgaaatttac agtactttga cttacggtgt aaaacacttt     660
tcaattgcca gcttaattcc agaaagagca atttatatct ctggtttatc taaatcacat     720
gcgatgactg gttatcgttt aggctatgtt gccggacctg caaaaattat ggcagaaatt     780
ggtaaagttc atggccttat ggtgacgact acgacggatt catcacaagc tgccgcaatt     840
gaagcacttg aacacggact tgatgaccct gagaaatata gggaagttta tgaaaagcgt     900
cgtgactatg tttaaaagga attagccgag atagagatgc aagcagttaa gccagaaggt     960
gcattttata tctttgctaa aattccagct aagtatggca agacgatat gaaatttgcc    1020
ttggatttag cttttaaaga aaagtgggt atcactccag gtagtgcatt tggtcctggt    1080
ggtgaaggtc atattagatt atcttatgca tcaagtgatg aaaacttgca tgaggcaatg    1140
aagcgaatga agaaagtttt acaagaggac gaataa                             1176
```

<210> SEQ ID NO 12
<211> LENGTH: 391
<212> TYPE: PRT
<213> ORGANISM: Lactobacillus amylovorus

<400> SEQUENCE: 12

```
Met Pro Glu Leu Ala Asn Asp Leu Gly Leu Ser Lys Lys Ile Thr Asp
  1               5                  10                  15

Val Lys Ala Ser Gly Ile Arg Ile Phe Asp Asn Lys Val Ser Ala Ile
                 20                  25                  30

Pro Gly Ile Ile Lys Leu Thr Leu Gly Glu Pro Asp Met Asn Thr Pro
             35                  40                  45

Glu His Val Lys Gln Ala Ala Ile Lys Asn Ile Ala Asp Asn Asp Ser
         50                  55                  60

His Tyr Ala Pro Gln Lys Gly Lys Leu Glu Leu Arg Lys Ala Ile Ser
 65                  70                  75                  80

Lys Tyr Leu Lys Lys Ile Thr Gly Ile Glu Tyr Asp Pro Glu Thr Glu
                 85                  90                  95

Ile Val Val Thr Val Gly Ala Thr Glu Ala Ile Asn Ala Thr Leu Phe
            100                 105                 110

Ala Ile Thr Asn Pro Gly Asp Lys Val Ala Ile Pro Thr Pro Val Phe
        115                 120                 125

Ser Leu Tyr Trp Pro Val Ala Thr Leu Ala Asp Ala Asp Tyr Val Leu
    130                 135                 140

Met Asn Thr Ala Glu Asp Gly Phe Lys Leu Thr Pro Lys Lys Leu Glu
145                 150                 155                 160

Glu Thr Ile Lys Glu Asn Pro Thr Ile Lys Ala Val Ile Leu Asn Tyr
```

```
                        165                 170                 175
Pro Thr Asn Pro Thr Gly Val Glu Tyr Ser Glu Asp Glu Ile Lys Ala
            180                 185                 190

Leu Ala Lys Val Ile Lys Asp Asn His Leu Tyr Val Ile Thr Asp Glu
        195                 200                 205

Ile Tyr Ser Thr Leu Thr Tyr Gly Val Lys His Phe Ser Ile Ala Ser
    210                 215                 220

Leu Ile Pro Glu Arg Ala Ile Tyr Ile Ser Gly Leu Ser Lys Ser His
225                 230                 235                 240

Ala Met Thr Gly Tyr Arg Leu Gly Tyr Val Ala Gly Pro Ala Lys Ile
            245                 250                 255

Met Ala Glu Ile Gly Lys Val His Gly Leu Met Val Thr Thr Thr Thr
        260                 265                 270

Asp Ser Ser Gln Ala Ala Ile Glu Ala Leu Glu His Gly Leu Asp
    275                 280                 285

Asp Pro Glu Lys Tyr Arg Glu Val Tyr Glu Lys Arg Arg Asp Tyr Val
290                 295                 300

Leu Lys Glu Leu Ala Glu Ile Glu Met Gln Ala Val Lys Pro Glu Gly
305                 310                 315                 320

Ala Phe Tyr Ile Phe Ala Lys Ile Pro Ala Lys Tyr Gly Lys Asp Asp
            325                 330                 335

Met Lys Phe Ala Leu Asp Leu Ala Phe Lys Glu Lys Val Gly Ile Thr
        340                 345                 350

Pro Gly Ser Ala Phe Gly Pro Gly Glu Gly His Ile Arg Leu Ser
    355                 360                 365

Tyr Ala Ser Ser Asp Glu Asn Leu His Glu Ala Met Lys Arg Met Lys
370                 375                 380

Lys Val Leu Gln Glu Asp Glu
385                 390

<210> SEQ ID NO 13
<211> LENGTH: 1413
<212> TYPE: DNA
<213> ORGANISM: Rhodobacter sphaeroides

<400> SEQUENCE: 13
atgcgcgagc ctcttgccct cgagatcgac ccgggccacg gcggcccgct gttcctcgcc      60
atcgccgagg cgatcaccct cgacatcacc cgcgggcggc tgaggcccgg agcgagactg     120
cccggcacac gcgcgctggc gcgggcgctc ggcgtgcatc gcaacacggt ggatgccgcc     180
tatcaggagt tgctgaccca gggctggctg caggccgagc ccgcgcgggg caccttcgtg     240
gcgcaggatc tgccgcaggg gatgctggtg cacaggcccg cgcccgcgcc ggtcgagccg     300
gtcgcgatgc gcgcggggct cgccttctcc gatggcgcgc cggaccccga gctggtgccc     360
gacaaggcgc tggcgcgggc ctttcgccgg gcgctcctgt cgcccgcctt ccgcgccgga     420
gcggattacg gcgatgcccg cggcacctcc tcgctgcggg aggcgctggc agcctatctc     480
gcctcggacc gggcgtggt cgcggatcct gcgcggctgc tgatcgcgcg gggcagccag     540
atggcgctgt cctggtagc ccgggcggcg ctggcgccgg agaggcgat cgcggtcgag     600 gagccgggct atccgctggc ctgggaggcg ttccgcgcag cggagcgga ggtgcgcggc     660 gtgccggtgg atggcggcgg cctcaggatc gacgcgctcg aggccgcgct ggcccgggat     720
ccgcgaatcc gggcggtcta tgtcacgccc atcaccagt atccgacgac cgtcaccatg     780
ggcgcggcgc ggcggttgca gcttctggaa ctggcagagc gccaccggct cgcgctgatc     840
```

```
gaggacgact acgaccacga ataccgcttc gagggccgtc cggtgctgcc gctggctgcc    900
cgcgcgccgg aaggtctgcc gctgatctat gtgggctcgc tgtcgaaact gctctcgccc    960
ggtatccggc tgggatacgc gctggcgccc gagcggctgc tgacccgcat ggccgcggcg   1020
cgcgccgcca tcgaccggca gggcgacgcg ccgctcgagg cggcgctggc cgagctgatc   1080
cgcgacggcg atctgggccg tcatgcccgc aaggcgcgca gggtctaccg ggcgcggcgg   1140
gatctgctgg cggagcgtct cacggcgcag ctggccgggc gcgccgcctt cgatctgccg   1200
gccgggggcc tcgcgctgtg gctgcgctgc cgggcgtct cggccgagac ctgggccgaa   1260
gccgcagggc aggcggggct cgccctgctg ccgggcacgc gcttcgcgct ggagagcccg   1320
gcgccgcagg ccttccggct gggctatgcg cgctggacg aggggcagat cgcccgggcg   1380
gtggagatcc tcgcccggag cttccccggc tga                                1413
```

<210> SEQ ID NO 14
<211> LENGTH: 470
<212> TYPE: PRT
<213> ORGANISM: Rhodobacter sphaeroides

<400> SEQUENCE: 14

```
Met Arg Glu Pro Leu Ala Leu Glu Ile Asp Pro Gly His Gly Gly Pro
  1               5                  10                  15

Leu Phe Leu Ala Ile Ala Glu Ala Ile Thr Leu Asp Ile Thr Arg Gly
             20                  25                  30

Arg Leu Arg Pro Gly Ala Arg Leu Pro Gly Thr Arg Ala Leu Ala Arg
         35                  40                  45

Ala Leu Gly Val His Arg Asn Thr Val Asp Ala Ala Tyr Gln Glu Leu
     50                  55                  60

Leu Thr Gln Gly Trp Leu Gln Ala Glu Pro Ala Arg Gly Thr Phe Val
 65                  70                  75                  80

Ala Gln Asp Leu Pro Gln Gly Met Leu Val His Arg Pro Ala Pro Ala
                 85                  90                  95

Pro Val Glu Pro Val Ala Met Arg Ala Gly Leu Ala Phe Ser Asp Gly
            100                 105                 110

Ala Pro Asp Pro Glu Leu Val Pro Asp Lys Ala Leu Ala Arg Ala Phe
        115                 120                 125

Arg Arg Ala Leu Leu Ser Pro Ala Phe Arg Ala Gly Ala Asp Tyr Gly
    130                 135                 140

Asp Ala Arg Gly Thr Ser Ser Leu Arg Glu Ala Leu Ala Ala Tyr Leu
145                 150                 155                 160

Ala Ser Asp Arg Gly Val Val Ala Asp Pro Ala Arg Leu Leu Ile Ala
                165                 170                 175

Arg Gly Ser Gln Met Ala Leu Phe Leu Val Ala Arg Ala Ala Leu Ala
            180                 185                 190

Pro Gly Glu Ala Ile Ala Val Glu Glu Pro Gly Tyr Pro Leu Ala Trp
        195                 200                 205

Glu Ala Phe Arg Ala Ala Gly Ala Glu Val Arg Gly Val Pro Val Asp
    210                 215                 220

Gly Gly Gly Leu Arg Ile Asp Ala Leu Glu Ala Leu Ala Arg Asp
225                 230                 235                 240

Pro Arg Ile Arg Ala Val Tyr Val Thr Pro His His Gln Tyr Pro Thr
                245                 250                 255

Thr Val Thr Met Gly Ala Ala Arg Arg Leu Gln Leu Leu Glu Leu Ala
            260                 265                 270
```

Glu Arg His Arg Leu Ala Leu Ile Glu Asp Asp Tyr Asp His Glu Tyr
            275                 280                 285

Arg Phe Glu Gly Arg Pro Val Leu Pro Leu Ala Ala Arg Ala Pro Glu
        290                 295                 300

Gly Leu Pro Leu Ile Tyr Val Gly Ser Leu Ser Lys Leu Leu Ser Pro
305                 310                 315                 320

Gly Ile Arg Leu Gly Tyr Ala Leu Ala Pro Glu Arg Leu Leu Thr Arg
                325                 330                 335

Met Ala Ala Ala Arg Ala Ile Asp Arg Gln Gly Asp Ala Pro Leu
            340                 345                 350

Glu Ala Ala Leu Ala Glu Leu Ile Arg Asp Gly Asp Leu Gly Arg His
            355                 360                 365

Ala Arg Lys Ala Arg Arg Val Tyr Arg Ala Arg Arg Asp Leu Leu Ala
            370                 375                 380

Glu Arg Leu Thr Ala Gln Leu Ala Gly Arg Ala Ala Phe Asp Leu Pro
385                 390                 395                 400

Ala Gly Gly Leu Ala Leu Trp Leu Arg Cys Ala Gly Val Ser Ala Glu
                405                 410                 415

Thr Trp Ala Glu Ala Ala Gly Gln Ala Gly Leu Ala Leu Leu Pro Gly
            420                 425                 430

Thr Arg Phe Ala Leu Glu Ser Pro Ala Pro Gln Ala Phe Arg Leu Gly
            435                 440                 445

Tyr Ala Ala Leu Asp Glu Gly Gln Ile Ala Arg Ala Val Glu Ile Leu
    450                 455                 460

Ala Arg Ser Phe Pro Gly
465                 470

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggtattgagg gtcgcatgaa ggttttagtc aatgg                              35

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agaggagagt tagagcctta tgaaatgcta gcagcct                            37

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggtattgagg gtcgcatgtt cgacgccctc gcccg                              35

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agaggagagt tagagcctca gagactggtg aacttgc                              37

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggtattgagg gtcgcatgga acatttgctg aatcc                                35

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agaggagagt tagagcctta aacgccgttg tttatcg                              37

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggtattgagg gtcgcatgcg cgagcctctt gccct                                35

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agaggagagt tagagcctca gccggggaag ctccggg                              37

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggtattgagg gtcgcatgtc cacgcaggcg gccat                                35

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agaggagagt tagagcctca ctcacgattc acattgc                         37

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggtattgagg gtcgcatgcc agaattagct aatga                           35

<210> SEQ ID NO 26
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agaggagagt tagagcctta ttcgtcctct tgtaaaa                         37

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggtattgagg gtcgcatgcg ctctacgacg gctcc                           35

<210> SEQ ID NO 28
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agaggagagt tagagcctca gccgcgcagc accttgg                         37

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggtattgagg gtcgcatgtt tgagaacatt accgc                           35

<210> SEQ ID NO 30

```
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agaggagagt tagagcctta cagcactgcc acaatcg                                37

<210> SEQ ID NO 31
<211> LENGTH: 1194
<212> TYPE: DNA
<213> ORGANISM: Escherichia coli

<400> SEQUENCE: 31
gtgtttcaaa aagttgacgc ctacgctggc gacccgattc ttacgcttat ggagcgtttt        60
aaagaagacc ctcgcagcga caaagtgaat ttaagtatcg gtctgtacta caacgaagac       120
ggaattattc cacaactgca agccgtggcg gaggcggaag cgcgcctgaa tgcgcagcct       180
catggcgctt cgctttattt accgatgaaa gggcttaact gctatcgcca tgccattgcg       240
ccgctgctgt ttggtgcgga ccatccggta ctgaaacaac agcgcgtagc aaccattcaa       300
acccttggcg ctccggggc attgaaagtg ggcgcggatt tcctgaaacg ctacttcccg        360
gaatcaggcg tctgggtcag cgatcctacc tgggaaaacc gcgtagcaat attcgccggg       420
gctggattcg aagtgagtac ttaccccctgg tatgacgaag cgactaacgg cgtgcgcttt      480
aatgacctgt tggcgacgct gaaaacatta cctgcccgca gtattgtgtt gctgcatcca       540
tgttgccaca acccaacggg tgccgatctc actaatgatc agtgggatgc ggtgattgaa       600
attctcaaag cccgcgagct tattccattc ctcgatattg cctatcaagg atttggtgcc       660
ggtatggaag aggatgccta cgctattcgc gccattgcca gcgctggatt acccgctctg       720
gtgagcaatt cgttctcgaa atttctctcc ctttacggcg agcgcgtcgg cggactttct       780
gttatgtgtg aagatgccga agccgctggc cgcgtactgg ggcaattgaa agcaacagtt       840
cgccgcaact actccagccc gccgaatttt ggtgcgcagg tggtggctgc agtgctgaat       900
gacgaggcat tgaaagccag ctggctggcg gaagtagaag agatgcgtac tcgcattctg       960
gcaatgcgtc aggaattggt gaaggtatta agcacagaga tgccagaacg caatttcgat      1020
tatctgctta atcagcgcgg catgttcagt tataccggtt aagtgccgc tcaggttgac       1080 cgactacgtg aagaatttgg tgtctatctc atcgccagcg gtcgcatgtg tgtcgccggg      1140
ttaaatacgg caaatgtaca acgtgtggca aaggcgtttg ctgcggtgat gtaa            1194

<210> SEQ ID NO 32
<211> LENGTH: 397
<212> TYPE: PRT
<213> ORGANISM: Escherichia coli

<400> SEQUENCE: 32

Val Phe Gln Lys Val Asp Ala Tyr Ala Gly Asp Pro Ile Leu Thr Leu
 1               5                   10                  15

Met Glu Arg Phe Lys Glu Asp Pro Arg Ser Asp Lys Val Asn Leu Ser
                20                  25                  30

Ile Gly Leu Tyr Tyr Asn Glu Asp Gly Ile Ile Pro Gln Leu Gln Ala
            35                  40                  45

Val Ala Glu Ala Glu Ala Arg Leu Asn Ala Gln Pro His Gly Ala Ser
        50                  55                  60
```

Leu Tyr Leu Pro Met Glu Gly Leu Asn Cys Tyr Arg His Ala Ile Ala
 65                  70                  75                  80

Pro Leu Leu Phe Gly Ala Asp His Pro Val Leu Lys Gln Gln Arg Val
                 85                  90                  95

Ala Thr Ile Gln Thr Leu Gly Gly Ser Gly Ala Leu Lys Val Gly Ala
            100                 105                 110

Asp Phe Leu Lys Arg Tyr Phe Pro Glu Ser Gly Val Trp Val Ser Asp
            115                 120                 125

Pro Thr Trp Glu Asn Arg Val Ala Ile Phe Ala Gly Ala Gly Phe Glu
130                 135                 140

Val Ser Thr Tyr Pro Trp Tyr Asp Glu Ala Thr Asn Gly Val Arg Phe
145                 150                 155                 160

Asn Asp Leu Leu Ala Thr Leu Lys Thr Leu Pro Ala Arg Ser Ile Val
                165                 170                 175

Leu Leu His Pro Cys Cys His Asn Pro Thr Gly Ala Asp Leu Thr Asn
                180                 185                 190

Asp Gln Trp Asp Ala Val Ile Glu Ile Leu Lys Ala Arg Glu Leu Ile
            195                 200                 205

Pro Phe Leu Asp Ile Ala Tyr Gln Gly Phe Gly Ala Gly Met Glu Glu
            210                 215                 220

Asp Ala Tyr Ala Ile Arg Ala Ile Ala Ser Ala Gly Leu Pro Ala Leu
225                 230                 235                 240

Val Ser Asn Ser Phe Ser Lys Ile Phe Ser Leu Tyr Gly Glu Arg Val
                245                 250                 255

Gly Gly Leu Ser Val Met Cys Glu Asp Ala Glu Ala Ala Gly Arg Val
                260                 265                 270

Leu Gly Gln Leu Lys Ala Thr Val Arg Arg Asn Tyr Ser Ser Pro Pro
            275                 280                 285

Asn Phe Gly Ala Gln Val Val Ala Ala Val Leu Asn Asp Glu Ala Leu
            290                 295                 300

Lys Ala Ser Trp Leu Ala Glu Val Glu Glu Met Arg Thr Arg Ile Leu
305                 310                 315                 320

Ala Met Arg Gln Glu Leu Val Lys Val Leu Ser Thr Glu Met Pro Glu
                325                 330                 335

Arg Asn Phe Asp Tyr Leu Leu Asn Gln Arg Gly Met Phe Ser Tyr Thr
                340                 345                 350

Gly Leu Ser Ala Ala Gln Val Asp Arg Leu Arg Glu Glu Phe Gly Val
            355                 360                 365

Tyr Leu Ile Ala Ser Gly Arg Met Cys Val Ala Gly Leu Asn Thr Ala
            370                 375                 380

Asn Val Gln Arg Val Ala Lys Ala Phe Ala Ala Val Met
385                 390                 395

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggtattgagg gtcgcgtgtt tcaaaaagtt gacgc                         35

<210> SEQ ID NO 34
<211> LENGTH: 37

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agaggagagt tagagcctta catcaccgca gcaaacg                                    37

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggtattgagg gtcgcatgga gtccaaagtc gttga                                      35

<210> SEQ ID NO 36
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agaggagagt tagagcctta cacttggaaa acagcct                                    37

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggtattgagg gtcgcatgaa aaactggaaa acaag                                      35

<210> SEQ ID NO 38
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
agaggagagt tagagcctta cagcttagcg ccttcta                                    37

<210> SEQ ID NO 39
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggtattgagg gtcgcatgcg agggcatta ttcaa                                       35

<210> SEQ ID NO 40
<211> LENGTH: 36
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 40
agaggagagt tagagcctca gcccttgagc gcgaag                              36

<210> SEQ ID NO 41
<211> LENGTH: 1416
<212> TYPE: DNA
<213> ORGANISM: Escherichia coli

<400> SEQUENCE: 41
atggaaaact ttaaacatct ccctgaaccg ttccgcattc gtgttattga gccagtaaaa    60
cgtaccaccc gcgcttatcg tgaagaggca attattaaat ccggtatgaa cccgttcctg   120
ctggatagcg aagatgtttt tatcgattta ctgaccgaca gcggcaccgg ggcggtgacg   180
cagagcatgc aggctgcgat gatgcgcggc gacgaagcct acagcggcag tcgtagctac   240
tatgcgttag ccgagtcagt gaaaaatatc tttggttatc aatacaccat tccgactcac   300
cagggccgtg gcgcagagca atctatatt ccggtactga ttaaaaaacg cgagcaggaa   360
aaaggcctgg atcgcagcaa aatggtggcg ttctctaact atttctttga taccacgcag   420
ggccatagcc agatcaacgg ctgtaccgtg cgtaacgtct atatcaaaga agccttcgat   480
acgggcgtgc gttacgactt aaaggcaac tttgaccttg agggattaga acgcggtatt   540
gaagaagttg gtccgaataa cgtgccgtat atcgttgcaa ccatcaccag taactctgca   600
ggtggtcagc cggtttcact ggcaaactta aaagcgatgt acagcatcgc gaagaaatac   660
gatattccgg tggtaatgga ctccgcgcgc tttgctgaaa acgcctattt catcaagcag   720
cgtgaagcag aatacaaaga ctggaccatc gagcagatca cccgcgaaac ctacaaatat   780
gccgatatgc tggcgatgtc cgccaagaaa gatgcgatgg tgccgatggg cggcctgctg   840
tgcatgaaag acgacagctt ctttgatgtg tacaccgagt gcagaaccct ttgcgtggtg   900
caggaaggct ccccgacata tggcggcctg gaaggcggcg cgatggagcg tctggcggta   960
ggtctgtatg acggcatgaa tctcgactgg ctggcttatc gtatcgcgca ggtacagtat  1020
ctggtcgatg gtctggaaga gattggcgtt gtctgccagc aggcgggcgg tcacgcggca  1080
ttcgttgatg ccggtaaact gttgccgcat atcccggcag accagttccc ggcacaggcg  1140
ctggcctgcg agctgtataa agtcgccggt atccgtgcgg tagaaattgg ctcttttcctg  1200
ttaggccgcg atccgaaaac cggtaaacaa ctgccatgcc cggctgaact gctgcgttta  1260
accattccgc gcgcaacata tactcaaaca catatggact tcattattga agcctttaaa  1320
catgtgaaag agaacgcggc gaatattaaa ggattaacct ttacgtacga accgaaagta  1380
ttgcgtcact tcaccgcaaa acttaaagaa gtttaa                            1416

<210> SEQ ID NO 42
<211> LENGTH: 1371
<212> TYPE: DNA
<213> ORGANISM: Citrobacter freundii

<400> SEQUENCE: 42
atgaattatc cggcagaacc cttccgtatt aaaagcgttg aaactgtatc tatgatcccg    60
cgtgatgaac gcctcaagaa aatgcaggaa gcgggttaca atacttttcct gttaaattcg   120
aaagatattt atattgacct gctgacagac agtggcacta acgcaatgag cgacaagcag   180

-continued

```
tgggccggaa tgatgatggg tgatgaagcg tacgcgggca gcgaaaactt ctatcatctg      240
gaaagaaccg tgcaggaact gtttggcttt aaacatattg ttccgactca ccagggggcgt     300 ggcgcagaaa acctgttatc gcagctggct attaaacctg gcaatatgt tgccgggaat      360 atgtatttca ctaccacccg ttatcaccag gaaaaaaatg gtgcggtgtt tgtcgatatc      420
gttcgtgacg aagcgcacga tgccggtctg aatattgcgt ttaaaggtga tatcgatctt     480
aaaaaattac aaaagctgat tgatgaaaaa ggcgcagaga atattgcgta tatctgcctg     540
gcggtgacgg ttaacctcgc gggcggccaa ccggtctcga tggctaacat gcgtgcggtg    600
cgtgaactga cagaagcgca tggcattaaa gtgttctacg acgctacccg ctgcgtagaa    660
aacgcctact ttatcaaaga gcaagagcag ggctttgaga acaagagcat cgccgagatc    720
gtgcatgaga tgttcagcta cgccgacggt tgtaccatga gtggtaaaaa agactgtctg    780
gtgaacatcg gcggcttcct gtgcatgaac gatgacgaaa tgttctcttc tgccaaagag    840
ttagtcgtgg tctacgaagg gatgccatct tacgcggcc tggccggacg tgatatggaa    900
gcgatggcga ttggcctgcg tgaagccatg cagtacgaat atattgagca ccgcgtgaag    960
caggttcgct acctgggcga taagctgaaa gccgctggcg taccgattgt tgaaccggta   1020
ggcggtcacg cggtattcct cgatgcgcgt cgcttctgcg agcatctgac gcaagatgag  1080
ttcccggcac aaagtctggc tgccagcatc tatgtgaaaa ccggcgtgcg cagtatggag  1140
cgcggaatta tctctgcggg ccgtaataac gtgaccggtg aacaccacag accgaaactg  1200
gaaaccgtgc gtctgactat tccacgtcgt gtttatacct acgcacatat ggatgttgtg  1260
gctgacggta ttattaaact ttaccagcac aaagaagata ttcgcgggct gaagtttatt  1320
tacgagccga agcagttgcg tttctttact gcacgctttg attacatcta a           1371
```

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ggtattgagg gtcgcatgga aaactttaaa catct                               35

<210> SEQ ID NO 44
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
agaggagagt tagagcctta aacttcttta agttttg                             37

<210> SEQ ID NO 45
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggtattgagg gtcgcatgaa ttatccggca gaacc                               35

```
<210> SEQ ID NO 46
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
agaggagagt tagagcctta gatgtaatca aagcgtg                              37

<210> SEQ ID NO 47
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ccagggcacc ggcgcagagc aaatctatat t                                   31

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tgcgccggtg ccctggtgag tcggaatggt                                     30

<210> SEQ ID NO 49
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tcctgcacgc ggcaaagggt tctgcactcg gt                                  32

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ctttgccgcg tgcaggaagg cttcccgaca                                     30

<210> SEQ ID NO 51
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aggggaccgg cgcagaaaac ctgttatcg                                      29
```

```
<210> SEQ ID NO 52
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tctgcgccgg tcccctggtg agtcggaaca at                                    32

<210> SEQ ID NO 53
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gttagtccgc gtctacgaag ggatgccat                                        29

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gtagacgcgg actaactctt tggcagaag                                        29

<210> SEQ ID NO 55
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggtattgagg gtcgcatgta cgaactggga gttgt                                 35

<210> SEQ ID NO 56
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
agaggagagt tagagcctta gtcaatatat ttcaggc                               37

<210> SEQ ID NO 57
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ggtattgagg gtcgcatgtc cggcatcgtt gtcca                                 35

<210> SEQ ID NO 58
```

<210> SEQ ID NO 58
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
agaggagagt tagagcctca gacatatttc agtccca                37

<210> SEQ ID NO 59
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
ggtattgagg gtcgcatgcg actgaacaac ctcgg                35

<210> SEQ ID NO 60
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
agaggagagt tagagcctca gttctccacg tattcca                37

<210> SEQ ID NO 61
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
ggtattgagg gtcgcatgag cgtggttcac cggaa                35

<210> SEQ ID NO 62
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
agaggagagt tagagcctca atcgatatat ttcagtc                37

<210> SEQ ID NO 63
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
ggtattgagg gtcgcatgag cctggttaat atgaa                35

<210> SEQ ID NO 64
<211> LENGTH: 37

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
agaggagagt tagagcctta tgactttaac gcgttga                              37

<210> SEQ ID NO 65
<211> LENGTH: 684
<212> TYPE: DNA
<213> ORGANISM: Comamonas testosteroni

<400> SEQUENCE: 65
atgtacgaac tgggagttgt ctaccgcaat atccagcgcg ccgaccgcgc tgctgctgac    60
ggcctggccg ccctgggctc cgccaccgtg cacgaggcca tgggccgcgt cggtctgctc   120
aagccctata tgcgccccat ctatgccggc aagcaggtct cgggcaccgc cgtcacggtg   180
ctgctgcagc ccggcgacaa ctggatgatg catgtggctg ccgagcagat tcagcccggc   240
gacatcgtgg tcgcagccgt caccgcagag tgcaccgacg gctacttcgg cgatctgctg   300
gccaccagct tccaggcgcg cggcgcacgt gcgctgatca tcgatgccgg cgtgcgcgac   360
gtgaagacgc tgcaggagat ggactttccg gtctggagca aggccatctc ttccaagggc   420
acgatcaagg ccaccctggg ctcggtcaac atccccatcg tctgcgccgg catgctggtc   480
acgcccggtg acgtgatcgt ggccgacgac gacggcgtgg tctgcgtgcc cgccgcgcgt   540
gccgtggaag tgctggccgc cgcccagaag cgtgaaagct cgaaggcga aaagcgcgcc    600 aagctggcct cgggcatcct cggcctggat atgtacaaga tgcgcgagcc cctggaaaag   660
gccggcctga atatattga ctaa                                            684

<210> SEQ ID NO 66
<211> LENGTH: 227
<212> TYPE: PRT
<213> ORGANISM: Comamonas testosteroni

<400> SEQUENCE: 66

Met Tyr Glu Leu Gly Val Val Tyr Arg Asn Ile Gln Arg Ala Asp Arg
  1               5                  10                  15

Ala Ala Ala Asp Gly Leu Ala Ala Leu Gly Ser Ala Thr Val His Glu
                 20                  25                  30

Ala Met Gly Arg Val Gly Leu Leu Lys Pro Tyr Met Arg Pro Ile Tyr
             35                  40                  45

Ala Gly Lys Gln Val Ser Gly Thr Ala Val Thr Val Leu Leu Gln Pro
         50                  55                  60

Gly Asp Asn Trp Met Met His Val Ala Ala Glu Gln Ile Gln Pro Gly
 65                  70                  75                  80

Asp Ile Val Val Ala Ala Val Thr Ala Glu Cys Thr Asp Gly Tyr Phe
                 85                  90                  95

Gly Asp Leu Leu Ala Thr Ser Phe Gln Ala Arg Gly Ala Arg Ala Leu
            100                 105                 110

Ile Ile Asp Ala Gly Val Arg Asp Val Lys Thr Leu Gln Glu Met Asp
        115                 120                 125

Phe Pro Val Trp Ser Lys Ala Ile Ser Ser Lys Gly Thr Ile Lys Ala
    130                 135                 140

Thr Leu Gly Ser Val Asn Ile Pro Ile Val Cys Ala Gly Met Leu Val
145                 150                 155                 160
```

Thr Pro Gly Asp Val Ile Val Ala Asp Asp Gly Val Val Cys Val
              165                 170                 175

Pro Ala Ala Arg Ala Val Glu Val Leu Ala Ala Ala Gln Lys Arg Glu
            180                 185                 190

Ser Phe Glu Gly Glu Lys Arg Ala Lys Leu Ala Ser Gly Ile Leu Gly
        195                 200                 205

Leu Asp Met Tyr Lys Met Arg Glu Pro Leu Glu Lys Ala Gly Leu Lys
    210                 215                 220

Tyr Ile Asp
225

<210> SEQ ID NO 67
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
actcggatcc gaaggagata tacatatgta cgaactggga ct                          42

<210> SEQ ID NO 68
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cggctgtcga ccgttagtca atatatttca ggc                                   33

<210> SEQ ID NO 69
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cgcggatcca taatggttga gaacattacc g                                     31

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
acgcgtcgac ttacagcact gccacaatcg                                       30

<210> SEQ ID NO 71
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71

<210> SEQ ID NO 72
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
gaatgcggcc gcttagtcaa tatatttcag gcc        33

<210> SEQ ID NO 73
<211> LENGTH: 15
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
ggtattgagg gtcgc        15

<210> SEQ ID NO 74
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
agaggagagt tagagcc        17

<210> SEQ ID NO 75
<211> LENGTH: 1191
<212> TYPE: DNA
<213> ORGANISM: Escherichia coli

<400> SEQUENCE: 75

```
atgtttgaga acattaccgc cgctcctgcc gacccgattc tgggcctggc cgatctgttt     60
cgtgccgatg aacgtccgg caaaattaac ctcgggattg gtctctatta cgatgagacg    120
ggcaaaatcc cggtactgac cagcgtgaaa aaggctgaac agtatctgct cgaaaatgaa    180
accaccaaac tttacctcgg cattgacggc atccctgaat tggtcgctg cactcaggaa    240
ctgctgtttg gtaaaggtag cgccctgatc aatgacaaac gtgctcgcac ggcacagact    300
ccggggggct ctggcgcact acgcgtggct gccgatttcc tggcaaaaaa taccagcgtt    360
aagcgtgtgt gggtgagcaa cccaagctgg ccgaaccata gagcgtctt taactctgca    420
ggtctggaag ttcgtgaata cgcttattat gatgcgaaa atcacactct tgacttcgat    480
gcactgatta acagcctgaa tgaagctcag gctggcgacg tagtgctgtt ccatggctgc    540
tgccataacc caaccggtat cgaccctacg ctgaacaat ggcaaacact ggcacaactc    600
tccgttgaga aaggctggtt accgctgttt gacttcgctt accaggggttt tgcccgtggt    660
ctggaagaag atgctgaagg actgcgcgct ttcgcggcta tgcataaaga gctgattgtt    720
gccagttcct actctaaaaa ctttggcctg tacaacgagc gtgttggcgc ttgtactctg    780
gttgctgccg acagtgaaac cgttgatcgc gcattcagcc aaatgaaagc ggcgattcgc    840
gctaactact cttcccccacc agcacacggc gcttctgttg ttgccaccat cctgagcaac    900
```

```
gatgcgttac gtgcgatttg ggaacaagag ctgactgata tgcgccagcg tattcagcgt    960
atgcgtcagt tgttcgtcaa tacgctgcag gaaaaaggcg caaaccgcga cttcagcttt   1020
atcatcaaac agaacggcat gttctccttc agtggcctga caaaagaaca agtgctgcgt   1080
ctgcgcgaag agtttggcgt atatgcggtt gcttctggtc gcgtaaatgt ggccgggatg   1140
acaccagata acatggctcc gctgtgcgaa gcgattgtgg cagtgctgta a            1191

<210> SEQ ID NO 76
<211> LENGTH: 396
<212> TYPE: PRT
<213> ORGANISM: Escherichia coli

<400> SEQUENCE: 76
```

| | | | | | | | | | | | | | | |
|---|---|---|---|---|---|---|---|---|---|---|---|---|---|---|
| Met | Phe | Glu | Asn | Ile | Thr | Ala | Ala | Pro | Ala | Asp | Pro | Ile | Leu | Gly | Leu |
| 1 | | | | 5 | | | | | 10 | | | | | 15 | |
| Ala | Asp | Leu | Phe | Arg | Ala | Asp | Glu | Arg | Pro | Gly | Lys | Ile | Asn | Leu | Gly |
| | | 20 | | | | | 25 | | | | | 30 | | | |
| Ile | Gly | Leu | Tyr | Tyr | Asp | Glu | Thr | Gly | Lys | Ile | Pro | Val | Leu | Thr | Ser |
| | | | 35 | | | | | 40 | | | | | 45 | | |
| Val | Lys | Lys | Ala | Glu | Gln | Tyr | Leu | Leu | Glu | Asn | Glu | Thr | Thr | Lys | Leu |
| 50 | | | | | 55 | | | | | 60 | | | | | |
| Tyr | Leu | Gly | Ile | Asp | Gly | Ile | Pro | Glu | Phe | Gly | Arg | Cys | Thr | Gln | Glu |
| 65 | | | | 70 | | | | | 75 | | | | | 80 | |
| Leu | Leu | Phe | Gly | Lys | Gly | Ser | Ala | Leu | Ile | Asn | Asp | Lys | Arg | Ala | Arg |
| | | | 85 | | | | | 90 | | | | | 95 | | |
| Thr | Ala | Gln | Thr | Pro | Gly | Gly | Ser | Gly | Ala | Leu | Arg | Val | Ala | Ala | Asp |
| | | | 100 | | | | | 105 | | | | | 110 | | |
| Phe | Leu | Ala | Lys | Asn | Thr | Ser | Val | Lys | Arg | Val | Trp | Val | Ser | Asn | Pro |
| | | 115 | | | | | 120 | | | | | 125 | | | |
| Ser | Trp | Pro | Asn | His | Lys | Ser | Val | Phe | Asn | Ser | Ala | Gly | Leu | Glu | Val |
| 130 | | | | | 135 | | | | | 140 | | | | | |
| Arg | Glu | Tyr | Ala | Tyr | Tyr | Asp | Ala | Glu | Asn | His | Thr | Leu | Asp | Phe | Asp |
| 145 | | | | 150 | | | | | 155 | | | | | 160 | |
| Ala | Leu | Ile | Asn | Ser | Leu | Asn | Glu | Ala | Gln | Ala | Gly | Asp | Val | Val | Leu |
| | | | 165 | | | | | 170 | | | | | 175 | | |
| Phe | His | Gly | Cys | Cys | His | Asn | Pro | Thr | Gly | Ile | Asp | Pro | Thr | Leu | Glu |
| | | | 180 | | | | | 185 | | | | | 190 | | |
| Gln | Trp | Gln | Thr | Leu | Ala | Gln | Leu | Ser | Val | Glu | Lys | Gly | Trp | Leu | Pro |
| | | 195 | | | | | 200 | | | | | 205 | | | |
| Leu | Phe | Asp | Phe | Ala | Tyr | Gln | Gly | Phe | Ala | Arg | Gly | Leu | Glu | Glu | Asp |
| 210 | | | | | 215 | | | | | 220 | | | | | |
| Ala | Glu | Gly | Leu | Arg | Ala | Phe | Ala | Ala | Met | His | Lys | Glu | Leu | Ile | Val |
| 225 | | | | | 230 | | | | | 235 | | | | | 240 |
| Ala | Ser | Ser | Tyr | Ser | Lys | Asn | Phe | Gly | Leu | Tyr | Asn | Glu | Arg | Val | Gly |
| | | | | 245 | | | | | 250 | | | | | 255 | |
| Ala | Cys | Thr | Leu | Val | Ala | Ala | Asp | Ser | Glu | Thr | Val | Asp | Arg | Ala | Phe |
| | | | 260 | | | | | 265 | | | | | 270 | | |
| Ser | Gln | Met | Lys | Ala | Ala | Ile | Arg | Ala | Asn | Tyr | Ser | Ser | Pro | Pro | Ala |
| | | 275 | | | | | 280 | | | | | 285 | | | |
| His | Gly | Ala | Ser | Val | Val | Ala | Thr | Ile | Leu | Ser | Asn | Asp | Ala | Leu | Arg |
| | 290 | | | | | 295 | | | | | 300 | | | | |
| Ala | Ile | Trp | Glu | Gln | Glu | Leu | Thr | Asp | Met | Arg | Gln | Arg | Ile | Gln | Arg |
| 305 | | | | | 310 | | | | | 315 | | | | | 320 |
| Met | Arg | Gln | Leu | Phe | Val | Asn | Thr | Leu | Gln | Glu | Lys | Gly | Ala | Asn | Arg |

-continued

```
                        325                 330                 335
Asp Phe Ser Phe Ile Ile Lys Gln Asn Gly Met Phe Ser Phe Ser Gly
            340                 345                 350

Leu Thr Lys Glu Gln Val Leu Arg Leu Arg Glu Glu Phe Gly Val Tyr
        355                 360                 365

Ala Val Ala Ser Gly Arg Val Asn Val Ala Gly Met Thr Pro Asp Asn
    370                 375                 380

Met Ala Pro Leu Cys Glu Ala Ile Val Ala Val Leu
385                 390                 395

<210> SEQ ID NO 77
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gcggaacata tgtttgagaa cattaccgcc                                        30

<210> SEQ ID NO 78
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ataaccggat ccttacagca ctgccacaat cg                                     32

<210> SEQ ID NO 79
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gcggcgcata tggtgtttca aaaagttgac gc                                     32

<210> SEQ ID NO 80
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ccaataggat ccttacatca ccgcagcaaa cg                                     32

<210> SEQ ID NO 81
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ggccggcata tgcgtgatat cgattccgta at                                     32
```

```
<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ggaattctcg agttaggcaa cagcagcgcg                                          30

<210> SEQ ID NO 83
<211> LENGTH: 627
<212> TYPE: DNA
<213> ORGANISM: Zymomonas mobilis

<400> SEQUENCE: 83
atgcgtgata tcgattccgt aatgcgtttg gcaccggtta tgccggtcct cgtcattgaa         60
gatattgctg atgcaaaacc tatcgcagaa gctttggttg ctggtggtct gaacgttctt        120
gaagtaacgc ttcgcacccc ttgtgctctt gaagccatca agatcatgaa agaagttccg        180
ggtgccgttg ttggtgccgg tacggttctg aacgcaaaaa tgctcgacca agctcaggaa        240
gctggttgcg aattttttcgt tagcccgggt ctgaccgctg acctcggcaa gcatgctgtt        300
gcccagaaag cagctttgct tccaggtgtt gctaatgctg ctgatgtgat gcttggtctt        360
gaccttggtc ttgatcgctt caaattcttc ccggctgaaa atatcggtgg tttacctgcc        420
ctgaagtcca tggcttctgt tttccgtcag gttcgtttct gcccgaccgg cggtatcacc        480
ccgacgtcag ctcctaaata tcttgaaaac ccgtccattc tttgcgtcgg tggtagctgg        540
gttgttccgg ctggcaaacc agatgtcgca aaaatcacgg cactcgctaa agaagcttct        600
gctttcaagc gcgctgctgt tgcctaa                                            627

<210> SEQ ID NO 84
<211> LENGTH: 208
<212> TYPE: PRT
<213> ORGANISM: Zymomonas mobilis

<400> SEQUENCE: 84

Met Arg Asp Ile Asp Ser Val Met Arg Leu Ala Pro Val Met Pro Val
  1               5                  10                  15

Leu Val Ile Glu Asp Ile Ala Asp Ala Lys Pro Ile Ala Glu Ala Leu
                 20                  25                  30

Val Ala Gly Gly Leu Asn Val Leu Glu Val Thr Leu Arg Thr Pro Cys
             35                  40                  45

Ala Leu Glu Ala Ile Lys Ile Met Lys Glu Val Pro Gly Ala Val Val
         50                  55                  60

Gly Ala Gly Thr Val Leu Asn Ala Lys Met Leu Asp Gln Ala Gln Glu
 65                  70                  75                  80

Ala Gly Cys Glu Phe Phe Val Ser Pro Gly Leu Thr Ala Asp Leu Gly
                 85                  90                  95

Lys His Ala Val Ala Gln Lys Ala Leu Leu Pro Gly Val Ala Asn
            100                 105                 110

Ala Ala Asp Val Met Leu Gly Leu Asp Leu Gly Leu Asp Arg Phe Lys
            115                 120                 125

Phe Phe Pro Ala Glu Asn Ile Gly Gly Leu Pro Ala Leu Lys Ser Met
        130                 135                 140

Ala Ser Val Phe Arg Gln Val Arg Phe Cys Pro Thr Gly Gly Ile Thr
```

```
                 145                 150                 155                 160
Pro Thr Ser Ala Pro Lys Tyr Leu Glu Asn Pro Ser Ile Leu Cys Val
                165                 170                 175

Gly Gly Ser Trp Val Val Pro Ala Gly Lys Pro Asp Val Ala Lys Ile
            180                 185                 190

Thr Ala Leu Ala Lys Glu Ala Ser Ala Phe Lys Arg Ala Ala Val Ala
        195                 200                 205

<210> SEQ ID NO 85
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tgaccctcta gataagaagg agatatacat atggctgaca ctcgccctga ac           52

<210> SEQ ID NO 86
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ttctcaagct tttattccgc gttttcgtga atatgtttg                          39

<210> SEQ ID NO 87
<211> LENGTH: 672
<212> TYPE: DNA
<213> ORGANISM: Rhizobium leguminosarum

<400> SEQUENCE: 87
atgggcatcg tcgtacagaa cataccacgg gcggaagctg atgtgatcga caggctcgcc   60
aaatcaggcg tcgcgacggt ccacgaagcc caggggcgca aaggcatgct cgccagccat  120
atgagaccaa tctattcagg tgcgcagatc gccggctccg ccattacgat ctccgcaccg  180
cccggtgata actggatgat ccatgtggcg atcgagcaga tccaggccgg cgacatcctg  240
gtgctttcgc cgacctcgcc ctgtgacaac ggttatttcg gcgacctgct tgccacctcg  300
gcgcgggcgc gaggttgccg cggccttgtc atcgacgccg tgtccgcga tatcagggat  360
ctgacccaga tgcagttccc cgtgtggtcc aaggccgtgt ccgcgcaggg gaccgtcaag  420
gaaacgctcg gttcggtcaa cgttccgatc gtctgcgctg cgccttcat cgaagccggc   480
gacatcatcg tcgccgacga cgacggggtg tgcgtggtga agctcaacgc ggccgaggag  540
gttctgactg ctgccgagaa ccgtgtggcg aacgaggagg ccaagcggca acgcctcgcc  600
gccggcgaac tcgggctcga tatctatgac atgcggtcga agctccggga aaaggggctt  660
aaatatgtat ga                                                      672

<210> SEQ ID NO 88
<211> LENGTH: 224
<212> TYPE: PRT
<213> ORGANISM: Rhizobium leguminosarum

<400> SEQUENCE: 88

Met Gly Ile Val Val Gln Asn Ile Pro Arg Ala Glu Ala Asp Val Ile
 1               5                  10                  15
```

```
Asp Arg Leu Ala Lys Ser Gly Val Ala Thr Val His Glu Ala Gln Gly
            20                  25                  30

Arg Lys Gly Met Leu Ala Ser His Met Arg Pro Ile Tyr Ser Gly Ala
        35                  40                  45

Gln Ile Ala Gly Ser Ala Ile Thr Ile Ser Ala Pro Pro Gly Asp Asn
    50                  55                  60

Trp Met Ile His Val Ala Ile Glu Gln Ile Gln Ala Gly Asp Ile Leu
65                  70                  75                  80

Val Leu Ser Pro Thr Ser Pro Cys Asp Asn Gly Tyr Phe Gly Asp Leu
                85                  90                  95

Leu Ala Thr Ser Ala Arg Ala Arg Gly Cys Arg Gly Leu Val Ile Asp
            100                 105                 110

Ala Gly Val Arg Asp Ile Arg Asp Leu Thr Gln Met Gln Phe Pro Val
            115                 120                 125

Trp Ser Lys Ala Val Ser Ala Gln Gly Thr Val Lys Glu Thr Leu Gly
130                 135                 140

Ser Val Asn Val Pro Ile Val Cys Ala Gly Ala Phe Ile Glu Ala Gly
145                 150                 155                 160

Asp Ile Ile Val Ala Asp Asp Gly Val Cys Val Val Lys Leu Asn
            165                 170                 175

Ala Ala Glu Glu Val Leu Thr Ala Ala Glu Asn Arg Val Ala Asn Glu
            180                 185                 190

Glu Ala Lys Arg Gln Arg Leu Ala Ala Gly Glu Leu Gly Leu Asp Ile
            195                 200                 205

Tyr Asp Met Arg Ser Lys Leu Arg Glu Lys Gly Leu Lys Tyr Val Trp
            210                 215                 220
```

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 89
aggtcgtgta ctgtcagtca                                          20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 90
acgtggtgaa ctgccagtga                                          20

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

```
<400> SEQUENCE: 91

His His His His His His
  1               5
```